United States Patent
Farnet et al.

(10) Patent No.: US 7,297,524 B2
(45) Date of Patent: Nov. 20, 2007

(54) POLYNUCLEOTIDES FOR PRODUCTION OF FARNESYL DIBENZODIAZEPINONES

(75) Inventors: Chris M. Farnet, Montreal (CA); Emmanuel Zazopoulos, Montreal (CA)

(73) Assignee: Thallion Pharmceuticals Inc., Montreal (CA)

(*) Notice: Subject to any disclaimer, the term of this patent is extended or adjusted under 35 U.S.C. 154(b) by 0 days.

(21) Appl. No.: 11/330,123

(22) Filed: Jan. 12, 2006

(65) Prior Publication Data

US 2006/0172395 A1    Aug. 3, 2006

Related U.S. Application Data

(63) Continuation-in-part of application No. 10/762,107, filed on Jan. 21, 2004, now Pat. No. 7,101,872.

(60) Provisional application No. 60/518,286, filed on Nov. 10, 2003.

(51) Int. Cl.
| | |
|---|---|
| C12N 9/10 | (2006.01) |
| C12N 15/70 | (2006.01) |
| C12N 1/20 | (2006.01) |
| C12P 17/16 | (2006.01) |
| C12P 21/06 | (2006.01) |
| C07H 21/04 | (2006.01) |

(52) U.S. Cl. .................. 435/193; 438/118; 438/69.1; 438/320.1; 438/252.3; 536/23.2

(58) Field of Classification Search ............... 435/193, 435/118, 69.1, 320.1, 252.3; 536/23.2
See application file for complete search history.

(56) References Cited

U.S. PATENT DOCUMENTS

| | | |
|---|---|---|
| 5,283,173 A | 2/1994 | Fields |
| 5,393,665 A | 2/1995 | Fayerman |
| 5,466,590 A | 11/1995 | Sariaslani |
| 5,541,181 A | 7/1996 | Ohkuma |
| 5,556,772 A | 9/1996 | Sorge |
| 5,830,695 A | 11/1998 | Serizawa |
| 2003/0052268 A1 | 3/2003 | Doroshenko |

FOREIGN PATENT DOCUMENTS

WO    WO-2004-065591 A1 *   8/2004

OTHER PUBLICATIONS

Whisstock et al. Quaterly Reviews of Biophysics, 2003, "Prediction of protein function from protein sequence and structure", 36(3): 307-340.*
Branden et al. Introduction to protein structure, Gerald Publishing Inc., New York, p. 247, 1991.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Seffernick et al. Melamine deaminase and atrazine chlorohydrolase: 98 percent identical but functionally different, J Bacteriol. Apr. 2001;183(8):2405-10.*
Carillo H. and Lipman D., Siam J. Applied Math. (1988)vol. 48, No. 5, pp. 1073-1082 "The Multiple Sequence Alignment Problem in Biology".
Goodfellow M., Bergey's Manual of Systematic Bacteriology (1989) vol. 4, pp. 2322-2339 "Suprageneric Classification of Actinomycetes".
Embley T. M. and Stackebrandt E., Ann. Rev. Microbiol. (1994) vol. 48, pp. 257-289 "The molecular phylogeny and systematics of the actinomycetes".
Herlt A. J. et al., Aust. J. Chem. (1981) vol. 34, pp. 1319-1324 "Synthesis of Unlabelled and Carboxyl-Labelled 3-Amino-5-hydroxybenzoic Acid".
Murakami T. et al., J. Bacteriol. (1989) vol. 171, No. 3, pp. 1459-1466 "Thiostrepton-Induced Gene Expression in *Streptomyces lividans*".
Thompson C. J. et al., J. Bacteriol. (1982) vol. 151, No. 2, pp. 668-677 "Cloning of Antibiotic Resistance and Nutritional Genes in Streptomycetes".
Nielson K. B. et al., Strategies (1994) vol. 7, pp. 27 "Taq Extender PCR Additive for Improved Length, Yield and Reliability of PCR Products".
Gluzman Y., Cell (1981) vol. 23, pp. 175-182 "SV40-Transformer Simian Cells Support the Replication of Early SV40 Mutants".
Workman P. et al., British Journal of Cancer, Second Edition (1997) vol. 77, pp. 1-10 "UKCCCR guidelines for the welfare of animals in experimental neoplasma".
Premont J., Biochim Biophys Acta. (1975), vol. 381, pp. 368-376 "[3H] Norepinephrine binding by rat glial cells in culture lack of correlation between binding and adenylate cyclase activation".
Zazopoulos et al., Nature Biotechnol. (2003) vol. 21, pp. 187-190 "A genomics-guided approach for discovering and expressing cryptic metabolic pathways".
Stryer L., Biochemisty 3rd edition (1988) W.H. Freeman and Co., New York, pp. 752-754.
Altschul S. F. et al. J. Mol. Biol. (1990)vol. 215, pp. 403-410 "Basic Local Alignment Search Tool".
Takagi M. et al., J. Bacteriol. (2000) vol. 182, No. 15, pp. 4153-4157 "A Gene Cluster for the Mevalonate Pathway from Streptomyces sp. Strain CL190".
Birnboim H. C. and Doly J., Nucleic Acids Research (1979)vol. 7, No. 6, pp. 1513-1523 "A rapid alkaline extraction procedure for screening recombinant plasmid DNA".

* cited by examiner

*Primary Examiner*—Rebecca E. Prouty
*Assistant Examiner*—Iqbal Chowdhury

(57) ABSTRACT

This invention provides genes and their encoded proteins, involved in the biosynthesis of farnesyl dibenzodiazepinones, including ECO-04601. The invention relates to expression vectors comprising the genes and to host cell transformed with these vectors. The invention further relates to methods of producing farnesyl dibenzodiazepinone compounds using the genes and proteins of the invention, for example, involving expression of biosynthetic pathway genes in transformed host cells.

4 Claims, 10 Drawing Sheets

Saline

ECO-04601
(20 mg/kg)

Figure 9

```
Locus A      ------VAELYSTIEESARQLDVPCSRDRVWPILSAYGDAFAHPEAVVAFRVATALRHAG
Locus B      MPGTSEAVELCSTIEESARLLNVACSRDRVWSLLSAYGDAFAHPGAVVAFRVATAMRHVG
Locus C      MFATAGAAELHAVVEDSARLLGVTCSPDTVAPILSTYGDTFEHDATVVAFRVATGKRHIG
                   ..**  :..:*:*** *.*.** * *  .:**:***:* *  :********. ** *

Locus A      ELDCRFRTHPDDRDPYASALARGLTPRTDHPVGALLSEVHRRCPVESHGIDFGVVGGFKK
Locus B      ELDCRFTTHPDDRDPYARALSRGLTPETDHPVGTLLSEVQGRCPVESHGIDFGVVGGFKK
Locus C      ELDCRFTTHPTHRDPYALALSNGLTPKTGHPVGSLLSALQERLPIDSYGIDFGVVGGFKK
             ****** *** .***** **:.****.*.****:*** ::  * *::*:************

Locus A      IYAAFAPDELQVATSLAGIPAMPRSLAANADFFTRHGLDDRVGVLGFDYPARTVNVYFND
Locus B      IYAFFTPDDLQETSKLAEIPAMPRSLAGNVEFFARHGLDDRVGVFGIDYPSRTVNVYFND
Locus C      IYSFFTPDALQEVAALAGIPSMPRSLAG-RDFFERYGCTTGR-VIGIDYPH---------
             **: *:** **  .: ** **:******.   :** *:*       *:*:*** ********

Locus A      VPRECFEPETIRSTLRRTGMAEPSEQMLRLGTGAFGLYVTLGWDSPEIERICYAAATTDL
Locus B      VPAESFHSETIRSTLREIGMAEPSERMLKLGEKAFGLYVTLGWDSSRIERICYAAATTDL
Locus C      ------------------------------------------------------------
             ** *.*..********. *******:**:**  :**  ***********..***********

Locus A      TTLPVPVEPEIEKFVKSVPYGGGDRKFVYGVALTPKGEYYKLESHYKWKPGAVNFI
Locus B      TTLPVPVEPEIEKFVRSVPYGGEDRKFVYGVALTPHGEYYKLESHYRWKPGAMDFI
Locus C      -------------------------------------------------------
             ***************:****** **************:***********:*****::**
```

Figure 10

```
Locus A    VSEPSSSLPRLGQWHGLEDLRRLQEKQLAETFTWAARSPFYRARLASGAPPVTPADLADL
Locus B    VNDPRPSLPQLGQWHGPEDLQRLQEKQLSQTVTWATRSPFYRDRLDPGALPATAADLADL
Locus C    VNPTRSSLPRLGQWNGPEDLRLLQEKQLQQTVGWASRSPFYRGRLDTAALPTTIDDLASL
            *.  . .***:****:* ***: ****** :*. **:****** **  ..* *.*   ***.*

Locus A    PLTTKQDLRDNYPFGMLAVPRERLATYHESSGTAGKPTPSYYTAEDWTDLAERFARKWIG
Locus B    PLTTKQDLRDNYPFGMLAVPKERLATYHESSGTAGRPTPSYYTAEDWTDLAERFARKWIG
Locus C    PLTTKQDLRDNYPFGMLAVPKERLATYHESSGTAGRPTPSYYTADDWIDLAERFARKWIG
           ********************:**************:*******:** ************

Locus A    MSADDVFLVRTPYALLLTGHLAHAAARLRGATVVPGDNRSLAMPYARVVRVMHDLDVTLT
Locus B    MSAEDVFLVRTPYALLLTGHLAHAAGRLRGATVVPGDNRSLAMPYARVVRVMHDLGVTLT
Locus C    ITAEDVFLVRTPYALLLTGHLAHAAGRLHGATVVPGDNRSLAMPYARVVRVMHDLGVTLT
           ::*:********************.**:********************.****

Locus A    WSVPTECLIWAAAAIAAGHRPDIDFPALRALFVGGEPMTDARRRRISRLWGVPVIEEYGS
Locus B    WSVPTECLIWAAAATAAGHRPDVDFPALRALFVGGEPLTDARRRRISRLWGVPVIEEYGS
Locus C    WSVPTECLIWAAAATAAGHRPSEDFPALRALFVGGEPLTTARRDRISRLWGVPVIEEYGS
           ************** ******. **************:* *** *****************

Locus A    TETGSLAGECPEGRLHLWADRALFEVYDPDTGAVRADGDGQLVVTPLFREAMPLLRYNLE
Locus B    TETGSLAGECPNGRMHLWADRALFEVYDPRTGTVSADGDGQLVVTPLFREAMPLLRYNLE
Locus C    TETGSLAGECPHGRMHLWADRALFEVYDPQTGTVRAEGEGQLVVTPLYREAMPLLRYNLE
           ***********.**:************** **:* *:*:*******:************

Locus A    DNVSVSYDDCGCGWKLPTVRVLGRSAFGYRVGGTTITQHQLEELVFSLPEAHRVMFWRAK
Locus B    DDVTVSYDDCACGWNLPTVRVLGRAAFGYRVGAATITQHRLEEVVFSLPESHGVVFWRAK
Locus C    DNVSVAYDDCACGWKLPTVQVLGRAAFGHRVGATTVTQHRLEELVFSLPDAYQVVFWRAR
           *:*:*:****.***:****:****:***:***..*:***:***:******:  *:****:

Locus A    AEPALLRVEIEVAAAHRVAAEAELTAAIRAAFGVDSEVTGLAPGTLIPLDALTSMPDVVK
Locus B    AEPTVLRIEIEVAEEHRTAAQAELTASVRATFGIDSEVTGLTPGTLVPREALTSMPDVVK
Locus C    AEPAALRIEIEVPEEHRAAAEAELVHSVRTAFGVDSTVTGLPPGTLIPHGALTAMPDVVK
           ***: **:****. **.**:***. ::*::**:** ****.****:* ***:******

Locus A    PRSLFGPDEDWSKALLYY
Locus B    PRSLFGPDEDWGKALLYY
Locus C    PRSLFGPDEDWGKALLYY
           **********.******
```

US 7,297,524 B2

POLYNUCLEOTIDES FOR PRODUCTION OF FARNESYL DIBENZODIAZEPINONES

RELATED APPLICATIONS

This application is a continuation-in-part of U.S. patent application Ser. No. 10/762,107, filed Jan. 21, 2004, now issued as U.S. patent No. 7,101,872, which claims priority to U.S. Provisional Application 60/518,286, filed Nov. 10, 2003. The entire disclosure of each of these applications is incorporated herein by reference.

SEQUENCE LISTING ON COMPACT DISK

The content of the following submissions on compact discs are incorporated herein by reference in its entirety: A compact disc copy of the Sequence Listing (COPY 1) (file name: 3005-5US-50US.ST25.txt, date recorded Jan. 10, 2006, size: 298 KB) and a duplicate compact disc copy of the Sequence Listing (COPY 2) (file name: 3005-5US-50US.ST25.txt, date recorded Jan. 10, 2006, size: 298 KB).

FIELD OF THE INVENTION

The invention relates to novel polynucleotide sequences and their encoded proteins, which are involved in the biosynthesis of a farnesyl dibenzodiazepinone compound and analogs. The invention relates to the use of such polynucleotides and proteins to produce farnesyl dibenzodiazepinone compounds and analogs. One method of obtaining the compound is by cultivation of a novel modified strain of *Micromonospora* sp., i.e., 046-ECO11 or [S01]046; another method involves expression of biosynthetic pathway genes in transformed host cells. The present invention further relates to cosmids 046KM and 046KQ and their methods of use.

BACKGROUND OF THE INVENTION

The euactinomycetes are a subset of a large and complex group of Gram-positive bacteria known as actinomycetes. Over the past few decades these organisms, which are abundant in soil, have generated significant commercial and scientific interest as a result of the large number of therapeutically useful compounds produced as secondary metabolites. The intensive search for strains able to produce new secondary metabolites having potential therapeutic applications has led to the identification of hundreds of new species. Many of the euactinomycetes, particularly *Streptomyces* and the closely related *Saccharopolyspora* genera, have been extensively studied. Both of these genera produce a notable diversity of biologically active metabolites. Because of the commercial significance of these compounds, much is known about the genetics and physiology of these organisms.

Microbial genomic information is unique in that, unlike the organization of genomic information in higher life forms, microbial secondary metabolic biosynthetic genes are known to cluster together within the genome. This information allows identification of the gene locus encoding the enzymes responsible for the biosynthesis of a specific molecule. Equally, the identification of the genes present within a cluster allows prediction of the structure of the secondary metabolite. The identification of the genes and proteins responsible for the production of active molecules allows for example, generation of structural analogs or improvement of the production process.

U.S. patent application Ser. No. 10/762,107 describes a dibenzodiazepinone secondary metabolite, specifically 10-farnesyl-4,6,8-trihydroxy-dibenzodiazepin-11-one (named ECO-04601) produced by a known euactinomycetes strain, *Micromonospora* sp. (IDAC 231203-01). Likewise, U.S. Pat. No. 5,541,181 (Ohkuma et al.) also discloses a dibenzodiazepinone secondary metabolite, specifically 5-farnesyl-4,7,9-trihydroxy-dibenzodiazepin-11-one (named "BU-4664L"), produced by a known euactinomycetes strain, *Micromonospora* sp. M990-6 (ATCC 55378). Both these dibenzodiazepinones have been reported to have anti-tumor activity.

Although many biologically active compounds have been identified from bacteria, there remains the need to obtain novel naturally occurring compounds with enhanced properties. Current methods of obtaining such compounds include screening of natural isolates and chemical modification of existing compounds, both of which are costly and time consuming. Current screening methods are based on general biological properties of the compound, which require prior knowledge of the structure of the molecules. Methods for chemically modifying known active compounds exist, but still suffer from practical limitations as to the type of compounds obtainable.

Thus, there exists a considerable need to obtain pharmaceutically active compounds in a cost-effective manner and with high yield. The present invention solves these problems by providing polynucleotides, polypeptides, vectors comprising the polynucleotides and host cells comprising the vectors for production of dibenzodiazepinones, as well as methods to generate farnesyl dibenzodiazepinones by de novo biosynthesis (heterologous or homologous expression of biosynthetic genes) or semi-synthesis rather than by chemical synthesis.

SUMMARY OF THE INVENTION

The invention further encompasses an isolated polynucleotide comprising one or more of SEQ ID NOs. 1, 64 and 73, wherein the polynucleotide encodes a polypeptide that participates in a biosynthetic pathway for a farnesyl dibenzodiazepinone.

The invention further encompasses an isolated polynucleotide comprising SEQ ID NOs. 1, 64 and 73, wherein the polynucleotide encodes a polypeptide that participates in a biosynthetic pathway for a farnesyl dibenzodiazepinone.

The invention further encompasses an isolated polynucleotide that encodes a polypeptide selected from the group consisting of SEQ ID NOs. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 65, 67, 69, 71, 74, 76, 78, 80, 82, 84, 86, 88, 90, 92, 94 and 96.

The invention further provides an isolated nucleic acid comprising a nucleotide sequence identical or complementary to a polynucleotide encoding a polypeptide having at least 70%, at least 75%, at least 80%, at least 85%, at least 90%, at least 95% or at least 99% identity to a sequence selected from the group consisting of SEQ ID NOs. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 65, 67, 69, 71, 74, 76, 78, 80, 82, 84, 86, 88, 90, 92, 94 and 96 said polypeptide having the same biological function as its corresponding protein.

The invention further provides an isolated nucleic acid comprising a nucleotide sequence hybridizing under low, moderate, high or very high stringency conditions to the complement of a polynucleotide encoding a sequence selected from the group consisting of SEQ ID NOs. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 65, 67, 69, 71, 74, 76, 78, 80, 82, 84, 86, 88, 90, 92, 94 and 96, said polypeptide having the same biological function as its corresponding protein.

The invention provides an isolated, purified or enriched nucleic acid comprising a polynucleotide, or a nucleotide sequence complementary thereto, said polynucleotide encoding a polypeptide selected from an adenylating amide synthetase (ADSA) having at least 80%, at least 90%, or at least 95% identity to the adenylating amide synthetase of SEQ ID NO: 48; and an isoprenyl transferase (IPTN) having at least 80%, at least 90%, or at least 95% identity to the isoprenyl transferase of SEQ ID NO: 22. In one embodiment, the invention provides an expression vector comprising said ADSA or IPTN-encoding nucleic acid. In another embodiment, the invention provides host cells transformed which such vector.

The invention further provides a polypeptide selected from an adenylating amide synthetase (ADSA) having at least 80%, at least 90%, or at least 95% identity to the adenylating amide synthetase of SEQ ID NO: 48; and an isoprenyl transferase (IPTN) having at least 80%, at least 90%, or at least 95% identity to the isoprenyl transferase of SEQ ID NO: 22.

In one embodiment, the isolated polynucleotide comprising SEQ ID No. 1 encodes a polypeptide selected from the group consisting of SEQ ID Nos. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60 and 62.

In another embodiment, the isolated polynucleotide comprising SEQ ID No. 64 encodes a polypeptide selected from the group consisting of SEQ ID NOS: 65, 67, 69 and 71.

In another embodiment, the isolated polynucleotide comprising SEQ ID No. 73, encodes a polypeptide selected from the group consisting of SEQ ID NOS: 74, 76, 78, 80, 82, 84, 86 and 88.

The invention further encompasses an isolated polypeptide of SEQ ID NO. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 65, 67, 69, 71, 74, 76, 78, 80, 82, 84, 86, 88, 90, 92, 94 and 96.

The invention further provides an isolated polypeptide having at least 70%, at least 75%, at least 80%, at least 85%, at least 90%, at least 95% or at least 99% identity to a sequence selected from the group consisting of SEQ ID NOs. 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 65, 67, 69, 71, 74, 76, 78, 80, 82, 84, 86, 88, 90, 92, 94 and 96, said polypeptide having the same biological function as its corresponding protein.

In one embodiment, the polypeptide participates in a biosynthetic pathway for a farnesyl dibenzodiazepinone.

The invention further encompasses an expression vector comprising one or more of the polynucleotides described herein.

The invention further encompasses a recombinant prokaryotic organism comprising one or more such expression vectors.

In one embodiment, the organism is an actinomycete.

In another embodiment, the organism requires the expression vector to synthesize a farnesyl dibenzodiazepinone. That is, the organism is deficient in the ability to synthesize a farnesyl dibenzodiazepinone before transformation with a polynucleotide as described herein.

The invention further encompasses a method of making a farnesyl dibenzodiazepinone de novo in a prokaryote, comprising the steps of: (a) providing a prokaryote that is incapable of synthesizing a farnesyl dibenzodiazepinone; (b) transforming the prokaryote with an expression vector as described herein; and (c) culturing the prokaryote under conditions such that a polypeptide of the invention is expressed and catalyses the synthesis of a farnesyl dibenzodiazepinone compound or analog.

In one embodiment, the prokaryote is an actinomycete.

In another embodiment, the vector expresses a polypeptide of SEQ ID NO: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 65, 67, 69, 71, 74, 76, 78, 80, 82, 84, 86, 88, 90, 92, 94 and 96.

BRIEF DESCRIPTION OF THE FIGURES

FIG. 5: shows a schematic diagram of the biosynthetic pathway for the production of farnesyl-diphosphate, providing the farnesyl group of ECO-04601.

FIG. 6: shows a schematic diagram of the biosynthetic pathway for the production of 3-hydroxy-anthranilate-adenylate precursor of the dibenzodiazepinone group.

FIG. 7: shows a schematic diagram of the biosynthetic pathway for the production of 2-amino-6-hydroxy-[1,4] benzoquinone precursor of the core dibenzodiazepinone.

FIG. 8: shows a schematic diagram of the biosynthetic pathway for the assembly of the ECO-04601 precursors, farnesyl-diphosphate, 3-hydroxy-anthranilate-adenylate and 2-amino-6-hydroxy-[1,4]benzoquinone.

FIGS. 9 and 10: show clustal alignments respectively of isoprenyl transferase and adenylating amide synthetase enzymes of locus A with the corresponding enzymes present in loci B and C. In each of the clustal alignments: (i) an asterisk "*" indicates positions which have a single, fully conserved residues; (ii) a colon ":" indicates that one of the following strong groups is fully conserved in a specific position: (S, T or A); (N, E, Q or K); (N, H, Q or K); (N, D, E or Q); (Q, H, R or K); (M, I, L or V); (M, I, L or F); (H or Y); and (F, Y or W); and (iii) a period "." indicates that one of the following weaker groups is fully conserved: (C, S or A); (A, T or V); (S, A or G); (S, T, N or K); (S, T, P or A); (S, G, N or D); (S, N, D, E, Q or K); (N, D, E, Q, H or K); (N, E, Q, H, R or K); (F, V, L, I or M): and (H, F or Y). The number at the end of each line indicates the position of the last amino acid of the line within the specific domain.

FIG. 9: shows an amino acid alignment comparing the isoprenyl transferase (IPTN) enzyme of locus A (SEQ ID NO: 22), isolated from *Micronospora* sp. strain 046-ECO11, with the isoprenyl transferase enzyme of locus B (SEQ ID NO 90) isolated from *Micromonospora echinospora challisensis* NRRL 12255, and the partial isoprenyl transferase enzyme of locus C (SEQ ID NO: 94) isolated from *Streptomyces carzinostaticus neocarzinostaticus* ATCC 15944.

FIG. 10: shows an amino acid alignment comparing the adenylating amide synthetase (ADSA) enzyme of locus A (SEQ ID NO: 48), isolated from *Micronospora* sp. strain 046-ECO11, with the adenylating amide synthetase of locus B (SEQ ID NO 92) isolated from *Micromonospora echinospora challisensis* NRRL 12255, and locus C (SEQ ID NO: 96) isolated from *Streptomyces carzinostaticus neocarzinostaticus* ATCC 15944.

DETAILED DESCRIPTION OF THE INVENTION

Figure 1:
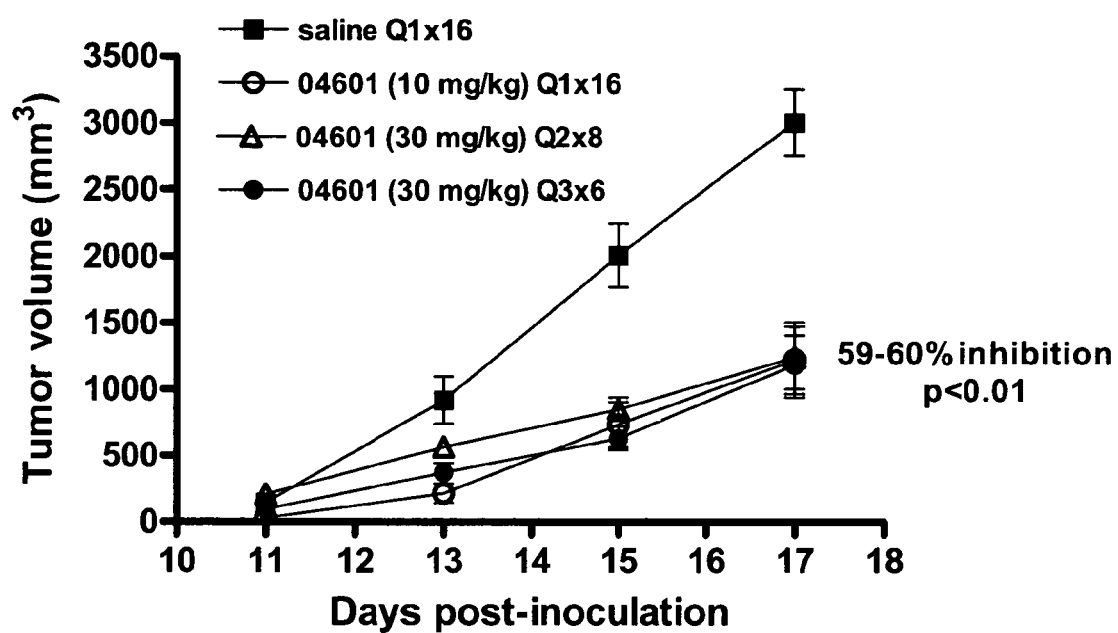
FIG. 1: shows inhibition of tumor growth resulting from administration of 10 to 30 mg/kg of ECO-04601 to glioblastoma-bearing mice beginning one day after tumor cell inoculation.

The present invention provides isolated and purified polynucleotides that encode farnesyl dibenzodiazepinone-producing enzymes, i.e., polypeptides from farnesyl dibenzodiazepinone-producing microorganisms, fragments thereof, vectors containing those polynucleotides, and host cells transformed with those vectors. These polynucleotides, fragments thereof, and vectors comprising the polynucleotides can be used as reagents in the production of farnesyl dibenzodiazepinones. The invention also relates to a method for producing new farnesyl dibenzodiazepinones, by selectively altering the genetic information of an organism or by feeding the proteins or a host cell transformed with vectors comprising nucleic acids encoding them, with close analogs of the key intermediates. Portions of the polynucleotide sequences disclosed herein are also useful as primers for the amplification of DNA or as probes to identify related domains from other farnesyl dibenzodiazepinone producing microorganisms.

I. Definitions

For convenience, the meaning of certain terms and phrases used in the specification, examples, and appended claims, are provided below.

As used herein, the term "farnesyl dibenzodiazepinone" refers to a class of dibenzodiazepinone compounds containing a farnesyl moiety. The term includes, but is not limited to, the exemplified compound of the present invention, 10-farnesyl-4,6,8-trihydroxy-dibenzodiazepin-11-one, which is referred to herein as "ECO-04601."

The terms "farnesyl dibenzodiazepinone-producing microorganism" and "producer of farnesyl dibenzodiazepinone," as used herein, refer to a microorganism that carries genetic information necessary to produce a farnesyl dibenzodiazepinone compound, whether or not the organism naturally produces the compound. The terms apply equally to organisms in which the genetic information to produce the farnesyl dibenzodiazepinone compound is found in the organism as it exists in its natural environment, and to organisms (host cells) in which the genetic information is introduced by recombinant techniques.

Specific organisms contemplated herein include, without limitation, organisms of the family Micromonosporaceae, of which preferred genera include *Micromonospora, Actinoplanes* and *Dactylosporangium*; the family Streptomycetaceae, of which preferred genera include *Streptomyces* and *Kitasatospora*; the family Pseudonocardiaceae, of which preferred genera are *Amycolatopsis* and *Saccharopolyspora*; and the family Actinosynnemataceae, of which preferred genera include *Saccharothrix* and *Actinosynnema*; however the terms are intended to encompass all organisms containing genetic information necessary to produce a farnesyl dibenzodiazepinone compound. A preferred producer of a farnesyl dibenzodiazepinone compound includes microbial strain 046-ECO11, a deposit of which was made on Mar. 7, 2003, with the International Depository Authority of Canada (IDAC), Bureau of Microbiology, Health Canada, 1015 Arlington Street, Winnipeg, Manitoba, Canada R3E 3R2, under Accession No. IDAC 070303-01.

The term "gene" means the segment of DNA involved in producing a polypeptide chain; it includes regions preceding and following the coding region (leader and trailer) as well as, where applicable, intervening regions (introns) between individual coding segments (exons).

The terms "gene locus, "gene cluster," and "biosynthetic locus" refer to a group of genes or variants thereof involved in the biosynthesis of a farnesyl dibenzodiazepinone compound. For example, the biosynthetic locus in strain 046-ECO11 that directs the production of ECO-04601 referred to herein as "046D" or "locus A", the biosynthetic locus in *Micromonospora echinospora challisensis* NRRL 12255 referred to herein as "052E" or "locus B", the biosynthetic locus in *Streptomyces carzinostaticus neocarzinostaticus* ATCC 15944 referred to herein as "237C" or "locus C", or the corresponding biosynthetic locus from a farnesyl dibenzodiazepinone-producing microorganism. Genetic modification of gene locus, gene cluster or biosynthetic locus refers to any genetic recombinant techniques known in the art including mutagenesis, inactivation, or replacement of nucleic acids that can be applied to generate variants of ECO-04601.

A DNA or nucleotide "coding sequence" or "sequence encoding" a particular polypeptide or protein, is a DNA sequence which is transcribed and translated into a polypeptide or protein when placed under the control of an appropriate regulatory sequence.

"Oligonucleotide" refers to a nucleic acid, generally of at least 10, preferably 15 and more preferably at least 20 nucleotides in length, preferably no more than 100 nucleotides in length, that are hybridizable to a genomic DNA molecule, a cDNA molecule, or an mRNA molecule encoding a gene, mRNA, cDNA or other nucleic acid of interest.

A promoter sequence is "operably linked to" a coding sequence recognized by RNA polymerase which initiates transcription at the promoter and transcribes the coding sequence into mRNA.

The term "replicon" as used herein means any genetic element, such as a plasmid, cosmid, chromosome or virus, that behaves as an autonomous unit of polynucleotide replication within a cell. An "expression vector" or "vector" is a replicon in which another polynucleotide fragment is attached, such as to bring about the replication and/or expression of the attached fragment. "Plasmids" are designated herein by a lower case "p" preceded or followed by capital letters and/or numbers. The starting plasmids disclosed herein are commercially available, publicly available on an unrestricted basis, or can be constructed from available plasmids in accordance with published procedures. In addition, equivalent plasmids to those described herein are known in the art and will be apparent to the skilled artisan.

The terms "express" and "expression" means allowing or causing the information in a gene or DNA sequence to become manifest, for example producing a protein by activating the cellular functions involved in transcription and translation of a corresponding gene or DNA sequence. A DNA sequence is expressed in or by a cell to form an "expression product" such as a protein. The expression product itself, e.g. the resulting protein, may also be said to be "expressed" by the cell. An expression product can be characterized as intracellular, extracellular or secreted.

"Digestion" of DNA refers to enzymatic cleavage of the DNA with a restriction enzyme that acts only at certain sequences in the DNA. The various restriction enzymes used herein are commercially available and their reaction conditions, cofactors and other requirements were used as would be known to the ordinary skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular enzymes are specified by the manufacturer. Incubation times of about 1 hour at 37° C. are ordinarily used, but may vary in accordance with the supplier's instructions. After digestion the gel electrophoresis may be performed to isolate the desired fragment.

The term "isolated" as used herein means that the material is removed from its original environment (e.g. the natural environment where the material is naturally occurring). For example, a naturally occurring polynucleotide or polypeptide present in a living animal is not isolated, but the same polynucleotide or polypeptide, which is separated from some or all of the coexisting materials in the natural system, is isolated. Such polynucleotides could be part of a vector and/or such polynucleotides or polypeptides could be part of a composition, and still be isolated in that the vector or composition is not part of the natural environment.

The term "restriction fragment" as used herein refers to any linear DNA generated by the action of one or more restriction enzymes.

The term "transformation" means the introduction of a foreign gene, foreign nucleic acid, DNA or RNA sequence to a host cell, so that the host cell will express the introduced gene or sequence to produce a desired substance, typically a protein or enzyme coded by the introduced gene or sequence. The introduced gene or sequence may also be called a "cloned" or "foreign" gene or sequence, may include regulatory or control sequences, such as start, stop, promoter, signal, secretion, or other sequences used by a cell's genetic machinery. The gene or sequence may include nonfunctional sequences or sequences with no known function. A host cell that receives and expresses introduced DNA or RNA has been "transformed" and is a "transformant" or a "clone" or "recombinant". The DNA or RNA introduced to a host cell can come from any source, including cells of the same genus or species as the host cell, or cells of a different genus or species.

The terms "recombinant polynucleotide" and "recombinant polypeptide" as used herein mean a polynucleotide or polypeptide which by virtue of its origin or manipulation is not associated with all or a portion of the polynucleotide or polypeptide with which it is associated in nature and/or is linked to a polynucleotide or polypeptide other than that to which it is linked in nature.

The term "host cell" as used herein, refer to both prokaryotic and eukaryotic cells which are used as recipients of the recombinant polynucleotides and vectors provided herein. In one embodiment, the host cell is a prokaryote.

The terms "open reading frame" and "ORF" as used herein refers to a region of a polynucleotide sequence which encodes a polypeptide; this region may represent a portion of a coding sequence or a total coding sequence.

As used herein and as known in the art, the term "identity" is the relationship between two or more polynucleotide sequences, as determined by comparing the sequences. Identity also means the degree of sequence relatedness between polynucleotide sequences, as determined by the match between strings of such sequences. Identity can be readily calculated (see, e.g., *Computation Molecular Biology*, Lesk, A. M., eds., Oxford University Press, New York (1998), and *Biocomputing: Informatics and Genome Projects*, Smith, D. W., ed., Academic Press, New York (1993), both of which are incorporated by reference herein). While there exist a number of methods to measure identity between two polynucleotide sequences, the term is well known to skilled artisans (see, e.g., *Sequence Analysis in Molecular Biology*, von Heinje, G., Academic Press (1987); and *Sequence Analysis Primer*, Gribskov., M. and Devereux, J., eds., M. Stockton Press, New York (1991)). Methods commonly employed to determine identity between sequences include, for example, those disclosed in Carillo, H., and Lipman, D., *SIAM J. Applied Math.* (1988) 48:1073. "Substantially identical," as used herein, means there is a very high degree of homology (preferably 100% sequence identity) between subject polynucleotide sequences. However, polynucleotides having greater than 90%, or 95% sequence identity may be used in the present invention, and thus sequence variations that might be expected due to genetic mutation, strain polymorphism, or evolutionary divergence can be tolerated.

II. Method of Making a Farnesyl Dibenzodiazepinone by Fermentation

The farnesyl dibenzodiazepinone compounds of the present invention may be biosynthesized by various microorganisms. Microorganisms that may synthesize the compounds of the present invention include but are not limited to bacteria of the order Actinomycetales, also referred to as actinomycetes. Non-limiting examples of members belonging to the genera of *Actinomycetes* include *Nocardia, Geodermatophilus, Actinoplanes, Micromonospora, Nocardioides, Saccharothrix, Amycolatopsis, Kutzneria, Saccharomonospora, Saccharopolyspora, Kitasatospora, Streptomyces, Microbispora, Streptosporangium,* and *Actinomadura*. The taxonomy of *actinomycetes* is complex and reference is made to Goodfellow, *Suprageneric Classification of Actinomycetes* (1989); *Bergey's Manual of Systematic Bacteriology*, Vol. 4 (Williams and Wilkins, Baltimore, pp. 2322-2339); and to Embley and Stackebrandt, "The molecular phylogeny and systematics of the actinomycetes," *Annu. Rev. Microbiol.* (1994) 48:257-289, each of which is hereby incorporated by reference in its entirety, for genera that may synthesize the compounds of the invention.

Farnesyl dibenzodiazepinone-producing microorganisms are cultivated in culture medium containing known nutritional sources for actinomycetes. Such media having assimilable sources of carbon, nitrogen, plus optional inorganic salts and other known growth factors at a pH of about 6 to about 9. Suitable media include, without limitation, the growth media provided in Table 1. Microorganisms are cultivated at incubation temperatures of about 18° C. to about 40° C. for about 3 to about 40 days.

TABLE 1

Examples of Fermentation Media

| Component | QB | MA | KH | RM | JA | FA | HI | CL |
|---|---|---|---|---|---|---|---|---|
| pH*[1] | 7.2 | 7.5 | 7 | 6.85 | 7.3 | 7.0 | 7.0 | 7.0 |
| Glucose | 12 | | 10 | 10 | | 10 | | |
| Sucrose | | | | 100 | | | | |
| Cane molasses | | | | | | 15 | | |
| Corn starch | | | | | 30 | | | |
| Soluble starch | 10 | 25 | | | | | | |
| Potato dextrin | | | 20 | | | 40 | 20 | 20 |
| Corn steep solid | 5 | | | | | | | |
| Corn steep liquor | 5 | | | | 15 | | | |
| Dried yeast | | 2 | | | | | | |
| Yeast extract | | | 5 | | | | 8.34 | |
| Malt extract | | | | | 35 | | | |
| Pharmamedia ™ | 10 | | | | 15 | | | |
| Glycerol | | | | | | | 30 | 20 |
| NZ-Amine A | | | 5 | | | 10 | | |
| Soybean powder | | 15 | | | | | | |
| Fish meal | | | | | | | | 10 |
| Bacto-peptone | | | | | | | 2.5 | 5 |
| MgSO$_4$.7H$_2$O | | | | | 1 | | | |
| CaCO$_3$ | | 4 | 1 | | 2 | 2 | 3 | 2 |
| NaCl | | 5 | | | | | | |
| (NH$_4$)$_2$SO$_4$ | | 2 | | | | | | 2 |
| K$_2$SO$_4$ | | | | 0.25 | | | | |
| MgCl$_2$.6H$_2$O | | | | 10 | | | | |
| Na$_2$HPO$_4$ | | | | | | 3 | | |
| Casamino acid | | | | 0.1 | | | | |
| Proflo oil ™ (mL/L) | 4 | | | | | | | |
| MOPS | | | | 21 | | | | |
| Trace element solution*[2] ml/L | | | | 2 | | | | |

Unless otherwise indicated all the ingredients are in g/L.
*[1]The pH is to adjusted as marked prior to the addition of CaCO$_3$.
*[2]Trace elements solution contains: ZnCl$_2$ 40 mg; FeCl$_3$6H$_2$O (200 mg); CuCl$_2$2H$_2$O (10 mg); MnCl$_2$.4H$_2$O; Na$_2$B$_4$O$_7$.10H$_2$O (10 mg); (NH$_4$)$_6$MO$_7$O$_{24}$.4H$_2$O (10 mg) per liter.

The culture media inoculated with the farnesyl dibenzodiazepinone-producing microorganisms may be aerated by incubating the inoculated culture media with agitation, for example, shaking on a rotary shaker, or a shaking water bath. Aeration may also be achieved by the injection of air, oxygen or an appropriate gaseous mixture to the inoculated culture media during incubation. Following cultivation, the farnesyl dibenzodiazepinone compounds can be extracted and isolated from the cultivated culture media by techniques known to a skilled person in the art and/or disclosed herein, including for example centrifugation, chromatography, adsorption, filtration. For example, the cultivated culture media can be mixed with a suitable organic solvent such as n-butanol, n-butyl acetate or 4-methyl-2-pentanone, the organic layer can be separated for example, by centrifugation followed by the removal of the solvent, by evaporation to dryness or by evaporation to dryness under vacuum. The resulting residue can optionally be reconstituted with for example water, ethanol, ethyl acetate, methanol or a mixture thereof, and re-extracted with a suitable organic solvent such as hexane, carbon tetrachloride, methylene chloride or a mixture thereof. Following removal of the solvent, the compounds may be further purified by the use of standard techniques, such as chromatography.

III. Method of Making a Farnesyl Dibenzodiazepinone by Recombinant Technology

In another embodiment, the present invention relates to nucleic acid molecules that encode proteins useful in the production of farnesyl benzodiazepinones. Specifically, the present invention provides recombinant DNA vectors and nucleic acid molecules that encode all or part of the biosynthetic locus in strain 046-ECO11, which directs the production of ECO-04601, and is referred to herein as "046D." The invention further includes genetic modification of 046D using conventional genetic recombinant techniques, such as mutagenesis, inactivation, or replacement of nucleic acids, to produce chemical variants of ECO-04601.

The invention thus provides a method for making a farnesyl benzodiazepinone compound using a transformed host cell comprising a recombinant DNA vector that encodes one or more of the polypeptides of the present invention, and culturing the host cell under conditions such that farnesyl benzodiazepinone is produced. In one embodiment, the host cell is a prokaryote. In another embodiment, the host cell is an actinomycete. In another embodiment, the host cell is a *Streptomyces* host cell. In a further embodiment, the host cell is a non-*Streptomyces* actinomycete such as a *Rhodococcus*, a *Mycobaterium*, or an *Amycolatopsis* specie.

The invention provides recombinant nucleic acids that produce a variety of farnesyl dibenzodiazepinone compounds that cannot be readily synthesized by chemical methodology alone. The invention allows direct manipulation of 046D biosynthetic locus via genetic engineering of the enzymes involved in the biosynthesis of a farnesyl dibenzodiazepinone according to the invention. The 046D biosynthetic locus is described in Example 5.

Farnesyl dibenzodazepinones and analogs are also produced by feeding one or more key intermediates or biosynthetic precursors (as defined in FIGS. 5-8) or close structural analogs, to a host cell comprising a recombinant DNA vector that encodes one or more of the polypeptides of the present invention, and culturing the host cell under conditions such that the farnesyl benzodiazepinone or analog is produced. Key intermediates are contacted directly with an isolated protein of the invention to perform the necessary steps for the production of a farnesyl dibenzodiazepinone (e.g., the farnesyl diphopshate and dibenzodiazepinone precursors can be coupled using an IPTN protein of the invention).

Key intermediates may be commercially available or may be prepared using standard chemical procedures or using the proteins of this invention. For example, farnesyl diphosphate and 3-hydroxyanthranilic acid are commercially available (e.g., Fluka F6892 and Aldrich 148776). 3-Amino-5-hydroxybenzoic acid, a precursor of the 2-amino-6-hydroxybenzoquinone, is prepared as described in Herlt et al (1981), *Aust. J. Chem.*, vol 34, 1319-1324.

Recombinant DNA Vectors

Vectors of the invention typically comprise the DNA of a transmissible agent, into which foreign DNA is inserted. A common way to insert one segment of DNA into another segment of DNA involves the use of specific enzymes called restriction enzymes that cleave DNA at specific sites (specific groups of nucleotides) called restriction sites. A "cassette" refers to a DNA coding sequence or segment of DNA that codes for an expression product that can be inserted into a vector at defined restriction sites. The cassette restriction sites are designed to ensure insertion of the cassette in the proper reading frame. Generally, a nucleic acid molecule that encodes a protein useful in the production of a farnesyl dibenzodiazepinone is inserted at one or more restriction sites of the vector DNA, and then is carried by the vector into a prokaryote e.g. actinomycte, by transformation (see below). A segment or sequence of DNA having inserted or added DNA, such as an expression vector, can also be called a "DNA construct". A common type of vector is a "plasmid" which generally is a self-contained molecule of double-stranded DNA, usually of bacterial origin, that can readily accept additional (foreign) DNA and which can be readily introduced into a suitable host cell. A plasmid vector often contains coding DNA and promoter DNA and has one or more restriction sites suitable for inserting foreign DNA. Coding DNA is a DNA sequence that encodes a particular amino acid sequence for a particular protein or enzyme. In one embodiment of the invention, the coding DNA encodes for polypeptides of SEQ ID NO: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86, 88, 90, 92, 94, 96 or 98 that may be useful for the biosynthesis of a farnesyl dibenzodiazepinone.

Promoter DNA of a recombinant vector is a DNA sequence that initiates, regulates, or otherwise mediates or controls the expression of the coding DNA. Promoter DNA and coding may be from the same or different organisms. Recombinant cloning vectors will often include one or more replication systems for cloning or expression, one or more markers for selection in the host, e.g. antibiotic resistance, and one or more expression cassettes. Vector constructs may be produced using conventional molecular biology and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes 1 and 11 (D. N. Glover ed. 1985); F. M. Ausubel et al. (eds.), Current Protocols in Molecular Biology, John Wiley & Sons, Inc. (1994).

Examples of promoters that function in actinomycetes, e.g. *Streptomyces*, are taught in U.S. Pat. Nos. 5,830,695 and 5,466,590. Another example of a transcription promoter useful in *Actinomycetes* expression vectors is tipA, a promoter inducible by the antibiotic thiostrepton [c.f. Murakami, T., et al., (1989), J. Bacteriol, 171, 1459].

Transformation of *Actinomycetes*

A suitable transformation method for use with an actinomycete comprises forming the *actinomycete* culture into spheroplasts using lysozyme. A buffer solution containing recombinant DNA vectors and polyethylene glycol is then added, in order to introduce the vector into the host cells, by using either of the methods of Thompson or Keiser [c. f. Thompson, C. J., et al., (1982), J. Bacteriol., 151, 668-677 or Keiser, T. et al. (2000), "Practical *Streptomyces* Genetics", The John Innes Foundation, Norwich], for example. A thiostrepton-resistance gene is frequently used as a selective marker in the transformation plasmid [c.f. Hopwood, D. A., et al., (1987), "Methods in Enzymology" 153, 116, Academic Press, New York], but the present invention is not limited thereto. Additional methods for the transformation of *actinomycetes* are taught in U.S. Pat. No. 5,393,665.

Assay for Farnesyl Dibenzodiazepinone or Biosynthetic Intermediates

*Actinomycetes* defective in farnesyl dibenzodiazepinone biosynthesis are transformed with one or more expression vectors encoding one or more proteins in the farnesyl benzodiazepinone biosynthetic pathway, thus restoring farnesyl benzodiazepinone biosynthesis by genetic complementation of the specific defect.

The presence or absence of farnesyl dibenzodiazepinone or intermediates in the biosynthetic pathway (see FIGS. 5 to 8) in a recombinant actinomycete can be determined using methodologies that are well known to persons of skill in the art. For example, ethyl acetate extracts of fermentation media used for the culture of a recombinant actinomycete are processed as described in Example 2 and fractions containing farnesyl dibenzodiazepinone or intermediates detected by TLC on commercial Kieselgel $60F_{254}$ plates. Farnesyl dibenzodiazepinone and intermediate compounds are visualized by inspection of dried plates under UV light or by spraying the plates with a spray containing vanillin (0.75%) and concentrated sulfuric acid (1.5%, v/v) in ethanol and subsequently heating the plate. The exact identity of the compounds separated by TLC is then determined using gas chromatography-mass spectroscopy. Methods of mass spectroscopy are taught in the published U.S. Patent Application No. US2003/0052268.

Mutagenesis

The invention allows direct manipulation of 046D biosynthetic locus via genetic engineering of the enzymes involved in the biosynthesis of a farnesyl benzodiazepinone according to the invention.

A number of methods are known in the art that permit the random as well as targeted mutation of the DNA sequences of the invention (see for example, Ausubel et. al. Short Protocols in Molecular Biology (1995) 3rd Ed. John Wiley & Sons, Inc.). In addition, there are a number of of commercially available kits for site-directed mutagenesis, including both conventional and PCR-based methods. Examples include the EXSITE™ PCR-Based Site-directed Mutagenesis Kit available from Stratagene (Catalog No. 200502) and the QUIKCHANGE™ Site-directed mutagenesis Kit from Stratagene (Catalog No. 200518), and the CHAMELEON® double-stranded Site-directed mutagenesis kit, also from Stratagene (Catalog No. 200509).

In addition the nucleotides of the invention may be generated by insertional mutation or truncation (N-terminal, internal or C-terminal) according to methodology known to a person skilled in the art.

Older methods of site-directed mutagenesis known in the art rely on sub-cloning of the sequence to be mutated into a vector, such as an M13 bacteriophage vector, that allows the isolation of single-stranded DNA template. In these methods, one anneals a mutagenic primer (i.e., a primer capable of annealing to the site to be mutated but bearing one or more mismatched nucleotides at the site to be mutated) to the single-stranded template and then polymerizes the complement of the template starting from the 3' end of the mutagenic primer. The resulting duplexes are then transformed into host bacteria and plaques are screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

The protocol described below accommodates these considerations through the following steps. First, the template concentration used is approximately 1000-fold higher than that used in conventional PCR reactions, allowing a reduction in the number of cycles from 25-30 down to 5-10 without dramatically reducing product yield. Second, the restriction endonuclease Dpn I (recognition target sequence: 5-Gm6ATC-3, where the A residue is methylated) is used to select against parental DNA, since most common strains of *E. coli* Dam methylate their DNA at the sequence 5-GATC-3. Third, Taq Extender is used in the PCR mix in order to increase the proportion of long (i.e., full plasmid length) PCR products. Finally, Pfu DNA polymerase is used to polish the ends of the PCR product prior to intramolecular ligation using T4 DNA ligase.

A non-limiting example for the isolation of mutant polynucleotides is described in detail as follows:

Plasmid template DNA (approximately 0.5 pmole) is added to a PCR cocktail containing: 1× mutagenesis buffer (20 mM Tris HCl, pH 7.5; 8 mM $MgCl_2$; 40 µg/ml BSA); 12-20 pmole of each primer (one of skill in the art may design a mutagenic primer as necessary, giving consideration to those factors such as base composition, primer length and intended buffer salt concentrations that affect the annealing characteristics of oligonucleotide primers; one primer must contain the desired mutation, and one (the same or the other) must contain a 5' phosphate to facilitate later ligation), 250 µM each dNTP, 2.5 U Taq DNA polymerase, and 2.5 U of Taq Extender (Available from Stratagene; See Nielson et al. (1994) Strategies 7: 27, and U.S. Pat. No. 5,556,772). Primers can be prepared using the triester method of Matteucci et al., 1981, J. Am. Chem. Soc. 103:3185-3191, incorporated herein by reference. Alternatively automated synthesis may be preferred, for example, on a Biosearch 8700 DNA Synthesizer using cyanoethyl phosphoramidite chemistry.

The PCR cycling is performed as follows: 1 cycle of 4 min at 94° C., 2 min at 50° C. and 2 min at 72° C.; followed by 5-10 cycles of 1 min at 94° C., 2 min at 54° C. and 1 min at 72° C. The parental template DNA and the linear, PCR-generated DNA incorporating the mutagenic primer are treated with Dpnl (10 U) and Pfu DNA polymerase (2.5 U). This results in the Dpnl digestion of the in vivo methylated parental template and hybrid DNA and the removal, by Pfu DNA polymerase, of the non-template-directed Taq DNA polymerase-extended base(s) on the linear PCR product. The reaction is incubated at 37° C. for 30 min and then transferred to 72° C. for an additional 30 min. Mutagenesis buffer (115 ul of 1×) containing 0.5 mM ATP is added to the Dpnl-digested, Pfu DNA polymerase-polished PCR products. The solution is mixed and 10 ul are removed to a new microfuge tube and T4 DNA ligase (2-4 U) is added. The ligation is incubated for greater than 60 min at 37° C. Finally, the treated solution is transformed into competent *E. coli* according to standard methods.

Methods of random mutagenesis, which will result in a panel of mutants bearing one or more randomly situated mutations, exist in the art. Such a panel of mutants may then be screened for those exhibiting reduced uracil detection activity relative to the wild-type polymerase (e.g., by measuring the incorporation of 10 nmoles of dNTPs into polymeric form in 30 minutes in the presence of 200 µM dUTP and at the optimal temperature for a given DNA polymerase). An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase.

Genes for desired mutant polypeptides generated by mutagenesis may be sequenced to identify the sites and number of mutations. For those mutants comprising more than one mutation, the effect of a given mutation may be evaluated by introduction of the identified mutation to the wild-type gene by site-directed mutagenesis in isolation from the other mutations borne by the particular mutant. Screening assays of the single mutant thus produced will then allow the determination of the effect of that mutation alone.

IV. Genes and Proteins for the Production of ECO-04601

As discussed in more detail below, the isolated, purified or enriched nucleic acids of one of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89 may be used to prepare one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88, respectively, or fragments comprising at least 50, 75, 100, 200, 300, 500 or more consecutive amino acids of one of the polypeptides of SEQ ID NO: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88.

Accordingly, another aspect of the present invention is an isolated, purified or enriched nucleic acid which encodes one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200, 300 or more consecutive amino acids of one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88. The coding sequences of these nucleic acids may be identical to one of the coding sequences of one of the nucleic acids of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89 or a fragment thereof, or may be different coding sequences which encode one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200, 300 consecutive amino acids of one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 as a result of the redundancy or degeneracy of the genetic code. The genetic code is well known to those of skill in the art and can be obtained, for example, from Stryer, Biochemistry, $3^{rd}$ edition, W. H. Freeman & Co., New York.

The isolated, purified or enriched nucleic acid which encodes one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 may include, but is not limited to: (1) only the coding sequences of one of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89; (2) the coding sequences of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89 and additional coding sequences, such as leader sequences or proprotein; and (3) the coding sequences of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89 and non-coding sequences, such as non-coding sequences 5' and/or 3' of the coding sequence. Thus, as used herein, the term "polynucleotide encoding a polypeptide" encompasses a polynucleotide that includes only coding sequence for the polypeptide as well as a polynucleotide that includes additional coding and/or non-coding sequence.

The invention relates to polynucleotides based on SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89 but having polynucleotide changes that are "silent", for example changes which do not alter the amino acid sequence encoded by the polynucleotides of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89. The invention also relates to polynucleotides which have nucleotide changes which result in amino acid substitutions, additions, deletions, fusions and truncations of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88. Such nucleotide changes may be introduced using techniques such as site directed mutagenesis, random chemical mutagenesis, exonuclease III deletion, and other recombinant DNA techniques.

The isolated, purified or enriched nucleic acids of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89, the sequences complementary thereto, or a fragment comprising at least 100, 150, 200, 300, 400 or more consecutive bases of one of the sequence of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89, or the sequences complementary thereto may be used as probes to identify and isolate DNAs encoding the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 respectively. In such procedures, a genomic DNA library is constructed from a sample microorganism or a sample containing a microorganism capable of producing a farnesyl dibenzodiazepinone. The genomic DNA library is then contacted with a probe comprising a coding sequence or a fragment of the coding sequence, encoding one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88, or a fragment thereof under conditions which permit the probe to specifically hybridize to sequences complementary thereto. In a preferred embodiment, the probe is an oligonucleotide of about 10 to about 30 nucleotides in length designed based on a nucleic acid of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89. Genomic DNA clones which hybridize to the probe are then detected and isolated. Procedures for preparing and identifying DNA clones of interest are disclosed in Ausubel et al., Current Protocols in Molecular Biology, John Wiley 503 Sons, Inc. 1997; and Sambrook et al., Molecular Cloning: A Laboratory Manual 2d Ed., Cold Spring Harbor Laboratory Press, 1989. In another embodiment, the probe is a restriction fragment or a PCR amplified nucleic acid derived from SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89.

The isolated, purified or enriched nucleic acids of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89, the sequences complementary thereto, or a fragment comprising at least 10, 15, 20, 25, 30, 35, 40, 50, 75, 100, 150, 200, 300, 400 or 500 consecutive bases of one of the sequences of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89 or the sequences complementary thereto may be used as probes to identify and isolate related nucleic acids. In some embodiments, the related nucleic acids may be genomic DNAs (or cDNAs) from potential farnesyl dibenzodiazepinone producers. In such procedures, a nucleic acid sample containing nucleic acids from a potential farnesyl dibenzodiazepinone producer is contacted with the probe under conditions that permit the probe to specifically hybridize to related sequences. The nucleic acid sample may be a genomic DNA (or cDNA) library from the potential farnesyl dibenzodiazepinone-producer. Hybridization of the probe to nucleic acids is then detected using any of the methods described above.

Hybridization may be carried out under conditions of low stringency, moderate stringency or high stringency. As an example of nucleic acid hybridization, a polymer membrane containing immobilized denatured nucleic acids is first prehybridized for 30 minutes at 45° C. in a solution consisting of 0.9M NaCl, 50 mM $NaH_2PO_4$, pH 7.0, 5.0 mM $Na_2EDTA$, 0.5% SDS, 10× Denhardt's, and 0.5 mg/ml polyriboadenylic acid. Approximately $2 \times 10^7$ cpm (specific activity $4-9 \times 10^8$ cpm/ug) of $^{32}P$ end-labeled oligonucleotide probe are then added to the solution. After 12-16 hours of incubation, the membrane is washed for 30 minutes at room temperature in 1× SET (150 mM NaCl, 20 mM Tris hydrochloride, pH 7.8, 1 mM $Na_2EDTA$) containing 0.5% SDS, followed by a 30 minute wash in fresh 1× SET at Tm-10° C. for the oligonucleotide probe where Tm is the melting temperature. The membrane is then exposed to autoradiographic film for detection of hybridization signals.

By varying the stringency of the hybridization conditions used to identify nucleic acids, such as genomic DNAs or cDNAs, which hybridize to the detectable probe, nucleic acids having different levels of homology to the probe can be identified and isolated. Stringency may be varied by conducting the hybridization at varying temperatures below the melting temperatures of the probes. The melting temperature of the probe may be calculated using the following formulas:

For oligonucleotide probes between 14 and 70 nucleotides in length the melting temperature (Tm) in degrees Celcius may be calculated using the formula: Tm=81.5+16.6(log [Na+])+0.41(fraction G+C)−(600/N) where N is the length of the oligonucleotide.

If the hybridization is carried out in a solution containing formamide, the melting temperature may be calculated using the equation Tm=81.5+16.6(log [Na+])+0.41(fraction G+C)−(0.63% formamide)−(600/N) where N is the length of the probe.

Prehybridization may be carried out in 6×SSC, 5× Denhardt's reagent, 0.5% SDS, 0.1 mg/ml denatured fragmented salmon sperm DNA or 6×SSC, 5× Denhardt's reagent, 0.5% SDS, 0.1 mg/ml denatured fragmented salmon sperm DNA, 50% formamide. The composition of the SSC and Denhardt's solutions are listed in Sambrook et al., supra.

Hybridization is conducted by adding the detectable probe to the hybridization solutions listed above. Where the probe comprises double stranded DNA, it is denatured by incubating at elevated temperatures and quickly cooling before addition to the hybridization solution. It may also be desirable to similarly denature single stranded probes to eliminate or diminish formation of secondary structures or oligomerization. The filter is contacted with the hybridization solution for a sufficient period of time to allow the probe to hybridize to cDNAs or genomic DNAs containing sequences complementary thereto or homologous thereto. For probes over 200 nucleotides in length, the hybridization may be carried out at 15-25° C. below the Tm. For shorter probes, such as oligonucleotide probes, the hybridization may be conducted at 5-10° C. below the Tm. Preferably, the hybridization is conducted in 6×SSC, for shorter probes. Preferably, the hybridization is conducted in 50% formamide containing solutions, for longer probes. All the foregoing hybridizations would be considered to be examples of hybridization performed under conditions of high stringency.

Following hybridization, the filter is washed for at least 15 minutes in 2×SSC, 0.1% SDS at room temperature or higher, depending on the desired stringency. The filter is then washed with 0.1×SSC, 0.5% SDS at room temperature (again) for 30 minutes to 1 hour. Nucleic acids which have hybridized to the probe are identified by conventional autoradiography and non-radioactive-detection methods.

The above procedure may be modified to identify nucleic acids having decreasing levels of homology to the probe sequence. For example, to obtain nucleic acids of decreasing homology to the detectable probe, less stringent conditions may be used. For example, the hybridization temperature may be decreased in increments of 5° C. from 68° C. to 42° C. in a hybridization buffer having a Na+ concentration of approximately 1M. Following hybridization, the filter may be washed with 2×SSC, 0.5% SDS at the temperature of hybridization. These conditions are considered to be "moderate stringency" conditions above 50° C. and "low stringency" conditions below 50° C. A specific example of "moderate stringency" hybridization conditions is when the above hybridization is conducted at 55° C. A specific example of "low stringency" hybridization conditions is when the above hybridization is conducted at 45° C.

Alternatively, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate stringency" conditions above 25% formamide and "low stringency" conditions below 25% formamide. A specific example of "moderate stringency" hybridization conditions is when the above hybridization is conducted at 30% formamide. A specific example of "low stringency" hybridization conditions is when the above hybridization is conducted at 10% formamide. Nucleic acids which have hybridized to the probe are identified by conventional autoradiography and non-radioactive detection methods. Examples of conditions of different stringency are also provided in Table 2.

TABLE 2

| Very High Stringency (detects sequences sharing at least 90% identity) | | | |
|---|---|---|---|
| Hybridization | in 5x SCC | at 65° C. | 16 hours |
| Wash twice | in 2x SCC | at room temeprature | 15 mnutes each |
| Wash twice | in 0.5x SCC | at 65° C. | 20 minutes each |
| High Stringency (detects sequences sharing at least 80% identity) | | | |
| Hybridization | in 5x SCC | at 65° C. | 16 hours |
| Wash twice | in 2x SCC | at room temeprature | 20 mnutes each |
| Wash once | in 1x SCC | at 55° C. | 30 minutes each |
| Low Stringency (detects sequences sharing at least 50% identity) | | | |
| Hybridization | in 6x SCC | at room temeprature | 16 hours |
| Wash twice | in 3x SCC | at room temeprature | 20 minutes each |

The preceding methods may be used to isolate nucleic acids having at least 97%, at least 95%, at least 90%, at least 85%, at least 80%, or at least 70% sequence identity to a nucleic acid sequence selected from the group consisting of the sequences of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89. The isolated nucleic acid may have a coding sequence that is a naturally occurring allelic variant of one of the coding sequences described herein. Such allelic variant may have a substitution, deletion or addition of one or more nucleotides when compared to the nucleic acids of SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 66, 68, 70, 72, 75, 77, 79, 81, 83, 85, 87 and 89, or the sequences complementary thereto.

Additionally, the above procedures may be used to isolate nucleic acids which encode polypeptides having at least 99%, at least 95%, at least 90%, at least 85%, at least 80%, or at least 70% identity to a polypeptide having the sequence of one of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200, 300 consecutive amino acids thereof.

Another aspect of the present invention is an isolated or purified polypeptide comprising the sequence of one of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200 or 300 consecutive amino acids thereof. As discussed herein, such polypeptides may be obtained by inserting a nucleic acid encoding the polypeptide into a vector such that the coding sequence is operably linked to a sequence capable of driving the expression of the encoded polypeptide in a suitable host cell. For example, the expression vector may comprise a promoter, a ribosome binding site for translation initiation and a transcription terminator. The vector may also include appropriate sequences for modulating expression levels, an origin of replication and a selectable marker.

Promoters suitable for expressing the polypeptide or fragment thereof in bacteria include the E. coli lac or trp promoters, the lacI promoter, the lacZ promoter, the T3 promoter, the T7 promoter, the gpt promoter, the lambda $P_R$ promoter, the lambda $P_L$ promoter, promoters from operons encoding glycolytic enzymes such as 3-phosphoglycerate kinase (PGK), and the acid phosphatase promoter. Fungal promoters include the a factor promoter. Eukaryotic promoters include the CMV immediate early promoter, the HSV thymidine kinase promoter, heat shock promoters, the early and late SV40 promoters, LTRs from retroviruses, and the mouse metallothionein-1 promoter. Other promoters known to control expression of genes in prokaryotic or eukaryotic cells or their viruses may also be used.

Mammalian expression vectors may also comprise an origin of replication, any necessary ribosome binding sites, a polyadenylation site, splice donors and acceptor sites, transcriptional termination sequences, and 5' flanking nontranscribed sequences. In some embodiments, DNA sequences derived from the SV40 splice and polyadenylation sites may be used to provide the required nontranscribed genetic elements.

Vectors for expressing the polypeptide or fragment thereof in eukaryotic cells may also contain enhancers to increase expression levels. Enhancers are cis-acting elements of DNA, usually from about 10 to about 300 bp in length that act on a promoter to increase its transcription. Examples include the SV40 enhancer on the late side of the replication origin bp 100 to 270, the cytomegalovirus early promoter enhancer, the polyoma enhancer on the late side of the replication origin, and the adenovirus enhancers.

In addition, the expression vectors preferably contain one or more selectable marker genes to permit selection of host cells containing the vector. Examples of selectable markers that may be used include genes encoding dihydrofolate reductase or genes conferring neomycin resistance for eukaryotic cell culture, genes conferring tetracycline or ampicillin resistance in E. coli, and the S. cerevisiae TRP1 gene.

The appropriate DNA sequence may be inserted into the vector by a variety of procedures. In general, the DNA sequence is ligated to the desired position in the vector following digestion of the insert and the vector with appropriate restriction endonucleases. Alternatively, appropriate restriction enzyme sites can be engineered into a DNA sequence by PCR. A variety of cloning techniques are disclosed in Ausbel et al. Current Protocols in Molecular Biology, John Wiley 503 Sons, Inc. 1997 and Sambrook et al., Molecular Cloning: A Laboratory Manual 2d Ed., Cold Spring Harbour Laboratory Press, 1989. Such procedures and others are deemed to be within the scope of those skilled in the art.

The vector may be, for example, in the form of a plasmid, a viral particle, or a phage. Other vectors include derivatives of chromosomal, nonchromosomal and synthetic DNA sequences, viruses, bacterial plasmids, phage DNA, baculovirus, yeast plasmids, vectors derived from combinations of plasmids and phage DNA, viral DNA such as vaccinia, adenovirus, fowl pox virus, and pseudorabies. A variety of cloning and expression vectors for use with prokaryotic and eukaryotic hosts are described by Sambrook et al., Molecular Cloning: A Laboratory Manual, Second Edition, Cold Spring Harbor, N.Y., (1989), incorporated by reference in its entirety for all purposes.

Particular bacterial vectors which may be used include the commercially available plasmids comprising genetic elements of the well known cloning vector pBR322 (ATCC 37017), pKK223-3 (Pharmacia Fine Chemicals, Uppsala, Sweden), pGEM1 (Promega Biotec, Madison, Wis., USA) pQE70, pQE60, pQE-9 (Qiagen), pD10, phiX174, pBluescript™ 11 KS, pNH8A, pNH16a, pNH18A, pNH46A (Stratagene), ptrc99a, pKK223-3, pKK233-3, pDR540, pRIT5 (Pharmacia), pKK232-8 and pCM7. Particular eukaryotic vectors include pSV2CAT, pOG44, pXT1, pSG (Stratagene) pSVK3, pBPV, pMSG, and pSVL (Pharmacia). However, any other vector may be used as long as it is replicable and stable in the host cell.

The host cell may be any of the host cells familiar to those skilled in the art, including prokaryotic cells or eukaryotic cells. As representative examples of appropriate hosts, there may be mentioned: bacteria cells, such as E. coli, Streptomyces lividans, Streptomyces griseofuscus, Streptomyces ambofaciens, Rhodococcus, Amycolatopsis, Bacillus subtilis, Salmonella typhimurium and various species within the genera Pseudomonas, Streptomyces, Bacillus, and Staphylococcus, fungal cells, such as yeast, insect cells such as Drosophila S2 and Spodoptera Sf9, animal cells such as CHO, COS or Bowes melanoma, and adenoviruses. The selection of an appropriate host is within the abilities of those skilled in the art, see for example Manual of Industrial Microbiology and Biotechnology, $2^{nd}$ Edition, ASM Press, Washington D.C., incorporated by reference in its entirety, and more particularly Sections IV, V and VII.

The vector may be introduced into the host cells using any of a variety of techniques, including electroporation transformation, transfection, transduction, viral infection, gene guns, or Ti-mediated gene transfer. Where appropriate, the engineered host cells can be cultured in conventional nutrient media modified as appropriate for activating promoters, selecting transformants or amplifying the genes of the present invention. Following transformation of a suitable host strain and growth of the host strain to an appropriate cell density, the selected promoter may be induced by appropriate means (e.g., temperature shift or chemical induction) and the cells may be cultured for an additional period to allow them to produce the desired polypeptide or fragment thereof.

Cells are typically harvested by centrifugation, disrupted by physical or chemical means, and the resulting crude extract is retained for further purification. Microbial cells employed for expression of proteins can be disrupted by any convenient method, including freeze-thaw cycling, sonication, mechanical disruption, or use of cell lysing agents. Such methods are well known to those skilled in the art. The expressed polypeptide or fragment thereof can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the polypeptide. If desired, high performance liquid chromatography (HPLC) can be employed for final purification steps.

Various mammalian cell culture systems can also be employed to express recombinant protein. Examples of mammalian expression systems include the COS-7 lines of monkey kidney fibroblasts (described by Gluzman, Cell, 23:175(1981)), and other cell lines capable of expressing proteins from a compatible vector, such as the C127, 3T3, CHO, HeLa and BHK cell lines. The constructs in host cells can be used in a conventional manner to produce the gene product encoded by the recombinant sequence. Polypeptides of the invention may or may not also include an initial methionine amino acid residue.

Alternatively, the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200 or 300 consecutive amino acids thereof can be synthetically produced by conventional peptide synthesizers. In other embodiments, fragments or portions of the polynucleotides may be employed for producing the corresponding full-length polypeptide by peptide synthesis; therefore, the fragments may be employed as intermediates for producing the full-length polypeptides.

Cell-free translation systems can also be employed to produce one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200 or 300 consecutive-amino acids thereof using mRNAs transcribed from a DNA construct comprising a promoter operably linked to a nucleic acid encoding the polypeptide or fragment thereof. In some embodiments, the DNA construct may be linearized prior to conducting an in vitro transcription reaction. The transcribed mRNA is then incubated with an appropriate cell-free translation extract, such as a rabbit reticulocyte extract, to produce the desired polypeptide or fragment thereof.

The present invention also relates to variants of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments comprising at least 50, 75, 100, 150, 200 or 300 consecutive amino acids thereof. The term "variant" includes derivatives or analogs of these polypeptides. In particular, the variants may differ in amino acid sequence from the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 by one or more substitutions, additions, deletions, fusions and truncations, which may be present in any combination.

The variants may be naturally occurring or created in vitro. In particular, such variants may be created using genetic engineering techniques such as site directed mutagenesis, random chemical mutagenesis, exonuclease III deletion procedures, and standard cloning techniques. Alternatively, such variants, fragments, analogs, or derivatives may be created using chemical synthesis or modification procedures.

Other methods of making variants are also familiar to those skilled in the art. These include procedures in which nucleic acid sequences obtained from natural isolates are modified to generate nucleic acids that encode polypeptides having characteristics which enhance their value in industrial or laboratory applications. In such procedures, a large number of variant sequences having one or more nucleotide differences with respect to the sequence obtained from the natural isolate are generated and characterized. Preferably, these nucleotide differences result in amino acid changes with respect to the polypeptides encoded by the nucleic acids from the natural isolates.

The variants of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 may be variants in which one or more of the amino acid residues of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 are substituted with a conserved or non-conserved amino acid residue (preferably a conserved amino acid residue) and such substituted amino acid residue may or may not be one encoded by the genetic code.

Conservative substitutions are those that substitute a given amino acid in a polypeptide by another amino acid of like characteristics. Typically seen as conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp or Glu with another acidic residue; replacement of a residue bearing an amide group, such as Asn or Gln, with another residue bearing an amide group; exchange of a basic residue such as Lys or Arg with another basic residue; and replacement of an aromatic residue such as Phe or Tyr with another aromatic residue.

Other variants are those in which one or more of the amino acid residues of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 include a substituent group. Still other variants are those in which the polypeptide is associated with another compound, such as a compound to increase the half-life of the polypeptide (for example, polyethylene glycol). Additional variants are those in which additional amino acids are fused to the polypeptide, such as leader sequence, a secretory sequence, a proprotein sequence or a sequence that facilitates purification, enrichment, or stabilization of the polypeptide.

In some embodiments, the fragments, derivatives and analogs retain the same biological function or activity as the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88. In other embodiments, the fragment, derivative or analogue includes a fused heterologous sequence that facilitates purification, enrichment, detection, stabilization or secretion of the polypeptide that can be enzymatically cleaved, in whole or in part, away from the fragment, derivative or analogue.

Another aspect of the present invention are polypeptides or fragments thereof which have at least 70%, at least 80%, at least 85%, at least 90%, or more than 95% identity to one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or a fragment comprising at least 50, 75, 100, 150, 200 or 300 consecutive amino acids thereof. It will be appreciated that amino acid "substantially identity" includes conservative substitutions such as those described above.

The polypeptides or fragments having homology to one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or a fragment comprising at least 50, 75, 100, 150, 200 or 300 consecutive amino acids thereof may be obtained by isolating the nucleic acids encoding them using the techniques described above.

Alternatively, the homologous polypeptides or fragments may be obtained through biochemical enrichment or purification procedures. The sequence of potentially homologous polypeptides or fragments may be determined by proteolytic digestion, gel electrophoresis and/or microsequencing. The sequence of the prospective homologous polypeptide or fragment can be compared to one of the polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or a fragment comprising at least 5, 10, 15, 20, 25, 30, 35, 40, 50, 75, 100, or 150 consecutive amino acids thereof.

The polypeptides of SEQ ID NOS: 2, 4, 6, 8, 10, 12, 14, 16, 18, 20, 22, 24, 26, 28, 30, 32, 34, 36, 38, 41, 42, 44, 46, 48, 50, 52, 54, 56, 58, 60, 62, 65, 67, 69, 70, 71, 74, 76, 78, 80, 82, 84, 86 and 88 or fragments, derivatives or analogs thereof comprising at least 40, 50, 75, 100, 150, 200 or 300 consecutive amino acids thereof invention may be used in a variety of applications. For example, the polypeptides or fragments, derivatives or analogs thereof may be used to catalyze biochemical reactions as described elsewhere in the specification.

EXAMPLES

Unless otherwise indicated, all numbers expressing quantities of ingredients, properties such as molecular weight, reaction conditions, $IC_{50}$ and so forth used in the specification and claims are to be understood as being modified in all instances by the term "about". Accordingly, unless indicated to the contrary, the numerical parameters set forth in the present specification and attached claims are approximations. At the very least, and not as an attempt to limit the application of the doctrine of equivalents to the scope of the claims, each numerical parameter should at least be construed in light of the number of significant figures and by applying ordinary rounding techniques. Notwithstanding that the numerical ranges and parameters setting forth the broad scope of the invention are approximations, the numerical values set in the examples, Tables and Figures are reported as precisely as possible. Any numerical values may inherently contain certain errors resulting from variations in experiments, testing measurements, statistical analyses and such.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Example 1

Preparation of Production Culture

Unless otherwise noted, all reagents were purchased from Sigma Chemical Co. (St. Louis, Mo.), (Aldrich). *Micromonospora* spp. (deposit accession number IDAC 070303-01) was maintained on agar plates of ISP2 agar (Difco Laboratories, Detroit, Mich.). An inoculum for the production phase was prepared by transferring the surface growth of the *Micromonospora* spp. from the agar plates to 125-mL flasks containing 25 mL of sterile medium comprised of 24 g potato dextrin, 3 g beef extract, 5 g Bacto-casitone, 5 g glucose, 5 g yeast extract, and 4 g $CaCO_3$ made up to one liter with distilled water (pH 7.0). The culture was incubated at about 28° C. for approximately 60 hours on a rotary shaker set at 250 rpm. Following incubation, 10 mL of culture was transferred to a 2L baffled flask containing 500 mL of sterile production medium containing 20 g/L potato dextrin, 20 g/L glycerol, 10 g/L Fish meal, 5 g/L Bacto-peptone, 2 g/L $CaCO_3$, and 2 g/L $(NH_4)_2SO_4$, pH 7.0. Fermentation broth was prepared by incubating the production culture at 28° C. in a rotary shaker set at 250 rpm for one week.

Example 2

Isolation 500 mL ethyl acetate was added to 500 mL of fermentation broth prepared as described in Example 1 above. The mixture was agitated for 30 minutes on an orbital shaker at 200 rpm to create an emulsion. The phases were separated by centrifugation and decantation. Between 4 and 5 g of anhydrous $MgSO_4$ was added to the organic phase, which was then filtered and the solvents removed in vacuo.

An ethyl acetate extract from 2 L fermentation was mixed with HP-20 resin (100 mL; Mitsubishi Casei Corp., Tokyo, Japan) in water (300 mL). Ethyl acetate was removed in vacuo, the resin was filtered on a Buchner funnel and the filtrate was discarded. The adsorbed HP-20 resin was then washed successively with 2×125 mL of 50% acetonitrile in water, 2×125 mL of 75% acetonitrile in water and 2×125 mL of acetonitrile.

Fractions containing ECO-04601 were evaporated to dryness and 100 mg was digested in the 5 mL of the upper phase of a mixture prepared from chloroform, cyclohexane, methanol, and water in the ratios, by volume, of 5:2:10:5. The sample was subjected to centrifugal partition chromatography using a High Speed Countercurrent (HSCC) system (Kromaton Technologies, Angers, France) fitted with a 200 mL cartridge and prepacked with the upper phase of this two-phase system. The HSCC was run with the lower phase mobile and ECO-04601 was eluted at approximately one-half column volume. Fractions were collected and ECO-04601 was detected by TLC of aliquots of the fractions on commercial Kieselgel 60F$_{254}$ plates. Compound could be visualized by inspection of dried plates under UV light or by spraying the plates with a spray containing vanillin (0.75%) and concentrated sulfuric acid (1.5%, v/v) in ethanol and subsequently heating the plate. Fractions contained substantially pure ECO-04601, although highly colored. A buff-colored sample could be obtained by chromatography on HPLC as follows.

6 mg of sample was dissolved in acetonitrile and injected onto a preparative HPLC column (XTerra ODS (10 µm), 19×150 mm, Waters Co., Milford, Mass.), with a 9 mL/min flow rate and UV peak detection at 300 nm. The column was eluted with acetonitrile/buffer (20 mM of NH$_4$HCO$_3$) according to the following gradient shown in Table 3.

TABLE 3

| Time (min) | Water (%) | Acetonitrile (%) |
|---|---|---|
| 0 | 70 | 30 |
| 10 | 5 | 95 |
| 15 | 5 | 95 |
| 20 | 70 | 30 |

Fractions containing ECO-04061 eluted at approximately 11:0 min and were combined, concentrated and lyophilized to give a yield of 3.8 mg compound.

Example 3

Elucidation of the Structure of ECO-04601

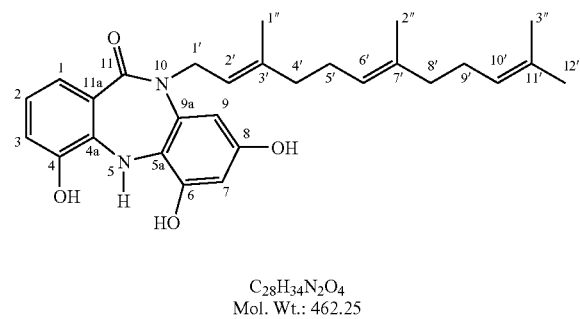

C$_{28}$H$_{34}$N$_2$O$_4$
Mol. Wt.: 462.25

The structure of ECO-04601 above was derived from spectroscopic data, including mass, UV, and NMR spectroscopy. Mass was determined by electrospray mass spectrometry to be 462.6, UVmax 230 nm with a shoulder at 290 nm. NMR data were collected dissolved in MeOH-d4 including proton, and multidimensional pulse sequences. Proton and carbon NMR data are detailed in Table 4 below.

TABLE 4

$^1$H and $^{13}$C NMR ($\delta_H$, ppm) of ECO-04601 in MeOH-D$_4$

| Assignment | $^1$H | $^{13}$C | Group |
|---|---|---|---|
| 1 | 7.15 | 122.3 | CH |
| 2 | 6.74 | 121.0 | CH |
| 3 | 6.83 | 116.9 | CH |
| 4 | — | 146.0 | C—OH |
| 4a | — | 142.0 | C |
| 5a | — | 126.0 | C |
| 6 | — | 148.2 | C—OH |
| 7 | 6.20 | 100.0 | CH |
| 8 | — | 153.0 | C—OH |
| 9 | 6.25 | 101.0 | CH |
| 9a | — | 135.0 | C |
| 11 | — | 170.0 | C(O) |
| 11a | — | 125.0 | C |
| 1' | 4.52 | 48.7 | CH$_2$ |
| 2' | 5.35 | 121.1 | CH |
| 3' | — | 138.5 | C |
| 4' | 2.03 | 39.5 | CH$_2$ |
| 5' | 2.08 | 26.7 | CH$_2$ |
| 6' | 5.09 | 124.1 | CH |
| 7' | — | 135.0 | C |
| 8' | 1.95 | 39.6 | CH$_2$ |
| 9' | 2.02 | 26.3 | CH$_2$ |
| 10' | 5.06 | 124.4 | CH |
| 11' | — | 130.9 | C |
| 12' | 1.64 | 24.8 | CH$_3$ |
| 1" | 1.72 | 15.5 | CH$_3$ |
| 2" | 1.59 | 14.9 | CH$_3$ |
| 3" | 1.55 | 16.5 | CH$_3$ |

A number of cross peaks in the 2D spectra of ECO-04601 are key in the structural determination. For example, the farnesyl chain is placed on the amide nitrogen by a strong cross peak between the proton signal of the terminal methylene of that chain at 4.52 ppm and the amide carbonyl carbon at 170 ppm in the gHMBC experiment. This conclusion is confirmed by a cross peak in the NOESY spectrum between the same methylene signals at 4.52 ppm and the aromatic proton signal at 6.25 ppm from one of the two protons of the tetra substituted benzenoid ring.

Based on the mass, UV and NMR spectroscopy data, the structure of the compound was determined to be the structure of ECO-04601.

Example 4

In Vivo Efficacy in a Glioma Model

The aim of this study was to test whether ECO-04601 when administered by the i.p. route prevents or delays tumor growth in C6 glioblastoma cell-bearing mice, and to determine an effective dosage regimen.

Animals: A total of 60 six-week-old female mice (Mus musculus nude mice), ranging between 18 to 25 g in weight, were observed for 7 days before treatment. Animal experiments were performed according to ethical guidelines of animal experimentation (Charte du comité d'éthique du CNRS, juillet 2003) and the English guidelines for the welfare of animals in experimental neoplasia (WORKMAN, P., TWENTYMAN, P., BALKWILL, F., et al. (1998). United Kingdom Coordinating Committee on Cancer Research (UKCCCR) Guidelines for the welfare of animals in experimental neoplasia (Second Edition, July 1997; British Journal of Cancer, 77:1-10). Any dead or apparently sick mice were promptly removed and replaced with healthy mice. Sick mice were euthanized upon removal from the cage. Animals were maintained in rooms under controlled conditions of temperature (23±2° C.), humidity (45±5%), photoperiodicity (12 hrs light/12 hrs dark) and air exchange. Animals were housed in polycarbonate cages (5/single cage) that were equipped to provide food and water. Animal bedding consisted of sterile wood shavings that were replaced every other day. Food was provided ad libitum, being placed in the metal lid on the top of the cage. Autoclaved tap water was provided ad libitum. Water bottles were equipped with rubber stoppers and sipper tubes. Water bottles were cleaned, sterilized and replaced once a week. Two different numbers engraved on two earrings identified the animals. Each cage was labeled with a specific code.

Tumor Cell Line: The C6 cell line was cloned from a rat glial tumor induced by N-nitrosomethyurea (NMU) according to Premont et al. (*Premont J, Benda P, Jard S., [3H] norepinephrine binding by rat glial cells in culture. Lack of correlation between binding and adenylate cyclase activation. Biochim Biophys Acta.* 1975 Feb. 13; 381(2):368-76.) after series of alternate culture and animal passages. Cells were grown as adherent monolayers at 37° C. in a humidified atmosphere (5% $CO_2$, 95% air). The culture medium was DMEM supplemented with 2 mM L-glutamine and 10% fetal bovine serum. For experimental use, tumor cells were detached from the culture flask by a 10 min treatment with trypsin-versen. The cells were counted in a hemocytometer and their viability assessed by 0.25% trypan blue exclusion.

Preparation of the Test Article: For the test article, the following procedure was followed for reconstitution (performed immediately preceding injection). The vehicle consisted of a mixture of benzyl alcohol (1.5%), ethanol (8.5%), propylene glycol (27%), PEG 400 (27%), dimethylacetamide (6%) and water (30%). The vehicle solution was first vortexed in order to obtain a homogeneous liquid. 0.6 mL of the vortexed vehicle solution was added to each vial containing the test article (ECO-04601). Vials were mixed thoroughly by vortexing for 1 minute and inverted and shaken vigorously. Vials were mixed again prior to injection into each animal.

Animal Inoculation with tumor cells: Experiment started at day 0 ($D_0$). On $D_0$, mice received a superficial intramuscular injection of C6 tumor cells ($5 \times 10^5$ cells) in 0.1 mL of DMEM complete medium into the upper right posterior leg.

Treatment Regimen and Results:

First series of experiments: In a first series of experiments, treatment started 24 hrs following inoculation of C6 cells. On the day of the treatment, each mouse was slowly injected with 100 μL of test or control articles by the i.p. route. For all groups, treatment was performed until the tumor volume of the saline-treated mice (group 1) reached approximately 3 cm³ (around day 16). Mice of group 1 were treated daily with a saline isosmotic solution for 16 days. Mice of group 2 were treated daily with the vehicle solution for 16 days. Mice of group 3 were treated daily with 10 mg/kg of ECO-04601 for 16 days. Mice of group 4 were treated every two days with 30 mg/kg of ECO-04601 and received 8 treatments. Mice of group 5 were treated every three days with 30 mg/kg of ECO-04601 and received 6 treatments. Measurement of tumor volume started as soon as tumors became palpable (>100 mm³; day 11 post-inoculation) and was evaluated every second day until the end of the treatment using callipers. As shown in Table 5 and FIG. 1, the mean value of the tumor volume of all ECO-4061-treated groups (6 mice/group) was significantly reduced as demonstrated by the one-way analysis of variance (Anova) test followed by the non-parametric Dunnett's multiple comparison test comparing treated groups to the saline group. An asterisk in the P value column of Table 5 indicates a statistically significant value, while "ns" signifies not significant.

TABLE 5

ECO-04601 in vivo antitumor efficacy against C6 glioblastoma

| Treatment | Treatment regimen | Tumor volume (mm³) (mean ± SEM) | % Inhibition | P value |
|---|---|---|---|---|
| Saline | Q1 × 16 | 3,004.1 ± 249.64 | — | — |
| Vehicle solution | Q1 × 16 | 2,162.0 ± 350.0 | 28.0% | >0.05 ns |
| ECO-04601 (10 mg/kg) | Q1 × 16 | 1,220.4 ± 283.46 | 59.4% | <0.01* |
| ECO-04601 (30 mg/kg) | Q2 × 8 | 1,236.9 ± 233.99 | 58.8% | <0.01* |
| ECO-04601 (30 mg/kg) | Q3 × 6 | 1,184.1 ± 221.45 | 60.6% | <0.01* |

Figure 2:
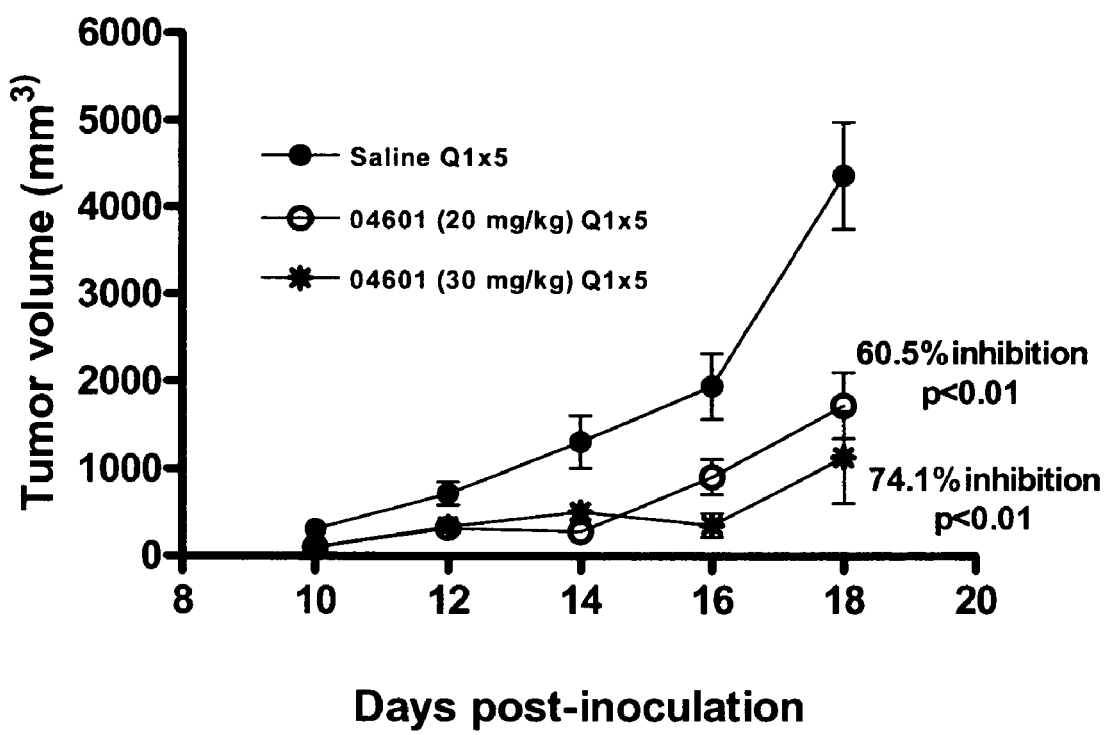
FIG. 2: shows inhibition of tumor growth resulting from administration of 20-30 mg/kg of ECO-04601 to glioblastoma-bearing mice beginning ten days after tumor cell inoculation.

Second series experiments: In a second series of experiments, treatment started at day 10 following inoculation of C6 cells when tumors became palpable (around 100 to 200 mm³). Treatment was repeated daily for 5 consecutive days. On the day of the treatment, each mouse was slowly injected with 100 μL of ECO-04601 by i.p. route. Mice of group 1 were treated daily with saline isosmotic solution. Mice of group 2 were treated daily with the vehicle solution. Mice of group 3 were treated daily with 20 mg/kg of ECO-04601. Mice of group 4 were treated daily with 30 mg/kg of ECO-04601. Mice were treated until the tumor volume of the saline-treated control mice (group 1) reached around 4 cm³. Tumor volume was measured every second day until the end of the treatment using callipers. As shown in Table 6 and FIG. 2, the mean value of the tumor volume of all ECO-04601-treated groups (6 mice/group) was significantly reduced as demonstrated by the one-way analysis of variance (Anova) test followed by the non-parametric Dunnett's multiple comparison test comparing treated groups to the saline group. An asterisk in the P value column of Table 6 indicates a statistically significant value, while "ns" signifies not significant.

Figure 3:
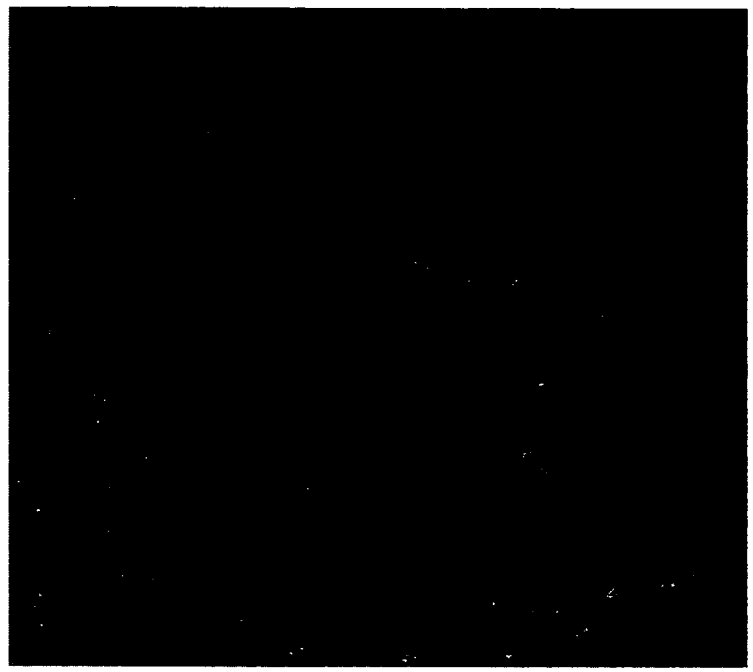
FIG. 3: shows micrographs of tumor sections from mice bearing glioblastoma tumors and treated with saline or ECO-04601. The cell density of tumor treated with ECO-04601 appears decreased and nuclei from ECO-04601-treated tumor cells are larger and pynotic suggesting a cytotoxic effect.
Figure 3:
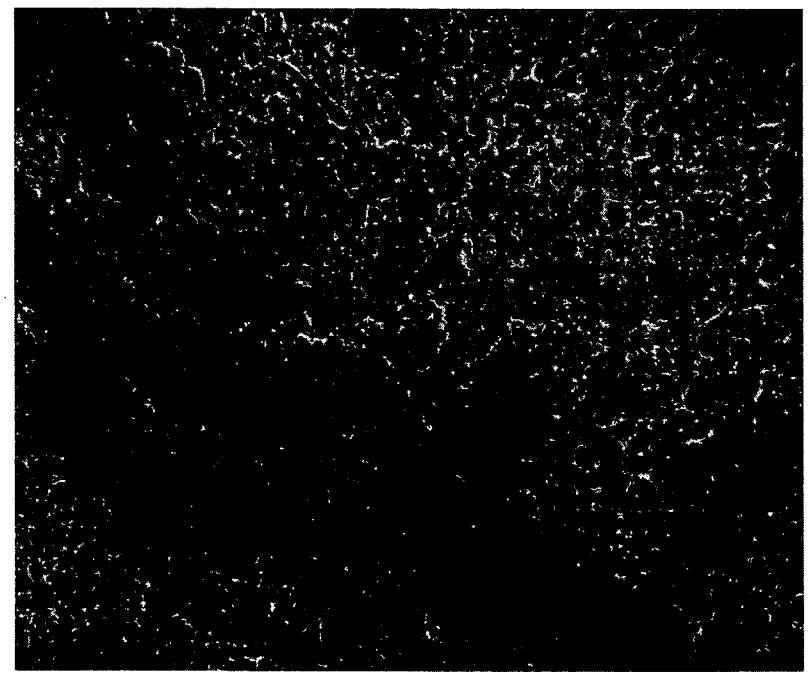

Histological analysis of tumor sections showed pronounced morphological changes between tumors from ECO-04601-treated mice and those from mice in the control groups. In tumors from mice treated with ECO-04601 (20-30 mg/kg), cell density was decreased and the nuclei of remaining tumor cells appeared larger and pycnotic while no such changes were observed for tumors from vehicle-treated mice (FIG. 3).

TABLE 6

ECO-04601 in vivo antitumor efficacy against C6 glioblastoma

| Treatment | Treatment regimen | Tumor volume (mm³) (mean ± SEM) | % Inhibition | P value |
|---|---|---|---|---|
| Saline | Q1 × 5 | 4,363.1 ± 614.31 | — | — |
| Vehicle solution | Q1 × 5 | 3,205.0 ± 632.37 | 26.5% | >0.05 ns |
| ECO-04601 (20 mg/kg) | Q1 × 5 | 1,721.5 ± 374.79 | 60.5% | <0.01* |
| ECO-04601 (30 mg/kg) | Q1 × 5 | 1,131.6 ± 525.21 | 74.1% | <0.01* |

Example 5

Genes and Proteins for the Production of Farnesyl Dibenzodiazepinones

*Micromonospora* sp. strain 046-ECO11 is a representative microorganism useful in the production of the compound of the invention. Strain 046-ECO11 has been deposited with the International Depositary Authority of Canada (IDAC), Bureau of Microbiology, Health Canada, 1015 Arlington Street, Winnipeg, Manitoba, Canada R3E 3R2 on Mar. 7, 2003 and was assigned IDAC accession no. 070303-01. The biosynthetic locus for the production of ECO-04601 was identified in the genome of *Micromonospora* sp. strain 046-ECO11 using the genome scanning method described in U.S. Ser. No. 10/232,370, CA 2,352,451 and Zazopoulos et. al., *Nature Biotechnol.*, 21,187-190 (2003).

Figure 4:
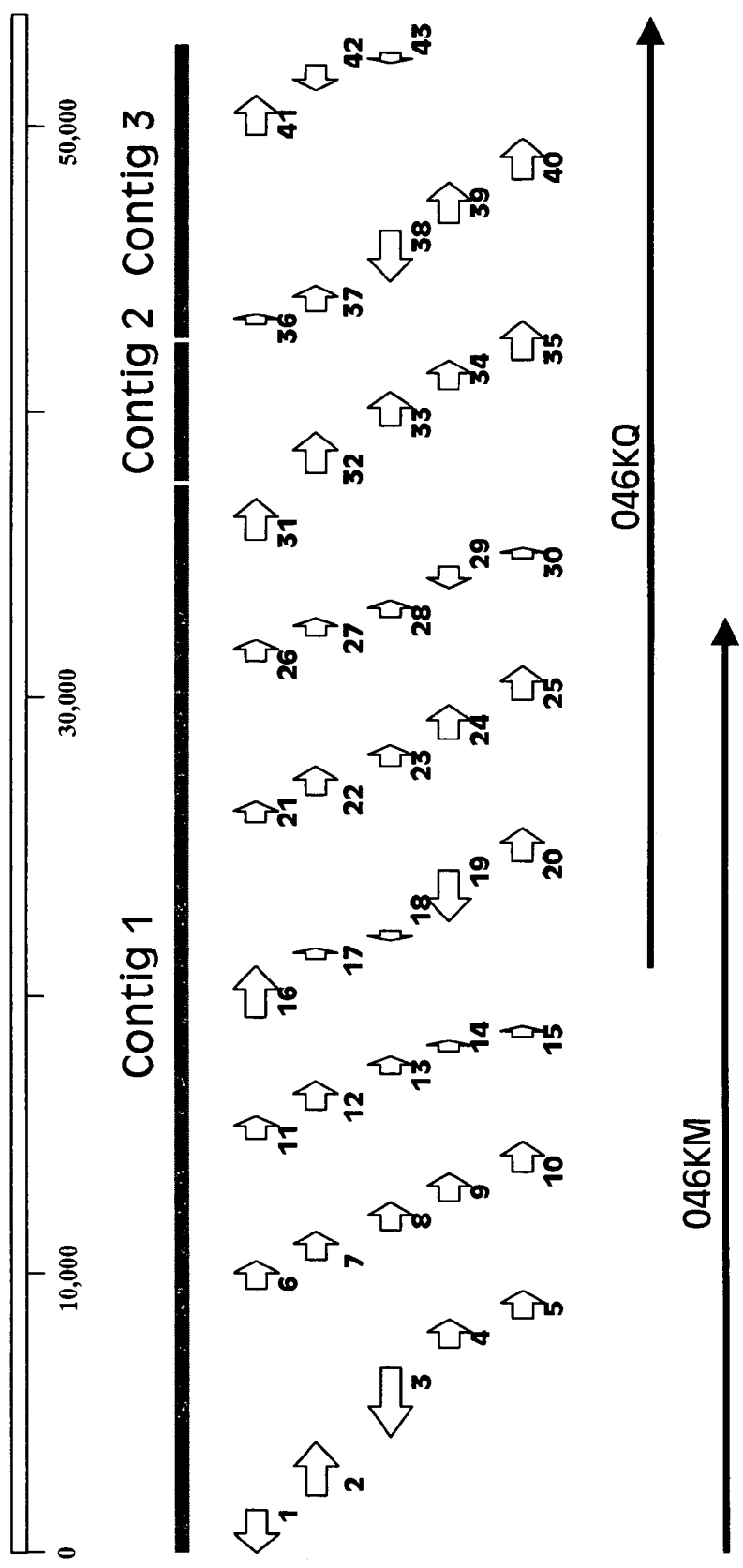
FIG. 4: shows the biosynthetic locus of ECO-04601, isolated from *Micromonospora* sp. strain. 046-ECO11, including the positions of cosmids 046KM and 046KQ.

The biosynthetic locus spans approximately 52,400 base pairs of DNA and encodes 43 proteins. More than 10 kilobases of DNA sequence were analyzed on each side of the locus and these regions were deemed to contain primary genes or genes unrelated to the synthesis of ECO-04601. As illustrated in FIG. 4, the locus is contained within three sequences of contiguous base pairs, namely Contig 1 having the 36,602 contiguous base pairs of SEQ ID NO: 1 and comprising ORFs 1 to 31 (SEQ ID NOS: 3, 5, 7, 9, 11, 13, 15, 17, 19, 21, 23, 25, 27, 29, 31, 33, 35, 37, 39, 41, 43, 45, 47, 49, 51, 53, 55, 57, 59, 61 and 63), Contig 2 having the 5,960 contiguous base pairs of SEQ ID NO: 64 and comprising ORFs 32 to 35 (SEQ ID NOS: 66, 68, 70 and 72), and Contig 3 having the 9,762 base pairs of SEQ ID NO: 73 and comprising ORFs 36 to 43 (SEQ ID NOS: 75, 77, 79, 81, 83, 85, 87 and 89). The order, relative position and orientation of the 43 open reading frames representing the proteins of the biosynthetic locus are illustrated schematically in FIG. 4. The top line in FIG. 4 provides a scale in base pairs. The gray bars depict the three DNA contigs (SEQ ID NOS: 1, 64 and 73) that cover the locus. The empty arrows represent the 43 open reading frames of this biosynthetic locus. The black arrows represent the two deposited cosmid clones covering the locus.

The biosynthetic locus will be further understood with reference to the sequence listing which provides contiguous nucleotide sequences and deduced amino acid sequences of the locus from *Micromonospora* sp. strain 046-ECO11. The contiguous nucleotide sequences are arranged such that, as found within the biosynthetic locus, Contig 1 (SEQ ID NO: 1) is adjacent to the 5' end of Contig 2 (SEQ ID NO: 64), which in turn is adjacent to Contig 3 (SEQ ID NO: 73). The ORFs illustrated in FIG. 4 and provided in the sequence listing represent open reading frames deduced from the nucleotide sequences of Contigs 1, 2 and 3 (SEQ ID NOS: 1, 64 and 73). Referring to the Sequence Listing, ORF 1 (SEQ ID NO: 3) is the polynucleotide drawn from residues 2139 to 424 of SEQ ID NO: 1, and SEQ ID NO: 2 represents that polypeptide deduced from SEQ ID NO: 3. ORF 2 (SEQ ID NO: 5) is the polynucleotide drawn from residues 2890 to 4959 of SEQ ID NO: 1, and SEQ ID NO: 4 represents the polypeptide deduced from SEQ ID NO: 5. ORF 3 (SEQ ID NO: 7) is the polynucleotide drawn from residues 7701 to 5014 of SEQ ID NO: 1, and SEQ ID NO: 6 represents the polypeptide deduced from SEQ ID NO: 7. ORF 4 (SEQ ID NO: 9) is the polynucleotide drawn from residues 8104 to 9192 of SEQ ID NO: 1, and SEQ ID NO: 8 represents the polypeptide deduced from SEQ ID NO: 9. ORF 5 (SEQ ID NO: 11) is the polynucleotide drawn from residues 9192 to 10256 of SEQ ID NO: 1, and SEQ ID NO: 10 represents the polypeptide deduced from SEQ ID NO: 11. ORF 6 (SEQ ID NO: 13) is the polynucleotide drawn from residues 10246 to 11286 of SEQ ID NO: 1, and SEQ ID NO: 12 represents the polypeptide deduced from SEQ ID NO: 13. ORF 7 (SEQ ID NO: 15) is the polynucleotide drawn from residues 11283 to 12392 of SEQ ID NO: 1, and SEQ ID NO: 14 represents the polypeptide deduced from SEQ ID NO: 15. ORF 8 (SEQ ID NO: 17) is the polynucleotide drawn from residues 12389 to 13471 of SEQ ID NO: 1, and SEQ ID NO: 16 represents the polypeptide deduced from SEQ ID NO: 17. ORF 9 (SEQ ID NO: 19) is the polynucleotide drawn from residues 13468 to 14523 of SEQ ID NO: 1, and SEQ ID NO: 18 represents the polypeptide deduced from SEQ ID NO: 19. ORF 10 (SEQ ID NO: 21) is the polynucleotide drawn from residues 14526 to 15701 of SEQ ID NO: 1, and SEQ ID NO: 20 represents the polypeptide deduced from SEQ ID NO: 21. ORF 11 (SEQ ID NO: 23) is the polynucleotide drawn from residues 15770 to 16642 of SEQ ID NO: 1, and SEQ ID NO: 22 represents the polypeptide deduced from SEQ ID NO: 23. ORF 12 (SEQ ID NO: 25) is the polynucleotide drawn from residues 16756 to 17868 of SEQ ID NO: 1, and SEQ ID NO: 24 represents the polypeptide deduced from SEQ ID NO: 25. ORF 13 (SEQ ID NO: 27) is the polynucleotide drawn from residues 17865 to 18527 of SEQ ID NO: 1, and SEQ ID NO: 26 represents the polypeptide deduced from SEQ ID NO: 27. ORF 14 (SEQ ID NO: 29) is the polynucleotide drawn from residues 18724 to 19119 of SEQ ID NO: 1, and SEQ ID NO: 28 represents the polypeptide deduced from SEQ ID NO: 29. ORF 15 (SEQ ID NO: 31) is the polynucleotide drawn from residues 19175 to 19639 of SEQ ID NO: 1, and SEQ ID NO: 30 represents the polypeptide deduced from SEQ ID NO: 31. ORF 16 (SEQ ID NO: 33) is the polynucleotide drawn from residues 19636 to 21621 of SEQ ID NO: 1, and SEQ ID NO: 32 represents the polypeptide deduced from SEQ ID NO: 33. ORF 17 (SEQ ID NO: 35) is the polynucleotide drawn from residues 21632 to 22021 of SEQ ID NO: 1, and SEQ ID NO: 34 represents the polypeptide deduced from SEQ ID NO: 35. ORF 18 (SEQ ID NO: 37) is the polynucleotide drawn from residues 22658 to 22122 of SEQ ID NO: 1, and SEQ ID NO: 36 represents the polypeptide deduced from SEQ ID NO: 37. ORF 19 (SEQ ID NO: 39) is the polynucleotide drawn from residues 24665 to 22680 of SEQ ID NO: 1, and SEQ ID NO: 38 represents the polypeptide deduced from SEQ ID NO: 39. ORF 20 (SEQ ID NO: 41) is the polynucleotide drawn from residues 24880 to 26163 of SEQ ID NO: 1, and SEQ ID NO: 40 represents the polypeptide deduced from SEQ ID NO: 41. ORF 21 (SEQ ID NO: 43) is the polynucleotide drawn from residues 26179 to 27003 of SEQ ID NO: 1, and SEQ ID NO: 42 represents the polypeptide deduced from SEQ ID NO: 43. ORF 22 (SEQ ID NO: 45) is the polynucleotide drawn from residues 27035 to 28138 of SEQ ID NO: 1, and SEQ ID NO: 44 represents the polypeptide deduced from SEQ ID NO: 45. ORF 23 (SEQ ID NO: 47) is the polynucleotide drawn from residues 28164 to 28925 of SEQ ID NO: 1, and SEQ ID NO: 46 represents the polypeptide deduced from SEQ ID NO: 47. ORF 24 (SEQ ID NO: 49) is the polynucleotide drawn from residues 28922 to 30238 of SEQ ID NO: 1, and SEQ ID NO: 48 represents the polypeptide deduced from SEQ ID NO: 49. ORF 25 (SEQ ID NO: 51) is the polynucleotide drawn from residues 30249 to 31439 of SEQ ID NO: 1, and SEQ ID NO: 50 represents the polypeptide deduced from SEQ ID NO: 51. ORF 26 (SEQ ID NO: 53) is the polynucleotide drawn from residues 31439 to 32224 of SEQ ID NO: 1, and SEQ ID NO: 52 represents the polypeptide deduced from SEQ ID NO: 53. ORF 27 (SEQ ID NO: 55) is the polynucleotide drawn from residues 32257 to 32931 of SEQ ID NO: 1, and SEQ ID NO: 54 represents the polypeptide deduced from SEQ ID NO: 55.

ORF 28 (SEQ ID NO: 57) is the polynucleotide drawn from residues 32943 to 33644 of SEQ ID NO: 1, and SEQ ID NO: 56 represents the polypeptide deduced from SEQ ID NO: 57. ORF 29 (SEQ ID NO: 59) is the polynucleotide drawn from residues 34377 to 33637 of SEQ ID NO: 1, and SEQ ID NO: 58 represents the polypeptide deduced from SEQ ID NO: 59. ORF 30 (SEQ ID NO: 61) is the polynucleotide drawn from residues 34572 to 34907 of SEQ ID NO: 1, and SEQ ID NO: 60 represents the polypeptide deduced from SEQ ID NO: 61. ORF 31 (SEQ ID NO: 63) is the polynucleotide drawn from residues 34904 to 36583 of SEQ ID NO: 1, and SEQ ID NO: 62 represents the polypeptide deduced from SEQ ID NO: 63. ORF 32 (SEQ ID NO: 66) is the polynucleotide drawn from residues 23 to 1621 of SEQ ID NO: 64, and SEQ ID NO: 65 represents the polypeptide deduced from SEQ ID NO: 66. ORF 33 (SEQ ID NO: 68) is the polynucleotide drawn from residues 1702 to 2973 of SEQ ID NO: 64, and SEQ ID NO: 67 represents the polypeptide deduced from SEQ ID NO: 68. ORF 34 (SEQ ID NO: 70) is the polynucleotide drawn from residues 3248 to 4270 of SEQ ID NO: 64, and SEQ ID NO: 69 represents the polypeptide deduced from SEQ ID NO: 70. ORF 35 (SEQ ID NO: 72) is the polynucleotide drawn from residues 4452 to 5933 of SEQ ID NO: 64, and SEQ ID NO: 71 represents the polypeptide deduced from SEQ ID NO: 72. ORF 36 (SEQ ID NO: 75) is the polynucleotide drawn from residues 30 to 398 of SEQ ID NO: 73, and SEQ ID NO: 74 represents the polypeptide deduced from SEQ ID NO: 75. ORF 37 (SEQ ID NO: 77) is the polynucleotide drawn from residues 395 to 1372 of SEQ ID NO: 73, and SEQ ID NO: 76 represents the polypeptide deduced from SEQ ID NO: 77. ORF 38 (SEQ ID NO: 79) is the polynucleotide drawn from residues 3388 to 1397 of SEQ ID NO: 73, and SEQ ID NO: 78 represents the polypeptide deduced from SEQ ID NO: 79. ORF 39 (SEQ ID NO: 81) is the polynucleotide drawn from residues 3565 to 5286 of SEQ ID NO: 73, and SEQ ID NO: 80 represents the polypeptide deduced from SEQ ID NO: 81. ORF 40 (SEQ ID NO: 83) is the polynucleotide drawn from residues 5283 to 7073 of SEQ ID NO: 73, and SEQ ID NO: 82 represents the polypeptide deduced from SEQ ID NO: 83. ORF 41 (SEQ ID NO: 85) is the polynucleotide drawn from residues 7108 to 8631 of SEQ ID NO: 73, and SEQ ID NO: 84 represents the polypeptide deduced from SEQ ID NO: 85. ORF 42 (SEQ ID NO: 87) is the polynucleotide drawn from residues 9371 to 8673 of SEQ ID NO: 73, and SEQ ID NO: 86 represents the polypeptide deduced from SEQ ID NO: 87. ORF 43 (SEQ ID NO: 89) is the polynucleotide drawn from residues 9762 to 9364 of SEQ ID NO: 73, and SEQ ID NO: 88 represents the polypeptide deduced from SEQ ID NO: 89.

Some open reading frames provided in the Sequence Listing, namely ORF 2 (SEQ ID NO: 5), ORF 5 (SEQ ID NO: 11), ORF 12 (SEQ ID NO: 25), ORF 13 (SEQ ID NO: 27), ORF 15 (SEQ ID NO: 31), ORF 17 (SEQ ID NO: 35), ORF 19 (SEQ ID NO: 39), ORF 20 (SEQ ID NO: 41), ORF 22 (SEQ ID NO: 45), ORF 24 (SEQ ID NO: 49), ORF 26 (SEQ ID NO: 53) and ORF 27 (SEQ ID NO: 55) initiate with non-standard initiation codons (eg. GTG—Valine, or CTG—Leucine) rather than standard initiation codon ATG methionine. All ORFs are listed with the appropriate M, V or L amino acids at the amino-terminal position to indicate the specificity of the first codon of the ORF. It is expected, however, that in all cases the biosynthesized protein will contain a methionine residue, and more specifically a formylmethionine residue, at the amino terminal position, in keeping with the widely accepted principle that protein synthesis in bacteria initiate with methionine (formylmethionine) even when the encoding gene specifies a non-standard initiation codon (e.g. Stryer BioChemistry $3^{rd}$ edition, 1998, W.H. Freeman and Co., New York, pp. 752-754).

ORF 32 (SEQ ID NO: 65) is incomplete and contains a truncation of 10 to 20 amino acids from its carboxy terminus. This is due to incomplete sequence information between Contigs 2 and 3 (SEQ ID NOS: 64 and 73, respectively).

Deposits of *E. coli* DH10B vectors, each harbouring a cosmid clone (designated in FIG. 4 as 046KM and 046KQ respectively) of a partial biosynthetic locus for the farnesyl dibenzodiazepinone from *Micromonospora* sp. strain 046-ECO11 and together spanning the full biosynthetic locus for production of ECO-04601 have been deposited with the International Depositary Authority of Canada, Bureau of Microbiology, Health Canada, 1015 Arlington Street, Winnipeg, Manitoba, Canada R3E 3R2 on Feb. 25, 2003. The cosmid clone designated 046KM was assigned deposit accession numbers IDAC 250203-06, and the cosmid clone designated 046KQ was assigned deposit accession numbers IDAC 250203-07. Cosmid 046KM covers residue 1 to residue 32,250 of Contig 1 (SEQ ID NO: 1). Cosmid 046KQ covers residue 21,700 of Contig 1 (SEQ ID NO: 1) to residue 9,762 of Contig 3 (SEQ ID NO: 73). The sequence of the polynucleotides comprised in the deposited strains, as well as the amino acid sequence of any polypeptide encoded thereby are controlling in the event of any conflict with any description of sequences herein.

The deposit of the deposited strains has been made under the terms of the Budapest Treaty on the International Recognition of the Deposit of Micro-organisms for Purposes of Patent Procedure. The deposited strains will be irrevocably and without restriction or condition released to the public upon the issuance of a patent. The deposited strains are provided merely as convenience to those skilled in the art and are not an admission that a deposit is required for enablement, such as that required under 35 U.S.C. §112. A license may be required to make, use or sell the deposited strains, and compounds derived therefrom, and no such license is hereby granted.

In order to identify the function of the proteins coded by the genes forming the biosynthetic locus for the production of ECO-04601 the gene products of ORFs 1 to 43, namely SEQ ID NOS: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 65, 67, 69, 71, 74, 76, 78, 80, 82, 84, 86 and 88 were compared, using the BLASTP version 2.2.10 algorithm with the default parameters, to sequences in the National Center for Biotechnology Information (NCBI) nonredundant protein database and the DECIPHER® database of microbial genes, pathways and natural products (Ecopia BioSciences Inc. St.-Laurent, Q C, Canada).

The accession numbers of the top GenBank™ hits of this BLAST analysis are presented in Table 7 along with the corresponding E values. The E value relates the expected number of chance alignments with an alignment score at least equal to the observed alignment score. An E value of 0.00 indicates a perfect homolog. The E values are calculated as described in Altschul et al. *J. Mol. Biol.*, 215, 403-410 (1990). The E value assists in the determination of whether two sequences display sufficient similarity to justify an inference of homology.

TABLE 7

Sequence comparison and ORF correlation

| ORF | SEQ ID | Family | # aa | GenBank homology | Probability | % Identity (% Similarity) | Proposed function of GenBank match |
|---|---|---|---|---|---|---|---|
| 1 | 2 | ABCC | 571 | NP_736627.1 590aa | 1E-107 | 45% (56%) | ABC transporter Corynebacterium efficiens |
| | | | | NP_600638.1 510aa | 5E-80 | 37% (52%) | ABC transporter Corynebacterium efficiens |
| | | | | NP_600638.1 510aa | 3E-12 | 30% (43%) | ABC transporter Corynebacterium efficiens |
| 2 | 4 | RECH | 689 | CAC93719.1 923aa | 3E-17 | 36% (55%) | regulator [*Lechevalieria aerocolonigenes*] |
| | | | | BAC55205.1 943aa | 3E-12 | 30% (48%) | transcriptional activator [*Streptomyces* sp.] |
| | | | | NP_631154.1 932aa | 3E-07 | 46% (63%) | regulator. [*Streptomyces coelicolor* A3(2)] |
| 3 | 6 | REGD | 895 | CAC93719.1 923aa | 3E-20 | 28% (43%) | regulator [*Lechevalieria aerocolonigenes*] |
| | | | | BAC55205.1 943aa | 1E-15 | 29% (36%) | activator [*Streptomyces* sp. TP-A0274] |
| | | | | NP_733725.1 908aa | 3E-12 | 28% (41%) | regulator [*Streptomyces coelicolor* A3(2)] |
| 4 | 8 | IDSA | 362 | NP_601376.2 371aa | 2E-80 | 49% (65%) | GGPP synthase [*Corynebacterium glutamicum*] |
| | | | | NP_738677.1 366aa | 3E-79 | 48% (62%) | polyprenyl synthase, *Corynebacterium efficiens* |
| | | | | NP_216689.1 352aa | 2E-78 | 46% (61%) | idsA2 [*Mycobacterium tuberculosis* H37Rv] |
| 5 | 10 | MVKA | 354 | BAB07790.1 345aa | 2E-71 | 46% (59%) | mevalonate kinase [*Streptomyces* sp. CL190] |
| | | | | BAB07817.1 334aa | 5E-66 | 45% (57%) | mevalonate kinase [*Kitasatospora griseola*] |
| | | | | NP_720650.1 332aa | 3E-36 | 29% (48%) | mevalonate kinase [*Streptococcus mutans*] |
| 6 | 12 | DMDA | 346 | BAB07791.1 350aa | 2E-88 | 58% (65%) | diphosphomevalonate decarboxylase [*Streptomyces sp.*] |
| | | | | BAB07818.1 300aa | 2E-69 | 53% (61%) | mevalonate diPH decarboxylase [*Kitasatospora griseola*] |
| | | | | NP_785307.1 325aa | 3E-44 | 34% (46%) | diphosphomevalonate decarboxylase [*Lactobacillus plantarum*] |
| 7 | 14 | MVKP | 369 | BAB07792.1 374aa | 4E-93 | 50% (60%) | phosphomevalonate kinase [*Streptomyces* sp. CL190] |
| | | | | BAB07819.1 | 6E-77 | 48% (56%) | phosphomevalonate kinase [*Kitasatospora*] |
| | | | | AAG02442.1 368aa | 2E-31 | 29% (42%) | 3 phosphomevalonate kinase [*Enterococcus faecalis*] |
| 8 | 16 | IPPI | 360 | Q9KWF6 364aa | 1E-128 | 66% (74%) | Isopentenyl-diphosphate delta-isomerase |
| | | | | Q9KWG2 363aa | 1E-128 | 66% (77%) | Isopentenyl-diphosphate delta-isomerase |
| | | | | NP_814639.1 347aa | 5E-73 | 44% (61%) | isopentenyl diphosphate isomerase [*Enterococcus faecalis*] |
| 9 | 18 | HMGA | 351 | BAA70975.1 353aa | 1E-165 | 82% (91%) | 3-hydroxy-3-methylglutaryl coenzyme A reductase [*Streptomyces* sp.] |
| | | | | BAA74565.1 353aa | 1E-160 | 81% (89%) | 3-hydroxy-3-methylglutaryl coenzyme A reductase [*Kitasatospora griseola*] |
| | | | | BAA74566.1 353aa | 1E-155 | 80% (86%) | 3-hydroxy-3-methylglutaryl coenzyme A reductase [*Streptomyces* sp.] |
| 10 | 20 | KASH | 391 | BAB07795.1 389aa | 1E-148 | 67% (78%) | 3-hydroxy-3-methylglutaryl CoA synthase [*Streptomyces* sp. CL 190] |
| | | | | BAB07822.1 346aa | 1E-136 | 70% (78%) | HMG-CoA synthase [*Kitasatospora griseola*] |
| | | | | CAD24420.1 388aa | 6E-79 | 43% (54%) | HMG-CoA synthase [*Paracoccus zeaxanthinifaciens*] |
| 11 | 22 | IPTN | 290 | NP_631248.1 295aa | 5E-22 | 28% (44%) | hypothetical protein [*Streptomyces coelicolor* A3(2)] |
| | | | | AAN65239.1 324aa | 5E-06 | 25% (40%) | cloQ [*Streptomyces roseochromogenes* subsp. *oscitans*] |
| 12 | 24 | SPKG | 370 | AAM78435.1 344aa | 5E-48 | 54% (63%) | two-component sensor [*Streptomyces coelicolor* A3(2)] |
| | | | | NP_630507.1 382aa | 5E-48 | 54% (63%) | sensor kinase [*Streptomyces coelicolor* A3(2)] |
| | | | | ZP_00058991.1 407aa | 9E-34 | 44% (58%) | Signal transduction histidine kinase [*Thermobifida fusca*] |
| 13 | 26 | RREB | 220 | NP_630508.1 224aa | 3E-79 | 67% (81%) | regulatory protein [*Streptomyces coelicolor* A3(2)] |
| | | | | ZP_00058992.1 221aa | 4E-67 | 59% (75%) | Response regulator [*Thermobifida fusca*] |

TABLE 7-continued

Sequence comparison and ORF correlation

| ORF | SEQ ID | Family | # aa | GenBank homology | Probability | % Identity (% Similarity) | Proposed function of GenBank match |
|---|---|---|---|---|---|---|---|
| | | | | NP_625364.1 221aa | 6E-66 | 60% (74%) | response regulator [*Streptomyces coelicolor* A3(2)] |
| 14 | 28 | UNES | 131 | No hit | — | — | — |
| 15 | 30 | UNEZ | 154 | NP_649459.2 628aa | 7.6E-02 | 38% (60%) | CG1090-PB [*Drosophila melanogaster*] |
| | | | | NP_730819.1 473aa | 7.6E-02 | 38% (60%) | CG1090-PA [*Drosophila melanogaster*] |
| | | | | AAM11079.1 428aa | 7.6E-02 | 38% (60%) | GH23040p [*Drosophila melanogaster*] |
| 16 | 32 | OXDS | 661 | NP_242948.1 500aa | 1E-52 | 30% (46%) | unknown conserved protein [*Bacillus halodurans*] |
| | | | | ZP_00091617.1 480aa | 3E-32 | 29% (41%) | Putative multicopper oxidases [*Azotobacter vinelandii*] |
| | | | | NP_252457.1 463aa | 1E-31 | 28% (42%) | metallo-oxidoreductase [*Pseudomonas aeruginosa* PA01] |
| 17 | 34 | UNFD | 129 | NP_437360.1 127aa | 7E-33 | 60% (72%) | bleomycin resistance protein family [*Sinorhizobium meliloti*] |
| | | | | AAO91879.1 123aa | 1E-31 | 58% (74%) | unknown [uncultured bacterium] |
| | | | | NP_103287.1 131aa | 1E-23 | 48% (62%) | unknown protein [*Mesorhizobium loti*] |
| 18 | 36 | UNFA | 178 | | | | |
| 19 | 38 | CSMB | 661 | ZP_00137697.1 769aa | 1E-166 | 51% (66%) | Anthranilate/para-aminobenzoate synthase |
| | | | | NP_250594.1 627aa | 1E-166 | 51% (66%) | phenazine biosynthesis protein PhzE [*Pseudomonas aeruginosa* PA01] |
| | | | | ZP_00137701.1 | 1E-166 | 51% (66%) | [*Pseudomonas aeruginosa*] |
| 20 | 40 | AAKD | 427 | P41403 421aa | 1E-64 | 38% (51%) | Aspartokinase (Aspartate kinase) |
| | | | | ZP_00057166.1 445aa | 2E-64 | 37% (52%) | Aspartokinases [*Thermobifida fusca*] |
| | | | | AAD49567.1 421aa | 6E-64 | 37% (52%) | aspartokinase subunit A [*Amycolatopsis mediterranei*] |
| 21 | 42 | ALDB | 274 | NP_275722.1 266aa | 2E-53 | 45% (64%) | conserved protein [*Methanothermobacter thermautotrophicus*] |
| | | | | NP_614692.1 270aa | 2E-52 | 43% (61%) | Fructose-1,6-bisphosphate aldolase [*Methanopyrus kandleri* AV19] |
| | | | | NP_615406.1 267aa | 2E-50 | 43% (61%) | fructose-bisphosphate aldolase [*Methanosarcina acetivorans* str. C2A] |
| 22 | 44 | UNFC | 367 | NP_275723.1 378aa | 4E-46 | 38% (56%) | conserved protein [*Methanothermobacter thermautotrophicus*] |
| | | | | NP_614691.1 402aa | 2E-45 | 39% (55%) | alternative 3-dehydroquinate synthase [*Methanopyrus kandleri*] |
| | | | | NP_248244.1 361aa | 2E-43 | 40% (59%) | conserved hypothetical protein [*Methanococcus jannaschii*] |
| 23 | 46 | HYDK | 253 | NP_577771.1 247aa | 4E-14 | 31% (49%) | metal-dependent hydrolase [*Pyrococcus furiosus* DSM 3638] |
| | | | | NP_142108.1 247aa | 1E-12 | 33% (52%) | hypothetical protein PH0093 [*Pyrococcus horikoshii*] |
| | | | | NP_125791.1 248aa | 1E-11 | 28% (50%) | hypothetical protein [*Pyrococcus abyssi*] |
| 24 | 48 | ADSA | 438 | NP_070499.1 433aa | 2E-41 | 35% (49%) | coenzyme F390 synthetase [*Archaeoglobus fulgidus*] |
| | | | | NP_618724.1 434aa | 5E-41 | 34% (50%) | coenzyme F390 synthetase [*Methanosarcina acetivorans*] |
| | | | | NP_632700.1 437aa | 7E-41 | 35% (50%) | Coenzyme F390 synthetase [*Methanosarcina mazei* Goe1] |
| 25 | 50 | HOXV | 396 | ZP_00027430.1 442aa | 8E-76 | 42% (59%) | 2-polyprenyl-6-methoxyphenol hydroxylase [*Burkholderia fungorum*] |
| | | | | NP_627457.1 420aa | 1E-71 | 38% (51%) | salicylate hydroxylase [*Streptomyces coelicolor* A3(2)] |
| | | | | ZP_00033877.1 403aa | 2E-68 | 37% (51%) | 2-polyprenyl-6-methoxyphenol hydroxylase [*Burkholderia fungorum*] |
| 26 | 52 | SDRA | 261 | NP_391080.1 261aa | 6E-58 | 46% (57%) | 2,3-dihydro-2,3-dihydroxybenzoate dehydrogenase [*Bacillus subtilis*] |
| | | | | ZP_00059512.1 260aa | 1E-55 | 45% (56%) | Dehydrogenase [*Thermobifida fusca*] |
| | | | | AAG31126.1 257aa | 9E-55 | 46% (56%) | MxcC [*Stigmatella aurantiaca*] |
| 27 | 54 | DHBS | 224 | Q51790 207aa | 7E-60 | 56% (72%) | isochrismatase |
| | | | | Q51518 207aa | 1E-58 | 56% (71%) | isochonsmatase |

TABLE 7-continued

Sequence comparison and ORF correlation

| ORF | SEQ ID | Family | # aa | GenBank homology | Probability | % Identity (% Similarity) | Proposed function of GenBank match |
|---|---|---|---|---|---|---|---|
| | | | | NP_391077.1 312aa | 2E-58 | 52% (69%) | isochrismatase [*Bacillus subtilis*] |
| 28 | 56 | SDRA | 233 | NP_103491.1 242aa | 9E-21 | 32% (49%) | acyl-carrier protein reductase [*Mesorhizobium loti*] |
| | | | | AAL14912.1 245aa | 1E-15 | 28% (44%) | short-chain dehydrogenase [*Rhizobium leguminosarum* bv. *trifolii*] |
| | | | | NP_902480.1 235aa | 7E-15 | 29% (44%) | oxidoreductase [*Chromobacterium violaceum*] |
| 29 | 58 | UNIQ | 246 | S18541 281aa | 4.5E-02 | 29% (43%) | hypothetical protein 3 - *Streptomyces coelicolor* |
| | | | | NP_629228.1 281aa | 5.9E-02 | 29% (43%) | hypothetical protein [*Streptomyces coelicolor* A3(2)] |
| 30 | 60 | UNFE | 111 | ZP_00058149.1 130aa | 1E-10 | 36% (48%) | membrane protein [*Thermobifida fusca*] |
| | | | | NP_737701.1 120aa | 1E-09 | 33% (46%) | hypothetical protein [*Corynebacterium efficiens*] |
| | | | | NP_827629.1 118aa | 7E-09 | 33% (49%) | hypothetical protein [*Streptomyces avermitilis* MA-4680] |
| 31 | 62 | EFFT | 559 | ZP_00058148.1 537aa | 2E-67 | 32% (49%) | Predicted symporter [*Thermobifida fusca*] |
| | | | | NP_626090.1 544aa | 4E-66 | 31% (49%) | transport protein [*Streptomyces coelicolor* A3(2)] |
| | | | | NP_827630.1 549aa | 7E-63 | 31% (49%) | sodium-dependent symporter [*Streptomyces avermitilis*] |
| 32 | 65 | HOYH | 532 | AAM96655.1 544aa | 2E-92 | 39% (53%) | 2,4-dihydroxybenzoate monooxygenase [*Sphingobium chlorophenolicum*] |
| | | | | ZP_00029353.1 543aa | 1E-73 | 35% (49%) | 2-polyprenyl-6-methoxyphenol hydroxylase [*Burkholderia fungorum*] |
| | | | | NP_769326.1 569aa | 5E-62 | 33% (48%) | blr2686 [*Bradyrhizobium japonicum*] dbj |
| 33 | 67 | DAHP | 423 | T03226 391aa | 1E-111 | 54% (68%) | hypothetical protein - *Streptomyces hygroscopicus* |
| | | | | ZP_00137693.1 405aa | 3E-87 | 45% (61%) | DAHP synthase [*Pseudomonas aeruginosa* UCBPP-PA14] |
| | | | | NP_250592.1 405aa | 1E-86 | 45% (61%) | phenazine biosynthesis protein PhzC [*Pseudomonas aeruginosa*] |
| 34 | 69 | REGG | 340 | BAC53615.1 346aa | 1E-67 | 46% (62%) | regulator protein [*Streptomyces kasugaensis*] |
| | | | | S44506 424aa | 3E-66 | 46% (60%) | regulator protein - *Streptomyces glaucescens* |
| | | | | AAK81822.1 348aa | 1E-65 | 44% (59%) | transcriptional regulator [*Streptomyces lavendulae*] |
| 35 | 71 | UNFJ | 493 | ZP_00073237.1 678aa | 7E-35 | 27% (43%) | RTX toxins [*Trichodesmium erythraeum* IMS101] |
| | | | | NP_484716.1 433aa | 3E-05 | 23% (37%) | similar to vanadium chloroperoxidase [*Nostoc* sp.] |
| | | | | ZP_00067005.1 667aa | 7.4E-02 | 27% (37%) | hypothetical protein [*Microbulbifer degradans* 2–40] |
| 36 | 74 | RECI | 112 | NP_627088.1 125aa | 3E-17 | 48% (59%) | hypothetical protein. [*Streptomyces coelicolor* A3(2)] |
| | | | | NP_846017.1 109aa | 7E-15 | 40% (59%) | hypothetical protein [*Bacillus anthracis* str. Ames] |
| | | | | NP_241272.1 174aa | 9E-15 | 37% (58%) | unknown conserved protein [*Bacillus halodurans*] |
| 37 | 76 | UNIQ | 325 | NP_422203.1 187aa | 1E-03 | 39% (59%) | hypothetical protien [*Caulobacter crescentus* CB15] |
| 38 | 78 | OXAH | 663 | ZP_00058724.1 659aa | 0E+00 | 57% (67%) | Acyl-CoA dehydrogenases [*Thermobifida fusca*] |
| | | | | AAB97825.1 433aa | 5E-93 | 46% (56%) | acyl-CoA oxidase [*Myxococcus xanthus*] |
| | | | | AAF14635.1, 694aa | 5E-85 | 37% (52%) | 1 acyl-CoA oxidase [*Petroselinum crispum*] |
| 39 | 80 | ABCA | 537 | T14162 574aa | 9E-62 | 37% (47%) | hABC transport protein - *Mycobacterium smegmatis* |
| | | | | NP_624808.1 | 4E-60 | 35% (46%) | ABC transporter [*Streptomyces coelicolor* A3(2)] |
| | | | | NP_822745.1 | 8E-32 | 31% (42%) | ABC transportert [*Streptomyces avermitilis* MA-4680] |
| 40 | 82 | ABCA | 596 | T14180 1122aa | 1E-107 | 40% (51%) | exiT protein - *Mycobacterium smegmatis* |
| | | | | AAC82548.1 589aa | 1E-107 | 40% (51%) | unknown [*Mycobacterium smegmatis*] |
| | | | | NP_624810.1 601aa | 3E-97 | 37% (48%) | ABC-transporter [*Streptomyces coelicolor* A3(2)] |

TABLE 7-continued

Sequence comparison and ORF correlation

| ORF | SEQ ID | Family | # aa | GenBank homology | Probability | % Identity (% Similarity) | Proposed function of GenBank match |
|---|---|---|---|---|---|---|---|
| 41 | 84 | UNIQ | 507 | NP_831570.1 676aa | 8E−07 | 24% (44%) | methyltransferases [*Bacillus cereus* |
| | | | | NP_655735.1 676aa | 2E−06 | 23% (44%) | ubiE/COQ5 methyltransferase family [*Bacillus anthracis* |
| | | | | NP_844290.1 681aa | 2E−06 | 23% (44%) | hypothetical protein [*Bacillus anthracis* str. Ames] |
| 42 | 86 | | 232 | NP_830809.1 208aa | 8E−08 | 22% (35%) | Transporter, LysE family [*Bacillus cereus*] |
| | | | | NP_844737.1 210aa | 2E−07 | 22% (35%) | homoserine/threonine efflux protein[*Bacillus anthracis* |
| | | | | NP_655752.1 208aa | 1E−06 | 22% (36%) | LysE, LysE type translocator [*Bacillus anthracis* |
| 43 | 88 | | 132 | NP_827272.1 127aa | 4E−09 | 36% (49%) | hypothetical protein [*Streptomyces avermitilis* MA-4680] |
| | | | | NP_246491.1, 112aa | 5E−02 | 22% (47%) | unknown [*Pasteurella multocida*] |

The ORFs encoding proteins involved in the biosynthesis of farnesyl dibenzodiazepinones are assigned a putative function and grouped together in families based on sequence similarity to known proteins. To correlate structure and function, the protein families are given a four-letter designation used throughout the description and figures as indicated in Table 8. The meaning of the four letter designations is as follows: AAKD designates an amino acid kinase; ABCA and ABCC designate ABC transporters; ADSA designates an amide synthetase; ALDB designates an aldolase function; CSMB designates a chorismate transaminase; DAHP designates a 3,4-dideoxy-4-amino-D-arabino-heptulosonic acid 7-phosphate synthase activity; DHBS designates a 2,3-dihydro-2,3-dihydroxybenzoate synthase activity; DMDA designates a diphosphomevalonate decarboxylase; EFFT designates an efflux protein; HMGA designates a 3-hydroxy-3-methylglutaryl-CoA reductase; HOXV designates a monooxygenase activity; HOYH designates a hydroxylase/decarboxylase activity; HYDK designates a hydrolase activity; IDSA designates an isopentenyl diphosphate synthase; IPPI designates an isopentenyl diphosphate isomerase; IPTN designates an isoprenyltransferase; KASH designates 3-hydroxy-3-methylglutaryl-CoA synthase; MVKA designates a mevalonate kinase; MVPK designates a phosphomevalonate kinase; OXAH designates an acylCoA oxidase; OXDS designates an oxidoreductase; RECH, RECI, REGD, REGG and RREB designate regulators; SDRA designates a dehydrogenase/ketoreductase, SPKG designates a sensory protein kinase; UNES, UNEZ, UNFA, UNFC, UNFD, UNFE, UNFJ and UNIQ designate proteins of unknown function.

TABLE 8

| FAMILY | FUNCTION: |
|---|---|
| AAKD | amino acid kinase; strong homology to primary aspartate kinases, converting L-aspartate to 4-phospho-L-aspartate |
| ABCA | ABC transporter |
| ABCC | ABC transporter |
| ADSA | adenylating amide synthetase |
| ALDB | aldolase; similarity to fructose-1,6-biphosphate aldolase that generates D-glyceraldehyde-3Ph, precursor of D-erythrose-4Ph involved in the shikimate pathway |
| CSMB | chorismate transaminase, similarity to anthranilate synthase |
| DAHP | DAHP synthase, class II; involved in formation of aminoDAHP from PEP and erythrose-4-phosphate |
| DHBS | 2,3-dihydro-2,3-dihydroxybenzoate synthase (isochorismatase) |
| DMDA | diphosphomevalonate decarboxylase (mevalonate pyrophosphate decarboxylase) |
| EFFT | efflux protein |
| HMGA | HMG-CoA reductase; converts 3-hydroxy-3-methylglutaryl-CoA to mevalonate plus CoA in isoprenoid biosynthesis |
| HOXV | FAD monooxygenase; shows homology to a variety of monooxygenases including salicylate hydroxylases, zeaxanthin epoxidases |
| HOYH | hydroxylase/decarboxylase; FAD-dependent monooxygenase |
| HYDK | hydrolase |
| IDSA | isoprenyl diphosphate synthase, catalyzes the addition of 2 molecules of isopentenyl pyrophosphate to dimethylallyl pyrophosphate to generate GGPP |
| IPPI | isopentenyl diphosphate isomerase, catalyzes the isomerization of IPP to produce dimethylallyl diphosphate |
| IPTN | isoprenyltransferase; catalyzes covalent N-terminal attachment of isoprenyl units to amide groups of nitrogen-containing heterocycle rings |
| KASH | HMG-CoA synthase; condenses acetyl-CoA with acetoacetyl-CoA to form 3-hydroxy-3-methylglutaryl-CoA |
| MEBI | membrane protein |

TABLE 8-continued

| FAMILY | FUNCTION: |
|---|---|
| MVKA | mevalonate kinase; converts mevalonate to 5-phosphomevalonate in the mevalonate pathway of isoprenoid biosynthesis |
| MVKP | phosphomevalonate kinase; converts 5-phosphomevalonate to 5-diphosphomevalonate in the mevalonate pathway of isoprenoid biosynyhesis |
| OXAH | acyl CoA oxidase |
| OXDS | oxidoreductase |
| RECH | regulator |
| RECI | regulator; similarity to PadR transcriptional regulators involved in repression of phenolic acid metabolism |
| REGD | transcriptional regulator; relatively large regulators with an N-terminal ATP-binding domain containing Walker A and B motifs and a C-terminal LuxR type DNA-binding domain |
| REGG | regulator |
| RREB | response regulator; similar to response regulators that are known to bind DNA and act as transcriptional activators |
| SDRA | dehydrogenase/ketoreductase, NAD-dependent |
| SPKD | sensory protein kinase, two component system |
| SPKG | sensory protein kinase, two component system |
| UNES | unknown function |
| UNEZ | unknown function |
| UNFA | unknown function |
| UNFC | unknown function |
| UNFD | unknown function |
| UNFE | putative membrane protein |
| UNFJ | unknown function |
| UNIQ | unknown function |

Figure 7:
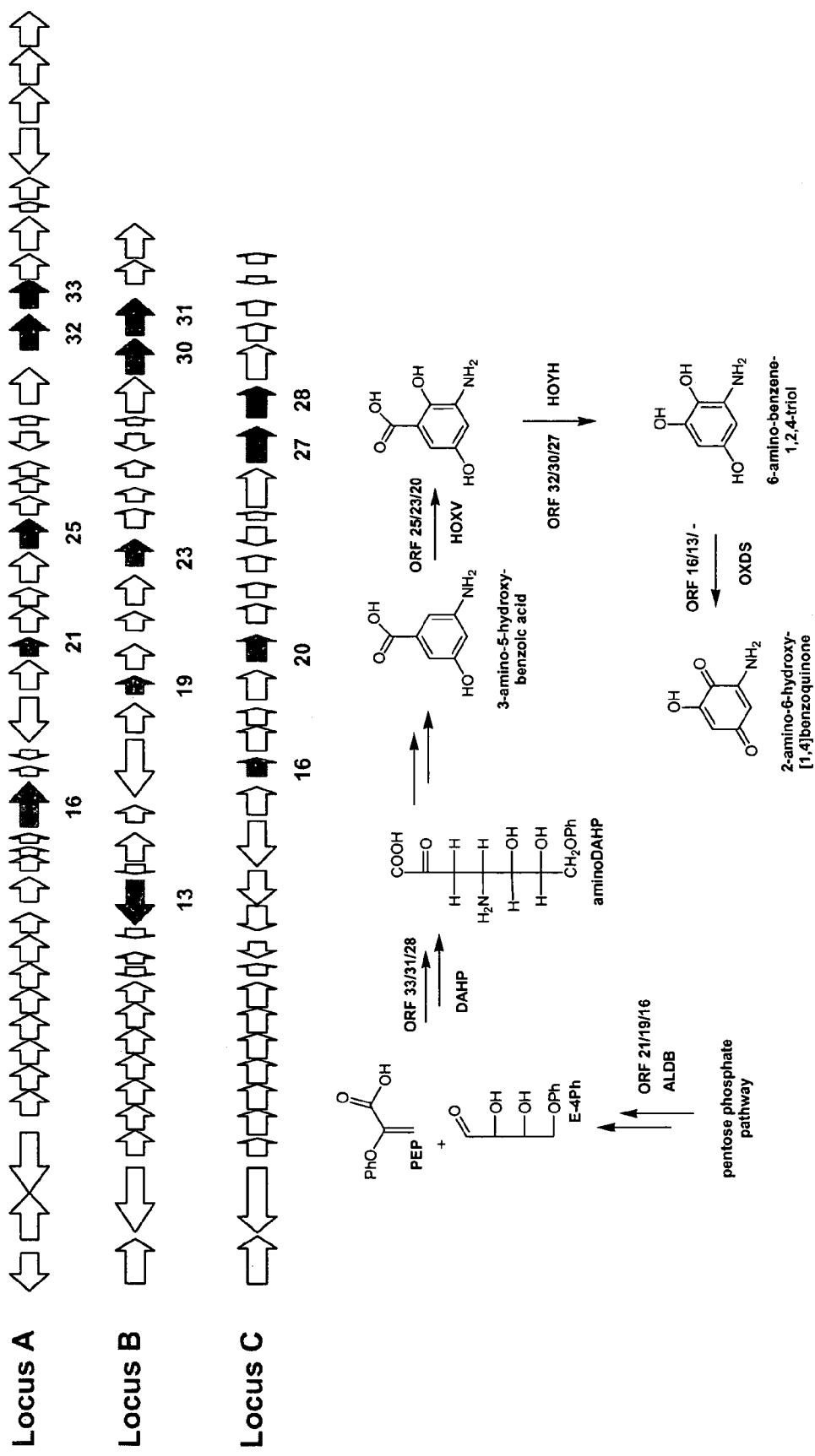
Figure 8:
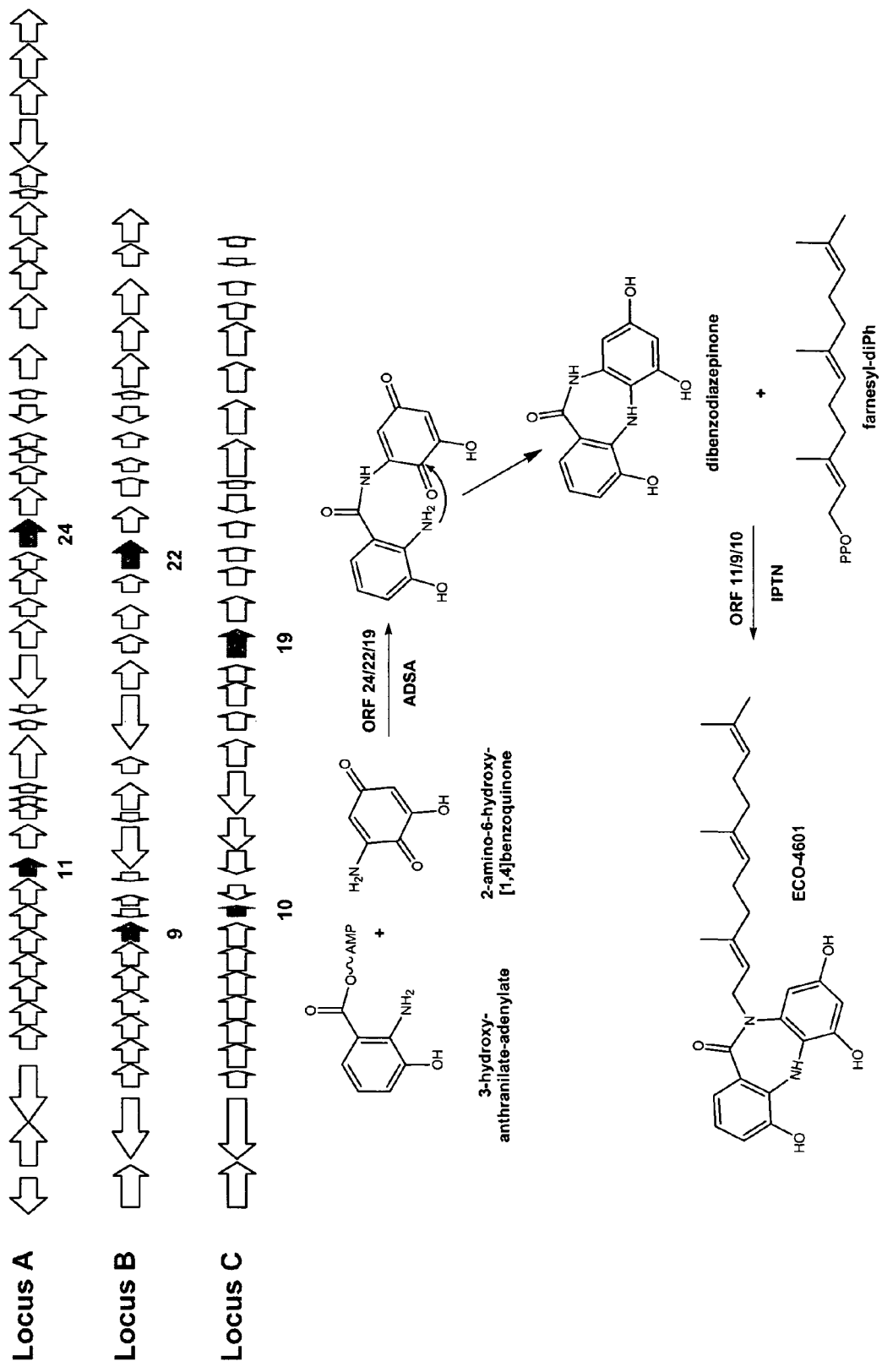

Biosynthesis of ECO-04601 involves the action of various enzymes that synthesize the three building blocks of the compound, namely the farnesyl-diphosphate component (FIG. 5), the 3-hydroxy-anthranilate-adenylate component (FIG. 6) and the 2-amino-6-hydroxy-benzoquinone component (FIG. 7) that are subsequently condensed to form the final compound (FIG. 8).

Figure 5:
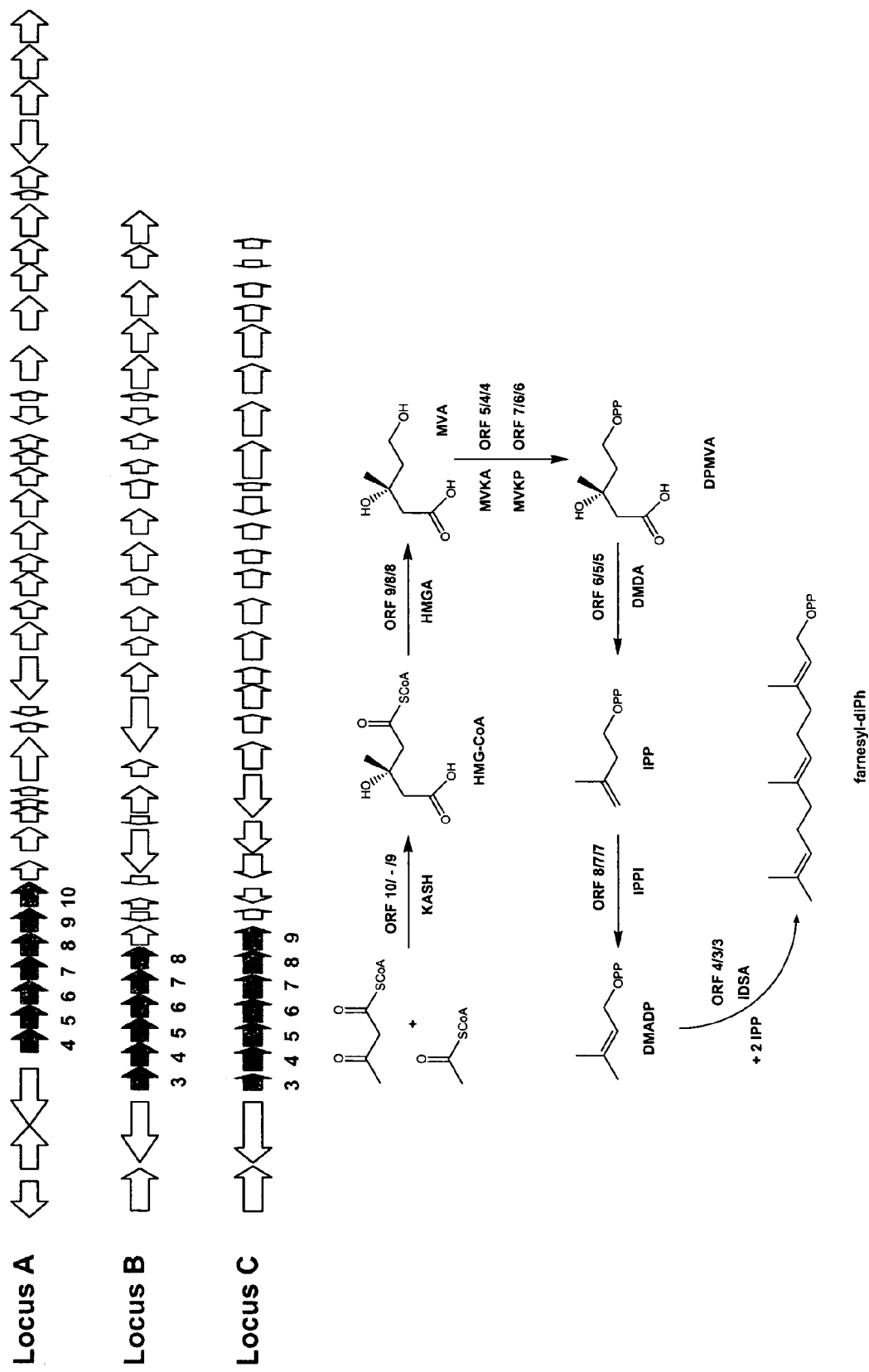
FIGS. 5 to 8: show the different steps involved in the biosynthetic pathway of ECO-04601. Each of FIGS. 5 to 8 shows the three biosynthetic loci A, B and C where ORFs are represented by arrows. Highlighted ORFs are involved in the steps described in the schematic diagram. The biosynthetic enzymes involved in the steps depicted in schematic diagrams are indicated by their family designation and the respective ORF number in each of Loci A, B and C (e.g., 8/7/7).

The farnesyl-diphosphate biosynthesis involves the concerted action of seven enzymes (FIG. 5). ORF 10 (KASH) (SEQ ID NO: 20) encodes a hydroxymethylglutaryl-CoA synthase that catalyzes an aldol addition of acetyl-CoA onto acetoacyl-CoA to yield 3-hydroxy-3-methylglutaryl-CoA (HMG-CoA). This product is subsequently reduced through the action of ORF 9 (HMGA) (SEQ ID NO: 18) to form mevalonic acid (MVA). ORF 5 (MVKA) (SEQ ID NO: 10) phosphorylates mevalonate to 5'-phosphomevalonate using ATP as the phosphate donor. The next step in the farnesyl-diphosphate biosynthesis is the phosphorylation reaction of the 5'-phosphomevalonate to 5'-pyrophosphomevalonate (DPMVA) that is catalyzed by ORF 7 (MVKP) (SEQ ID NO: 14). Subsequent decarboxylation of 5'-pyrophosphomevalonate catalyzed by ORF 6 (DMDA) (SEQ ID NO: 12) yields isopentenyl diphosphate (IPP) which is then converted to dimethylallyldiphosphate (DMADP) through the action of ORF 8 (IPPI) (SEQ ID NO: 16) that has isomerase enzymatic activity. The final step in the biosynthesis of farnesyl-diphosphate is the condensation of one molecule of dimethylallyldiphosphate with two molecules of isopentenyl diphosphate catalyzed by the isoprenyl diphosphate synthase ORF 4 (IDSA) (SEQ ID NO: 8). The described pathway involved in synthesis of farnesyl-diphosphate is entirely consistent with related mevalonate pathways described in other actinomycete species (Takagi et al., *J. Bacteriol.* 182, 4153-4157, (2000)).

Figure 6:
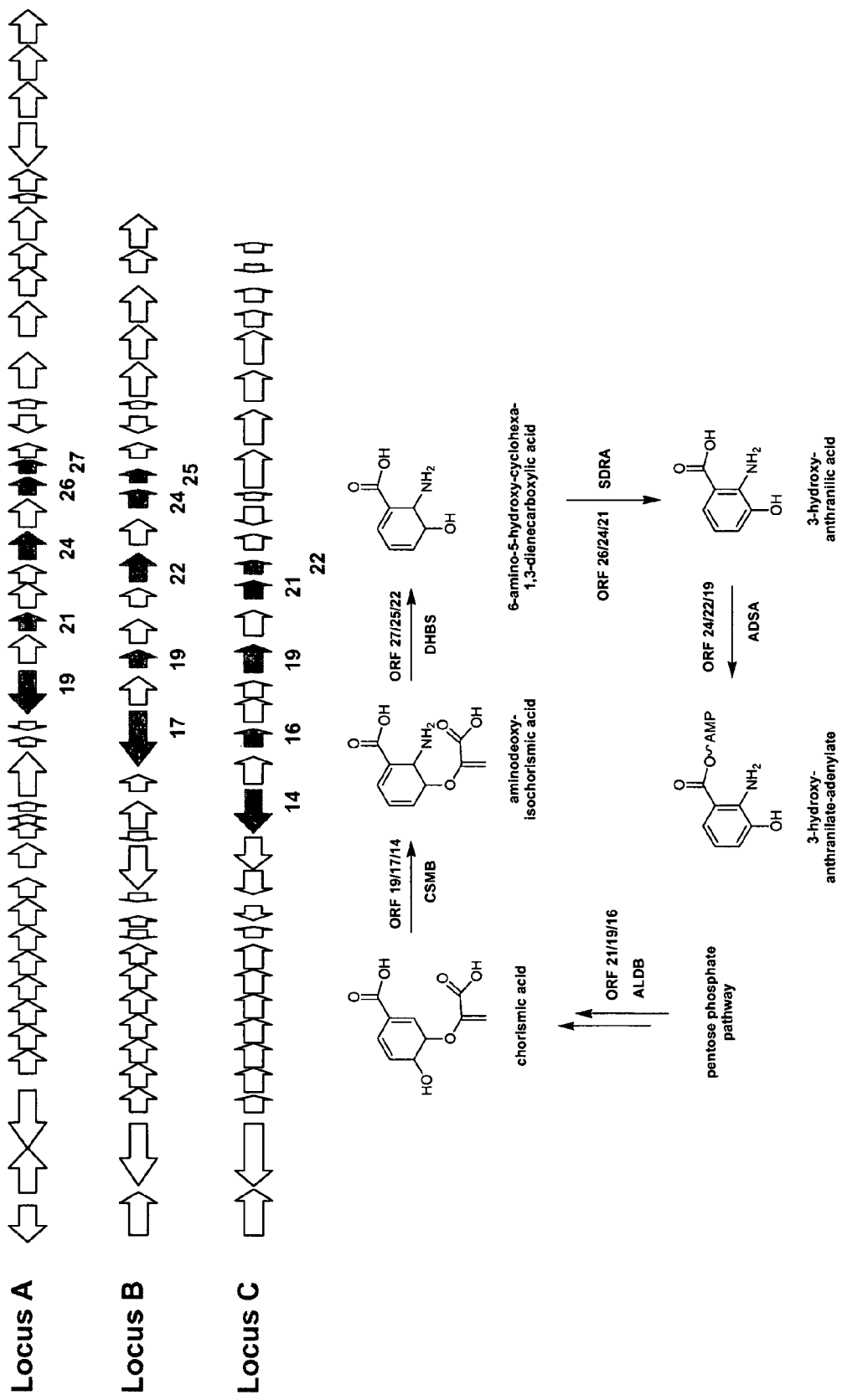

Biosynthesis of the 3-hydroxy-anthranilate component involves the use of precursors derived from the shikimate pathway (FIG. 6). Chorismic acid is transaminated through the action of ORF 19 (CSMB) (SEQ ID NO: 38) to form aminodeoxyisochorismic acid. This enzyme resembles anthranilate synthases and is likely to catalyze specifically the transfer of the amino group using glutamine as the amino donor. The next step involves isochorismatase activity and is mediated by ORF 27 (DHBS) (SEQ ID NO: 54). This reaction consists in the removal of the pyruvate side chain from aminodeoxyisochorismic acid to form 6-amino-5-hydroxy-cyclohexa-1,3-dienecarboxylic acid. This compound is subsequently oxidized through the action of ORF 26 (SDRA) (SEQ ID NO: 52) yielding 3-hydroxy-anthranilic acid. ORF 24 (ADSA) (SEQ ID NO: 48) catalyzes the activation of 3-hydroxy-anthranilic acid through adenylation generating the 3-hydroxy-anthranilate-adenylate component (FIG. 6).

Biosynthesis of the 2-amino-6-hydroxy-benzoquinone component of the farnesyl dibenzodiazepinone, requires components derived from the aminoshikimate pathway. FIG. 7 depicts the series of enzymatic reactions involved in the biosynthesis of this constituent. ORF 21 (ALDB) (SEQ ID NO: 42) resembles aldolases involved in the generation of precursors of D-erythrose-4-phosphate which is part of the aminoshikimate pathway used for the generation of 2-amino-6-hydroxy-[1,4]-benzoquinone. ORF 33 (DAHP) (SEQ ID NO: 67) catalyzes the initial step in the aminoshikimate pathway that corresponds to the formation of 3,4-dideoxy-4-amino-D-arabino-heptulosonic acid 7-phosphate (amino DAHP) from phosphoenolpyruvate (PEP) and erythrose 4-phosphate (E-4Ph). Subsequent reactions leading to 3-amino-5-hydroxy-benzoic acid are catalyzed by enzymes provided by primary metabolism biosynthetic pathways present in *Micromonospora* sp. strain 046-ECO11. ORF 25 (HOXV) (SEQ ID NO: 50) hydroxylates 3-amino-5-hydroxy-benzoic acid at position 2, generating 3-amino-2,5-dihydroxy-benzoic acid. This intermediate is further modified by ORF 32 (HOYH) (SEQ ID NO: 65) that catalyzes a decarboxylative oxidation reaction yielding 6-amino-benzene-1,2,4-triol. A final oxidation reaction is performed by ORF 16 (OXDS) (SEQ ID NO: 32) yielding 2-amino-6-hydroxy-[1,4]-benzoquinone (FIG. 7).

Assembly of the three components resulting in the farnesyl dibenzodiazepinone is catalyzed by ORFs 24 and 11 (FIG. 8). ORF 24 (ADSA) (SEQ ID NO: 48) catalyzes the condensation of the adenylated 3-hydroxy-anthranilate with the 2-amino-6-hydroxy-[1,4]-benzoquinone component. A spontaneous condensation between the free amino group of the 3-hydroxy-anthranilate and one of the carbonyl groups present on the 2-amino-6-hydroxy-[1,4]-benzoquinone component occurs yielding a dibenzodiazepinone intermediate. This compound is further modified through transfer of the farnesyl group of the farnesyl-diphosphate intermediate onto the nitrogen of the amide of the dibenzodiazepinone catalyzed by ORF 11 (IPTN) (SEQ ID NO: 22) and resulting in the formation of the farnesyl dibenzodiazepinone (FIG. 8).

Additional ORFs, namely ORF 2 (RECH) (SEQ ID NO: 4), ORF 3 (REGD) (SEQ ID NO: 6), ORF 12 (SPKG) (SEQ ID NO: 24), ORF 13 (RREB) (SEQ ID NO: 26), ORF 34 (REGG) (SEQ ID NO: 69) and ORF 36 (RECI) (SEQ ID NO: 74) are involved in the regulation of the biosynthetic locus encoding the farnesyl dibenzodiazepinone. Other ORFs, namely ORF 1 (ABCC) (SEQ ID NO: 2), ORF 31 (EFFT) (SEQ ID NO: 62), ORFs 39 and 40 (ABCA) (SEQ ID NOS: 80 and 82, respectively) and ORF 42 (SEQ ID NO: 86) are involved in transport. Other ORFs involved in the biosynthesis of the farnesyl dibenzodiazepinone include ORF 20 (MKD) (SEQ ID NO: 40), ORF 23 (HYDK) (SEQ ID NO: 46), ORF 38 (OXAH) (SEQ ID NO: 78) as well as ORFs 14, 15, 17, 18, 22, 29, 30, 35, 37, 41 and 43 (SEQ ID NOS: 28, 30, 34, 34, 44, 58, 60, 71, 76, 84 and 88, respectively) of unknown function.

Example 6

Farnesyl Dibenzodiazepinone Loci from *Actinomycetes* Species

A. Correlation of Loci A, B and C

Loci related to the biosynthetic locus present in *Micromonospora* sp. strain 046ECO-11 as described in Example 5 (referred to herein as locus A) and directing the biosynthesis of farnesyl diabenodiazepinones related to ECO-04601 were detected in the genome of two actinomycetes using the genome scanning method described in U.S. Ser. No. 10/232,370, CA 2,352,451 and Zazopoulos et. al., *Nature Biotechnol.*, 21,187-190 (2003).

Locus B (052E) was detected in *Micromonospora echinospora challisensis* NRRL 12255. The locus spans approximately 38,000 base pairs of DNA and encodes 33 proteins. Locus C (237C) was detected in *Streptomyces carzinostaticus neocarzinostaticus* ATCC 15944. This locus spans approximately 37,000 base pairs of DNA and encodes 33 proteins. More than 10 kilobases of DNA sequence were analyzed on each side of the two loci and these regions were deemed to contain primary genes.

In order to identify the function of the proteins coded by the genes forming the biosynthetic loci B an C the gene products of their ORFs 1 to 33, were compared, using the BLASTP version 2.2.10 algorithm with the default parameters, to sequences in the National Center for Biotechnology Information (NCBI) nonredundant protein database and the DECIPHER® database of microbial genes, pathways and natural products (Ecopia BioSciences Inc. St.-Laurent, Q C, Canada).

The ORFs encoding proteins present in loci A, B, and C are assigned a putative function and grouped together in families based on sequence similarity to known proteins. To correlate structure and function, the protein families are given a four-letter designation used throughout the description and figures as indicated in Table 8 of Example 5.

Comparison of loci A, B and C clearly indicates that all three loci are related and encode similar enzymatic functions. Therefore, the compounds produced by the enzymes encoded by loci B and C are structurally closely related to ECO-04601. Table 9 correlates the protein families of loci B and C to those of locus A. All 33 ORFs found in locus B have counterparts in locus A. Similarly, all 33 ORFs present in locus C have counterpart proteins in locus A, with the exception of ORFs 30, 31, and 32 that encode a sensory protein kinase protein, a response regulator and a membrane protein. These observations suggest that the compounds produced by loci B and C encoded proteins share a high degree of similarity with ECO-04601.

TABLE 9

Loci A, B and C ORFs function and correlation

| | A | B | C |
|---|---|---|---|
| ABCC | 1 | — | — |
| RECH | 2 | 1 | 1 |
| REGD | 3 | 2 | 2 |
| IDSA | 4 | 3 | 3 |
| MVKA | 5 | 4 | 4 |
| DMDA | 6 | 5 | 5 |
| MVKP | 7 | 6 | 6 |
| IPPI | 8 | 7 | 7 |
| HMGA | 9 | 8 | 8 |
| KASH | 10 | — | 9 |
| IPTN | 11 | 9 | 10 |
| SPKG | 12 | 15 | 12 |
| RREB | 13 | 16 | 11 |
| UNES | 14 | 10 | 33 |
| UNEZ | 15 | 14 | — |
| OXDS | 16 | 13 | — |
| UNFD | 17 | 12 | — |
| UNFA | 18 | 11 | — |
| CSMB | 19 | 17 | 14 |
| AAKD | 20 | 18 | 15 |
| ALDB | 21 | 19 | 16 |
| UNFC | 22 | 20 | 17 |
| HYDK | 23 | 21 | 18 |
| ADSA | 24 | 22 | 19 |
| HOXV | 25 | 23 | 20 |
| SDRA | 26 | 24 | 21 |
| DHBS | 27 | 25 | 22 |
| SDRA | 28 | 26 | 23 |
| UNGA | 29 | 27 | 24 |
| UNFE | 30 | 28 | 25 |
| EFFT | 31 | 29 | 26 |
| HOYH | 32 | 30 | 27 |
| DAHP | 33 | 31 | 28 |
| REGG | 34 | 32 | — |
| UNFJ | 35 | 33 | 13/29 |
| RECI | 36 | — | — |
| UNIQ | 37 | — | — |
| OXAH | 38 | — | — |
| ABCA | 39 | — | — |
| ABCA | 40 | — | — |
| UNIQ | 41 | — | — |
| SPKD | — | — | 30 |
| RREB | — | — | 31 |
| MEBI | — | — | 32 |

FIG. 5 depicts the three biosynthetic loci A, B and C. All ORFs are represented by arrows and their orientation indicate the direction of the transcription of each ORF; highlighted ORFs are involved in the biosynthesis of the farnesyl unit. ORFs 4, 5, 6, 7, 8, 9, and 10 in locus A participate in the synthesis of the farnesyl unit present in the farnesyl dibenzodiazepinone. Counterparts of these ORFs are found in locus B (ORFs 3, 4, 5, 6, 7 and 8) as well as in locus C(ORFs 3, 4, 5, 6, 7, 8 and 9). As shown in FIG. 5, proteins encoded by these ORFs participate in an orderly fashion in the biosynthesis of farnesyl-diphosphate component starting with acetoacetyl-CoA and acetyl-CoA. All enzymes necessary for the synthesis of farnesyl-diphosphate are present in all three loci with the exception of a hydroxymethylglutaryl-CoA synthase (KASH) which is absent from locus B. The product of this enzymatic reaction, 3-hydroxy-3 methylglutaryl-CoA is provided by an alternative biosynthetic pathway of the primary metabolism of the microorganism or by a hydroxymethylglutaryl-CoA synthase located elsewhere in the genome. The described pathway involved in synthesis of farnesyl-diphosphate is entirely consistent with related mevalonate pathways described in other actinomycete species (Takagi et al., *J. Bacteriol.* 182, 4153-4157, (2000) and FIG. 5).

FIG. 6 depicts ORFs 19, 21, 24, 26 and 27 in locus A involved in the biosynthesis of the 3-hydroxy-anthranilate component of the farnesyl dibenzodiazepinone. Counterparts of these ORFs are found in locus B (ORFs 17, 19, 22, 24 and 25) as well as in locus C(ORFs 14, 16, 19, 21 and 22). As shown in FIG. 6, proteins encoded by these ORFs participate in an orderly fashion to the biosynthesis of the 3-hydroxy-anthranilate-adenylate component starting with precursors from the pentose phosphate pathway and chorismic acid. In particular, the enzyme responsible for the adenylation of 3-hydroxy-anthranilic acid (ADSA) that corresponds to ORFs 24, 22 and 19 in loci A, B and C respectively is present in all three loci as well as the remaining enzymes that participate in the biosynthesis of 3-hydroxy-anthranilate component present in dibenzodiazepinones.

FIG. 7 highlights ORFs 16, 24, 25, 32 and 33 in locus A involved in the biosynthesis of the 2-amino-6-hydroxy-[1,4]benzoquinone component of the farnesyl dibenzodiazepinone. Counterparts of these ORFs are found in locus B (ORFs 13, 19, 23, 30 and 31) as well as in locus C(ORFs 16, 20, 27 and 28) with the exception of ORF corresponding to the oxidoreductase (OXDS) present in loci A and B. As shown in FIG. 7, proteins encoded by these ORFs participate in an orderly fashion in the biosynthesis of the 2-amino-6-hydroxy-[1,4]benzoquinone component starting with precursors from the pentose phosphate pathway and 3,4-dideoxy-4-amino-D-arabino-heptulosonic acid 7-phosphate (amino DAHP).

FIG. 8 highlights ORFs 11 (SEQ ID NO: 22) and 24 (SEQ ID NO: 48) in locus A involved in the assembly of all three components, 3-hydroxy-anthranilate, 2-amino-6-hydroxy-[1,4]benzoquinone and farnesyl-diphosphate to form the farnesyl dibenzodiazepinone. Counterparts of these ORFs are found in locus B (ORFs 9 (SEQ ID NO: 90) and 22 (SEQ ID NO: 92)) as well as in locus C(ORFs 10 (SEQ ID NO: 94) and 19 (SEQ ID NO: 96)). The isoprenyltransferase ORF 10 of locus C (SEQ ID NO: 96) is partial and represents the N-terminal part of the protein. IPTN ORFs 11 (SEQ ID NO: 22), 9 (SEQ ID NO: 90) and 10 (SEQ ID NO: 94) in loci A, B and C respectively catalyze the transfer of the farnesyl unit onto the core element of the farnesyl dibenzodiazepinone and related compounds produced by loci B and C. ADSA ORFs 24 (SEQ ID NO: 48), 22 (SEQ ID NO: 92) and 19 (SEQ ID NO: 96) in loci A, B and C respectively catalyze the condensation of 3-hydroxy-anthranilate and 2-amino-6-hydroxy-[1,4]benzoquinone and farnesyl-diphosphate to form the dibenzodiazepinone core element of ECO-04601 and related compounds produced by loci B and C.

B. Clustal™ Alignments

Alignements of isoprenyl transferases (IPTN) and adenylating amide synthetases (ADSA) of loci A, B and C, respectively presented in FIGS. 9 and 10, were generated by the Clustal™ alignment method.

FIG. 9 shows an alignment of ORFs 11 (SEQ ID NO: 22), 9 (SEQ ID NO: 90, which represents the polypeptide deduced from SEQ ID NO:91) and 10 (SEQ ID NO: 94, which represents the polypeptide deduced from SEQ ID NO:95) in loci A, B and C respectively, highlighting the phylogenetic relatedness of these three proteins. The amino acid sequence of all three proteins is extremely conserved as shown by the codes on the fourth line, suggesting that these proteins share a well-conserved and related isoprenyltransferase enzymatic function. The following consensus amino acid sequence (also as SEQ ID NO: 98) that represents all three sequences was generated using the hmmemit algorithm (HMMER, Washington University in St-Louis, School of Medicine, MO, USA, http://hmmer.wustl.edu):

"AaELysviEesARILdvaCsrDrvwpiL-saYGDaFaHpaawAFRvAtalRHvGELD CRFttHPddRD-PYAIALsrGLtPktdHPvGsLLsevqeR-lPvesyGiDFGwGGFKKiYafFtPDe LqevaaLAgiPamPRsLAgnadFFeR-yGlddrvGvlGiDYPartvnvyfndvpaesfesetirstlreiGma epsermIklGekafGlyvtlGwdsseieri-cyaaattdlttlpvpvepeiekfvksvpyGGedrkfvyGvaltpkGey ykleshykwkpGavdfi"

FIG. 10 shows an alignment of ORFs 24 (SEQ ID NO: 48), 22 (SEQ ID NO: 92, which represents the polypeptide deduced from SEQ ID NO: 93) and 19 (SEQ ID NO: 96, which represents the polypeptide deduced from SEQ ID NO: 97) in loci A, B and C respectively, highlighting the phylogenetic relatedness of these three proteins. The amino acid sequence of all three proteins is extremely conserved as shown by the codes on the fourth line, suggesting that these proteins share a well-conserved and related adenylating amide synthetase enzymatic function. The following consensus amino acid sequence (also as SEQ ID NO: 99) that represents all three sequences was generated using the hmmemit algorithm:

"VneprssLPrLGqWhGpEDLr-rLqEKqLaqtvtWAaRsPFYRdRLdsgAlPvtaaDL AdLPLtt-KqDLRDnYPFGmLAvPkERLAtYHEssG-tAGrPtPsYYtAeDWtDLAERFARKWi GmsAeDvFLvRtPYALLLtGHLAHAAgR-LrGAtwPGDnRsLAmPYARwRvmHDLgvtLt WsvPtECLi-WAAAAtAAGHRPdvDFPALRALFvGGE-PltdARRrRisRLWGvPviEEYGstE tGsLAGECPeGRIHLWADRALFEvYDP-dtGtvrAdGdGqLvvtPLfREAmPLLRYnLEDnvs vsYD-DCaCGWkLPtvrvLGRaAFGyRvGat-titqHrLEEIvFsLPeahrvvFWRAkAEPavLRiEi EvaeeHRvMeAELtasvRaaFGvDsevt-GLaPGtLiPreALtsmPDwKPRsLFGPDEDWgK ALLYY"

The amino acid shown for the consensus sequences (SEQ ID NOs: 98 and 99) are the highest probability amino acid at that position according to the HMM (hidden Markov model). Highly conserved residues (those with a probability of >0.5) are shown by capital letters while other residues (lowercase letters) are deduced by the program from the most common amino acid found at the specific position in the aligned proteins (*HMMER User's Guide*, Sean Eddy, October 2003, Washington University of Medicine, MO, USA, p 23-24).

Example 7

Labeled 3-Hydroxyanthranilic Acid Feeding

This experiment was designed to confirm the farnesyl dibenzodiazepinone biosynthetic pathway involves a 3-hydroxyanthranilate intermediate. First, labeled 4,6-dideuterio-3-hydroxyanthranilic acid was prepared. Then the labeled intermediate was fed to the *Micromonospora* sp. strain, the product was purified (see Example 2) and the results were analyzed. The following is an exemplary procedure to accomplish the feeding experiment:

A. Preparation of 4,6-dideuterio-3-hydroxyanthranilic acid

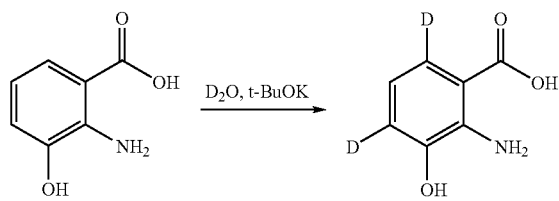

3-Hydroxyanthranilic acid (108 mg, Sigma-Aldrich) was suspended in $D_2O$ (2 mL). Potassium t-butoxide (154 mg) was added to give a brown solution. The solution was stirred at 100° C. under nitrogen for about 6 days. The reaction mixture was cooled to room temperature. The solution was acidified to pH 6 with 10N hydrochloric acid and white solid precipitated. The solid was filtered and dried in vacuo (93 mg). The $^1$H NMR of the isolated product showed about 92-96% reduction of the proton signals (doublets) at the 4 and 6 positions. The $^1$H NMR signal of the unchanged proton (5 position) also reflected the incorporation of the two deuterium; coupling to the 4 and 6 protons was nearly lost (triplet changed to a singlet having two very small side peaks).

B. 4,6-dideuterio-3-hydroxyanthranilic acid feeding

B. 1. Culture Conditions:

To prepare a vegetative culture, *Micromonospora* sp. 046-Eco11 was grown on ISP2 agar (Difco) for 10 to 15 days, and the surface growth from the agar plate was homogenized and transferred to a 125 ml flask containing three glass beads (5 mm diameter), and 25 ml of sterile medium KH composed of 10 g glucose, 20 g potato dextrin, 5 g yeast extract, 5 g NZ-Amine A, and 1 g CaCO3 made up to one liter with tap water and adjusted to pH 7 with 1M NaOH.). This vegetative culture was incubated at 28° C. for about 70 hours on a shaker at 250 rpm with a 1-inch throw.

Following incubation, 18 ml was used to inoculate 2 L baffled flasks each containing 600 ml of sterile HI production medium consisting of 20 g potato dextrin, 30 g glycerol, 2.5 g Bacto-peptone, 8.34 g yeast extract, and 3 g CaCO3 made to one liter with distilled water and adjusted at pH 7.0 with 1M NaOH. The culture was incubated at 28° C. for about 96 hours on a shaker at 250 rpm with 1-inch throw.

B.2. Feeding Experiment:

Vegetative cultures of *Micromonospora* sp. 046-Eco11 prepared in medium KH as explained above were used to inoculate HI medium (four 125-mL flasks containing 25 mL). The medium was fed with 4,6-$D_2$-3-hydroxyanthranilic acid at 0.5 mg/mL before inoculation with the vegetative culture at 2% level. Control cultures without adding the labeled compound were prepared for each medium in the same way mentioned above. Effect of adding 4,6-$D_2$-3-hydroxyanthranilic acid on the production titre and growth was measured by adding the unlabeled compound to each medium in the same fashion explained above. The purified compound obtained from each experiment was tested by $^1$H-NMR for incorporation ratio of the labeled substrate.

C. Results

The purified farnesyl dibenzodiazepinone from the feeding experiment was analyzed both by $^1$H NMR and mass spectrum. The $^1$H NMR (in DMSO-$d_6$) was compared to the unlabelled standard. About 31% reduction in the intensity of the signals at 6.82 and 7.06 ppm in DMSO-$d_6$ (correspond to protons signals at 6.83 and 7.14 ppm in MeOH-$d_4$) was observed, which reflected a 31% incorporation of the deuterium at these positions. Mass spectral analysis gave about 47% incorporation of the deuterium labeled precursor.

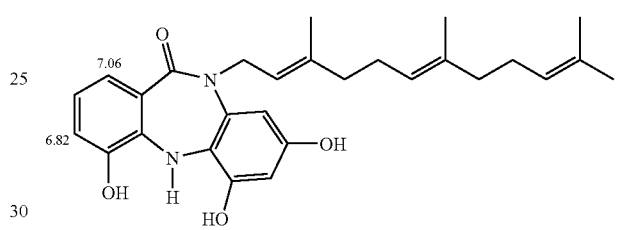

The result indicated a direct incorporation of 3-hydroxyanthranilate as a precursor in the biosynthesis of ECO-04601.

Example 8

Methods of Using the Deposited Cosmids

Two deposits of *E. coli* DH10B vectors (046KM and 046KQ), having deposit accession numbers IDAC 250203-06 and IDAC 250203-07 respectively, each contain a cosmid clone and together span the whole biosynthetic locus of ECO-04601. The coverage of the locus by each deposited cosmid is described in Example 5 and shown on FIG. 4.

Culture conditions to be employed for growing the deposited cosmid-containing DH10B™ *E. coli* are understood by a person of skill in the art (Sambrook et al. (1989) Molecular Cloning: A Laboratory Manual, $2^{nd}$ ed., *Cold Spring Harbor Laboratory Press*). As a non-limiting example, upon receiving a sample of the deposited strain, either as a frozen glycerol stock or as an agar stab or in a liquid media, a small aliquot of the strain is gathered using a sterile metal loop and thereafter streaked onto a selective media agar on freshly prepared growth plates (e.g. disposable plastic Petri® plates). The aliquot is streaked so that single bacterial colonies can be isolated. A number of different growth media can be used, provided that the media contain an appropriate amount of a selective agent, for example an antibiotic. Standard growth media are known in the art, such as standard Luria Bertani (LB) media (10 grams of NaCl, 10 grams of tryptone, 5 grams of yeast extract, 20 grams of agar, with pH adjusted to 7.0 with 5.0 N NaOH add deionized water to a final volume of 1.0 liters, autoclaved then cooled to 55° C. followed by addition of 10 mL of 10-mg/mL filter-sterilized ampicilin or 5 ml of 10-mg/mL filter-sterilized kanamycin). Plates with streaked bacteria are incubated overnight (approximately 16 hours) at 37° C. to allow for growth of the bacterial colonies.

Cosmid DNA containing insert DNA are prepared from the above-noted strains by methods that are known in the art. As a non-limiting example, a single bacterial colony is selected from an agar plate (as referred to above) and re-streaked onto a fresh agar plate, containing the appropriate selective agent as noted above, and allowed to grow overnight at 37° C. From this second agar plate, a single bacterial colony is selected and inoculated into 2.0 to 5.0 ml of liquid broth containing the appropriate amount of a selective agent, for example LB broth (prepared as per LB media, but lacking agar) containing ampicillin or kanamycin in a concentration as noted in the preceding paragraph, in order to generate a liquid starter culture of the single bacterial colony. This starter culture is grown to late logarithmic stage (approximately 8 hours), at which time an aliquot of the starter culture is withdrawn and diluted, by a factor of 500 to 1000, into a volume of broth containing the selective agent and grown with vigorous shaking (approximately 300 revolutions per minute) to late logarithmic/stationary phase (approximately 10 to 12 hours) to achieve a cell density of approximately 3 to $4 \times 10^9$ cells per ml. Cell density is estimated by taking an aliquot of the liquid culture and obtaining an $OD_{600}$ reading using a spectrophotometer, or by centrifuging the liquid culture and thereafter measuring the weight of the resulting bacterial pellet. Typically, 1.0 liter volume of an liquid culture of *E. coli* that is grown overnight at 37° C., 300 rpm with a cell density of approximately 3 to $4 \times 10^9$ cells per ml will correspond to a pellet weight of approximately 3 g/l. Depending on the desired amount of insert-bearing cosmid DNA that is required, a person skilled in the art would understand that either a liquid "mini-culture" of 2.0 to 5.0 ml or a liquid "maxi-culture" of 500 ml may be required to be grown to result in the desired amount of cosmid DNA to be isolated.

Cosmid DNA, bearing the insert DNA of interest, is isolated from the bacteria grown in liquid cultures, as described in the preceding paragraph, using procedures that are known in the art. Non-limiting examples include the use of commercially available kits, for example the QIAGEN® Large-Construct Kit (QIAGEN Inc., Catalogue No. 12462) or Perfectprep® BAC 96 Kit (catalogue order number 955150431) available from Eppendorf North America (Westbury, N.Y.). Alternatively, the insert-bearing cosmid DNA is isolated by following procedures detailed for a traditional alkaline lysis method as described in Birnboim and Doly (1979) *Nucleic Acids Research* 7(6): 1513-1523, or in a cosmid-specific manual (e.g. the SuperCos™ 1 Cosmid Vector Kit Instruction Manual published online at www.stratagene.com). As an example of an alkaline lysis procedure, insert-bearing cosmid-containing bacterial cells from a 5.0 ml culture are collected by centrifugation (using an appropriate, sterile centrifuge tube) for 2 minutes followed by aspiration of the supernatant and resuspension of the pellet by vortexing in 200 µl of an ice cold solution of 50 mM glucose, 10 mM EDTA, 25 Mm Tris-HCl (pH 8.0). Following resuspension of the bacteria, 400 µl of a freshly prepared solution of 0.2 N NaOH, 1% SDS is added and the contents gently mixed by inversion (vortexing must be avoided), followed by incubation on ice for 5 minutes. Following incubation on ice, 300 µl of ice-cold potassium acetate (approximate pH 4.8) is added, and the tube gently inverted twice and incubated on ice for a further 5 minutes. The tube is then centrifuged for 5 minutes at 4° C. and 500 µl of the supernatant is transferred to a fresh (sterile) tube. The transferred supernatant is deproteinated by extraction with phenol-chloroform, keeping the upper phase to which is then added 1.0 ml of ethanol. The tube is left standing at room temperature for 5 minutes, and thereafter microfuged for 30 minutes, followed by aspiration of the liquid from the tube. The remaining DNA pellet is washed in 70% ethanol, centrifuged (in a microfuge), and after aspiration of the liquid and drying (avoiding complete dryness) of the pellet, the DNA is resuspended in 50 µl of Tris-EDTA (TE). DNA concentration is estimated by taking an $OD_{600}$ reading on a 1/100 diluted aliquot of the purified insert-bearing cosmid DNA. The insert-bearing cosmid DNA is thereafter used in any number of downstream applications that would be appreciated by a person skilled in the art.

Segments or regions of the insert DNA can be generated by performing a restriction digestion on the insert-bearing cosmid DNA using protocols that are known to those of skill in the art. The segments or regions of the insert DNA may be of interest to the person of skill in the art as the particular nucleotide may be that for a gene(s) that is to be manipulated for a downstream application. As well, the segments or regions of the insert DNA may be of interest to the person of skill in the art as the particular nucleotide may be that for an entire biosynthetic locus, or a portion thereof, that encodes for the production of a natural product. It is possible that the nucleotide sequence of the insert DNA encodes one or more modules, which may be comprised of one or more domains, of a nonribosomal peptide synthetase or a polyketide synthase locus encodes for the production of a bioactive natural product.

As an example that is not intended to be limiting, if the sequence of the insert DNA is known, the presence of particular restriction enzyme sites within the insert DNA are determined and the region (i.e. the fragment) of DNA situated between two restriction enzyme sites cut or digested from the cosmid DNA. Generally, it is preferred in the art to use a restriction enzyme that recognizes a six base pair (bp) DNA recognition sequence as opposed to a four base pair recognition site, as there will be fewer restriction sites in a given stretch of DNA for six bp restriction enzyme, thereby offering less chance of digesting the cosmid (i.e. the vector) DNA per se. Selection of a given restriction enzyme may also be dependent upon whether the ends of the generated DNA fragment are to be blunt or are to possess overhangs so as to facilitate sub-cloning of the DNA fragment. Restriction digestion conditions are known to those skilled in the art. While not intending to be limiting, a digestion is usually performed using a minimum of 0.2 µg of DNA. If the DNA fragment to be generated is to be used as a probe, for example in Southern blotting, then an amount of DNA of at least 10 µg will be required for digestion. A restriction digestion can usually be performed in a range of reaction volume between 10 µl to 50 µl, using a requisite number of units of the given restriction endonuclease plus the particular buffer for the restriction enzyme and a necessary amount of sterile water to give the desired reaction volume. One unit of a restriction endonuclease will digest 1 µg of DNA in one hour, and it is common to use a ten-fold excess of the restriction enzyme to ensure complete digestion, provided that the volume of the restriction enzyme used does not exceed 10% of the final reaction volume. Upon addition of the restriction enzyme as the last component of the reaction mixture, the tube containing the mixture should be gently flicked with a finger to ensure proper mixing of the tube contents, followed by a brief centrifugation and incubation of the tube at 37° C., or at an elevated temperature 50-65° C. if the restriction enzyme is one isolated from a thermophilic bacteria, for a time span ranging from one to four hours. The reaction time may be extended beyond for greater lengths of time if it is desired. Reaction and deproteination may be accomplished by heat inactivating the restriction enzyme followed by phenol-chloroform extraction of the reaction (as described above), or by using a commercially available kit such as the MinElute® Reaction Cleanup Kit from QIAGEN.

Downstream uses of the insert DNA are discussed in Section VII above and include: Labeling and use of the fragments as probes to detect the presence of the given gene or the expression of the given gene in a different organism; Use of the fragment in hybridization experiments; PCR amplification of the insert DNA or regions of interest of the insert DNA; Mutagenesis of the particular DNA segment of interest in order to produce substitutions, additions, deletions, fusions or truncations in the expressed polypeptide, which can be accomplished by random chemical mutagenesis, site directed mutagenesis, error-prone PCR, exonuclease II deletion, oligonucleotide mutagenesis for PCR; Generation of variant forms of the peptide of interest with conservative vs. non-conservative changes in the amino acid sequence to result in the production of novel end-product compounds; Cloning and use of the DNA sequence of interest in a heterologous expression system (yeast, mammalian, insect, plant expression vectors) for the production of the peptide of interest, and the creation of tagged (e.g. His, c-myc, Ni-tagged, etc.) fusion proteins; Use of the peptide that is produced to raise polyclonal or monoclonal antibodies (via the production of hybridomas).

Antibodies (Ab's) are also used as probes to isolate interacting proteins—Ab's are generated against the peptides resulting from the heterologous expression of the DNA sequence of interest. Proteins that may potentially interact with that encoded by the DNA sequence of interest may also be identified by yeast two-hybird screening as described in U.S. Pat. No. 5,283,173.

All patents, patent applications, and published references cited herein are hereby incorporated by reference in their entirety. While this invention has been particularly shown and described with references to preferred embodiments thereof, it will be understood by those skilled in the art that various changes in form and details may be made therein Without departing from the scope of the invention encompassed by the appended claims.

We claim:

1. An isolated polypeptide selected from the group consisting of:
   a) a polypeptide comprising amino acids 1-438 of SEQ ID NO: 48:
   b) a polypeptide having at least 95% identity to a polypeptide comprising amino acids 1-438 of SEQ ID NO: 48 and having adenylating amide synthetase activity; and
   c) a polypeptide encoded by a polynucleotide, the complement of which hybridizes under stringent hybridization conditions to a polynucleotide encoding a polypeptide comprising amino acids 1-438 of SEQ ID NO: 48, wherein said stringent hybridization conditions comprise: (i) hybridization in 5×SCC at 65° C. for 16 hours, (ii) two washes in 2×SSC at room temperature for 15 minutes for each wash, and (iii) two washes in 0.5×SSC at 65° C. for 20 minutes for each wash.

2. The isolated polypeptide of claim 1, wherein said polypeptide comprises amino acids 1-438 of SEQ ID NO: 48.

3. The isolated polypeptide of claim 1, wherein said polypeptide consist of amino acids 1-438 of SEQ ID NO: 48.

4. The isolated polypeptide of claim 1, wherein said polypeptide b) has at least 99% identity to a polypeptide comprising amino acids 1-438 of SEQ ID NO: 48.

* * * * *

SEQUENCE LISTING

<160> NUMBER OF SEQ ID NOS: 99

<210> SEQ ID NO 1
<211> LENGTH: 36602
<212> TYPE: DNA
<213> ORGANISM: Micromonospora sp. strain 046-ECO11

<400> SEQUENCE: 1

```
ccggtgcacc gggttctcca ggatcgccgt cgcgcccacc ggccccgaca ggtagacgac      60
gttcagggac ttgccgcgcc cttcgtagtt ggcccgcacc acctgcgcgt cgccgatccg     120
gccgctggtc tccagcgtgc ggttctccca cacctgccat ccgacgaagg tcaggaacag    180
cgcggtgaac agggacgtga cgagcagcca gaggccagct gtcagcacgg tcgcccctc     240 gccccgtagc aggccgagga cgacctcctc gtagcgcgag gggcggccga cggggccggt    300
gcccgctccg tcgacagcca tcccgccgct ccttcgccga ctgccccgga catccacggt    360
agccagcgag tccagtccgg tgaggaaggg gtggcgagaa gtcgatatga ctgagaggca    420
tatttatgac tcccagtcat atcgctcgga agtgaccgaa cgacctgacg ccgccgggc     480 tgtgagcggc agcgtgggcc aggccgcgag gtcctggagc atctgccggt cgtgggtggc    540
gacgaccacc gccgcccggg tcgtcagcag ggcggcggtg aggtcgtcga ccagcggcgc    600
cgacaggtgg ttcgtcggtt cgtcgaggat cagcaggtcg ggacgttcgg ccaggcgcag    660
cgccaggttc agccgccgtt gctgtccgtg cgacatccgg ccgacggggg tacgccgggc    720
ctcggcgtcg agcaggttcg tcgcgctcag cggcagggcc gtgccggagc cgacgcgccc    780
gctggagcgg agccggccca cgtgctgctc gtacaggtcg tgcgcgagca gcgccggcgg    840
ccagtcgggc acctcctgac cgaggtacgc gacgcgcgcg ccggacaggt gccggacctc    900
cccggtcgac ggcgtgaggt cgccggccag cacggagagc agcgtcgact tgcccgcgcc    960
gttgggtccg gtcaccagca ggcggtcccc gccgtcgagc gtgagcgtga cccgggtacg   1020
caggcgcccg gccaccgtga cgtcgtggca tcgcaggatg ggcagtccgg cacgggtgtc   1080
cagcggcggc cagcgcagcg gctgcggtgg ctccggcacg gtgacgcggt gcgcgtcgag   1140
```

-continued

```
cgcctcctgc cggcggcgca gcgcctggac cagtccgggc gcgcgggact ggcgctggtg    1200
cttgccgtgc cccttctccg gccgccagcc ggtgctgagc cggtcccgcg cctcccgtac    1260
cccgtcggca agccgctggt gctcggcctg ctgcgcctcg tggtcgcgta cccagtgcgc    1320
gaagtcgcgg cggcgcccgt cctgccaggc gacgtagtcc ccggcgtagc ggcgcgggcg    1380
cccgtccgcg ctggggtcga ggtccaggaa ctccgtggcg acgtcccgca gcagggcgcg    1440
gtcgtgggtc accagcacga cgccgcccgg gtggtcgcgt agccgggcgg tgaggaaggc    1500
caggctgtcg gcgtcgaggt ggttcgtcgg ctcgtccagc atcagcaggt cgaccctcgc    1560
tcccagcagg cacgccagcc gtacccggta gcgctggccg acggacaacg tggccagctg    1620
ccggtccccgg tccgggcacg cgtcgaggcc ggccagcgcc acgtcgacgc gccgctgcgc    1680
gtcccaggcg tccagccggg tcgccgcgtc gagcgcggcc gcgtacgcgt cgtccgcgcc    1740
cgccccgccc tcggtgagcg cgatcgtcgc ctcgtcgagc gcccgcagcg cgcgttcgga    1800
ctcccggatc gcctcccgga cgagcgtgcc cactgtctcg ccgtggcgcg actccaggtt    1860
ctgccgggcg acgccgatcg tgcccagccg ttccaccacg ccctggtcgg gcgcgatgag    1920
gccggccagc acgtgcagca gggtggtctt gccgcggccg ttctcgccga cgactgcgag    1980
gcgggaagcg gcggagacgg tcacgctgac gtcggacagc acgacccggc cgccgcgtac    2040
gacgcggacg ccgtcggccc gcacgtgcgc ccggtgcccg gcgggcagcg aaccgcccga    2100
ggtggatggg gaggaaggaa tgttgtcgag gttgtgcaca gtccgctctt cggctcgtcg    2160
tggagccggg cagcgcgagg acaccgcccg gcgggaacgc cgggacggcg gagcagagct    2220
ggtacgtcag aagaagccgg tcaccctgcc gccgtcagcg gagggaccag ggcttcatga    2280
cagcggcgta gaacctcatg cggtcaacac tacccggggc cgggccggag atcgccgcag    2340
ttatcggcgg cggcgggcgt cggcctcggc gtcgagcagg tcgttcaccg ccagcgccga    2400
gttgatcaga gcgaggtggc tgaacgcctg cggatccacg gttgcggtac tccatttgca    2460
gtacacctgt cggtatccgg tcagcgccgt atcctgcgct ttctctgtcg gcagagcggc    2520
gcggtcgccc gccgcccgcc gacgtggctg cggggccggt cgggctcgga ccgctcggtg    2580
cggcgtcgcg gcccggccgt agcatgtttc acctgttcag agcggcttcc gggcgctcgg    2640
gccgtcggcc gcgtggggtta ccggcgaggg ctatttcggt catgcgagag ggttctgcca    2700
atcgtggcat tgtttagtta agtccgatat cagcgggatg ctgcctgata tatgacggct    2760
gcgcccgggc ctgccggata gctatgatga gcgacgacgg tgatcgatgg caaatgttgt    2820
tgctgtgggg tagcgtcacc gccgagtcca ggcttttctt gagctgtgtg cgcatattcc    2880
ggggggatta tgacaacggg acggccgggg gagaaccggg cgacagacgc ggcacgaaat    2940
ccggggtggg ccgccggggg gccggcgtcc cagccatggg gcggggggaa cgacgagcag    3000
gtcctgcgcg agatcctcgg ggtcgacgtg caccgcgagc tgattgactt cgcgggtggt    3060
gccggcggaa atccgcacct ggtcgccgaa ctcgcgcgcg ggctcgccga agagggattg    3120
attcgggaga caaacggtcg ggcggaattg tgtcccggc gaattccccg gcgcgtgctg    3180
agttttgtca tgcgtcgatt gaatgatgtc agcgccggct gccagcagtt cttgaaggtt    3240
gccgcggcat tggcagatc cttcatgctg gaggacgttt cgagaatgct gggccgatcg    3300
tcggcggccc tgctcccgcc ggtggacgag gcgatcgcat cgggcttcgt cgtcgccgcc    3360
gagcatcaac tcgcctttca gagcgacttc ctgctgcgcg gcatcatcga gtccattccc    3420
gggcccgccc gcgacgcctt acgacgtgag gcgatgagcc tttccgggcg acggcgcccg    3480
```

```
gcggccgacc agaatcgccg gttggacgcg gcgcctaccg cgccggtgag cgcgaccggg    3540
gaggacgcca ccggatcctg ttcccgggcg caccgcctga taatgaacgg gaacgcgaag    3600
gccggcattc gcgtcgccga ggcggttctc gccggcccgg ccgcgtcgct cgctgcccgg    3660
cgtgacgcgg aggcgtgtct ggtgctggcc gatctgctgc tcggcgggga gggcggcggc    3720
ccgatgaccg aggcgatcct gcgcgaacgc gacgccgagt ccggtgacgc cgcactggcg    3780
atggcgctga ccgcccggtc caccgggctg tggtcggcgg gaaagctggc ggagggcctg    3840
aagctgggac gggcggcggt gcgggcgggc gcggaggccg aaccggtgtg gcgtctgcac    3900
gcccagctcg cgctcgccgg gaaactcgcg aacctccgcg agttcgacga ggccgaggcg    3960
ttgatcaacg aggcggaagc gggcctgcgc ggactgcccg cgccgatctg gacggccgcg    4020
acggcggtga tgcggtcccg gttgctgctc caggcgggc ggatcgggga ggcgcgtcgg    4080
gaggcggcgc tggccaccac cgccgtggag ggggacgcgg tgccgatgct gcggcctctc    4140
gcctacgcgg tgctcagcac cgcctccttc tacatggggg acctgcccgc cgcgatcgag    4200
tacctcaggc gggggcagcg ggacgcggac cgccacgtgg tcctcgactc ggtgcagtac    4260
tcgtgggcgg aagtgctgat cacggtcaag caggaaggcc cgcggccgc cgcccagctg    4320
ctcgcgggca agcaccaccg cctgcccacg cagcgccgcc tctacgtcga ggtgccgagc    4380
gccgccgcct tcctggtcct gctcgcccgc gacgtggacg accgtgacct cgaacgccgc    4440
gtcctcgaca cggtcaacgg gctcgccgcg gacaacccca ggatccaggt cgtcagcctc    4500
accgccatgc acgcccacgc gctggcgaac agcgctccgg ccgccctggc gctcatcatc    4560
gtgcagtcac gggacccgat ctcggtggcg ctggccaccg aggaactcgc caagctctac    4620
gccgcgcagg cccaggcggg gggacggccg gcgacgccgg cccgcgccga ggaggccgcc    4680
accccgccgg cgagctgctg gtcgaccctg tccgacatgg agcagcggat cgcctacctg    4740
gtgagcgtgg gtctgacgaa ccggcagatc gccaagcagg tccacctgtc cgcgcacacc    4800
gtcaactacc acctgcggaa gatctaccgg aaactgggtt tcaacacccg ggccgagctg    4860
gcgcacgccg cggccacgta ctccggccgg cggcgatct actccatgag cggcgaccag    4920
gactggggcg ccggatccat gaccggcaag gccagctgaa ccgcattccc ggcgtccgcc    4980
ggctgaaccg cgcccggcg tacgccggcc ggttcagccg gcggacgccg gctggcgtgt    5040
ggtggccagc gccggccgga ccgcctcgtg cgcgatgaag cagcgggtca gttccacccg    5100
gctgttgatg tcgagcttgg agaagacgcg ccgcaggtga ctgtcgacgg tgtgcgggga    5160
caggaacagc gaactcgccg cctcgcggtt ggtcatcccg tccacgatgg cccgcacgac    5220
ccgcagctcc gcgctggtca ggctctccca ccccgaccgg ggccggtcgg ggaccagcgg    5280
gcggacgttg tgagccggca ggccacgcag ctcggcctcc acgcgctcca ggtcgcgtcg    5340
cgcgccgcac tcccggtagc cgtccgtcgc ggcctcgagc agacgggtgg cctcggcccg    5400
gtcccgggtg ctgcgggccg cgtcctccac cgcgccggcc gccgcgagcg tacgccggc    5460
gagccggtgc agatccgcgg cccgcagcag cgccgccgga tcgtcgcgca ggagacccgc    5520
ggcgtgttcc gccgccgccg ccagcgactg gacgaacggg ttgccgcggg cgacgcgccg    5580
ggcgacctcc acggcgcgct cggcctccgc gtcgagcccc gccggcgggg cctggcgtac    5640
gagcgtcgcc gcagcggccg gcgcctcggt gaacagcagc ggatcgggtg cgacctgtcc    5700
ggcgacgttg atcagcgtct gcaccatcat cgccggacgg ccgctggcag cgtggaaccg    5760
ggccagcgcc cagtccatcc gcgccgagtc gtcggcggag ccagccgct cggccgcccg    5820
caactggtcg ctggccgtgg cgaggtcacc gtggtgcacg ccgaggtggg ccaggaccag    5880
```

```
gcgcgccggc acgcagtcgc ccggccggga gtggtcggcg gctcgcagcg ccgcctccgc    5940
ctcggcgcgt gcctcgtcca gccgtccggc cgctgccagc agctcggccc ggtggccgcg    6000
ccagagcgac tccgagccgg tgtgactggg ctcctgcgcc agcggtcgta cggtgtccag    6060
caccgcctgc gcctcgtcga gctgatcggc cgcgcccagc gcccggacca gccaggtcca    6120
cagcggccgc cggccgggcg cgcagcccgg ggactggtgc cggggctcca gctcggcgga    6180
ggaggcaccg cccaggtgct cgtggtgtc cgcgagcgcc cggtccagct ggcgcggtc     6240
cagctcgcac acgtcgtggc gggcctgcgt ccggcgcagg aagccggccg ccaggcggtg    6300
gctgccggcg gcccgcatcc cgtgtcccag ttcgagcacg agctgcgcct cgacgtccgc    6360
cgcgaggtcg cggcggagca tcacctccgc gaggcggccg gcctcggcgg cccgccccgc    6420
cccggccagc aggcgcagcg cacgggccag tgctcgtggc gcctcggcgg atccgttctc    6480
caggtgggac acgcggctg ccgccacgtc gtcgcacccg caccggcccg agcgcggccc    6540
cgccgtcgcg gcgggcgtgg ccgcgtccgg cgcggagcgc gtgacgcgta cgccggcggg    6600
ggagtggggc gtcccgggcc gcggatcggg ccgcccgcgc cggaccgggt cgcccgccgc    6660
cggtgccggc gcggatccgg gctcggcacg ctccggttcc gggtacgcgg cgtggcgaag    6720
cgcctctccg agcaccgggt gggcgaaggt cagctccgcg ccgtcgcgtc gtatcagccc    6780
gacccgcacc gcctcgtcga tcgcggcgga cacgtcggcg gccgagccgt ccagcaggcc    6840
cgtcacccgg tcgacgggaa acgtgtggcc gagccggccg ccggccgcga gcaggcgccg    6900
cagcggggc ggcagctcct ccagcagccc gcgaacggcg gcgaggacac cgtcgggcag    6960
ctcgtcggac accaccgacg ccgccccgtc cacgatgatc atctggccgg ccttgatgaa    7020
cgcgctgaag acgatctcca tcaccttcgg gttgccgccg cagcgggccg cccagcgcag    7080
gacggaggcg tccggccggg cgccgaggat gccggcgcac aggtcggcca ccgcctcctc    7140
gcccggctcg cgcagccgta cccgtaccgc gacgtgctcg ccagccagt cgacggcgtg    7200
ctgagcgatc gacccggcgg cgaccggccg gcgggccagc agccagagca ccggcgagga    7260
cgccaggcgc ggcacgagcc cgcgcagggc cagggcgctg acgtcgtcga tgcgctgggc    7320
gtcgtccagg gcgaccacga gcgggcgccg gcgcgccgcg acctcgacca gatcgccgac    7380
ccgtcgatc agccagaacg ggttggcgcc cggcagggcg agctgctcga ccgccgcttc    7440
gccgggcatc gcgtggcgca ggaagttgac gagcaggtgt acgggcaccg gctgatccgt    7500
gacgcttgcc cgcccggcca ccactgtcag cccgcgggcc gccgcctcca ggccggtgac    7560
cttcagcagg tgggtcttgc cgatgccgaa cggcccgtcg acgacgacgc agcccccgga    7620
tccccgcatg gtggcgtcga gcagttcccc caatgaggac aattcctgcc cgcgcccccgc   7680
catgcgattc atgatgacca tcccgttttc ctctgctgaa tcgtccgacg tgcgccgcga    7740
gccgatgtcc caccgcgttc gaccgtccgt tctggacagt gaacgccgg atcggggcgg    7800
gctactcagt tatacgggat ctgcggccgt tcgtcggcga cgtcgctggc agcgcgcact    7860
actcgcgtga gtagtgggca gggtgtcagg ccgcgattac tgtcaggcca tgccgggctc    7920
ggcgtgccgg cgcggacgaa atggcgacgc cgatgggag atcggcgtcg tttccgcgcc    7980
ggcgcaaaac gtcggaacg gaatcgacta atcgccgctc gacgcgactg gtccagcgaa    8040
tccaggggag tccgagatgc gtgagtgtaa tggtgaccgc cgtcttgatc gggagacgcg    8100
ggcatgaccg tcggatatct cgggacggtc accgactcgg cgcccgtcga cgccgcgctg    8160
cgcgacttct tcgccgagcg ccgcgccgag gcacgcgagc tcggcgacga cttcgcggcc    8220
```

```
ctggtcgccg agctggagag ctacgtcctg cggggcggca agcgcatccg gcccgccttc   8280
gcctggctgg gctggatcgg cgccggcggc gacccggagg acccggtggc gaccgcggtg   8340
ctgaacgcct gcgccgggtt cgagctgctg cacgcgtccg gcctcatcca cgacgacatc   8400
atcgacgcgt cgcagacccg ccgcggccat cccgccgcgc acgtcgcgta cgccgaacgg   8460
catcgggcgc ggcgcttctc cggtgacccg ggaacgttcg gcaccggcac cgccatcctg   8520
atcggagacc tcgtcctgat ctgggccgac gtcctggtcc gcgcctccgg cctgccggcc   8580
gacgcgcacg tgcgggtctc gccggtgtgg tcggcggtgc gctccgaggt catgtacggc   8640
cagctgctcg atctgatcag ccaggtgagc cggagcgagg acgtcgacgc ggcgctgcgc   8700
atcaaccagt acaagaccgc gtcgtacacg gtggagcggc cactgcagtt cggcgcggcg   8760
atcgccggcg cggacgacga cctcttcgcg gcctaccgcg ccttcggcgc cgacgtgggt   8820
attgccttcc agctgcgcga cgacctgctc ggcgtgttcg gcgacccggt ggtgacgggc   8880
aagccgtccg gcgacgacct gcgggagggc aagcggacgg tcctgctcgc cacggcgctc   8940
aagcgcgccg acgaacggga cccggacgcg gcggcctacc tgcgggcgaa ggtcggcacg   9000
gacctcgcgg acgaggagat cgcccgcatc cgcgccatct ccgcgacgt cggcgcggtc   9060
gaggagatcg agcggcagat ctcgcagcgc accgaccggg cgctggccgc gctggaggcg   9120
agcagcgcca ccgcccccgc gaagcatcag ctcgccgaca tggcgatcaa ggccacccag   9180
cgggcccagt gatgtccacg gaaccggtga ccgtcgtcgc ccgcggcgtt ctcgacggcc   9240
ggggtgacgg gccgggccgc ctcggcaccg gccgcgccca cggcaaggcc atcctgctgg   9300
gcgaacacgc cgtcgtgtac ggcgctccgg cgctcgccgt cccggtgccg caactgaccg   9360
ccgtggccaa ggcgcggcgg gccggcggcg acggcggcga cgaggtctcc ttcgccatcg   9420
ccgggctgga gagcccggag gtgacgtcgc ttccgaccga cggcctgcaa catctggtga   9480
cggagttccg gcagcgggcc gccgtcaccg agccgatgcg cgtcgacgtg ctcgtggact   9540
gcgccatccc gcagggccgg gggctcgggt cgagcgccgc ctgcgcccgc gccgcggtgc   9600
tggccctcgc ggacgcgttc gaccgccgcc tcgacgccgc cacggtgttc gatctggtgc   9660
agacctcgga gaacgtggcg cacggccggg ccagcggcat cgacgccctg ccaccggtg   9720
cgaccgcgcc gctgatcttc cgcaacggcg tgggccggga actgccggtc gccatggcgg   9780
gcgccgcgcg tgccgcgcga gggtcgggcc cggccggctt cgacgcggtg ctcgtcatcg   9840
ccgacagcgg cgtcagcggc agcacccggg acgcggtgga gctgctgcgg ggtgccttcg   9900
agcgctcccc gcgcacgcgc gacgagttcg tcagccgggt gaccagcctg accgaggcgg   9960
cggcgcacga cctgctccag ggccgggtcg ccgacttcgg cgcgcggctg accgagaacc  10020
accggctgtt gcgcgaggtc ggcatcagca ccgaacggat cgaccggatg gtcgacgccg  10080
cgctcgcggc gggcagcccg ggcgccaaga tcagcggcgg tggcctgggc ggctgcatga  10140
tcgcactggc ccgggaccgc caggaatccg gcggtggt gcggagcgtc cagcaggccg  10200
gcgccgtccg cacctggacc gtcccgatgg ggaggttcac cggccatgac gactgaccac  10260
cggcggagc cgtccgagcc ggcgctcgac cggcccgcga ccgccgtggc ccatccgaac  10320
atcgcgctga tcaagtactg gggcaagcgc gacgagcagc tgatgatccc gtacgccgac  10380
agcctgtcga tgacgctcga cgtcttcccg accaccacca ccgtccggat cgacagcggc  10440
gcggcggccg acgaggtcgt cctcgacggc tcgcccgccg acggcgaacg gcgacagcgc  10500
gtcgtcacct tcctggacct ggtacgcaag ctggccgggc gcacggaacg ggcctgcgtc  10560
gacacccgca actccgtgcc caccggcgcc ggcctggcgt cctcggcgag cggattcgcc  10620
```

-continued

```
gccctcgccc tcgccggcgc cgccgcgtac ggcctcgacc tggacaccac cgcgctgtcc    10680
cgcctggccc ggcggggatc cgtgtcggcc tcccggtcgg tcttcggcgg cttcgcgatg    10740
tgccacgcag gccccggcgc cgggaccgcc gcggacctcg gctcctacgc cgagccggtg    10800
cccgtcgcgc ccctcgacgt cgcgctggtg atcgcgatcg tcgacgccgg gccgaaggcg    10860
gtgtcgagcc gcgaggggat gcggcgaacc gtccggacct ccccgctcta tcagtcgtgg    10920
gtcgcctccg gccgcgccga cctggccgag atgcgggccg cgctgctcca gggagacctg    10980
gacgcggtcg gcgagatcgc cgaacgcaac gccctcggca tgcacgccac catgctggcc    11040
gcccggccgg cggtgcgcta cctggcgccg gtcactgtcg ccgtgctcga cagcgtgctg    11100
cgcctgcgcg ccgacggcgt ctccgcctac gccacgatgg acgcgggacc gaacgtcaag    11160
gtgctctgcc gccgcgcgga cgccgaccgg gtcgccgaca ccctgcgcga cgccgcgccg    11220
agctgcgccg tggtcgtcgc cggaccgggg ccggcggccc ggccgacccc gggcagccgg    11280
ccgtgaccgg cccgggcgcc gtgcgccgcc acgcgccggg caagctgttc gtcgccggtg    11340
agtacgcggt gctggagccg ggccaccccg cgctgctggt ggcggtcgac aggggagtgg    11400
acgtcaccgt ctccggcgcc gacgcccacc tcgttgtcga ctccgacctc tgcccggagc    11460
aggcgtgcct gcggtggcag gacggccggc tcgtcggcgc gggcgacggg cagccggcgc    11520
ccgacgccct cggcgccgtg gtctcggcga tcgaggtggt cggcgaactc ctgaccggac    11580
gagggctgcg cccgctgccc atgcgggtgg cgatcaccag ccggctgcac cgcgacggca    11640
cgaagttcgg cctcggtcg agcggggcgg tgacagtcgc cacggtgacc gcagtggccg    11700
cgtaccacgg ggtggagctg tcgctcgaat cgcggttccg gctggcgatg ctggcgacgg    11760
tgcgtgacgg cgccgacgcc tccggcggtg atctggccgc gagcgtctgg ggcggctgga    11820
tcgcctacca ggcgcccgac cgcgcggccg tgcgcgagat ggcgcggcgg cgcggcgtcg    11880
aggagacgat gcgcgcgccc tggccgggcc tgcgggtccg gcggctgcca ccaccgcgtg    11940
gcctcgcgct ggaggtgggc tggaccggcg agccggcgag cagcagctcg ttgaccgggc    12000
ggctggccgc ctcccggtgg cggggcagcc cggcgcggtg gagcttcacc agccgtagcc    12060
aggagtgtgt gcgtaccgcc atcgacgcgc tggagcgggg cgacgaccag gaactgctgc    12120
accaggtccg gcgggcccgg cacgtgcttg ccgagctgga cgacgaggtc cggctcggga    12180
tcttcacccc ccggctgacg gcgctgtgcg acgccgccga ccgtcggc ggcgcggcca    12240 aaccgtccgg cgccggtggc ggggactgcg gcatcgcgtt gctggacgcc accgccgcga    12300
cgcggaccgc gcggctgcgc gagcagtggg ccgccgccgg ggtgctcccc atgccgatcc    12360
aggtccatca gacgaacggg agcgcgcgat gatcgccaac cgcaaggacg accacgtccg    12420
gctcgccgcc gagcagcagg gccggctcgg cggtcaccac gagttcgacg acgtgtcctt    12480
cgtgcaccac gccctggccg gcatcgaccg gtccgacgtc tcgctggcca cgtcgttcgg    12540
cggcatcgac tggccggtgc cgctgtgcat caacgcgatg accggcggca gcaccaagac    12600
cggcctgatc aaccgggacc tggcgatcgc ggcccgggag accggcgtac cgatcgccac    12660
cgggtcgatg agcgcctact tcgccgacga gtcggtggcc gagagtttca gcgtgatgcg    12720
ccgggagaac cccgacgggt tcatcatggc caacgtcaac gccaccgcct ccgtcgaacg    12780
ggcccggcgg gctgtcgacc tgatgcgggc cgacgcgctg cagatccacc tgaacaccat    12840
ccaggagacg gtgatgccgg aggggaccg tcgttcgcc gcctgggggc gcggatcga    12900 acagatcgtc gccggcgtcg gtgtgccggt gatcgtcaag gaggtcggct tcgggctcag    12960
```

```
ccgcgaaacg ctgctgcggc tgcgggacat gggcgtccgg gtggccgacg tcgccggccg   13020
cggcggcacg aacttcgcgc gcatcgagaa cgaccggcgg gacgccgccg actactcctt   13080
cctcgacggg tggggacagt cgacacccgc ctgcctgctg gacgcccagg gcgtggacct   13140
gcccgtgctg gcctccggcg gcatccgcaa cccgctcgac gtggtccgcg ggctggcgct   13200
cggcgccggc gcggccgggg tgtccggact gttcctgcgc acgctcctgg acggcggcgt   13260
gccggcgctg ctgtcgctgc tgtccacctg gctcgaccag atcgaagccc tgatgaccgc   13320
cctgggcgcg cggaccccgg ccgacctgac ccgctgcgac ctgctgatcc agggtcggct   13380
gagcgcgttc tgcgcggccc ggggcatcga cacccaccgc ctcgccaccc gttccggcgc   13440
cacccacgag atgatcggag cattcgatg aacgacgcga tcgccggtgt gcccatgaaa   13500
tgggtaggtc ccgtgcggat ctcgggaaac gtggcgcaga tcgagacgga ggttccgctc   13560
gccacgtacg agtcgccgct ctggccgtcc gtcggccggg gcgcgaagat ctcccggatg   13620
gtcgaggcgg gcatcgtcgc cacgctcgtc gacgagcgca tgacccgctc ggtgttcgtg   13680
cgcgccaagg acgcgcagac cgcctacctg gcctcgcttg aggtcgacgc gcggttcgac   13740
gaactgcgtg acatcgtgcg cacctgcggc aggttcgtcg agctgatcgg gttccaccac   13800
gagatcaccg cgaacctgct gttcctgcgg ttcagtttca ccaccggcga cgcgtccggg   13860
cacaacatgg cgacgctggc cgccgacgcg ctgctgaagc acatcctgga caccattccg   13920
ggcatctcgt acggctcgat ctcgggcaac tactgcaccg acaagaaggc caccgcgata   13980
aacggcattc tcggccgggg caagaacgtg gtcaccgagc tggtcgtgcc gcgggagatc   14040
gtccacgaca gcctgcacac gacggcggcg gcgatcgccc agctgaacgt gcacaagaac   14100
atgatcggca cgttgctcgc cggcggtatc cgctcggcca acgcccacta cgcgaacatg   14160
ctgctcgggt tctacctggc cacgggtcag gacgccgcga acatcgtcga gggctcccag   14220
ggcgtgacgg tcgccgagga ccgcgacggc gacctctact tctcctgcac gctgcccaac   14280
ctgatcgtgg gcaccgtcgg caacggcaag gggctcggct tcgtcgagga gaacctggag   14340 cggctcgggct gccgcgcctc gcgtgatccg ggcgagaacg cccggcggct cgcggtcatc   14400
gcggccgcga cggtgctctg cggcgagctg tccctgctcg ccgcgcagac caacccgggc   14460
gagctgatgc gggcgcacgt ccggctcgaa cgcccgaccg agaccacgaa gatcggagcc   14520
tgacgatggc cgagagaccc gccgtcggca tccacgacct gtccgccgcg acggcgcatc   14580
acgtgctgac acacgagacc ctggccgcga gcaacggcgc cgacgtgccc aagtaccacc   14640
gtggcatcgg gctgcgggcg atgagcgtgc ccgccccgga cgaggacatc gtgacgatgg   14700
ctgctgccgc cgccgcgccg gtggtcgccc gccacggcac cgaccggatc cggaccgtcg   14760
tgttcgccac ggagtcgtcg gtcgaccagg cgaaggcggc cgggatacac gtccactccc   14820
tgctcggcct cccctcggcc acccgggtgg tcgagctgaa gcaggcctgc tacggcggta   14880
cggcgggact gcagttcgcc atcggcctgg tgcaccgtga cccgtcgcag caggtcctgg   14940
tgatcgccag cgacgtgtcg aagtacgcgc tgggtgagcc cggcgaggcg acccagggcg   15000
ccgcggcggt cgccatgctc gtcggcgcgg accggcgct ggtacgcgtc gaggaccgt   15060 cgggcatgtt caccgccgac gtcatggact ctggcggcc gaactaccgc accaccgccc   15120
tggtcgacgg gcacgagtcc atctccgcct acctgcaggc gctggagggc tcgtggaagg   15180
actacaccga gcgcggcggt cgcaccctgg acagttcgg cgcgttctgc taccaccagc   15240
cgttcccgag gatggccgac aaggcgcacc ggcacctgct caactactgc gggcgcgacg   15300
tcgacgacgc gctggtggcc ggggccatcg ggcacaccac cgcgtacaac gccgagatcg   15360
```

```
gcaacagcta cacggcgtcg atgtatctcg ggctcgcggc actgctcgac accgccgacg   15420
acctgaccgg ccggaccgtc ggcttcctca gctacgggtc cggcagcgtc gccgagttct   15480
tcgccggcac tgtcgtgccc gggtaccgcg cgcacacgcg acccgaccag caccgcgcgg   15540
cgatcgaccg gcggcaggag atcgactacg cgacgtaccg ggagttgcac gagcacgcct   15600
tcccggtcga cggcggcgac tatccggcgc cggaggtgac caccgggccg taccggctgg   15660
ccgggctctc cggtcacaag cgcgtctacg agccgcgata ggaccggcca cgccggccgc   15720
cctgaccgaa cgaaccatgc ttggaggatc gatgtccgga actcccgagg tggccgagct   15780
ctactcgacc atcgaggaat cggcccggca actggacgtg ccgtgttcgc gcgaccgggt   15840
ctggcccatc ctgtccgcgt acggcgacgc gttcgcccat cccgaggcgg tggtcgcctt   15900
ccgggtggcg accgcgctgc gtcacgcggg cgagctggac tgccggttcc ggacgcatcc   15960
ggacgaccgg gacccgtacg cctcggcgct cgcccggggc ctcacccgc gcacggacca   16020
ccccgtcggc gcgctgctct ccgaggtcca ccggcgctgc ccggtggaga gccacggcat   16080
cgacttcggg gtggtcggcg gcttcaagaa gatctacgcg gccttcgccc cggacgagct   16140
gcaggtggcc acgtcgctcg ccggcattcc ggcgatgccc cgcagcctcg ccgcgaacgc   16200
cgacttcttc acccggcacg gcctcgacga ccgggtcggc gtgctgggat tcgactaccc   16260
ggccccggacc gtgaacgtct acttcaacga cgtgccgcgt gagtgcttcg agccggagac   16320
catccggtcg acgctgcgcc ggaccgggat ggccgagccg agcgagcaga tgctccggct   16380
cggcaccggg gcgttcgggc tctacgtcac gctgggctgg gactccccgg agatcgagcg   16440
gatctgctac gccgcggcga ccacggacct gaccacgctt ccggtacccg tggaaccgga   16500
gatcgagaag ttcgtgaaaa gcgttccgta cggcggcggg gaccggaagt tcgtctacgg   16560
cgtggcgctg accccaagg gggagtacta caaactcgag tcgcactaca aatggaagcc   16620
gggcgcggtg aacttcattt gaacagcggc cggttccgcc gccgggcgg cggaaccggg   16680
atcaatgcct gttcgctcgg gttcaacact ggcgcgctcc gctaaagtgc gaacatgacg   16740
actgactgt ccagtgtgtg ggcccgggtg aagaactggg tcgtcgcgtt ggctgtggcg   16800
gcggtgctga tgatcagcgc gctggccggt gaccatcctg cccccgaggg cctcggtctg   16860
ctcggcttcg cgctggtggc ggcgagcggc ctggcgctgg ccgccagtcg tcgggccccg   16920
atcgccgtgc tggtcgccac cgggctgtgc gtggtgggct acaacgcgat cggcttcggg   16980
gtgcccgcca tcgcgtacct gttcgcggtc tacgcggcgg tccgggccgg gcaccggctc   17040
gtcacgctcg gggcgagcgc cgccctgctc gtcgtcctgc cgctggcgat catggtctcg   17100
cccgcggacg cgcgcctcaa ggaggcgctc cgcagtcgc ggggcgtgct ggaactggcc   17160
tggctgatcg ccgcggcggc ggccggtgag gcgctgcggc aggccgaacg gcgagcggac   17220
gaggcggaac ggaccgcga ggagaccgcc cggctgcgcg ccacccagga gcggctgcac   17280
atcgcacggg agctgcacga ctcgctcacc caccagatct cgatcatcaa ggtgcaggcg   17340
gaggtggcgg tccacctggc ccgcaagcgg ggcgagcagg tgccggagtc gctgctggcg   17400
atccaggagg ccggccgggc ggcgactcgc gagctgcgcg cgaccctgga cgctgcgt   17460
gacctgacca gtccccgtc gcacgggctc gaccacctcc cggagctgct ggccggggcc   17520
gagaagatcg gcctggccac cacgctgacc atcgagggcg accagcggga cgtgccggag   17580
gcggtggggcc gcaccgcgta ccggatcgtg caggagtcgc tcaccaacac cgcccggcac   17640
gcctccgccg cggccgccgc ggtccggatc gactaccgcc cggacgcgct gagcatccgg   17700
```

```
atcgacgacg acgggacggc cggccgggc gccgccccgg tgcccggcgt cgggctgctg    17760
gggatgcacg agcgcgtcct cgcgctgggc ggccggctgc gggcggaacc ccgcaccggc    17820
ggaggcttca ccgtccaggc cgaactcccg gtggtgcgcg tcccatgatc aggatcatgc    17880
tgctcgacga ccagccgctg ctgcgcagcg ggttccgcgc gctcctcgac gccgaggacg    17940
acatcgaggt ggtggccgag ggcgggaacg ccgggaggg cctggcgctg gcccggcagc    18000
acctgcccga tctcgccctg atcgacatcc agatgccggt catggacggc gtcgagacga    18060
cccggcagat cgtcgcggat ccggcgctgg ccggggtacg cgtcgtcatc ctcaccaact    18120
acggcctcga cgagtacgtc ttccacgcgc tgcgcgccgg cgccaccggc ttcctggtca    18180
aggacatcga gccggacgac ctgctgcacg ccgtgcgggt cgccgcgcgc ggtgacgcgc    18240
tgctcgcgcc gtcgatcacc cggatgctga tcaacaggta cgtgtcggag ccgctctgcg    18300
cggacgtcac gcccggcatg gaggagctga ccaaccggga acgcgaggcg gtcgccctgg    18360
ccgcccgggg cctgtccaac gacgagatcc ccgatcgcat ggtgatcagc ccgctgaccg    18420
cgaagaccca cgtcaaccgc gccatgacca agctgcaggc ccgcgaccgc gcccagctgg    18480
tggtgttcgc ctacgagtcc ggcctggtgt cacccggcaa tcgctgaccg ggcagcccgc    18540
ccggtctgtc gcctcggcag tgctgcggct gcggtatgcg gctgctcccg gcgcagacgc    18600
cggagcccgt ggataccgtc accgcagtag atcgatcgat tgtctccttc ggcatgacga    18660
cccgtagcgg ggtcgttacc tacgctggcg cagatgcctg ttcccgcagc cgaagggct    18720
tccatgttca tccgtcgttt gctcaccgcc gccgcagccg gcgtcctcgg tgggctcgca    18780
ctcgtcgcac cggcggccgc gcaggtgacg gccgccgacg gtgacggtgg ttccggccgc    18840
gccggatccg tgctggcgct cgcgctcgcg ttgctcggcc tcgtcctggg cgggtggcg    18900
ttgcgctccg cggggcgcgg cggcggtcgt ggcaacgcga tcgccgcgct ggtgctcgcg    18960
gtggccggcc tgatcgccgg cgtggtcgcc ctggccggct ccgacggtgg tgtcggcagc    19020
ggcaacggcc gtggtggcgc catcgtggcc gtcgtgctgg cgctgatcgg gatcgccgtc    19080
ggcggcctgg cattcacccg ctcccggcgc gccgcctgac cggcgctgcc gaccgaacac    19140
cccggtgacc caaccgaacc cgaaggggag tcccatgcgc aaagtgttcg ccggactggc    19200
agcgttcctg ctgctcgtgc tcgtggtgca gttcttcctg gccgccagcg gcgcgttcag    19260
caacgaggcc aacgaggagg cgttccgccc tcaccggatc ctgggcctgg ggagcatcct    19320
cgtcgccgtg gtgctgacgg tggccgccgc ggtgatgcgg atgcccggcc ggatcatcgg    19380
cctgtccggc ctggtcgccg ggctgggcat cctgcaggcc ctgatcgcgg tcatcgccaa    19440
ggcgttcggc gactcggccg gtgactcggc cgtcggccgg tacgtgttcg gcctgcacgc    19500
ggtcaacgga ctggtgatgg tggccgtcgc ccgcgtcatc ctgcgcagcg tccgggcggc    19560
gccggacacg accaccacgc ccggcgtgga cacgacggtc accggtccgg cggccgactc    19620
ggcgcgaacg gcgtcatgag cacgctccaa tggatcctcg tggaccacgt cgtggcgctg    19680
ctcggtgtcg cgacgtggtt cgcaacgggt gtcacggcag ctctcggccg ccaccggatc    19740
gcgttggcgc tcctcggcgc cgcggtgctg gtgacagtcg cccgcctggg caccgtggcg    19800
ctgctggccg accgcggctg gtggttcgtc caggagaagg ttctgctggg gctgccgatg    19860
ctcggcgccg cggggctcgt cgcggtgctc tggccggcc cgcgcctgct cgcggcccgg    19920
cagtcaccgg cggcggacct gccggccggc gcgctggtcg cggtgctgac cgccggcttc    19980
gccgcgctgg ccggcctggt ggtgacgttc accgccgggt accgctgac gtggagcacc    20040
gcgctgatcg ccgtcgccct cgtctgcgcc gccgcgctgc tcaccgcgcg ggtggtcgga    20100
```

-continued

```
cgacccgccg ccccggccgc ggaggccggc tccccggagc acacgccggc ggcggccggg   20160
cccacggcgc tgtcccgccg ccggttcctc ggcgtggccg ggggagtggt cgcggcgggc   20220
gccggcgcca ccggcgtcgg cctgctcttc cgcgacccgg aggcgatggt caccggaggc   20280
ggccccggac acgccggtgg cgcccgcccc aaggtctccg tggcggacct gcgcggcccc   20340
ggcgctccgg cggcgggcgg cacggcgcga cgccacgtgc tcaccgcccg gacgggcacc   20400
gtcacgattc cgtccggacg tccgatcgac gcctggagct acgagggccg cctgcccggg   20460
ccggccatca ccgcgaccga gggcgacctg atcgaggtga cgctccgcaa cgccgacatc   20520
gaggacggcg tcaccgtgca ctggcacggg tacgacgtgc cgtgcggcga ggacggcgcg   20580
ccgggcgcca cgcagcacgc ggtgcagccc ggcggcgagt tcgtctaccg gttccaggcg   20640
gaccaggtgg ggacgtactg gtaccacacc caccaggcgt cgcacccccgc cgtgcgcaaa   20700 gggctgtacg ggacgctcgt cgtgacgccg cgcgaggacc ggccggaagc ggagcgcggg   20760
ctggacctga cgctgccggt gcacacgttc gacgacgtca cgatcctcgg cgaccaggag   20820
ggacgcgccg tccacgacgt ccgccccggc cagccggtgc gactgcgtct gatcaacacc   20880
gactccaacc cgcactggtt cgccgtcgtc ggctcgccct ccgcgtggt ggccgtcgac   20940 ggccgcgacc tcaaccagcc gggcgaggta cgcgaggtcg ggctccgcct gcccgccgga   21000
ggccggtacg acctgaccct ggccatgccg gacgccaagg tcacgctgct gctcgacaac   21060
gactccgacc agggcgtcct gctgcgcccc ccgggcgtcg gcgtggtga ccgcccgctg   21120 ccggacaccg ccgactggcc cgagttcgac ctgctgggct acggcgagcc ggcgcccgtg   21180
ccgttcgacg ccgacgacgc cgaccgccac ttcaccatcg tcctcgaccg ggccctggcc   21240
atggtcgacg gcaagcccgc gtacgcccag accgtcgacg gtcgcgcaca tccctccgtc   21300
cccgaccagc tcgtccggga gggggacgtc gtgcgcttca cggtggtcaa ccggagcctc   21360
gaaacccacc cgtggcacct gcacggccat ccggtgctga tcctgtcccg cgacggccgg   21420
ccgtactccg gcagcccgct gtggatggac accttcgacg tgcggccggg agaggtgtgg   21480
gaggtggcgt tccggggcgga caatccgggt gtctggatga accactgcca caacctgccg   21540
caccaggagc agggcatgat gctgcggctc gtctacgacg gtgtcaccac gcccttcgcc   21600
agcacgagcc acgcacactg aggggactcg catgaccgca gacctgcacg gcctggccag   21660
cgtccgctac atcgtcgacg acgtgtcggc ggcgatcgag ttctacacca cccacctggg   21720
tttcacggtg tcgaccgcgt tcccgccggc cttcgccgac gtggtgcgcg ggccgctgcg   21780
gctcctgctg tccgggccga ccagctcggg cgcccgggtc accccggcgg acgcggccgg   21840
gtgcgggcgc aaccgcatcc acctgatcgt cgacgatctc gacgccgaac gggagcggct   21900
ggagcgcgcc ggggtgacgt tgcgcagcga cgtcgtggcc gggccggggcg gccgtcagtt   21960 cctgatcgcc gacccggcgg gcaacctggt cgaggtgttc gagccggcag cccgcggctg   22020
aaccgccgac ggacgccctc ccacctcgcg acgcccgaag cccgacacct ggccgcgtcg   22080
cggccacgat caccgtggcc gcgacgcggt gacggggtgc cttaccgggg cggggtgggc   22140
gcggcgagcc gcgcggccag gatggagatg atcacggcgc cggcgatcac gtgggtgccg   22200
gcgaggacga gctgcgtcga caccggggtg tccggggcga aggcgggcgc ggcgagggac   22260
agcacggtga acgcgacggt gccggccacg aaggcacgca cggccgccg ggcccgccgc   22320 gccacgacca ccgccaggac gattccgccg atcgaccaga gcacgacgct gcgggcgatg   22380 gccccaccg ggatcgcctg cgcctgctcc tcccagacgc cggccgcctc catcggtacg   22440
```

```
ccgaagcccc gggcggcgag cgtgaacgcc tccgcggcca cggccccggc gagggtggcc    22500
agcacgccga ccagccacac cggagcggtg gccggcgacc aggtgggccg tgccgcgacg    22560
ggagttcggg gagtggcctc atccacggcg tcgcctccgg tcgggtgcct cgatgtgttc    22620
tcgggagaat gcgggacgc cacgacggca gtcaacatgg acagttgaac gccctggcgt    22680
cacgggcggt tcccgcgccg gcccgccgcc tcggccgcgg cggcggccgt gccgtcggcg    22740
agcagggaga ccagcaggtc gcccaggatc cgtgggccgt gctgggtgag gacggactcc    22800
aggtggaact ggacggaacg gaatcccggg ccgcgcagcg cgtgcacgtc cccgctgtcc    22860
gggctgcggc tgatctcgat cgggccccgc cggccaccgg ccaccacgtc gtgcgcggag    22920
cgggcggtgt aggtgttgta gaaccccacg agttccggcc ggccgaacag gtcgatccgc    22980
ttctgcacac cctggtttggg caccgcgcgc cgggcgaggg ggaacccccag ttcggcggc    23040 agcacctggt ggcccaggca gatggacagg aacggcaccg ttccggcgag caggtcgcgg    23100
gtgagcccgc gcagggtccg catacgcggg tcggtcaggt cgcccgggtc gccggggccg    23160
ggaccgacga cgacgaggtc gtgtccgtcc ggccgcagcc ggctgtcgaa ccgggcgatg    23220
ctcgaccgca gcccgagggc ccgcaactgg tggtcgagca tggccatgaa cgtgtcctcg    23280
ttgtcgacga cgagcacgcg gcgtccggtc agcgccgggt tcggggtgcg ccgctccgcg    23340
ccgtcgagcc agaacctcga cagtgtggtg ttgcgctcgc gcaacgcccg ccgtacccgg    23400
gggtcggtgg ccagggacga acgagcccgc gcggccgtgg tccgcccgcc gtccgggccg    23460
tccgggtcga cgccgaggcc gagcgccgcg cgcatggcgc ccgccttggc ccgcgtctcg    23520
gccacctccg actccggctt ggagtcccgc acgagggtgg cgccgacgcc caggcgcagc    23580
gtgcccgcgt cgtcgatctc ggcggtgcgg atcatgatgg ccgagtcgag cgtacggctg    23640
ccggccgagt cacggcccat caacgcgagc acgccgccgt agtagccgcg gccggtcgtc    23700
tcgtggcggg tgatgacccg gaacgcgttc tcgatcgggc tgccggtgac cgtcggcgcg    23760
agcagggtct cccgcagcac gtcgcgcacg tccaggtcgc tgcggccggt caggatgtac    23820
tcggagtgcg tcacccgcgc catttccttg aggaacgggc cgtgcacctg ccgccggag    23880 gcgcacatcc gcgccatcat tttcagttcc tcgtcgacga ccatgtagag ttcgttagcc    23940
tctttcgggt cgttcaggaa ttccagcaga ccggaaacgg ccgggccgtt cgggggggtgc    24000 cggtaggtcc cgctgatggg attcatcgag acggttccgt cgatcatgct gacgtgtcgt    24060
tccggtgacg cgccgatgaa cgtgccggcg ccggagtgga acagaaacgt ccagtaggaa    24120
cccagttcgc cggtcagcaa ccggcggaag agcgccagtt ccgtggcgat cgagtagtcg    24180
gccagccgcg cggtgaaggt gcgccggatg acgaagttgg atccggcgcc cagcccgatc    24240
tcgtcaccca ccacccgctt gacgatcgcg gcgtagtcct cgtcgctgag gtcgaagtcg    24300
gcgtcggtca ccggcacacc gcgttcgggc aggcccgcca gcgcctgtcc gcggtcgagc    24360
ccgaactgct cgtggacgcg catcgcgagc agcggcgcgc cgtcgtcgtg gcagtcgaac    24420
ccccgttcgg tgacctgccg gtacggcacc gccacgagca ggtcgtgccg cgcgccggtc    24480
gccggctcgg tgggcagggg cagctcgccg agagtgtcca cgtcgcacac ctcgccggtc    24540
agaacctcca cgtacgcgca cccggccgcg ccgggccggt gcagcagggc gaaggcgcgc    24600
ccgtcgccgc cgagaccgga cagcagatcg gggaatccgg tcacgttcga ttccgtcccg    24660
tccatgtcgc tcccctttgcc tgagagatcg cctgtcgata ctgcgtccgg caaaaggcgt    24720
cgcacatgac gtgaagtcgc cgacggcatc acgtgttcc ggtaacgcgc cgacgttatg    24780
gcgtgaacga ctgaatcggc gggctactac tcgggcgagt agtgcccacg cagatcgacc    24840
```

```
gcgattactg tcgaccgcaa tgccgatacg acgagggcgg tgaagacgac tgtggacgtg    24900
ctggtccaga aatacggggg cacctcgctg cagaccctcg accgcgttcg gcacgccgcg    24960
ctgcggatcg ccgaggcgcg gcggcacggc tccgccgtga cagtggtcgt gtcggcgcgc    25020
ggcagccgga ccgacgacct gctgcggctg gcggccgacg tcggcgccgc gggtccgtcc    25080
cgggaactcg accagttgct cgcagtcggc gagtccgagt cggcggcgct gatgcgcgtg    25140
gcgttgaccg ggctgggagt gccggccgtc tcgctgaccg ggcaccaggc ggagatccac    25200
accaccgacc ggcacggcga cgcgctgatc tcgcggatcg gggcggcgcg ggtggaagcg    25260
gcgctgggcc gtggcgaggt cgccgtggtc accggattcc agggcatcga ccgggccggt    25320
gacgtcgcca cgctggggcg cggcggctcc gacacgacag cggtggcgct cgcggcccgg    25380
ctccgcgcgt cggcgtgcga gatctacacc gacgtggacg gcgtcttcag cgccgacccc    25440
cgcatccttc cggcggcgcg ttgcctgccg tgggtggagc ccggcgtcat ggcggagatg    25500
gcgttcgccg gcgcgcgggt cctgcacacc cgatgcatcg agctggccgc catggaaggg    25560
gtcgaagtgc gcgtgcgcaa cgcgtcgtcg caggcgcccg gaacgatagt cgtggaccgg    25620
cccgacgacc ggccgctgga gacccggcgg gccgtggtgg cggtcaccca cgacaccgat    25680
gtcgtccgcg tgctggtgca ctgccgcgac ggccgccggg acatggcacc cgacgtgttc    25740
gaggtgctgg ccgcccatgg ggcggtggcg gacctggtgg cccggtccgg gccctacgag    25800
agcgagttcc ggatgggggtt caccatccgc cgcagccagg ccgaagcggt gcggaccgcg    25860
ctgcacgacc tcaccgcgtc cttcgacggc ggggtccact tcgacgagaa cgtcggcaag    25920
gtgtccgtgg tcggcatggg cctgctcagc cgccccgagc acacggcccg gctgatggcg    25980
gcgctggccg cggcggggat ctcgacgagc tggatctcca cctcccagat gcggctgtcg    26040
gtgatcgtgt cgcgggaccg caccgtcgac gccgtcgaag ccctgcaccg cgcgttccgc    26100
ctggaccggt ccgagccggc ggacgccacg tccctgacct cccgccgttc cgccaccgcc    26160
tgagagaggt aggaaaccgt ggccgtactc aacgcttcgt tcgctcgtgg cctgcgtctg    26220
cgccgactgt tccgacgcgg cgacggacgc ctgctcgtcg tcccgctcga ccactccgtc    26280
accgacgggc cgctgcgccg cggcgacctg aactcgctgc tcggtgagct cgccggcacc    26340
ggcgtggacg ccgtggtgct gcacaagggc agcctgcggc acgtcgacca cggctggttc    26400
ggcgacatgt cgctgatcgt gcatctgagc gtgagcaccc ggcacgcccc ggacccggac    26460
gcgaagtacc tggtcgcgca cgtggaggag gcgctgcggc tgggcgccga cgcggtcagc    26520
gtgcacgtca acctcggctc accgcaggag gcgcggcaga tcgccgacct ggcggcggtg    26580
gcgggggagt gcgaccgctg gaacgtcccg ctgctggcca tggtgtacgc ccgcgggccg    26640
cagatcaccg actcccgggc accggagctg gtggcgcacg ccgcgacgct cgccgcggac    26700
ctcgcgcccg acatcgtcaa gaccgactac gtgggcacgc ccgagcagat ggccgaggtg    26760
gtgcgcggct gcccgatccc gctgatcgtg gccggcggcc cgcgctcggc cgacactccg    26820
acggtgctcg cctacgtctc ggacgcgctg cgcggcggcg tggccgggat ggccatgggc    26880
cgcaacgtgt tccaggccga gcagcccggc ctgatggccg ccgccgtggc acggctggtg    26940
cacgagccac ggcacgtgcc ggaccggtac gacgtcgacg accggctcgc ccttacgtcc    27000
tgagactccc tgaccgtcca ccgaggagaa cccgtgaag ctgtgctggc tggacatccg    27060
taacgtcaac ggcgccaagg aggcaatcgt cgaggaggcg gtccaccagc gggtggacgc    27120
cgtcgtggcg gccgatccgg ccgacctgga gacgcttccc ccgacggtga agaaggtgct    27180
```

```
gttcccgcag ggcgggccgc tgccggagaa gctggaaccg gccgacctgg tgatcgtcga  27240
gccggcccgg cacggcgagc cgccgagct ggcggcccgg tacccggagg tggagttcgg  27300
ccggttcgtc gagatcgtcg acgcggacag cctggaggac gcctgccggt ccgcgcgcca  27360
cgaccggtgg agcctgctgt acttccgcga ccccaccaag atcccgctgg agatcgtgct  27420
ggcggccgcg gcgggcgcgg agggcagcat catcacccag gtcgccgacg tcgaggaggc  27480
ggagatcgtc ttcggcgtcc tggagcacgg ctcggacgga gtgatgctgg cgccccgcgc  27540
cgtgggggag gccaccgagc tgcggaccgc cgcggtgagc acggcggcgg acctgtcgct  27600
cgtggagctg gaggtcaccg gcatccggcg ggtgggcatg ggcgagcgcg cctgcgtcga  27660
cacgtgcacg aacttccgtc tggacgaggg catcctggtc ggctcgcact ccaccggcat  27720
gatcctgtgc tgcagcgaga cgcatccgct gccgtacatg ccgacccggc cgttccgggt  27780
caacgccggc gcgctgcact cgtacacgct ctccgccggc gggcggacca actacctcag  27840
cgagctggtc tccggcggcc gggtgctcgc cgtggactcg caggggaagt cccgcgtcgt  27900
cacagtggga cgggtcaaga tcgagacgcg tccgctgctg gcgatcgacg cggtctcccc  27960
ctccgggaca cgcgtcaacc tcatcgtcca ggacgactgg cacgtgcgcg tgctcgggcc  28020
gggcggcacc gtgctcaacg tgaccgagct gaccgccggc acgaaggtgc tcggttacct  28080
gccggtggag aagcggcacg tcggctaccc gatcgacgag ttctgcatcg agaagtgaca  28140
ggcggcggga aggggagcgg gcgatgaccg cgcagccggt gctggacttc cacgtacgcc  28200
tggcgccccg gccggggcg cgggagcggc tgctcgccgc gctgcgcgag tgcgggctgg  28260
cgcgggcggt ggtgtgcgcg ggcggcacca tcgacctgga ccggctgtcc cgccagctcg  28320
tcaccggcgg ccacgtcgag accgacgccg acaacgacgc ggtggcggcg gcctgcgccg  28380
gcaccgacgg ccggctggtg ccgttcttct cgccaaccc gcaccggccg gccgaggcgt  28440
accgggcccg cgccgccgag ttccgcggcc tggagatctc accgccgtc cacgcgtcg  28500 ccctgaccga cccgcgggtc gccgacctcg tggccgtggc ggcggagttc gaccatccgg  28560
tgtacgtggt ctgcctggac cgacccggcg cgggcgtggc cgacctggtc ggcctgagcc  28620
gccggttccc gcaggtgagc ttcgtgctcg ggcacagcgg cgtcggcaac atcgacctct  28680
acgccctgac cctgatccag gacgagccga catctcgct ggagacctcc ggcggctaca  28740
cctgcgtggc cgaggcggcg ctacgccgcc tcggcgacga ccgggtggtg ttcggctccg  28800
agtacccgct gcagcacccg gccgtggaac tggccaagtt ccaggcgttg cgactgccgc  28860
cggagcggtg gcggcggatc gcctgggaca acgcgcatcg actgctagga gaggagaagc  28920
ggtgagcgag ccaagttcga gcctgccccg gctcggccag tggcacggcc tcgaggacct  28980
gcggcgcctc caggagaagc aactggcgga gacgttcacc tgggcggccc ggtcgccgtt  29040
ctaccgggcg cggctggcct ccggcgcgcc gccggtgacg cccgccgacc tggccgacct  29100
gccgctgacc accaagcagg acctgcggga caactacccc ttcggcatgc tcgccgtgcc  29160
ccgcgaacgg ctggcgacct accacgagtc gagcgggacc gccgggaagc ccacccctc  29220 ctactacacc gcggaggact ggaccgacct ggcggagcgc ttcgcccgca agtggatcgg  29280
catgtccgcc gacgacgtct tcctggtccg cacgccgtac gcgctgctgc tgaccgggca  29340
tctcgcccac gccgcagccc ggctgcgtgg ggccacggtg gtacctggcg acaaccggtc  29400
gctggcgatg ccgtacgccc gggtggtccg ggtgatgcac gacctggacg tcacgctcac  29460
ctggtcggtg ccgacggagt gcctgatctg ggccgccgcg gcgatcgcgg ccgggcaccg  29520
gcccgacatc gacttcccgg cgctgcgcgc gctgttcgtc ggcggcgagc cgatgaccga  29580
```

```
cgcccgccgg cggcggatca gccgcctgtg gggggtgccg gtcatcgagg agtacggctc    29640
gacggagacc ggcagcctgg ccggggagtg ccccgaggga cgcctgcacc tgtgggccga    29700
ccgggcgctg ttcgaggtgt acgacccgga caccggcgcc gtccgcgcgg acggcgacgg    29760
ccagctcgtg gtcacgccgc tgttccggga ggcgatgccg ctgctgcggt acaacctgga    29820
ggacaacgtg tcggtctcct acgacgactg cggatgcggc tggaagctgc ccaccgtgcg    29880
ggtgctcggc cggtcggcgt tcggctaccg ggtcggcggc accaccatca cccagcacca    29940
gctggaggaa ctggtcttct ccctgccgga ggcgcaccgg gtgatgttct ggcgggccaa    30000
ggcggagccg gcgctgttgc gggtcgagat cgaggtggcc gccgcgcacc gggtcgccgc    30060
cgaggcggag ctgaccgccg cgatccgggc cgccttcggc gtggacagcg aggtcaccgg    30120
cctggcgccg ggaaccctga tcccgctcga cgcgctgacc agcatgccgg acgtggtgaa    30180
gccacgcagc ctgttcggtc cggacgagga ctggagcaaa cgctcctct actactgagg     30240 gaaccgacat gccgcagatg agggtcgccg tggccggcgc cggcatcgcc gggctcgcct    30300
tcgccgccgc cctgcgccgg accgggatcg actgccacgt gtacgaacag gccgaccagc    30360
tcatggaggt gggcgcgggc gtgcaggtcg cgccgaacgc cacccggctg ctgcaccggc    30420
tgggcctgcg tgaccgcctg cgtacggtgg ctgtcgcgcc gcaggcgatc gagatgcgcc    30480
gctgggacga cggcacgctg ctgcaacgca cccagctggg cagcgtgtgc ggacgccgct    30540
tcggcgcgcc gtactacgtg gtgcaccgcg cggacctgca cagcagcctg ctgtcgctgg    30600
tgccgccgga ccgggtgcac ctgggcgccc gcctcaccgc cgtgacgcag accgccgacg    30660
aggcgtacct gcacctgtcc aacggcacca cggtcgcggc ggatctcgtc gtgggcgccg    30720
acggcatcca ctcggtcgcg cgggagcaga tcgtggcgga ccggccgcgc ttctccggac    30780
agtccatcta ccgcgggctg gtgccggccg agcgggtgcc gttcctgctc accgaacccc    30840
gggtgcagtt gtggttcggg ccggaccagc actgcgtctg ctacccggtg tccgccggcc    30900
ggcaggtgag cttcggcgcg acggtgcccg ccaccgactg gcggcaggag tcgtggtcgg    30960
gccggggcga cgtgacgcaa ctcgcggccg cgtacgcggg ctggcacccg gacgtcaccc    31020
ggctgatcgc cgcggccgac cgggtcggca ggtgggcgct gcacgaccgg gacagcatcg    31080
accggctcag cgcgggacgg gtgaccctga tcggcgacgc cgcgcacccg atgctgccgt    31140
tccaggcgca gggcgcgaac caggccgtcg aggacgcggt ggtgctcgcg gtctgcctgg    31200
ccggcgtgga accggcgggc ctgggcgccg cgctgcgccg ctacgaacgg atccgcctgc    31260
cccggaccac ccggatccag cggcagtccc gggccaacgc cgagatgttc cacctggccg    31320
acggcgccga ccagcgccgc cgggacgtcg ccgcacaatc ctcgtccggc ctggaccgcc    31380
acgaatggct cttcgggtac gacgccgaga agccaccac gaccagcggg agcgcctgat     31440
ggaactgacc ggaatcgagt cgaaggtcgc cctggtcacg ggcgcggggc agggcatcgg    31500
cgccgccgtg gccggtgtcc tggcgagggc gggcgcgcag gtggcggcgg tggaccgcaa    31560
cgccgaggcg ctgaccaccg tcgtgacgaa gctcgccgcc gagggcgact cggcgcgcgc    31620
ctactgcgtc gacgtgtgcg acagcgaggc ggtggacgcg ctggtgcgcc gggtcgagga    31680
cgagatgggg ccggtcgcca tcctggtcaa cgccgccggc gtgctgcaca ccggacgggt    31740
cgtcgagctg tcggaccggc agtggcgccg gaccttctcg gtgaacgccg acggcgtgtt    31800
ccacgtgtcc cggcggtgg cgcggcggat gtgggccgc cgtcgtggcg cgatcgtcac      31860
cgtggcgtcg aacgccgccg gggtgccgcg taccgagatg gccgcgtacg ccgcctccaa    31920
```

```
ggccgcgtcc gcgcagttca cccgctgcct ggggcttgag ctgtccggct acggcatccg   31980
gtgcaacgtg gtctcgcccg gctccaccga cacccccatg ctgcgggcca tgctcggcga   32040
gggcgccgac ccgagcgcgg tgatcgaggg cacgccgggc gcgtaccgcg tcggcatccc   32100
gctgcgcaag ctggcccagc cgcgcgacgt ggccgaggcg gtcgcctatc tggtgtccga   32160
ccaggcgggc cacgtgacca tgcacgacct gtacgtcgac ggcggcgcgg ccctgcacgt   32220
gtgacgccct cgcacggaaa ccggaggcga gaaccgatgg ccatgacccc gatcgcgccg   32280
taccgcatgc ccggcgacgg cgacctgccc ggcaccgcgc tgccctggcg tccgcacccg   32340 gacccgggccg ccgtgctggt gcacgacctg caacgctact tcctgcgccc gttcgaggcc   32400
ggggagtccc cgatggccga actgctcccc aacgtcgcga agctgctcgc cacggcgcgg   32460
gcggccggcg tgccggtgct gtacaccgcg cagcccggcg catgagccg caggaccgc   32520 gggttgctgc acgacctgtg ggccccggc atgagcagcg ccgaggacga ccggggcatc   32580
gtcgacgacg tcgccccgca gccgggcgac acggtgctga ccaagtggcg ctacagcgcg   32640
ttcttccgca gcgacctgga ggagcgactg cgcggtgcgg gacgggacca gctcgtggtc   32700
tgcggcgtgt acgcgcacat ggggtgcctg atcaccgcct gcgacgcgtt cagccgcgac   32760
atcgaggcgt tcctggtggc ggacgcgctg gccgacctat cgcgcgagga ccacctgatg   32820
gcgctgcgct acgccgcgga ccgctgcgcg gtgccgttgt ggacggcgga tgtgctggac   32880
gggctggcgg acgccgccgg gcgtccggat cagagcagca cccaacgatg aggagaacat   32940
cgatgtcgga tcggacccgg gtcgtggtcg tcggcggaac ctcggggatc gggcggcact   33000
tcgcccgatt ctgcgccgaa cgcggagacg acgtggtgat caccggccgt tcggcggccc   33060
ggaccaagac cgtggcggac gagatcgcg ggcggacccg tgggctcgct ctcgacctgg   33120
ccgagccgga gacgatcgcg gacgcgctcg ccgacgtgcc gcacgtcgac cggctcgtgg   33180
tcgcggcgct ggaccgcgac tacaacaccg tccgcgcgta ccggccgggc gacgcggcgc   33240
ggctgctgac cgtcaagctg gtcggctaca cggcggtcct gcacgccctc gccccgcgga   33300
tgaccgacga gagcgcagtc gtgctgctcg gcggcctggc cagccaccgg ccgtatcccg   33360
gctccacctc cgtcacgacc gccaacggcg ggatcagcgc gctggtgcgg accctggctg   33420
tggaactctc gccggtccgg gtcaacgccc tgcacccgag catcgtctcc gacacgccgt   33480
tctggagcga caagcccgcc gcgcgggagg ccgccgcgac ccgcgcgctc agccgacggc   33540
cggtcaccat gcaggactgc gccgaggcga tcgacttcct gctgacgaac cgctcgataa   33600
acggggtcaa cctgaacatc gacggcgggg acgtgctcat ctgacgccgg aggcgatccg   33660
ccacggcccc caccacccgg tcgcgccctg cccgtgctcc cgctgctcgc ggggtaccg   33720 ggccaggtcg cgggcggaga agagcgccat gccggcgtgg aatccggtca ccggcaccgg   33780
gacccgcgcc cagtaggcga gccggccgtc gacgtggaac tccacctccg acgtcggcgc   33840
ccggtaggtg atggcgtatc cgtgcgcccg gcccggctcc gtcggcacgt ccaggaccac   33900
ccggtggatg tagtgctcgt gcggctgggt cacgccgggc agcaccaggc gctcgaccgt   33960
cgcgtacacg gtgtcgttcg tggcggcggc gttgaacacg acgccggtct ccaggtcgaa   34020
caggttcacc gtgccgaacg cgtccagcag gtcgtgcggg atctgccggt acgtccgcac   34080
gcccatctcc acctcgacgg tcagcgagcc ctccgccggc acggcgaagc gccgcaccga   34140
ccggtacatc tgcttggcgt tgttctgccg gggatcggtg tcgtggaagc gggtgaacgg   34200
gtcgacggtc agctccagcc gccgtcgcc ggtgcggacc tgggcgttgc ggtcctggta   34260
cctgtgggtc tgcccgtccg cgccggcgat cgacatgatc gcccagcggg cggggtccag   34320
```

-continued

```
ctcgcggctg gtgaagtcgt cgtacgtcca cgcgctggtt ctcagtgccg acgtcatgca    34380
gtcaccatcg gacgccggcc gggcgcgggc atcacccgtt cacgcggttc ggccggaccc    34440
ggcacgccaa tgcgccggcc acgccccgga aatcccgtga ttaagccatg ccggagcgtg    34500
aacggtcgcc gagactgacg ccgcacccat ctccgcatcg tctgcgacgt tctcaccagg    34560
gggagagagc aatggacacg gcagctccgg caacggacgg cggtcgctac ctcgccgtcc    34620
atcacagcgc agagttcagg gaactacggc gacgatcgag cacgttcacg ctctgggcca    34680
gcgtcgcctt cttcggctgg tggttcctcg gcagcctgct cgccacctac gcgccggact    34740
tcttccggga aaggtggcc ggcccggtca acgtgggtct gctcttcgtc ttcctgtcgt    34800
tcgccttcgt ggtgacgctc gccgccttct acctgcgtta cgcccgcacg catctcgatc    34860
cgctcagcga aagatccgt gccgacctgg aaggagcgtc ccgatgagcg tcatcctcgc    34920
cgacccgcca ccccggtcg acaacacgtg ggcgacgccc gcgatcgccg tgccggtcac    34980
catcgtcctc gcgctcgcgg tgctctacct ggtccggtcg gcgcgcgcca gcaccaccac    35040
cgcggacggg ttcctgctgg ccgaccggcg gatcggccg gtgcagaacg cgctggcggt    35100
ggcctccgcg ccgctgatgt actcgacgat gtacatcatc accggccaca tcgcgctcag    35160
cggctacgac gccatcctgc tgatgaccgc cttcaccatg ggcaccatgc tcgcgctgtt    35220
cctcttcgcc gggccggtgc gcaacgtggg cggctacacg ctcggtgacc tgctcgcggt    35280
ccgtacccgg gagcggccgg cgcggatcgc gtcggcggtg ctcacgctgc tgacgtacgt    35340
catgctgacg gtgatcatga tggccgccat cgcgttcatc ttcaaccgct ggttcggcgt    35400
cgacgccctc gtcggcctgg tcctcccggt gttcgtcgtc ggtctgatca cggtggggta    35460
cgtgtacctc ggcgggatgc tcggggtcac ccgcatcctg gtgttcaagc tggtgctgtc    35520
ggtggtcgtc gtgggcgtgc tgaccgcctg ggtgctggcc cgcttcgacc tgaacctctt    35580
cagcctgctg gagcgggccg aggcgaacgc ggcgccggtg cccagcggca gcgacctgct    35640
gggcccgggc cggctgttcg gcgagggcgc gaccacgctc gtgcacctgt cgaagctgtt    35700
cgccatcgcc gtcggagtgg cggccattcc gttcctgttc atgcgcaact tcgcggtgac    35760
cagcgggcgg gacgcgcgcc ggtcgaccgg gtgggcgtcg atgatcatcg tcgggttcta    35820
cctgtgcctg tccgtcgtcg ggctcggtgc cgtcgcgatc ctcggccggg acaacatcgg    35880
cgtcatcaag gccaccgcg acatcagctt ccccaagctc gccgacgagc tcggcggtcc    35940
ggtgatggtc ggctccctgg ccggcgtcgc ggtcctgacg atcgtcggcg tcttcgcgcc    36000
gctgctgcac agcgccgtga cgacggtgac caaggacctg aacgtgatcc gcggccggcg    36060
gctggatccg gccgccgagc tgcgggacat caagcgcaac accctgatca tcggcgtcgg    36120
ctccgtgctg ctggcggtcg tgatgctgcc ggtacggacc cacatcttca tcccgacctc    36180
gatcgacatt gccggcgcgg tggtcctgcc gatcgtcgtc tacgcgttgt tctgcgcgg    36240
tttcaacacc cgcggactgc agtggacggt ctacggcggc ctcgcgctca ccgcgttcct    36300
ggtgctgttc tccaacggtg tctcgggcga gccggacgcc atcttcccgg accgcaactt    36360
caagttcgtg gacgtcgagc ccgcgctgat cacggtgccg gtcggcttcc tgctcggcta    36420
cctcggctcg atcaccagcc gggagcgcga cgacgccgcg ttcgccgaga tgcaggtccg    36480
gtccctcacc ggagctgtcg tcacgggacc gccgcggccg gccgccgtgg acgacaggga    36540
ccgcgacggc cgccaggacc gggcgcccag cccggtgagc tgaacatccg caacggtgtg    36600
gg                                                                   36602
```

```
<210> SEQ ID NO 2
<211> LENGTH: 571
<212> TYPE: PRT
<213> ORGANISM: Micromonospora sp. strain 046-ECO11

<400> SEQUENCE: 2

Val His Asn Leu Asp Asn Ile Pro Ser Ser Pro Ser Thr Ser Gly Gly
1               5                   10                  15

Ser Leu Pro Ala Gly His Arg Ala His Val Arg Ala Asp Gly Val Arg
            20                  25                  30

Val Val Arg Gly Gly Arg Val Val Leu Ser Asp Val Ser Val Thr Val
        35                  40                  45

Ser Ala Ala Ser Arg Leu Ala Val Val Gly Glu Asn Gly Arg Gly Lys
    50                  55                  60

Thr Thr Leu Leu His Val Leu Ala Gly Leu Ile Ala Pro Asp Gln Gly
65                  70                  75                  80

Val Val Glu Arg Leu Gly Thr Ile Gly Val Ala Arg Gln Asn Leu Glu
                85                  90                  95

Ser Arg His Gly Glu Thr Val Gly Thr Leu Val Arg Glu Ala Ile Arg
            100                 105                 110

Glu Ser Glu Arg Ala Leu Arg Ala Leu Asp Glu Ala Thr Ile Ala Leu
        115                 120                 125

Thr Glu Gly Arg Ala Gly Ala Asp Asp Ala Tyr Ala Ala Leu Asp
    130                 135                 140

Ala Ala Thr Arg Leu Asp Ala Trp Asp Ala Gln Arg Arg Val Asp Val
145                 150                 155                 160

Ala Leu Ala Gly Leu Asp Ala Cys Pro Asp Arg Asp Arg Gln Leu Ala
                165                 170                 175

Thr Leu Ser Val Gly Gln Arg Tyr Arg Val Arg Leu Ala Cys Leu Leu
            180                 185                 190

Gly Ala Arg Val Asp Leu Leu Met Leu Asp Glu Pro Thr Asn His Leu
        195                 200                 205

Asp Ala Asp Ser Leu Ala Phe Leu Thr Ala Arg Leu Arg Asp His Pro
    210                 215                 220

Gly Gly Val Val Leu Val Thr His Asp Arg Ala Leu Leu Arg Asp Val
225                 230                 235                 240

Ala Thr Glu Phe Leu Asp Leu Asp Pro Ser Ala Asp Gly Arg Pro Arg
                245                 250                 255

Arg Tyr Ala Gly Asp Tyr Val Ala Trp Gln Asp Gly Arg Arg Asp
            260                 265                 270

Phe Ala His Trp Val Arg Asp His Glu Ala Gln Gln Ala Glu His Gln
    275                 280                 285

Arg Leu Ala Asp Gly Val Arg Glu Ala Arg Asp Arg Leu Ser Thr Gly
290                 295                 300

Trp Arg Pro Glu Lys Gly His Gly Lys His Gln Arg Gln Ser Arg Ala
305                 310                 315                 320

Pro Gly Leu Val Gln Ala Leu Arg Arg Gln Glu Ala Leu Asp Ala
                325                 330                 335

His Arg Val Thr Val Pro Glu Pro Pro Gln Pro Leu Arg Trp Pro Pro
            340                 345                 350

Leu Asp Thr Arg Ala Gly Leu Pro Ile Leu Arg Cys His Asp Val Thr
        355                 360                 365

Val Ala Gly Arg Leu Arg Thr Arg Val Thr Leu Thr Leu Asp Gly Gly
    370                 375                 380
```

```
Asp Arg Leu Leu Val Thr Gly Pro Asn Gly Ala Gly Lys Ser Thr Leu
385                 390                 395                 400

Leu Ser Val Leu Ala Gly Asp Leu Thr Pro Ser Thr Gly Glu Val Arg
            405                 410                 415

His Leu Ser Gly Ala Arg Val Ala Tyr Leu Gly Gln Glu Val Pro Asp
        420                 425                 430

Trp Pro Pro Ala Leu Leu Ala His Asp Leu Tyr Glu Gln His Val Gly
            435                 440                 445

Arg Leu Arg Ser Ser Gly Arg Val Gly Ser Gly Thr Ala Leu Pro Leu
    450                 455                 460

Ser Ala Thr Asn Leu Leu Asp Ala Glu Ala Arg Arg Thr Pro Val Gly
465                 470                 475                 480

Arg Met Ser His Gly Gln Gln Arg Arg Leu Asn Leu Ala Leu Arg Leu
            485                 490                 495

Ala Glu Arg Pro Asp Leu Leu Ile Leu Asp Glu Pro Thr Asn His Leu
        500                 505                 510

Ser Ala Pro Leu Val Asp Asp Leu Thr Ala Ala Leu Leu Thr Thr Arg
    515                 520                 525

Ala Ala Val Val Val Ala Thr His Asp Arg Gln Met Leu Gln Asp Leu
530                 535                 540

Ala Ala Trp Pro Thr Leu Pro Leu Thr Ala Pro Ala Ala Ser Gly Arg
545                 550                 555                 560

Ser Val Thr Ser Glu Arg Tyr Asp Trp Glu Ser
            565                 570

<210> SEQ ID NO 3
<211> LENGTH: 1716
<212> TYPE: DNA
<213> ORGANISM: Micromonospora sp. strain 046-ECO11

<400> SEQUENCE: 3
gtgcacaacc tcgacaacat tccttcctcc ccatccacct cgggcggttc gctgcccgcc    60
gggcaccggg cgcacgtgcg ggccgacggc gtccgcgtcg tacgcggcgg ccgggtcgtg   120
ctgtccgacg tcagcgtgac cgtctccgcc gcttcccgcc tcgcagtcgt cggcgagaac   180
ggccgcggca agaccaccct gctgcacgtg ctggccggcc tcatcgcgcc cgaccagggc   240
gtggtggaac ggctgggcac gatcggcgtc gcccggcaga acctggagtc gcgccacggc   300
gagacagtgg gcacgctcgt ccgggaggcg atccgggagt ccgaacgcgc gctgcgggcg   360
ctcgacgagg cgacgatcgc gctcaccgag ggccgggcgg gcgcggacga cgcgtacgcg   420
gccgcgctcg acgcggcgac ccggctggac gcctgggacg cgcagcggcg cgtcgacgtg   480
gcgctggccg gcctcgacgc gtgcccggac cgggaccggc agctggccac gttgtccgtc   540
ggccagcgct accgggtacg gctggcgtgc ctgctggagc gagggtcga cctgctgatg   600
ctggacgagc cgacgaacca cctcgacgcc gacagcctgg ccttcctcac cgcccggcta   660
cgcgaccacc cggcggcgt cgtgctggtg acccacgacc gcgccctgct gcgggacgtc   720
gccacggagt tcctggacct cgaccccagc gcggacgggc gcccgcgccg ctacgccggg   780
gactacgtcg cctggcagga cgggcgccgc cgcgacttcg cgcactgggt acgcgaccac   840
gaggcgcagc aggccgagca ccagcggctg gccgacgggg tacgggaggc gcgggaccgg   900
ctcagcaccg gctggcggcc ggagaagggg cacggcaagc accagcgcca gtcccgcgcg   960
cccggactgg tccaggcgct gcgccgccgg caggaggcgc tcgacgcgca ccgcgtcacc  1020
```

-continued

```
gtgccggagc caccgcagcc gctgcgctgg ccgccgctgg acacccgtgc cggactgccc    1080
atcctgcgat gccacgacgt cacgtggcc gggcgcctgc gtacccgggt cacgctcacg     1140
ctcgacggcg gggaccgcct gctggtgacc ggacccaacg gcgcgggcaa gtcgacgctg    1200
ctctccgtgc tggccggcga cctcacgccg tcgaccgggg aggtccggca cctgtccggc    1260
gcgcgcgtcg cgtacctcgg tcaggaggtg cccgactggc cgccggcgct gctcgcgcac    1320
gacctgtacg agcagcacgt gggccggctc cgctccagcg ggcgcgtcgg ctccggcacg    1380
gccctgccgc tgagcgcgac gaacctgctc gacgccgagg cccggcgtac ccccgtcggc    1440
cggatgtcgc acggacagca acggcggctg aacctggcgc tgcgcctggc cgaacgtccc    1500
gacctgctga tcctcgacga accgacgaac cacctgtcgg cgccgctggt cgacgacctc    1560
accgccgccc tgctgacgac ccgggcggcg gtggtcgtcg ccacccacga ccggcagatg    1620
ctccaggacc tcgcggcctg gcccacgctg ccgctcacag ccccggcggc gtcaggtcgt    1680
tcggtcactt ccgagcgata tgactgggag tcataa                              1716
```

<210> SEQ ID NO 4
<211> LENGTH: 689
<212> TYPE: PRT
<213> ORGANISM: Micromonospora sp. strain 046-ECO11

<400> SEQUENCE: 4

```
Met Thr Thr Gly Arg Pro Gly Glu Asn Arg Ala Thr Asp Ala Ala Arg
  1               5                  10                  15

Asn Pro Gly Trp Ala Ala Gly Gly Pro Ala Ser Gln Pro Trp Gly Gly
             20                  25                  30

Gly Asn Asp Glu Gln Val Leu Arg Glu Ile Leu Gly Val Asp Val His
         35                  40                  45

Arg Glu Leu Ile Asp Phe Ala Gly Ala Gly Gly Asn Pro His Leu
     50                  55                  60

Val Ala Glu Leu Ala Arg Gly Leu Ala Glu Glu Gly Leu Ile Arg Glu
 65                  70                  75                  80

Thr Asn Gly Arg Ala Glu Leu Val Ser Arg Arg Ile Pro Arg Arg Val
                 85                  90                  95

Leu Ser Phe Val Met Arg Arg Leu Asn Asp Val Ser Ala Gly Cys Gln
            100                 105                 110

Gln Phe Leu Lys Val Ala Ala Leu Gly Arg Ser Phe Met Leu Glu
        115                 120                 125

Asp Val Ser Arg Met Leu Gly Arg Ser Ser Ala Ala Leu Leu Pro Pro
    130                 135                 140

Val Asp Glu Ala Ile Ala Ser Gly Phe Val Val Ala Ala Glu His Gln
145                 150                 155                 160

Leu Ala Phe Gln Ser Asp Phe Leu Leu Arg Gly Ile Ile Glu Ser Ile
                165                 170                 175

Pro Gly Pro Ala Arg Asp Ala Leu Arg Arg Glu Ala Met Ser Leu Ser
            180                 185                 190

Gly Arg Arg Arg Pro Ala Ala Asp Gln Asn Arg Leu Asp Ala Ala
        195                 200                 205

Pro Thr Ala Pro Val Ser Ala Thr Gly Glu Asp Ala Thr Gly Ser Cys
    210                 215                 220

Ser Arg Ala His Arg Leu Ile Met Asn Gly Asn Ala Lys Ala Gly Ile
225                 230                 235                 240

Arg Val Ala Glu Ala Val Leu Ala Gly Pro Ala Ser Leu Ala Ala
                245                 250                 255
```

-continued

```
Arg Arg Asp Ala Glu Ala Cys Leu Val Leu Ala Asp Leu Leu Leu Gly
            260                 265                 270

Gly Glu Gly Gly Gly Pro Met Thr Glu Ala Ile Leu Arg Glu Arg Asp
            275                 280                 285

Ala Glu Ser Gly Asp Ala Ala Leu Ala Met Ala Leu Thr Ala Arg Ser
            290                 295                 300

Thr Gly Leu Trp Ser Ala Gly Lys Leu Ala Glu Gly Leu Lys Leu Gly
305                 310                 315                 320

Arg Ala Ala Val Arg Ala Gly Ala Glu Ala Pro Val Trp Arg Leu
                    325                 330                 335

His Ala Gln Leu Ala Leu Ala Gly Lys Leu Ala Asn Leu Arg Glu Phe
            340                 345                 350

Asp Glu Ala Glu Ala Leu Ile Asn Glu Ala Glu Ala Gly Leu Arg Gly
            355                 360                 365

Leu Pro Ala Pro Ile Trp Thr Ala Ala Thr Ala Val Met Arg Ser Arg
            370                 375                 380

Leu Leu Leu Gln Ala Gly Arg Ile Gly Glu Ala Arg Arg Glu Ala Ala
385                 390                 395                 400

Leu Ala Thr Thr Ala Val Glu Gly Asp Ala Val Pro Met Leu Arg Pro
                    405                 410                 415

Leu Ala Tyr Ala Val Leu Ser Thr Ala Ser Phe Tyr Met Gly Asp Leu
            420                 425                 430

Pro Ala Ala Ile Glu Tyr Leu Arg Arg Gly Gln Arg Asp Ala Asp Arg
            435                 440                 445

His Val Val Leu Asp Ser Val Gln Tyr Ser Trp Ala Glu Val Leu Ile
            450                 455                 460

Thr Val Lys Gln Glu Gly Pro Arg Ala Ala Ala Gln Leu Leu Ala Gly
465                 470                 475                 480

Lys His His Arg Leu Pro Thr Gln Arg Arg Leu Tyr Val Glu Val Pro
                    485                 490                 495

Ser Ala Ala Ala Phe Leu Val Leu Leu Ala Arg Asp Val Asp Asp Arg
            500                 505                 510

Asp Leu Glu Arg Arg Val Leu Asp Thr Val Asn Gly Leu Ala Ala Asp
            515                 520                 525

Asn Pro Arg Ile Gln Val Val Ser Leu Thr Ala Met His Ala His Ala
            530                 535                 540

Leu Ala Asn Ser Ala Pro Ala Ala Leu Ala Leu Ile Ile Val Gln Ser
545                 550                 555                 560

Arg Asp Pro Ile Ser Val Ala Leu Ala Thr Glu Glu Leu Ala Lys Leu
                    565                 570                 575

Tyr Ala Ala Gln Ala Gln Ala Gly Gly Arg Pro Ala Thr Pro Ala Arg
            580                 585                 590

Ala Glu Glu Ala Ala Thr Pro Pro Ala Ser Cys Trp Ser Thr Leu Ser
            595                 600                 605

Asp Met Glu Gln Arg Ile Ala Tyr Leu Val Ser Val Gly Leu Thr Asn
            610                 615                 620

Arg Gln Ile Ala Lys Gln Val His Leu Ser Ala His Thr Val Asn Tyr
625                 630                 635                 640

His Leu Arg Lys Ile Tyr Arg Lys Leu Gly Phe Asn Thr Arg Ala Glu
                    645                 650                 655

Leu Ala His Ala Ala Ala Thr Tyr Ser Gly Arg Ala Ala Ile Tyr Ser
            660                 665                 670
```

Met Ser Gly Asp Gln Asp Trp Gly Ala Gly Ser Met Thr Gly Lys Ala
    675                 680                 685
Ser

<210> SEQ ID NO 5
<211> LENGTH: 2070
<212> TYPE: DNA
<213> ORGANISM: Micromonospora sp. strain 046-ECO11

<400> SEQUENCE: 5

| | | | | |
|---|---|---|---|---|
| atgacaacgg | gacggccggg | ggagaaccgg | gcgacagacg | cggcacgaaa | tccggggtgg | 60 |
| gccgccgggg | ggccggcgtc | ccagccatgg | ggcgggggga | acgacgagca | ggtcctgcgc | 120 |
| gagatcctcg | gggtcgacgt | gcaccgcgag | ctgattgact | tcgcgggtgg | tgccggcgga | 180 |
| aatccgcacc | tggtcgccga | actcgcgcgc | gggctcgccg | aagagggatt | gattcgggag | 240 |
| acaaacggtc | gggcggaatt | ggtgtcccgg | cgaattcccc | ggcgcgtgct | gagttttgtc | 300 |
| atgcgtcgat | tgaatgatgt | cagcgccggc | tgccagcagt | tcttgaaggt | tgccgcggca | 360 |
| ttgggcagat | ccttcatgct | ggaggacgtt | tcgagaatgc | tgggccgatc | gtcggcggcc | 420 |
| ctgctcccgc | cggtggacga | ggcgatcgca | tcgggcttcg | tcgtcgccgc | cgagcatcaa | 480 |
| ctcgcctttc | agagcgactt | cctgctgcgc | ggcatcatcg | agtccattcc | cgggcccgcc | 540 |
| cgcgacgcct | tacgacgtga | ggcgatgagc | ctttccgggc | gacggcgccc | ggcggccgac | 600 |
| cagaatcgcc | ggttggacgc | ggcgcctacc | gcgccggtga | gcgcgaccgg | ggaggacgcc | 660 |
| accggatcct | gttcccgggc | gcaccgcctg | ataatgaacg | ggaacgcgaa | ggccggcatt | 720 |
| cgcgtcgccg | aggcggttct | cgccggcccg | gccgcgtcgc | tcgctgcccg | gcgtgacgcg | 780 |
| gaggcgtgtc | tggtgctggc | cgatctgctg | ctcggcgggg | agggcggcgg | cccgatgacc | 840 |
| gaggcgatcc | tgcgcgaacg | cgacgccgag | tccggtgacg | ccgcactggc | gatggcgctg | 900 |
| accgcccggt | ccaccgggct | gtggtcggcg | ggaaagctgg | cggagggcct | gaagctggga | 960 |
| cgggcggcgg | tgcgggcggg | cgcggaggcc | gaaccggtgt | ggcgtctgca | cgcccagctc | 1020 |
| gcgctcgccg | ggaaactcgc | gaacctccgc | gagttcgacg | aggccgaggc | gttgatcaac | 1080 |
| gaggcggaag | cgggcctgcg | cggactgccc | gcgccgatct | ggacggccgc | gacggcggtg | 1140 |
| atgcggtccc | ggttgctgct | ccaggcgggg | cggatcgggg | aggcgcgtcg | ggaggcggcg | 1200 |
| ctggccacca | ccgccgtgga | ggggacgcg | gtgccgatgc | tgcggcctct | cgcctacgcg | 1260 |
| gtgctcagca | ccgcctcctt | ctacatgggg | gacctgcccg | ccgcgatcga | gtacctcagg | 1320 |
| cgggggcagc | gggacgcgga | ccgccacgtg | gtcctcgact | cggtgcagta | ctcgtgggcg | 1380 |
| gaagtgctga | tcacggtcaa | gcaggaaggc | ccgcgggccg | ccgcccagct | gctcgcgggc | 1440 |
| aagcaccacc | gcctgcccac | gcagcgccgc | ctctacgtcg | aggtgccgag | cgccgccgcc | 1500 |
| ttcctggtcc | tgctcgcccg | cgacgtggac | gaccgtgacc | tcgaacgccg | cgtcctcgac | 1560 |
| acggtcaacg | ggctcgccgc | ggacaacccc | aggatccagg | tcgtcagcct | caccgccatg | 1620 |
| cacgcccacg | cgctggcgaa | cagcgctccg | gccgccctgg | cgctcatcat | cgtgcagtca | 1680 |
| cgggacccga | tctcggtggc | gctggccacc | gaggaactcg | ccaagctcta | cgccgcgcag | 1740 |
| gcccaggcgg | ggggacggcc | ggcgacgccg | gcccgcgccg | aggaggccgc | caccccgccg | 1800 |
| gcgagctgct | ggtcgaccct | gtccgacatg | gagcagcgga | tcgcctacct | ggtgagcgtg | 1860 |
| ggtctgacga | accggcagat | cgccaagcag | gtccacctgt | ccgcgcacac | cgtcaactac | 1920 |
| cacctgcgga | agatctaccg | gaaactgggt | ttcaacaccc | gggccgagct | ggcgcacgcc | 1980 |

```
gcggccacgt actccggccg ggcggcgatc tactccatga gcggcgacca ggactggggc    2040
gccggatcca tgaccggcaa ggccagctga                                     2070
```

<210> SEQ ID NO 6
<211> LENGTH: 895
<212> TYPE: PRT
<213> ORGANISM: Micromonospora sp. strain 046-ECO11

<400> SEQUENCE: 6

```
Met Val Ile Met Asn Arg Met Ala Gly Arg Gly Gln Glu Leu Ser Ser
 1               5                  10                  15

Leu Gly Glu Leu Leu Asp Ala Thr Met Arg Gly Ser Gly Gly Cys Val
            20                  25                  30

Val Val Asp Gly Pro Phe Gly Ile Gly Lys Thr His Leu Leu Lys Val
        35                  40                  45

Thr Gly Leu Glu Ala Ala Ala Arg Gly Leu Thr Val Val Ala Gly Arg
    50                  55                  60

Ala Ser Val Thr Asp Gln Pro Val Pro Val His Leu Leu Val Asn Phe
65                  70                  75                  80

Leu Arg His Ala Met Pro Gly Glu Ala Ala Val Glu Gln Leu Ala Leu
                85                  90                  95

Pro Gly Ala Asn Pro Phe Trp Leu Ile Asp Arg Val Gly Asp Leu Val
            100                 105                 110

Glu Val Ala Ala Arg Arg Pro Leu Val Val Ala Leu Asp Asp Ala
        115                 120                 125

Gln Arg Ile Asp Asp Val Ser Ala Leu Ala Leu Arg Gly Leu Val Pro
    130                 135                 140

Arg Leu Ala Ser Ser Pro Val Leu Trp Leu Leu Ala Arg Arg Pro Val
145                 150                 155                 160

Ala Ala Gly Ser Ile Ala Gln His Ala Val Asp Trp Leu Ala Glu His
                165                 170                 175

Val Ala Val Arg Val Arg Leu Arg Glu Pro Gly Glu Glu Ala Val Ala
            180                 185                 190

Asp Leu Cys Ala Gly Ile Leu Gly Ala Arg Pro Asp Ala Ser Val Leu
        195                 200                 205

Arg Trp Ala Ala Arg Cys Gly Gly Asn Pro Lys Val Met Glu Ile Val
    210                 215                 220

Phe Ser Ala Phe Ile Lys Ala Gly Gln Met Ile Ile Val Asp Gly Ala
225                 230                 235                 240

Ala Ser Val Val Ser Asp Glu Leu Pro Asp Gly Val Leu Ala Ala Val
                245                 250                 255

Arg Gly Leu Leu Glu Glu Leu Pro Pro Leu Arg Arg Leu Leu Ala
            260                 265                 270

Ala Gly Gly Arg Leu Gly His Thr Phe Pro Val Asp Arg Val Thr Gly
        275                 280                 285

Leu Leu Asp Gly Ser Ala Ala Asp Val Ser Ala Ala Ile Asp Glu Ala
    290                 295                 300

Val Arg Val Gly Leu Ile Arg Arg Asp Gly Ala Glu Leu Thr Phe Ala
305                 310                 315                 320

His Pro Val Leu Gly Glu Ala Leu Arg His Ala Ala Tyr Pro Glu Pro
                325                 330                 335

Glu Arg Ala Glu Pro Gly Ser Ala Pro Ala Pro Ala Ala Gly Asp Pro
            340                 345                 350

Val Arg Arg Gly Arg Pro Asp Pro Arg Pro Gly Thr Pro His Ser Pro
```

-continued

```
            355                 360                 365
Ala Gly Val Arg Val Thr Arg Ser Ala Pro Asp Ala Thr Pro Ala
    370                 375                 380
Ala Thr Ala Gly Pro Arg Ser Gly Arg Cys Gly Cys Asp Asp Val Ala
385                 390                 395                 400
Ala Ala Ala Val Ser His Leu Glu Asn Gly Ser Ala Glu Ala Pro Arg
                405                 410                 415
Ala Leu Ala Arg Ala Leu Arg Leu Leu Ala Gly Ala Gly Arg Ala Ala
                420                 425                 430
Glu Ala Gly Arg Leu Ala Glu Val Met Leu Arg Arg Asp Leu Ala Ala
                435                 440                 445
Asp Val Glu Ala Gln Leu Val Leu Glu Leu Gly His Gly Met Arg Ala
450                 455                 460
Ala Gly Ser His Arg Leu Ala Ala Gly Phe Leu Arg Arg Thr Gln Ala
465                 470                 475                 480
Arg His Asp Val Cys Glu Leu Asp Arg Ala Lys Leu Asp Arg Ala Leu
                485                 490                 495
Ala Asp Thr Thr Lys His Leu Gly Gly Ala Ser Ser Ala Glu Leu Glu
                500                 505                 510
Pro Arg His Gln Ser Pro Gly Cys Ala Pro Gly Arg Arg Pro Leu Trp
                515                 520                 525
Thr Trp Leu Val Arg Ala Leu Gly Ala Ala Asp Gln Leu Asp Glu Ala
                530                 535                 540
Gln Ala Val Leu Asp Thr Val Arg Pro Leu Ala Gln Glu Pro Ser His
545                 550                 555                 560
Thr Gly Ser Glu Ser Leu Trp Arg Gly His Arg Ala Glu Leu Leu Ala
                565                 570                 575
Ala Ala Gly Arg Leu Asp Glu Ala Arg Ala Glu Ala Glu Ala Ala Leu
                580                 585                 590
Arg Ala Ala Asp His Ser Arg Pro Gly Asp Cys Val Pro Ala Arg Leu
                595                 600                 605
Val Leu Ala His Leu Gly Val His His Gly Asp Leu Ala Thr Ala Ser
                610                 615                 620
Asp Gln Leu Arg Ala Ala Glu Arg Leu Ala Ser Ala Asp Asp Ser Ala
625                 630                 635                 640
Arg Met Asp Trp Ala Leu Ala Arg Phe His Ala Ala Ser Gly Arg Pro
                645                 650                 655
Ala Met Met Val Gln Thr Leu Ile Asn Val Ala Gly Gln Val Ala Pro
                660                 665                 670
Asp Pro Leu Leu Phe Thr Glu Ala Pro Ala Ala Ala Thr Leu Val
                675                 680                 685
Arg Gln Ala Arg Arg Ala Gly Leu Asp Ala Glu Ala Glu Arg Ala Val
                690                 695                 700
Glu Val Ala Arg Arg Val Ala Arg Gly Asn Pro Phe Val Gln Ser Leu
705                 710                 715                 720
Ala Ala Ala Ala Glu His Ala Ala Gly Leu Leu Arg Asp Asp Pro Ala
                725                 730                 735
Ala Leu Leu Arg Ala Ala Asp Leu His Arg Leu Ala Gly Arg Thr Leu
                740                 745                 750
Ala Ala Ala Gly Ala Val Glu Asp Ala Ala Arg Ser Thr Arg Asp Arg
                755                 760                 765
Ala Glu Ala Thr Arg Leu Leu Glu Ala Ala Thr Asp Gly Tyr Arg Glu
770                 775                 780
```

```
Cys Gly Ala Arg Arg Asp Leu Glu Arg Val Glu Ala Glu Leu Arg Gly
785                 790                 795                 800

Leu Pro Ala His Asn Val Arg Pro Leu Val Pro Asp Arg Pro Arg Ser
                805                 810                 815

Gly Trp Glu Ser Leu Thr Ser Ala Glu Leu Arg Val Val Arg Ala Ile
                820                 825                 830

Val Asp Gly Met Thr Asn Arg Glu Ala Ala Ser Ser Leu Phe Leu Ser
            835                 840                 845

Pro His Thr Val Asp Ser His Leu Arg Arg Val Phe Ser Lys Leu Asp
        850                 855                 860

Ile Asn Ser Arg Val Glu Leu Thr Arg Cys Phe Ile Ala His Glu Ala
865                 870                 875                 880

Val Arg Pro Ala Leu Ala Thr Thr Arg Gln Pro Ala Ser Ala Gly
                885                 890                 895

<210> SEQ ID NO 7
<211> LENGTH: 2688
<212> TYPE: DNA
<213> ORGANISM: Micromonospora sp. strain 046-ECO11

<400> SEQUENCE: 7
```

| | | | | |
|---|---|---|---|---|
| atggtcatca tgaatcgcat ggcggggcgc gggcaggaat tgtcctcatt gggggaactg | 60 |
| ctcgacgcca ccatgcgggg atccgggggc tgcgtcgtcg tcgacgggcc gttcggcatc | 120 |
| ggcaagaccc acctgctgaa ggtcaccggc ctggaggcgg cggcccgcgg gctgacagtg | 180 |
| gtggccgggc gggcaagcgt cacggatcag ccggtgcccg tacacctgct cgtcaacttc | 240 |
| ctgcgccacg cgatgcccgg cgaagcggcg gtcgagcagc tcgccctgcc gggcgccaac | 300 |
| ccgttctggc tgatcgaccg ggtcggcgat ctggtcgagg tcgggcgcg ccggcgcccg | 360 |
| ctcgtggtcg ccctggacga cgcccagcgc atcgacgacg tcagcgccct ggccctgcgc | 420 |
| gggctcgtgc gcgcctggc gtcctcgccg gtgctctggc tgctggcccg ccggccggtc | 480 |
| gccgccgggt cgatcgctca gcacgccgtc gactggctgg ccgagcacgt cgcggtacgg | 540 |
| gtacggctgc gcgagccggg cgaggaggcg gtggccgacc tgtgcgccgg catcctcggc | 600 |
| gcccggccgg acgcctccgt cctgcgctgg gcggccccgct cgcggcggcaa cccgaaggtg | 660 |
| atggagatcg tcttcagcgc gttcatcaag gccggccaga tgatcatcgt ggacggggcg | 720 |
| gcgtcggtgg tgtccgacga gctgcccgac ggtgtcctcg ccgccgttcg cgggctgctg | 780 |
| gaggagctgc gcccccgct gcggcgcctg ctcgcgcccg cggccggct cggccacacg | 840 |
| tttcccgtcg accgggtgac gggcctgctg gacggctcgg ccgccgacgt gtccgccgcg | 900 |
| atcgacgagg cggtgcgggt cggctgata cgacgcgacg cgcggagct gaccttcgcc | 960 |
| cacccggtgc tcggagaggc gcttcgccac gccgcgtacc cggaaccgga gcgtgccgag | 1020 |
| cccgatccg cgccggcacc ggcggcgggc gacccggtcc ggcgcgggcg gcccgatccg | 1080 |
| cggcccggga cgccccactc ccccgccggc gtacgcgtca cgcgctccgc gccggacgcg | 1140 |
| gccacgcccg ccgcgacggc ggggccgcgc tcgggccggt gcgggtgcga cgacgtggcg | 1200 |
| gcagccgccg tgtcccacct ggagaacgga tccgccgagg cgccacgagc actggcccgt | 1260 |
| gcgctgcgcc tgctggccgg gcggggcg ccgccgagg ccggccgcct cgcggaggtg | 1320 |
| atgctccgcc gcgacctcgc ggcggacgtc gaggcgcagc tcgtgctcga actgggacac | 1380 |
| gggatgcggg ccgccggcag ccaccgcctg cgggccggct tcctgcgccg gacgcaggcc | 1440 |
| cgccacgacg tgtgcgagct ggaccgcgcc aagctggacc gggcgctcgc ggacaccacg | 1500 |

```
aagcacctgg gcggtgcctc ctccgccgag ctggagcccc ggcaccagtc cccgggctgc   1560
gcgcccggcc ggcggccgct gtggacctgg ctggtccggg cgctgggcgc ggccgatcag   1620
ctcgacgagg cgcaggcggt gctggacacc gtacgaccgc tggcgcagga gcccagtcac   1680
accggctcgg agtcgctctg gcgcggccac cgggccgagc tgctggcagc ggccggacgg   1740
ctggacgagg cacgcgccga ggcggaggcg cgctgcgag ccgccgacca ctcccggccg    1800
ggcgactgcg tgccggcgcg cctggtcctg gcccacctcg gcgtgcacca cggtgacctc   1860
gccacggcca cgaccagtt cgggcggcc gagcggctgg cctccgccga cgactcggcg    1920
cggatggact gggcgctggc ccggttccac gctgccagcg gccgtccggc gatgatggtg   1980
cagacgctga tcaacgtcgc cggacaggtc gcacccgatc cgctgctgtt caccgaggcg   2040
ccggccgctg cggcgacgct cgtacgccag gcccgccggg cggggctcga cgcggaggcc   2100
gagcgcgccg tggaggtcgc ccggcgcgtc gcccgcggca acccgttcgt ccagtcgctg   2160
gcggcggcgg cggaacacgc cgcgggtctc ctgcgcgacg atccggcggc gctgctgcgg   2220
gccgcggatc tgcaccggct cgccggccgt acgctcgcgg cggccggcgc ggtggaggac   2280
gcggcccgca gcacccggga ccgggccgag gccacccgtc tgctcgaggc cgcgacggac   2340
ggctaccggg agtgcggcgc gcgacgcgac ctggagcgcg tggaggccga gctgcgtggc   2400
ctgccggctc acaacgtccg cccgctggtc cccgaccggc cccggtcggg gtgggagagc   2460
ctgaccagcg cggagctgcg ggtcgtgcgg gccatcgtgg acgggatgac caaccgcgag   2520
gcggcgagtt cgctgttcct gtccccgcac accgtcgaca gtcacctgcg gcgcgtcttc   2580
tccaagctcg acatcaacag ccgggtggaa ctgacccgct gcttcatcgc gcacgaggcg   2640
gtccggccgg cgctggccac cacacgccag ccggcgtccg ccggctga              2688
```

<210> SEQ ID NO 8
<211> LENGTH: 362
<212> TYPE: PRT
<213> ORGANISM: Micromonospora sp. strain 046-ECO11

<400> SEQUENCE: 8

```
Met Thr Val Gly Tyr Leu Gly Thr Val Thr Asp Ser Ala Pro Val Asp
1               5                   10                  15

Ala Ala Leu Arg Asp Phe Phe Ala Glu Arg Arg Ala Glu Ala Arg Glu
            20                  25                  30

Leu Gly Asp Asp Phe Ala Ala Leu Val Ala Glu Leu Glu Ser Tyr Val
        35                  40                  45

Leu Arg Gly Gly Lys Arg Ile Arg Pro Ala Phe Ala Trp Leu Gly Trp
    50                  55                  60

Ile Gly Ala Gly Gly Asp Pro Glu Asp Pro Val Ala Thr Ala Val Leu
65                  70                  75                  80

Asn Ala Cys Ala Gly Phe Glu Leu Leu His Ala Ser Gly Leu Ile His
                85                  90                  95

Asp Asp Ile Ile Asp Ala Ser Gln Thr Arg Arg Gly His Pro Ala Ala
            100                 105                 110

His Val Ala Tyr Ala Glu Arg His Arg Ala Arg Arg Phe Ser Gly Asp
        115                 120                 125

Pro Gly Thr Phe Gly Thr Gly Thr Ala Ile Leu Ile Gly Asp Leu Val
    130                 135                 140

Leu Ile Trp Ala Asp Val Leu Val Arg Ala Ser Gly Leu Pro Ala Asp
145                 150                 155                 160
```

-continued

```
Ala His Val Arg Val Ser Pro Val Trp Ser Ala Val Arg Ser Glu Val
            165                 170                 175
Met Tyr Gly Gln Leu Leu Asp Leu Ile Ser Gln Val Ser Arg Ser Glu
        180                 185                 190
Asp Val Asp Ala Ala Leu Arg Ile Asn Gln Tyr Lys Thr Ala Ser Tyr
    195                 200                 205
Thr Val Glu Arg Pro Leu Gln Phe Gly Ala Ala Ile Ala Gly Ala Asp
    210                 215                 220
Asp Asp Leu Phe Ala Ala Tyr Arg Ala Phe Gly Ala Asp Val Gly Ile
225                 230                 235                 240
Ala Phe Gln Leu Arg Asp Asp Leu Leu Gly Val Phe Gly Asp Pro Val
                245                 250                 255
Val Thr Gly Lys Pro Ser Gly Asp Asp Leu Arg Glu Gly Lys Arg Thr
            260                 265                 270
Val Leu Leu Ala Thr Ala Leu Lys Arg Ala Asp Glu Arg Asp Pro Asp
        275                 280                 285
Ala Ala Ala Tyr Leu Arg Ala Lys Val Gly Thr Asp Leu Ala Asp Glu
    290                 295                 300
Glu Ile Ala Arg Ile Arg Ala Ile Phe Arg Asp Val Gly Ala Val Glu
305                 310                 315                 320
Glu Ile Glu Arg Gln Ile Ser Gln Arg Thr Asp Arg Ala Leu Ala Ala
                325                 330                 335
Leu Glu Ala Ser Ser Ala Thr Ala Pro Ala Lys His Gln Leu Ala Asp
            340                 345                 350
Met Ala Ile Lys Ala Thr Gln Arg Ala Gln
        355                 360
```

<210> SEQ ID NO 9
<211> LENGTH: 1089
<212> TYPE: DNA
<213> ORGANISM: Micromonospora sp. strain 046-ECO11

<400> SEQUENCE: 9

```
atgaccgtcg gatatctcgg gacggtcacc gactcggcgc ccgtcgacgc cgcgctgcgc    60
gacttcttcg ccgagcgccg cgccgaggca cgcgagctcg gcgacgactt cgcggccctg   120
gtcgccgagc tggagagcta cgtcctgcgg ggcggcaagc gcatccggcc cgccttcgcc   180
tggctgggct ggatcggcgc cggcggcgac ccggaggacc cggtggcgac gcggtgctg    240
aacgcctgcg ccgggttcga gctgctgcac cgtccggcc tcatccacga cgacatcatc   300
gacgcgtcgc agacccgccg cggccatccc gccgcgcacg tcgcgtacgc cgaacggcat   360
cgggcgcggc gcttctccgg tgacccggga acgttcggca ccggcaccgc catcctgatc   420
ggagacctcg tcctgatctg gccgacgtc ctggtccgcg cctccggcct gccggccgac   480
gcgcacgtgc gggtctcgcc ggtgtggtcg gcggtgcgct ccgaggtcat gtacggccag   540
ctgctcgatc tgatcagcca ggtgagccgg agcgaggacg tcgacgcggc gctgcgcatc   600
aaccagtaca agaccgcgtc gtacacggtg gagcggccac tgcagttcgg cgcggcgatc   660
gccggcgcgg acgacgacct cttcgcggcc taccgcgcct tcggcgccga cgtgggtatt   720
gccttccagc tgcgcgacga cctgctcggc gtgttcggcg acccggtggt gacgggcaag   780
ccgtccggcg acgacctgcg ggagggcaag cggacggtc tgctcgccac ggcgctcaag   840
cgcgccgacg aacgggaccc ggacgcggcg gcctacctgc gggcgaaggt cggcacggac   900
ctcgcggacg aggagatcgc ccgcatccgc gccatcttcc gcgacgtcgg cgcggtcgag   960
```

-continued

```
gagatcgagc ggcagatctc gcagcgcacc gaccgggcgc tggccgcgct ggaggcgagc    1020
agcgccaccg cccccgcgaa gcatcagctc gccgacatgg cgatcaaggc cacccagcgg    1080
gcccagtga                                                            1089
```

<210> SEQ ID NO 10
<211> LENGTH: 354
<212> TYPE: PRT
<213> ORGANISM: Micromonospora sp. strain 046-ECO11

<400> SEQUENCE: 10

```
Met Ser Thr Glu Pro Val Thr Val Ala Arg Gly Val Leu Asp Gly
1               5                  10                  15

Arg Gly Asp Gly Pro Gly Arg Leu Gly Thr Gly Arg Ala His Gly Lys
            20                  25                  30

Ala Ile Leu Leu Gly Glu His Ala Val Val Tyr Gly Ala Pro Ala Leu
        35                  40                  45

Ala Val Pro Val Pro Gln Leu Thr Ala Val Ala Lys Ala Arg Arg Ala
    50                  55                  60

Gly Gly Asp Gly Gly Asp Glu Val Ser Phe Ala Ile Ala Gly Leu Glu
65                  70                  75                  80

Ser Pro Glu Val Thr Ser Leu Pro Thr Asp Gly Leu Gln His Leu Val
                85                  90                  95

Thr Glu Phe Arg Gln Arg Ala Ala Val Thr Glu Pro Met Arg Val Asp
            100                 105                 110

Val Leu Val Asp Cys Ala Ile Pro Gln Gly Arg Gly Leu Gly Ser Ser
        115                 120                 125

Ala Ala Cys Ala Arg Ala Ala Val Leu Ala Leu Ala Asp Ala Phe Asp
    130                 135                 140

Arg Arg Leu Asp Ala Ala Thr Val Phe Asp Leu Val Gln Thr Ser Glu
145                 150                 155                 160

Asn Val Ala His Gly Arg Ala Ser Gly Ile Asp Ala Leu Ala Thr Gly
                165                 170                 175

Ala Thr Ala Pro Leu Ile Phe Arg Asn Gly Val Gly Arg Glu Leu Pro
            180                 185                 190

Val Ala Met Ala Gly Ala Ala Arg Ala Ala Arg Gly Ser Gly Pro Ala
        195                 200                 205

Gly Phe Asp Ala Val Leu Val Ile Ala Asp Ser Gly Val Ser Gly Ser
    210                 215                 220

Thr Arg Asp Ala Val Glu Leu Leu Arg Gly Ala Phe Glu Arg Ser Pro
225                 230                 235                 240

Arg Thr Arg Asp Glu Phe Val Ser Arg Val Thr Ser Leu Thr Glu Ala
                245                 250                 255

Ala Ala His Asp Leu Leu Gln Gly Arg Val Ala Asp Phe Gly Ala Arg
            260                 265                 270

Leu Thr Glu Asn His Arg Leu Leu Arg Glu Val Gly Ile Ser Thr Glu
        275                 280                 285

Arg Ile Asp Arg Met Val Asp Ala Ala Leu Ala Gly Ser Pro Gly
    290                 295                 300

Ala Lys Ile Ser Gly Gly Leu Gly Gly Cys Met Ile Ala Leu Ala
305                 310                 315                 320

Arg Asp Arg Gln Glu Ser Ala Ala Val Val Arg Ser Val Gln Gln Ala
                325                 330                 335

Gly Ala Val Arg Thr Trp Thr Val Pro Met Gly Arg Phe Thr Gly His
            340                 345                 350
```

Asp Asp

<210> SEQ ID NO 11
<211> LENGTH: 1065
<212> TYPE: DNA
<213> ORGANISM: Micromonospora sp. strain 046-ECO11

<400> SEQUENCE: 11

| | | | |
|---|---|---|---|
| atgtccacgg aaccggtgac cgtcgtcgcc cgcggcgttc tcgacggccg gggtgacggg | | | 60 |
| ccgggccgcc tcggcaccgg ccgcgcccac ggcaaggcca tcctgctggg cgaacacgcc | | | 120 |
| gtcgtgtacg gcgctccggc gctcgccgtc ccggtgccgc aactgaccgc cgtggccaag | | | 180 |
| gcgcggcggg ccggcggcga cggcggcgac gaggtctcct tcgccatcgc cgggctggag | | | 240 |
| agcccggagg tgacgtcgct tccgaccgac ggcctgcaac atctggtgac ggagttccgg | | | 300 |
| cagcgggccg ccgtcaccga gccgatgcgc gtcgacgtgc tcgtggactg cgccatcccg | | | 360 |
| cagggccggg ggctcgggtc gagcgccgcc tgcgcccgcg ccgcggtgct ggccctcgcg | | | 420 |
| gacgcgttcg accgccgcct cgacgccgcc acggtgttcg atctggtgca gacctcggag | | | 480 |
| aacgtggcgc acgccgggc cagcggcatc gacgccctgg ccaccggtgc gaccgcgccg | | | 540 |
| ctgatcttcc gcaacggcgt gggccgggaa ctgccggtcg ccatggcggg cgccgcgcgt | | | 600 |
| gccgcgcgag ggtcgggccc ggccggcttc gacgcggtgc tcgtcatcgc cgacagcggc | | | 660 |
| gtcagcggca gcacccggga cgcggtggag ctgctgcggg gtgccttcga gcgctccccg | | | 720 |
| cgcacgcgcg acgagttcgt cagccgggtg accagcctga ccgaggcggc ggcgcacgac | | | 780 |
| ctgctccagg gccgggtcgc cgacttcggc gcgcggctga ccgagaacca ccggctgttg | | | 840 |
| cgcgaggtcg gcatcagcac cgaacggatc gaccggatgg tcgacgccgc gctcgcggcg | | | 900 |
| ggcagcccgg gcgccaagat cagcggcggt ggcctgggcg gctgcatgat cgcactggcc | | | 960 |
| cgggaccgcc aggaatccgc ggcggtggtg cggagcgtcc agcaggccgg cgccgtccgc | | | 1020 |
| acctggaccg tcccgatggg gaggttcacc ggccatgacg actga | | | 1065 |

<210> SEQ ID NO 12
<211> LENGTH: 346
<212> TYPE: PRT
<213> ORGANISM: Micromonospora sp. strain 046-ECO11

<400> SEQUENCE: 12

Met Thr Thr Asp His Arg Ala Glu Pro Ser Glu Pro Ala Leu Asp Arg
1               5                   10                  15

Pro Ala Thr Ala Val Ala His Pro Asn Ile Ala Leu Ile Lys Tyr Trp
            20                  25                  30

Gly Lys Arg Asp Glu Gln Leu Met Ile Pro Tyr Ala Asp Ser Leu Ser
        35                  40                  45

Met Thr Leu Asp Val Phe Pro Thr Thr Thr Val Arg Ile Asp Ser
    50                  55                  60

Gly Ala Ala Ala Asp Glu Val Val Leu Asp Gly Ser Pro Ala Asp Gly
65                  70                  75                  80

Glu Arg Arg Gln Arg Val Val Thr Phe Leu Asp Leu Val Lys Leu
            85                  90                  95

Ala Gly Arg Thr Glu Arg Ala Cys Val Asp Thr Arg Asn Ser Val Pro
            100                 105                 110

Thr Gly Ala Gly Leu Ala Ser Ser Ala Ser Gly Phe Ala Ala Leu Ala
        115                 120                 125

```
Leu Ala Gly Ala Ala Ala Tyr Gly Leu Asp Leu Asp Thr Thr Ala Leu
    130                 135                 140
Ser Arg Leu Ala Arg Arg Gly Ser Val Ser Ala Ser Arg Ser Val Phe
145                 150                 155                 160
Gly Gly Phe Ala Met Cys His Ala Gly Pro Gly Ala Gly Thr Ala Ala
                165                 170                 175
Asp Leu Gly Ser Tyr Ala Glu Pro Val Pro Val Ala Pro Leu Asp Val
            180                 185                 190
Ala Leu Val Ile Ala Ile Val Asp Ala Gly Pro Lys Ala Val Ser Ser
        195                 200                 205
Arg Glu Gly Met Arg Arg Thr Val Arg Thr Ser Pro Leu Tyr Gln Ser
    210                 215                 220
Trp Val Ala Ser Gly Arg Ala Asp Leu Ala Glu Met Arg Ala Ala Leu
225                 230                 235                 240
Leu Gln Gly Asp Leu Asp Ala Val Gly Glu Ile Ala Glu Arg Asn Ala
                245                 250                 255
Leu Gly Met His Ala Thr Met Leu Ala Ala Arg Pro Ala Val Arg Tyr
            260                 265                 270
Leu Ala Pro Val Thr Val Ala Val Leu Asp Ser Val Leu Arg Leu Arg
        275                 280                 285
Ala Asp Gly Val Ser Ala Tyr Ala Thr Met Asp Ala Gly Pro Asn Val
    290                 295                 300
Lys Val Leu Cys Arg Arg Ala Asp Ala Asp Arg Val Ala Asp Thr Leu
305                 310                 315                 320
Arg Asp Ala Ala Pro Ser Cys Ala Val Val Val Ala Gly Pro Gly Pro
                325                 330                 335
Ala Ala Arg Pro Asp Pro Gly Ser Arg Pro
            340                 345

<210> SEQ ID NO 13
<211> LENGTH: 1041
<212> TYPE: DNA
<213> ORGANISM: Micromonospora sp. strain 046-ECO11

<400> SEQUENCE: 13
atgacgactg accaccgggc ggagccgtcc gagccggcgc tcgaccggcc cgcgaccgcc      60
gtggcccatc cgaacatcgc gctgatcaag tactggggca agcgcgacga gcagctgatg     120
atcccgtacg ccgacagcct gtcgatgacg ctcgacgtct tcccgaccac caccaccgtc     180
cggatcgaca gcggcgcggc ggccgacgag gtcgtcctcg acggctcgcc cgccgacggc     240
gaacggcgac agcgcgtcgt caccttcctg gacctggtac gcaagctggc cgggcgcacg     300
gaacgggcct gcgtcgacac ccgcaactcc gtgcccaccg cgccggcct ggcgtcctcg      360 gcgagcggat tcgccgccct cgccctcgcc ggcgccgccg cgtacggcct cgacctggac     420
accaccgcgc tgtcccgcct ggccggcgg ggatccgtgt cggcctcccg gtcggtcttc      480
ggcggcttcg cgatgtgcca cgcaggcccc ggcgccggga ccgccgcgga cctcggctcc     540
tacgccgagc cggtgcccgt cgcgcccctc gacgtcgcgc tggtgatcgc gatcgtcgac     600
gccgggccga aggcggtgtc gagccgcgag gggatgcggc gaaccgtccg gacctccccg     660
ctctatcagt cgtgggtcgc ctccggccgc gccgacctgg ccgagatgcg ggccgcgctg     720
ctccagggag acctggacgc ggtcggcgag atcgccgaac gcaacgccct cggcatgcac     780
gccaccatgc tggccgcccg gccggcggtg cgctacctgg cgccggtcac tgtcgccgtg     840
ctcgacagcg tgctgcgcct gcgcgccgac ggcgtctccg cctacgccac gatggacgcg     900
```

-continued

```
ggaccgaacg tcaaggtgct ctgccgccgc gcggacgccg accgggtcgc cgacaccctg    960
cgcgacgccg cgccgagctg cgccgtggtc gtcgccggac cggggccggc ggcccggccg   1020
gacccgggca gccggccgtg a                                             1041
```

<210> SEQ ID NO 14
<211> LENGTH: 369
<212> TYPE: PRT
<213> ORGANISM: Micromonospora sp. strain 046-ECO11

<400> SEQUENCE: 14

| Val | Thr | Gly | Pro | Gly | Ala | Val | Arg | Arg | His | Ala | Pro | Gly | Lys | Leu | Phe |
|---|---|---|---|---|---|---|---|---|---|---|---|---|---|---|---|
| 1 |  |  |  | 5 |  |  |  |  | 10 |  |  |  |  | 15 |  |

Val Ala Gly Glu Tyr Ala Val Leu Glu Pro Gly His Pro Ala Leu Leu
              20                  25                  30

Val Ala Val Asp Arg Gly Val Asp Val Thr Val Ser Gly Ala Asp Ala
          35                  40                  45

His Leu Val Val Asp Ser Asp Leu Cys Pro Glu Gln Ala Cys Leu Arg
 50                  55                  60

Trp Gln Asp Gly Arg Leu Val Gly Ala Gly Asp Gly Gln Pro Ala Pro
65                  70                  75                  80

Asp Ala Leu Gly Ala Val Val Ser Ala Ile Glu Val Val Gly Glu Leu
              85                  90                  95

Leu Thr Gly Arg Gly Leu Arg Pro Leu Pro Met Arg Val Ala Ile Thr
          100                 105                 110

Ser Arg Leu His Arg Asp Gly Thr Lys Phe Gly Leu Gly Ser Ser Gly
      115                 120                 125

Ala Val Thr Val Ala Thr Val Thr Ala Val Ala Ala Tyr His Gly Val
  130                 135                 140

Glu Leu Ser Leu Glu Ser Arg Phe Arg Leu Ala Met Leu Ala Thr Val
145                 150                 155                 160

Arg Asp Gly Ala Asp Ala Ser Gly Gly Asp Leu Ala Ala Ser Val Trp
              165                 170                 175

Gly Gly Trp Ile Ala Tyr Gln Ala Pro Asp Arg Ala Ala Val Arg Glu
          180                 185                 190

Met Ala Arg Arg Arg Gly Val Glu Glu Thr Met Arg Ala Pro Trp Pro
      195                 200                 205

Gly Leu Arg Val Arg Arg Leu Pro Pro Arg Gly Leu Ala Leu Glu
  210                 215                 220

Val Gly Trp Thr Gly Glu Pro Ala Ser Ser Ser Leu Thr Gly Arg
225                 230                 235                 240

Leu Ala Ala Ser Arg Trp Arg Gly Ser Pro Ala Arg Trp Ser Phe Thr
              245                 250                 255

Ser Arg Ser Gln Glu Cys Val Arg Thr Ala Ile Asp Ala Leu Glu Arg
          260                 265                 270

Gly Asp Asp Gln Glu Leu Leu His Gln Val Arg Arg Ala Arg His Val
      275                 280                 285

Leu Ala Glu Leu Asp Asp Glu Val Arg Leu Gly Ile Phe Thr Pro Arg
  290                 295                 300

Leu Thr Ala Leu Cys Asp Ala Ala Glu Thr Val Gly Ala Ala Lys
305                 310                 315                 320

Pro Ser Gly Ala Gly Gly Asp Cys Gly Ile Ala Leu Leu Asp Ala
              325                 330                 335

Thr Ala Thr Arg Thr Ala Arg Leu Arg Glu Gln Trp Ala Ala Ala

```
                    340              345              350
      Gly Val Leu Pro Met Pro Ile Gln Val His Gln Thr Asn Gly Ser Ala
          355              360              365

Arg

<210> SEQ ID NO 15
<211> LENGTH: 1110
<212> TYPE: DNA
<213> ORGANISM: Micromonospora sp. strain 046-ECO11

<400> SEQUENCE: 15
gtgaccggcc cgggcgccgt gcgccgccac gcgccgggca agctgttcgt cgccggtgag        60
tacgcggtgc tggagccggg ccacccggcg ctgctggtgg cggtcgacag gggagtggac       120
gtcaccgtct ccggcgccga cgcccacctc gttgtcgact ccgacctctg cccggagcag       180
gcgtgcctgc ggtggcagga cggccggctc gtcggcgcgg gcgacgggca gccggcgccc       240
gacgccctcg gcgccgtggt ctcggcgatc gaggtggtcg gcgaactcct gaccggacga       300
gggctgcgcc gctgcccat gcgggtggcg atcaccagcc ggctgcaccg cgacggcacg        360
aagttcggcc tcgggtcgag cggggcggtg acagtcgcca cggtgaccgc agtggccgcg       420
taccacgggg tggagctgtc gctcgaatcg cggttccggc tggcgatgct ggcgacggtg       480
cgtgacggcc ccgacgcctc cggcggtgat ctggccgcga gcgtctgggg cggctggatc       540
gcctaccagg cgcccgaccg cgcggccgtg cgcgagatgg cgcggcggcg cggcgtcgag       600
gagacgatgc gcgcgccctg gccgggcctg cgggtccggc ggctgccacc accgcgtggc       660
ctcgcgctgg aggtgggctg gaccggcgag ccggcgagca gcagctcgtt gaccgggcgg       720
ctggccgcct cccggtggcg gggcagcccg gcgcggtgga gcttcaccag ccgtagccag       780
gagtgtgtgc gtaccgccat cgacgcgctg gagcggggcg acgaccagga actgctgcac       840
caggtccggc gggcccggca cgtgcttgcc gagctggacg acgaggtccg gctcgggatc       900
ttcacccccc ggctgacggc gctgtgcgac gccgccgaga ccgtcggcgg cgcggccaaa       960
ccgtccggcg ccggtggcgg ggactgcggc atcgcgttgc tggacgccac cgccgcgacg      1020
cggaccgcgc ggctgcgcga gcagtgggcc gccgccgggg tgctccccat gccgatccag      1080
gtccatcaga cgaacgggag cgcgcgatga                                      1110

<210> SEQ ID NO 16
<211> LENGTH: 360
<212> TYPE: PRT
<213> ORGANISM: Micromonospora sp. strain 046-ECO11

<400> SEQUENCE: 16

Met Ile Ala Asn Arg Lys Asp Asp His Val Arg Leu Ala Ala Glu Gln
1               5                   10                  15

Gln Gly Arg Leu Gly Gly His His Glu Phe Asp Asp Val Ser Phe Val
            20                  25                  30

His His Ala Leu Ala Gly Ile Asp Arg Ser Asp Val Ser Leu Ala Thr
        35                  40                  45

Ser Phe Gly Gly Ile Asp Trp Pro Val Pro Leu Cys Ile Asn Ala Met
    50                  55                  60

Thr Gly Gly Ser Thr Lys Thr Gly Leu Ile Asn Arg Asp Leu Ala Ile
65                  70                  75                  80

Ala Ala Arg Glu Thr Gly Val Pro Ile Ala Thr Gly Ser Met Ser Ala
                85                  90                  95
```

```
Tyr Phe Ala Asp Glu Ser Val Ala Glu Ser Phe Ser Val Met Arg Arg
            100                 105                 110

Glu Asn Pro Asp Gly Phe Ile Met Ala Asn Val Asn Ala Thr Ala Ser
        115                 120                 125

Val Glu Arg Ala Arg Ala Val Asp Leu Met Arg Ala Asp Ala Leu
    130                 135                 140

Gln Ile His Leu Asn Thr Ile Gln Glu Thr Val Met Pro Glu Gly Asp
145                 150                 155                 160

Arg Ser Phe Ala Ala Trp Gly Pro Arg Ile Glu Gln Ile Val Ala Gly
                165                 170                 175

Val Gly Val Pro Val Ile Val Lys Glu Val Gly Phe Gly Leu Ser Arg
            180                 185                 190

Glu Thr Leu Leu Arg Leu Arg Asp Met Gly Val Arg Val Ala Asp Val
        195                 200                 205

Ala Gly Arg Gly Gly Thr Asn Phe Ala Arg Ile Glu Asn Asp Arg Arg
    210                 215                 220

Asp Ala Ala Asp Tyr Ser Phe Leu Asp Gly Trp Gly Gln Ser Thr Pro
225                 230                 235                 240

Ala Cys Leu Leu Asp Ala Gln Gly Val Asp Leu Pro Val Leu Ala Ser
                245                 250                 255

Gly Gly Ile Arg Asn Pro Leu Asp Val Val Arg Gly Leu Ala Leu Gly
            260                 265                 270

Ala Gly Ala Ala Gly Val Ser Gly Leu Phe Leu Arg Thr Leu Leu Asp
        275                 280                 285

Gly Gly Val Pro Ala Leu Leu Ser Leu Leu Ser Thr Trp Leu Asp Gln
    290                 295                 300

Ile Glu Ala Leu Met Thr Ala Leu Gly Ala Arg Thr Pro Ala Asp Leu
305                 310                 315                 320

Thr Arg Cys Asp Leu Leu Ile Gln Gly Arg Leu Ser Ala Phe Cys Ala
                325                 330                 335

Ala Arg Gly Ile Asp Thr His Arg Leu Ala Thr Arg Ser Gly Ala Thr
            340                 345                 350

His Glu Met Ile Gly Gly Ile Arg
        355                 360

<210> SEQ ID NO 17
<211> LENGTH: 1083
<212> TYPE: DNA
<213> ORGANISM: Micromonospora sp. strain 046-ECO11

<400> SEQUENCE: 17
atgatcgcca accgcaagga cgaccacgtc cggctcgccg ccgagcagca gggccggctc      60
ggcggtcacc acgagttcga cgacgtgtcc ttcgtgcacc acgccctggc cggcatcgac     120
cggtccgacg tctcgctggc cacgtcgttc ggcggcatcg actggccggt gccgctgtgc     180
atcaacgcga tgaccggcgg cagcaccaag accggcctga tcaaccggga cctggcgatc     240
gcggcccggg agaccggcgt accgatcgcc accgggtcga tgagcgccta cttcgccgac     300
gagtcggtgg ccgagagttt cagcgtgatg cgccgggaga accccgacgg gttcatcatg     360
gccaacgtca acgccaccgc ctccgtcgaa cgggcccggc gggctgtcga cctgatgcgg     420
gccgacgcgc tgcagatcca cctgaacacc atccaggaga cggtgatgcc ggaggggggac     480 cggtcgttcg ccgcctgggg gccgcggatc gaacagatcg tcgccggcgt cggtgtgccg     540
gtgatcgtca aggaggtcgg cttcgggctc agccgcgaaa cgctgctgcg gctgcgggac     600
```

-continued

```
atgggcgtcc gggtggccga cgtcgccggc cgcggcggca cgaacttcgc gcgcatcgag        660
aacgaccggc gggacgccgc cgactactcc ttcctcgacg ggtggggaca gtcgacaccc        720
gcctgcctgc tggacgccca gggcgtggac ctgcccgtgc tggcctccgg cggcatccgc        780
aacccgctcg acgtggtccg cgggctggcg ctcgcgccg gcgcggccgg ggtgtccgga         840
ctgttcctgc gcacgctcct ggacggcggg gtgccggcgc tgctgtcgct gctgtccacc        900
tggctcgacc agatcgaagc cctgatgacc gccctgggcg cgcggacccc ggccgacctg        960
acccgctgcg acctgctgat ccagggtcgg ctgagcgcgt tctgcgcggc ccggggcatc       1020
gacacccacc gcctcgccac ccgttccggc gccacccacg agatgatcgg aggcattcga       1080
tga                                                                    1083
```

<210> SEQ ID NO 18
<211> LENGTH: 351
<212> TYPE: PRT
<213> ORGANISM: Micromonospora sp. strain 046-ECO11

<400> SEQUENCE: 18

```
Met Asn Asp Ala Ile Ala Gly Val Pro Met Lys Trp Val Gly Pro Val
1               5                   10                  15

Arg Ile Ser Gly Asn Val Ala Gln Ile Glu Thr Glu Val Pro Leu Ala
                20                  25                  30

Thr Tyr Glu Ser Pro Leu Trp Pro Ser Val Gly Arg Gly Ala Lys Ile
            35                  40                  45

Ser Arg Met Val Glu Ala Gly Ile Val Ala Thr Leu Val Asp Glu Arg
        50                  55                  60

Met Thr Arg Ser Val Phe Val Arg Ala Lys Asp Ala Gln Thr Ala Tyr
65                  70                  75                  80

Leu Ala Ser Leu Glu Val Asp Ala Arg Phe Asp Glu Leu Arg Asp Ile
                85                  90                  95

Val Arg Thr Cys Gly Arg Phe Val Glu Leu Ile Gly Phe His His Glu
            100                 105                 110

Ile Thr Ala Asn Leu Leu Phe Leu Arg Phe Ser Phe Thr Thr Gly Asp
        115                 120                 125

Ala Ser Gly His Asn Met Ala Thr Leu Ala Ala Asp Ala Leu Leu Lys
    130                 135                 140

His Ile Leu Asp Thr Ile Pro Gly Ile Ser Tyr Gly Ser Ile Ser Gly
145                 150                 155                 160

Asn Tyr Cys Thr Asp Lys Lys Ala Thr Ala Ile Asn Gly Ile Leu Gly
                165                 170                 175

Arg Gly Lys Asn Val Val Thr Glu Leu Val Val Pro Arg Glu Ile Val
            180                 185                 190

His Asp Ser Leu His Thr Thr Ala Ala Ile Ala Gln Leu Asn Val
        195                 200                 205

His Lys Asn Met Ile Gly Thr Leu Leu Ala Gly Ile Arg Ser Ala
    210                 215                 220

Asn Ala His Tyr Ala Asn Met Leu Leu Gly Phe Tyr Leu Ala Thr Gly
225                 230                 235                 240

Gln Asp Ala Ala Asn Ile Val Glu Gly Ser Gln Gly Val Thr Val Ala
                245                 250                 255

Glu Asp Arg Asp Gly Asp Leu Tyr Phe Ser Cys Thr Leu Pro Asn Leu
            260                 265                 270

Ile Val Gly Thr Val Gly Asn Gly Lys Gly Leu Gly Phe Val Glu Glu
        275                 280                 285
```

-continued

Asn Leu Glu Arg Leu Gly Cys Arg Ala Ser Arg Asp Pro Gly Glu Asn
            290                 295                 300

Ala Arg Arg Leu Ala Val Ile Ala Ala Thr Val Leu Cys Gly Glu
305                 310                 315                 320

Leu Ser Leu Leu Ala Ala Gln Thr Asn Pro Gly Glu Leu Met Arg Ala
                325                 330                 335

His Val Arg Leu Glu Arg Pro Thr Glu Thr Thr Lys Ile Gly Ala
            340                 345                 350

<210> SEQ ID NO 19
<211> LENGTH: 1056
<212> TYPE: DNA
<213> ORGANISM: Micromonospora sp. strain 046-ECO11

<400> SEQUENCE: 19
atgaacgacg cgatcgccgg tgtgcccatg aaatgggtag gtcccgtgcg gatctcggga      60
aacgtggcgc agatcgagac ggaggttccg ctcgccacgt acgagtcgcc gctctggccg     120
tccgtcggcc ggggcgcgaa gatctcccgg atggtcgagg cgggcatcgt cgccacgctc     180
gtcgacgagc gcatgacccg ctcggtgttc gtgcgcgcca aggacgcgca gaccgcctac     240
ctggcctcgc ttgaggtcga cgcgcggttc gacgaactgc gtgacatcgt gcgcacctgc     300
ggcaggttcg tcgagctgat cgggttccac cacgagatca ccgcgaacct gctgttcctg     360
cggttcagtt tcaccaccgg cgacgcgtcc gggcacaaca tggcgacgct ggccgccgac     420
gcgctgctga agcacatcct ggacaccatt ccgggcatct cgtacggctc gatctcgggc     480
aactactgca ccgacaagaa ggccaccgcg ataaacggca ttctcggccg gggcaagaac     540
gtggtcaccg agctggtcgt gccgcgggag atcgtccacg acagcctgca cacgacggcg     600
gcggcgatcg cccagctgaa cgtgcacaag aacatgatcg gcacgttgct cgccggcggt     660
atccgctcgg ccaacgccca ctacgcgaac atgctgctcg gttctacct ggccacgggt     720
caggacgccg cgaacatcgt cgagggctcc cagggcgtga cggtcgccga ggaccgcgac     780
ggcgacctct acttctcctg cacgctgccc aacctgatcg tgggcaccgt cggcaacggc     840
aaggggctcg gcttcgtcga ggagaacctg gagcggctcg gctgccgcgc ctcgcgtgat     900
ccgggcgaga cgcccggcg gctcgcggtc atcgcggccg cgacggtgct ctgcggcgag     960
ctgtccctgc tcgccgcgca gaccaacccg ggcgagctga tgcgggcgca cgtccggctc    1020
gaacgcccga ccgagaccac gaagatcgga gcctga                              1056

<210> SEQ ID NO 20
<211> LENGTH: 391
<212> TYPE: PRT
<213> ORGANISM: Micromonospora sp. strain 046-ECO11

<400> SEQUENCE: 20

Met Ala Glu Arg Pro Ala Val Gly Ile His Asp Leu Ser Ala Ala Thr
1               5                   10                  15

Ala His His Val Leu Thr His Glu Thr Leu Ala Ala Ser Asn Gly Ala
            20                  25                  30

Asp Val Ala Lys Tyr His Arg Gly Ile Gly Leu Arg Ala Met Ser Val
        35                  40                  45

Pro Ala Pro Asp Glu Asp Ile Val Thr Met Ala Ala Ala Ala Ala
    50                  55                  60

Pro Val Val Ala Arg His Gly Thr Asp Arg Ile Arg Thr Val Val Phe
65                  70                  75                  80

```
Ala Thr Glu Ser Ser Val Asp Gln Ala Lys Ala Gly Ile His Val
                85                  90                  95

His Ser Leu Leu Gly Leu Pro Ser Ala Thr Arg Val Val Glu Leu Lys
            100                 105                 110

Gln Ala Cys Tyr Gly Gly Thr Ala Gly Leu Gln Phe Ala Ile Gly Leu
        115                 120                 125

Val His Arg Asp Pro Ser Gln Gln Val Leu Val Ile Ala Ser Asp Val
    130                 135                 140

Ser Lys Tyr Ala Leu Gly Glu Pro Gly Glu Ala Thr Gln Gly Ala Ala
145                 150                 155                 160

Ala Val Ala Met Leu Val Gly Ala Asp Pro Ala Leu Val Arg Val Glu
                165                 170                 175

Asp Pro Ser Gly Met Phe Thr Ala Asp Val Met Asp Phe Trp Arg Pro
            180                 185                 190

Asn Tyr Arg Thr Thr Ala Leu Val Asp Gly His Glu Ser Ile Ser Ala
        195                 200                 205

Tyr Leu Gln Ala Leu Glu Gly Ser Trp Lys Asp Tyr Thr Glu Arg Gly
    210                 215                 220

Gly Arg Thr Leu Asp Glu Phe Gly Ala Phe Cys Tyr His Gln Pro Phe
225                 230                 235                 240

Pro Arg Met Ala Asp Lys Ala His Arg His Leu Leu Asn Tyr Cys Gly
                245                 250                 255

Arg Asp Val Asp Asp Ala Leu Val Ala Gly Ala Ile Gly His Thr Thr
            260                 265                 270

Ala Tyr Asn Ala Glu Ile Gly Asn Ser Tyr Thr Ala Ser Met Tyr Leu
        275                 280                 285

Gly Leu Ala Ala Leu Leu Asp Thr Ala Asp Asp Leu Thr Gly Arg Thr
    290                 295                 300

Val Gly Phe Leu Ser Tyr Gly Ser Gly Ser Val Ala Glu Phe Phe Ala
305                 310                 315                 320

Gly Thr Val Val Pro Gly Tyr Arg Ala His Thr Arg Pro Asp Gln His
                325                 330                 335

Arg Ala Ala Ile Asp Arg Arg Gln Glu Ile Asp Tyr Ala Thr Tyr Arg
            340                 345                 350

Glu Leu His Glu His Ala Phe Pro Val Asp Gly Asp Tyr Pro Ala
        355                 360                 365

Pro Glu Val Thr Thr Gly Pro Tyr Arg Leu Ala Gly Leu Ser Gly His
    370                 375                 380

Lys Arg Val Tyr Glu Pro Arg
385                 390

<210> SEQ ID NO 21
<211> LENGTH: 1176
<212> TYPE: DNA
<213> ORGANISM: Micromonospora sp. strain 046-ECO11

<400> SEQUENCE: 21
atggccgaga gacccgccgt cggcatccac gacctgtccg ccgcgacggc gcatcacgtg    60
ctgacacacg agaccctggc cgcgagcaac ggcgccgacg tggccaagta ccaccgtggc   120
atcgggctgc gggcgatgag cgtgcccgcc ccggacgagg acatcgtgac gatggctgct   180
gccgccgccg cgccggtggt cgcccgccca ggcaccgacc ggatccggac cgtcgtgttc   240
gccacggagt cgtcggtcga ccaggcgaag gcggccggga tacacgtcca ctccctgctc   300
```

-continued

```
ggcctcccct cggccacccg ggtggtcgag ctgaagcagg cctgctacgg cggtacggcg    360
ggactgcagt tcgccatcgg cctggtgcac cgtgacccgt cgcagcaggt cctggtgatc    420
gccagcgacg tgtcgaagta cgcgctgggt gagcccggcg aggcgaccca gggcgccgcg    480
gcggtcgcca tgctcgtcgg cgcggacccg gcgctggtac gcgtcgagga cccgtcgggc    540
atgttcaccg ccgacgtcat ggacttctgg cggccgaact accgcaccac cgccctggtc    600
gacgggcacg agtccatctc cgcctacctg caggcgctgg agggctcgtg gaaggactac    660
accgagcgcg gcggtcgcac cctggacgag ttcggcgcgt tctgctacca ccagccgttc    720
ccgaggatgg ccgacaaggc gcaccggcac ctgctcaact actgcgggcg cgacgtcgac    780
gacgcgctgg tggccggggc catcgggcac accaccgcgt acaacgccga gatcggcaac    840
agctacacgg cgtcgatgta tctcgggctc gcggcactgc tcgacaccgc cgacgacctg    900
accggccgga ccgtcggctt cctcagctac gggtccggca gcgtcgccga gttcttcgcc    960
ggcactgtcg tgcccgggta ccgcgcgcac acgcgacccg accagcaccg cgcggcgatc   1020
gaccggcggc aggagatcga ctacgcgacg taccgggagt tgcacgagca cgccttcccg   1080
gtcgacggcg cgactatcc ggcgccggag gtgaccaccg gccgtaccg gctggccggg    1140
ctctccggtc acaagcgcgt ctacgagccg cgatag                             1176
```

<210> SEQ ID NO 22
<211> LENGTH: 290
<212> TYPE: PRT
<213> ORGANISM: Micromonospora sp. strain 046-ECO11

<400> SEQUENCE: 22

```
Val Ala Glu Leu Tyr Ser Thr Ile Glu Glu Ala Arg Gln Leu Asp
1               5                  10                  15

Val Pro Cys Ser Arg Asp Arg Val Trp Pro Ile Leu Ser Ala Tyr Gly
            20                  25                  30

Asp Ala Phe Ala His Pro Glu Ala Val Val Ala Phe Arg Val Ala Thr
            35                  40                  45

Ala Leu Arg His Ala Gly Glu Leu Asp Cys Arg Phe Arg Thr His Pro
50                  55                  60

Asp Asp Arg Asp Pro Tyr Ala Ser Ala Leu Ala Arg Gly Leu Thr Pro
65                  70                  75                  80

Arg Thr Asp His Pro Val Gly Ala Leu Leu Ser Glu Val His Arg Arg
                85                  90                  95

Cys Pro Val Glu Ser His Gly Ile Asp Phe Gly Val Val Gly Gly Phe
            100                 105                 110

Lys Lys Ile Tyr Ala Ala Phe Ala Pro Asp Glu Leu Gln Val Ala Thr
            115                 120                 125

Ser Leu Ala Gly Ile Pro Ala Met Pro Arg Ser Leu Ala Ala Asn Ala
130                 135                 140

Asp Phe Phe Thr Arg His Gly Leu Asp Asp Arg Val Gly Val Leu Gly
145                 150                 155                 160

Phe Asp Tyr Pro Ala Arg Thr Val Asn Val Tyr Phe Asn Asp Val Pro
                165                 170                 175

Arg Glu Cys Phe Glu Pro Glu Thr Ile Arg Ser Thr Leu Arg Arg Thr
            180                 185                 190

Gly Met Ala Glu Pro Ser Glu Gln Met Leu Arg Leu Gly Thr Gly Ala
            195                 200                 205

Phe Gly Leu Tyr Val Thr Leu Gly Trp Asp Ser Pro Glu Ile Glu Arg
210                 215                 220
```

```
Ile Cys Tyr Ala Ala Ala Thr Thr Asp Leu Thr Thr Leu Pro Val Pro
225                 230                 235                 240

Val Glu Pro Glu Ile Glu Lys Phe Val Lys Ser Val Pro Tyr Gly Gly
            245                 250                 255

Gly Asp Arg Lys Phe Val Tyr Gly Val Ala Leu Thr Pro Lys Gly Glu
            260                 265                 270

Tyr Tyr Lys Leu Glu Ser His Tyr Lys Trp Lys Pro Gly Ala Val Asn
        275                 280                 285

Phe Ile
    290

<210> SEQ ID NO 23
<211> LENGTH: 873
<212> TYPE: DNA
<213> ORGANISM: Micromonospora sp. strain 046-ECO11

<400> SEQUENCE: 23
gtggccgagc tctactcgac catcgaggaa tcggcccggc aactggacgt gccgtgttcg      60
cgcgaccggg tctggcccat cctgtccgcg tacggcgacg cgttcgccca tcccgaggcg     120
gtggtcgcct ccgggtggc gaccgcgctg cgtcacgcgg gcgagctgga ctgccggttc     180
cggacgcatc cggacgaccg ggacccgtac gcctcggcgc tcgcccgggg cctcaccccg     240
cgcacggacc accccgtcgg cgcgctgctc tccgaggtcc accggcgctg cccggtggag     300
agccacggca tcgacttcgg ggtggtcggc ggcttcaaga agatctacgc ggccttcgcc     360
ccggacgagc tgcaggtggc cacgtcgctc gccggcattc cggcgatgcc ccgcagcctc     420
gccgcgaacg ccgacttctt cacccggcac ggcctcgacg accgggtcgg cgtgctggga     480
ttcgactacc cggcccggac cgtgaacgtc tacttcaacg acgtgccgcg tgagtgcttc     540
gagccggaga ccatccggtc gacgctcgcc cggaccggga tggccgagcc gagcgagcag     600
atgctccggc tcggcaccgg ggcgttcggg ctctacgtca cgctgggctg ggactccccg     660
gagatcgagc ggatctgcta cgccgcggcg accacggacc tgaccacgct tccggtaccc     720
gtggaaccgg agatcgagaa gttcgtgaaa gcgttccgt acggcggcgg ggaccggaag     780
ttcgtctacg gcgtggcgct gacccccaag ggggagtact acaaactcga gtcgcactac     840
aaatggaagc cgggcgcggt gaacttcatt tga                                 873

<210> SEQ ID NO 24
<211> LENGTH: 370
<212> TYPE: PRT
<213> ORGANISM: Micromonospora sp. strain 046-ECO11

<400> SEQUENCE: 24

Val Trp Ala Arg Val Lys Asn Trp Val Ala Leu Ala Val Ala Ala
1               5                   10                  15

Val Leu Met Ile Ser Ala Leu Ala Gly Asp His Pro Ala Pro Glu Gly
                20                  25                  30

Leu Gly Leu Leu Gly Phe Ala Leu Val Ala Ala Ser Gly Leu Ala Leu
            35                  40                  45

Ala Ala Ser Arg Arg Ala Pro Ile Ala Val Leu Val Ala Thr Gly Leu
        50                  55                  60

Cys Val Val Gly Tyr Asn Ala Ile Gly Phe Gly Val Pro Ala Ile Ala
65                  70                  75                  80

Tyr Leu Phe Ala Val Tyr Ala Ala Val Arg Ala Gly His Arg Leu Val
                85                  90                  95
```

-continued

```
Thr Leu Gly Ala Ser Ala Ala Leu Leu Val Val Leu Pro Leu Ala Ile
            100                 105                 110

Met Val Ser Pro Ala Asp Gly Ala Leu Lys Glu Ala Leu Ala Gln Ser
        115                 120                 125

Arg Gly Val Leu Glu Leu Ala Trp Leu Ile Ala Ala Ala Ala Ala Gly
    130                 135                 140

Glu Ala Leu Arg Gln Ala Glu Arg Ala Asp Glu Ala Glu Arg Thr
145                 150                 155                 160

Arg Glu Glu Thr Ala Arg Leu Arg Ala Thr Gln Glu Arg Leu His Ile
                165                 170                 175

Ala Arg Glu Leu His Asp Ser Leu Thr His Gln Ile Ser Ile Ile Lys
            180                 185                 190

Val Gln Ala Glu Val Ala Val His Leu Ala Arg Lys Arg Gly Glu Gln
        195                 200                 205

Val Pro Glu Ser Leu Leu Ala Ile Gln Glu Ala Gly Arg Ala Ala Thr
    210                 215                 220

Arg Glu Leu Arg Ala Thr Leu Glu Thr Leu Arg Asp Leu Thr Lys Ser
225                 230                 235                 240

Pro Ser His Gly Leu Asp His Leu Pro Glu Leu Leu Ala Gly Ala Glu
                245                 250                 255

Lys Ile Gly Leu Ala Thr Thr Leu Thr Ile Glu Gly Asp Gln Arg Asp
            260                 265                 270

Val Pro Glu Ala Val Gly Arg Thr Ala Tyr Arg Ile Val Gln Glu Ser
        275                 280                 285

Leu Thr Asn Thr Ala Arg His Ala Ser Ala Ala Ala Ala Val Arg
    290                 295                 300

Ile Asp Tyr Arg Pro Asp Ala Leu Ser Ile Arg Ile Asp Asp Gly
305                 310                 315                 320

Thr Ala Arg Pro Gly Ala Ala Pro Val Pro Gly Val Gly Leu Leu Gly
                325                 330                 335

Met His Glu Arg Val Leu Ala Leu Gly Gly Arg Leu Arg Ala Glu Pro
            340                 345                 350

Arg Thr Gly Gly Gly Phe Thr Val Gln Ala Glu Leu Pro Val Val Arg
        355                 360                 365

Val Pro
    370
```

<210> SEQ ID NO 25
<211> LENGTH: 1113
<212> TYPE: DNA
<213> ORGANISM: Micromonospora sp. strain 046-ECO11

<400> SEQUENCE: 25

| | |
|---|---|
| gtgtgggccc gggtgaagaa ctgggtcgtc gcgttggctg tggcggcggt gctgatgatc | 60 |
| agcgcgctgg ccggtgacca tcctgccccc gagggcctcg gtctgctcgg cttcgcgctg | 120 |
| gtggcggcga gcggcctggc gctggccgcc agtcgtcggg ccccgatcgc cgtgctggtc | 180 |
| gccaccgggc tgtgcgtggt gggctacaac gcgatcggct cggggtgcc cgccatcgcg | 240 |
| tacctgttcg cggtctacgc ggcggtccgg gccgggcacc ggctcgtcac gctcggggcg | 300 |
| agcgccgccc tgctcgtcgt cctgccgctg gcgatcatgg tctcgcccgc ggacggcgcc | 360 |
| ctcaaggagg cgctcgcgca gtcgcggggc gtgctggaac tggcctggct gatcgccgcg | 420 |
| gcggcggccg gtgaggcgct gcggcaggcc gaacggcgag cggacgaggc ggaacggacc | 480 |

```
cgcgaggaga ccgcccggct gcgcgccacc caggagcggc tgcacatcgc acgggagctg      540
cacgactcgc tcacccacca gatctcgatc atcaaggtgc aggcggaggt ggcggtccac      600
ctggcccgca agcggggcga gcaggtgccg gagtcgctgc tggcgatcca ggaggccggc      660
cgggcggcga ctcgcgagct gcgcgcgacc ctggagacgt gcgtgacct  gaccaagtcc      720 ccgtcgcacg gctcgacca  cctcccggag ctgctggccg gggccgagaa gatcggcctg      780
gccaccacgc tgaccatcga gggcgaccag cgggacgtgc cggaggcggt gggccgcacc      840
gcgtaccgga tcgtgcagga gtcgctcacc aacaccgccc ggcacgcctc cgccgcggcc      900
gccgcggtcc ggatcgacta ccgcccggac gcgctgagca tccggatcga cgacgacggg      960
acggcccggc cgggcgccgc cccggtgccc ggcgtcgggc tgctggggat gcacgagcgc     1020
gtcctcgcgc tgggcggccg gctgcgggcg aacccccgca ccggcggagg cttcaccgtc     1080
caggccgaac tcccggtggt gcgcgtccca tga                                  1113

<210> SEQ ID NO 26
<211> LENGTH: 220
<212> TYPE: PRT
<213> ORGANISM: Micromonospora sp. strain 046-ECO11

<400> SEQUENCE: 26

Met Ile Arg Ile Met Leu Leu Asp Asp Gln Pro Leu Leu Arg Ser Gly
1               5                   10                  15

Phe Arg Ala Leu Leu Asp Ala Glu Asp Asp Ile Glu Val Val Ala Glu
                20                  25                  30

Gly Gly Asn Gly Arg Glu Gly Leu Ala Leu Ala Arg Gln His Leu Pro
            35                  40                  45

Asp Leu Ala Leu Ile Asp Ile Gln Met Pro Val Met Asp Gly Val Glu
        50                  55                  60

Thr Thr Arg Gln Ile Val Ala Asp Pro Ala Leu Ala Gly Val Arg Val
65                  70                  75                  80

Val Ile Leu Thr Asn Tyr Gly Leu Asp Glu Tyr Val Phe His Ala Leu
                85                  90                  95

Arg Ala Gly Ala Thr Gly Phe Leu Val Lys Asp Ile Glu Pro Asp Asp
            100                 105                 110

Leu Leu His Ala Val Arg Val Ala Ala Arg Gly Asp Ala Leu Leu Ala
        115                 120                 125

Pro Ser Ile Thr Arg Met Leu Ile Asn Arg Tyr Val Ser Glu Pro Leu
    130                 135                 140

Cys Ala Asp Val Thr Pro Gly Met Glu Glu Leu Thr Asn Arg Glu Arg
145                 150                 155                 160

Glu Ala Val Ala Leu Ala Arg Gly Leu Ser Asn Asp Glu Ile Ala
                165                 170                 175

Asp Arg Met Val Ile Ser Pro Leu Thr Ala Lys Thr His Val Asn Arg
            180                 185                 190

Ala Met Thr Lys Leu Gln Ala Arg Asp Arg Ala Gln Leu Val Val Phe
        195                 200                 205

Ala Tyr Glu Ser Gly Leu Val Ser Pro Gly Asn Arg
    210                 215                 220

<210> SEQ ID NO 27
<211> LENGTH: 663
<212> TYPE: DNA
<213> ORGANISM: Micromonospora sp. strain 046-ECO11

<400> SEQUENCE: 27
```

```
atgatcagga tcatgctgct cgacgaccag ccgctgctgc gcagcgggtt ccgcgcgctc      60
ctcgacgccg aggacgacat cgaggtggtg gccgagggcg ggaacggccg ggagggcctg     120
gcgctggccc ggcagcacct gcccgatctc gccctgatcg acatccagat gccggtcatg     180
gacggcgtcg agacgacccg gcagatcgtc gcggatccgg cgctggccgg ggtacgcgtc     240
gtcatcctca ccaactacgg cctcgacgag tacgtcttcc acgcgctgcg cgccggcgcc     300
accggcttcc tggtcaagga catcgagccg gacgacctgc tgcacgccgt gcgggtcgcc     360
gcgcgcggtg acgcgctgct cgcgccgtcg atcacccgga tgctgatcaa caggtacgtg     420
tcggagccgc tctgcgcgga cgtcacgccc ggcatggagg agctgaccaa ccgggaacgc     480
gaggcggtcg ccctggccgc ccggggcctg tccaacgacg agatcgccga tcgcatggtg     540
atcagcccgc tgaccgcgaa gacccacgtc aaccgcgcca tgaccaagct gcaggcccgc     600
gaccgcgccc agctggtggt gttcgcctac gagtccggcc tggtgtcacc cggcaatcgc     660
tga                                                                    663

<210> SEQ ID NO 28
<211> LENGTH: 131
<212> TYPE: PRT
<213> ORGANISM: Micromonospora sp. strain 046-ECO11

<400> SEQUENCE: 28

Met Phe Ile Arg Arg Leu Leu Thr Ala Ala Ala Ala Gly Val Leu Gly
1               5                   10                  15

Gly Leu Ala Leu Val Ala Pro Ala Ala Ala Gln Val Thr Ala Ala Asp
            20                  25                  30

Gly Asp Gly Gly Ser Gly Arg Ala Gly Ser Val Leu Ala Leu Ala Leu
        35                  40                  45

Ala Leu Leu Gly Leu Val Leu Gly Gly Trp Ala Leu Arg Ser Ala Gly
    50                  55                  60

Arg Gly Gly Gly Arg Gly Asn Ala Ile Ala Ala Leu Val Leu Ala Val
65                  70                  75                  80

Ala Gly Leu Ile Ala Gly Val Val Ala Leu Ala Gly Ser Asp Gly Gly
                85                  90                  95

Val Gly Ser Gly Asn Gly Arg Gly Gly Ala Ile Val Ala Val Val Leu
            100                 105                 110

Ala Leu Ile Gly Ile Ala Val Gly Gly Leu Ala Phe Thr Arg Ser Arg
        115                 120                 125

Arg Ala Ala
    130

<210> SEQ ID NO 29
<211> LENGTH: 396
<212> TYPE: DNA
<213> ORGANISM: Micromonospora sp. strain 046-ECO11

<400> SEQUENCE: 29
atgttcatcc gtcgtttgct caccgccgcc gcagccggcg tcctcggtgg gctcgcactc      60
gtcgcaccgg cggccgcgca ggtgacggcc gccgacggtg acgtggttc cggccgcgcc     120 ggatccgtgc tggcgctcgc gctcgcgttg ctcggcctcg tcctgggcgg gtgggcgttg     180
cgctccgcgg ggcgcggcgg cggtcgtggc aacgcgatcg ccgcgctggt gctcgcggtg     240
gccgccctga tcgccggcgt ggtcgccctg gccggctccg acggtggtgt cggcagcggc     300
aacggccgtg gtggcgccat cgtggccgtc gtgctggcgc tgatcgggat cgccgtcggc     360
```

```
ggcctggcat tcacccgctc ccggcgcgcc gcctga                              396
```

<210> SEQ ID NO 30
<211> LENGTH: 154
<212> TYPE: PRT
<213> ORGANISM: Micromonospora sp. strain 046-ECO11

<400> SEQUENCE: 30

```
Met Arg Lys Val Phe Ala Gly Leu Ala Ala Phe Leu Leu Val Leu
1               5                   10                  15

Val Val Gln Phe Phe Leu Ala Ala Ser Gly Ala Phe Ser Asn Glu Ala
            20                  25                  30

Asn Glu Glu Ala Phe Arg Pro His Arg Ile Leu Gly Leu Gly Ser Ile
                35                  40                  45

Leu Val Ala Val Val Leu Thr Val Ala Ala Val Met Arg Met Pro
    50                  55                  60

Gly Arg Ile Ile Gly Leu Ser Gly Leu Val Ala Gly Leu Gly Ile Leu
65                  70                  75                  80

Gln Ala Leu Ile Ala Val Ile Ala Lys Ala Phe Gly Asp Ser Ala Gly
                85                  90                  95

Asp Ser Ala Val Gly Arg Tyr Val Phe Gly Leu His Ala Val Asn Gly
            100                 105                 110

Leu Val Met Val Ala Val Ala Arg Val Ile Leu Arg Ser Val Arg Ala
        115                 120                 125

Ala Pro Asp Thr Thr Thr Thr Pro Gly Val Asp Thr Thr Val Thr Gly
    130                 135                 140

Pro Ala Ala Asp Ser Ala Arg Thr Ala Ser
145                 150
```

<210> SEQ ID NO 31
<211> LENGTH: 465
<212> TYPE: DNA
<213> ORGANISM: Micromonospora sp. strain 046-ECO11

<400> SEQUENCE: 31

```
atgcgcaaag tgttcgccgg actggcagcg ttcctgctgc tcgtgctcgt ggtgcagttc    60
ttcctggccg ccagcggcgc gttcagcaac gaggccaacg aggaggcgtt ccgccctcac   120
cggatcctgg gcctggggag catcctcgtc gccgtggtgc tgacggtggc cgccgcggtg   180
atgcggatgc ccgccggat catcggcctg tccggcctgg tcgccgggct gggcatcctg   240
caggccctga tcgcggtcat cgccaaggcg ttcggcgact cggccggtga ctcggccgtc   300
ggccggtacg tgttcggcct gcacgcggtc aacggactgg tgatggtggc cgtcgcccgc   360
gtcatcctgc gcagcgtccg ggcggcgccg gacacgacca ccacgcccgg cgtggacacg   420
acggtcaccg gtccggcggc cgactcggcg cgaacggcgt catga                   465
```

<210> SEQ ID NO 32
<211> LENGTH: 661
<212> TYPE: PRT
<213> ORGANISM: Micromonospora sp. strain 046-ECO11

<400> SEQUENCE: 32

```
Met Ser Thr Leu Gln Trp Ile Leu Val Asp His Val Val Ala Leu Leu
1               5                   10                  15

Gly Val Ala Thr Trp Phe Ala Thr Gly Val Thr Ala Ala Leu Gly Arg
            20                  25                  30
```

-continued

```
His Arg Ile Ala Leu Ala Leu Leu Gly Ala Ala Val Leu Val Thr Val
        35                  40                  45

Ala Arg Leu Gly Thr Val Ala Leu Leu Ala Asp Arg Gly Trp Trp Phe
    50                  55                  60

Val Gln Glu Lys Val Leu Leu Gly Leu Pro Met Leu Gly Ala Ala Gly
65                  70                  75                  80

Leu Val Ala Val Leu Leu Ala Gly Pro Arg Leu Leu Ala Ala Arg Gln
                85                  90                  95

Ser Pro Ala Ala Asp Leu Pro Ala Gly Ala Leu Val Ala Val Leu Thr
            100                 105                 110

Ala Gly Phe Ala Ala Leu Ala Gly Leu Val Val Thr Phe Thr Ala Gly
            115                 120                 125

Tyr Pro Leu Thr Trp Ser Thr Ala Leu Ile Ala Val Ala Leu Val Cys
        130                 135                 140

Ala Ala Ala Leu Leu Thr Ala Arg Val Val Gly Arg Pro Ala Ala Pro
145                 150                 155                 160

Ala Ala Glu Ala Gly Ser Pro Glu His Thr Pro Ala Ala Ala Gly Pro
                165                 170                 175

Thr Ala Leu Ser Arg Arg Arg Phe Leu Gly Val Ala Gly Gly Val Val
            180                 185                 190

Ala Ala Gly Ala Gly Ala Thr Gly Val Gly Leu Leu Phe Arg Asp Pro
            195                 200                 205

Glu Ala Met Val Thr Gly Gly Pro Gly His Ala Gly Gly Ala Arg
        210                 215                 220

Pro Lys Val Ser Val Ala Asp Leu Arg Gly Pro Gly Ala Pro Ala Ala
225                 230                 235                 240

Gly Gly Thr Ala Arg Arg His Val Leu Thr Ala Arg Thr Gly Thr Val
                245                 250                 255

Thr Ile Pro Ser Gly Arg Pro Ile Asp Ala Trp Ser Tyr Glu Gly Arg
            260                 265                 270

Leu Pro Gly Pro Ala Ile Thr Ala Thr Glu Gly Asp Leu Ile Glu Val
            275                 280                 285

Thr Leu Arg Asn Ala Asp Ile Glu Asp Gly Val Thr Val His Trp His
        290                 295                 300

Gly Tyr Asp Val Pro Cys Gly Glu Asp Gly Ala Pro Gly Ala Thr Gln
305                 310                 315                 320

His Ala Val Gln Pro Gly Gly Glu Phe Val Tyr Arg Phe Gln Ala Asp
                325                 330                 335

Gln Val Gly Thr Tyr Trp Tyr His Thr His Gln Ala Ser His Pro Ala
            340                 345                 350

Val Arg Lys Gly Leu Tyr Gly Thr Leu Val Val Thr Pro Arg Glu Asp
        355                 360                 365

Arg Pro Glu Ala Glu Arg Gly Leu Asp Leu Thr Leu Pro Val His Thr
    370                 375                 380

Phe Asp Asp Val Thr Ile Leu Gly Asp Gln Glu Gly Arg Ala Val His
385                 390                 395                 400

Asp Val Arg Pro Gly Gln Pro Val Arg Leu Arg Leu Ile Asn Thr Asp
                405                 410                 415

Ser Asn Pro His Trp Phe Ala Val Val Gly Ser Pro Phe Arg Val Val
            420                 425                 430

Ala Val Asp Gly Arg Asp Leu Asn Gln Pro Gly Glu Val Arg Glu Val
            435                 440                 445

Gly Leu Arg Leu Pro Ala Gly Gly Arg Tyr Asp Leu Thr Leu Ala Met
```

```
              450                 455                 460
Pro Asp Ala Lys Val Thr Leu Leu Asp Asn Asp Ser Asp Gln Gly
465                 470                 475                 480

Val Leu Leu Arg Pro Pro Gly Val Gly Gly Asp Arg Pro Leu Pro
                485                 490                 495

Asp Thr Ala Asp Trp Pro Glu Phe Asp Leu Leu Gly Tyr Gly Glu Pro
            500                 505                 510

Ala Pro Val Pro Phe Asp Ala Asp Ala Asp Arg His Phe Thr Ile
            515                 520                 525

Val Leu Asp Arg Ala Leu Ala Met Val Asp Gly Lys Pro Ala Tyr Ala
530                 535                 540

Gln Thr Val Asp Gly Arg Ala His Pro Ser Val Pro Asp Gln Leu Val
545                 550                 555                 560

Arg Glu Gly Asp Val Val Arg Phe Thr Val Asn Arg Ser Leu Glu
                565                 570                 575

Thr His Pro Trp His Leu His Gly His Pro Val Leu Ile Leu Ser Arg
                580                 585                 590

Asp Gly Arg Pro Tyr Ser Gly Ser Pro Leu Trp Met Asp Thr Phe Asp
            595                 600                 605

Val Arg Pro Gly Glu Val Trp Glu Val Ala Phe Arg Ala Asp Asn Pro
            610                 615                 620

Gly Val Trp Met Asn His Cys His Asn Leu Pro His Gln Glu Gln Gly
625                 630                 635                 640

Met Met Leu Arg Leu Val Tyr Asp Gly Val Thr Thr Pro Phe Ala Ser
                645                 650                 655

Thr Ser His Ala His
                660

<210> SEQ ID NO 33
<211> LENGTH: 1986
<212> TYPE: DNA
<213> ORGANISM: Micromonospora sp. strain 046-ECO11

<400> SEQUENCE: 33
atgagcacgc tccaatggat cctcgtggac cacgtcgtgg cgctgctcgg tgtcgcgacg    60
tggttcgcaa cgggtgtcac ggcagctctc ggccgccacc ggatcgcgtt ggcgctcctc   120
ggcgccgcgg tgctggtgac agtcgcccgc ctgggcaccg tggcgctgct ggccgaccgc   180
ggctggtggt cgtccagga gaaggttctg ctggggctgc cgatgctcgg cgccgcgggg   240
ctcgtcgcgg tgctcctggc cggcccgcgc ctgctcgcgg cccggcagtc accggcggcg   300
gacctgccgg ccggcgcgct ggtcgcggtg ctgaccgccg gcttcgccgc gctggccggc   360
ctggtggtga cgttcaccgc cgggtacccg ctgacgtgga gcaccgcgct gatcgccgtc   420
gccctcgtct cgccgccgc gctgctcacc gcgcgggtgg tcggacgacc cgccgccccg   480
gccgcggagg ccggctcccc ggagcacacg ccggcggcgg ccgggcccac ggcgctgtcc   540
cgccgccggt tcctcggcgt ggccggggga gtggtcgcgg cgggcgccgg cgccaccggc   600
gtcggcctgc tcttccgcga cccggaggcg atggtcaccg gaggcggccc cggacacgcc   660
ggtggcgccc gccccaaggt ctccgtggcg gacctgcgcg ccccggcgc tccggcggcg   720 gcggcacgg cgcgacgcca cgtgctcacc gcccggacgg gcaccgtcac gattccgtcc   780
ggacgtccga tcgacgcctg gagctacgag ggccgcctgc ccgggccggc catcaccgcg   840
accgagggcg acctgatcga ggtgacgctc cgcaacgccg acatcgagga cggcgtcacc   900
```

```
gtgcactggc acgggtacga cgtgccgtgc ggcgaggacg gcgcgccggg cgccacgcag    960
cacgcggtgc agcccggcgg cgagttcgtc taccggttcc aggcggacca ggtggggacg   1020
tactggtacc acacccacca ggcgtcgcac ccgccgtgc gcaaagggct gtacgggacg    1080
ctcgtcgtga cgccgcgcga ggaccggccg gaagcggagc gcgggctgga cctgacgctg   1140
ccggtgcaca cgttcgacga cgtcacgatc ctcggcgacc aggagggacg cgccgtccac   1200
gacgtccgcc ccgccagcc ggtgcgactg cgtctgatca acaccgactc caacccgcac   1260
tggttcgccg tcgtcggctc gcccttccgc gtggtggccg tcgacggccg cgacctcaac   1320
cagccgggcg aggtacgcga ggtcgggctc cgcctgcccg ccggaggccg gtacgacctg   1380
accctggcca tgccggacgc caaggtcacg ctgctgctcg acaacgactc cgaccagggc   1440
gtcctgctgc gcccgccggg cgtcggcggt ggtgaccgcc cgctgccgga caccgccgac   1500
tggcccgagt tcgacctgct gggctacggc gagccggcgc ccgtgccgtt cgacgccgac   1560
gacgccgacc gccacttcac catcgtcctc gaccgggccc tggccatggt cgacggcaag   1620
cccgcgtacg cccagaccgt cgacggtcgc gcacatccct ccgtccccga ccagctcgtc   1680
cgggaggggg acgtcgtgcg cttcacggtg gtcaaccgga gcctcgaaac ccacccgtgg   1740
cacctgcacg gccatccggt gctgatcctg tcccgcgacg gccggccgta ctccggcagc   1800
ccgctgtgga tggacacctt cgacgtgcgg ccggagagg tgtgggaggt ggcgttccgg   1860
gcggacaatc cgggtgtctg gatgaaccac tgccacaacc tgccgcacca ggagcagggc   1920
atgatgctgc ggctcgtcta cgacggtgtc accacgccct cgccagcac gagccacgca   1980 cactga                                                              1986

<210> SEQ ID NO 34
<211> LENGTH: 129
<212> TYPE: PRT
<213> ORGANISM: Micromonospora sp. strain 046-ECO11

<400> SEQUENCE: 34

Met Thr Ala Asp Leu His Gly Leu Ala Ser Val Arg Tyr Ile Val Asp
1               5                   10                  15

Asp Val Ser Ala Ala Ile Glu Phe Tyr Thr Thr His Leu Gly Phe Thr
            20                  25                  30

Val Ser Thr Ala Phe Pro Pro Ala Phe Ala Asp Val Val Arg Gly Pro
        35                  40                  45

Leu Arg Leu Leu Leu Ser Gly Pro Thr Ser Ser Gly Ala Arg Val Thr
    50                  55                  60

Pro Ala Asp Ala Ala Gly Cys Gly Arg Asn Arg Ile His Leu Ile Val
65                  70                  75                  80

Asp Asp Leu Asp Ala Glu Arg Glu Arg Leu Glu Arg Ala Gly Val Thr
                85                  90                  95

Leu Arg Ser Asp Val Val Ala Gly Pro Gly Gly Arg Gln Phe Leu Ile
            100                 105                 110

Ala Asp Pro Ala Gly Asn Leu Val Glu Val Phe Glu Pro Ala Ala Arg
        115                 120                 125

Gly

<210> SEQ ID NO 35
<211> LENGTH: 390
<212> TYPE: DNA
<213> ORGANISM: Micromonospora sp. strain 046-ECO11

<400> SEQUENCE: 35
```

```
atgaccgcag acctgcacgg cctggccagc gtccgctaca tcgtcgacga cgtgtcggcg    60
gcgatcgagt tctacaccac ccacctgggt tcacggtgt cgaccgcgtt cccgccggcc   120
ttcgccgacg tggtgcgcgg gccgctgcgg ctcctgctgt ccgggccgac cagctcgggc   180
gcccgggtca ccccggcgga cgcggccggg tgcgggcgca accgcatcca cctgatcgtc   240
gacgatctcg acgccgaacg ggagcggctg gagcgcgccg gggtgacgtt gcgcagcgac   300
gtcgtggccg ggccgggcgg ccgtcagttc ctgatcgccg acccggcggg caacctggtc   360
gaggtgttcg agccggcagc ccgcggctga                                    390
```

<210> SEQ ID NO 36
<211> LENGTH: 178
<212> TYPE: PRT
<213> ORGANISM: Micromonospora sp. strain 046-ECO11

<400> SEQUENCE: 36

```
Met Leu Thr Ala Val Val Ala Ser Pro His Ser Pro Glu Asn Thr Ser
1               5                  10                  15

Arg His Pro Thr Gly Gly Asp Ala Val Asp Glu Ala Thr Pro Arg Thr
            20                  25                  30

Pro Val Ala Ala Arg Pro Thr Trp Ser Pro Ala Thr Ala Pro Val Trp
        35                  40                  45

Leu Val Gly Val Leu Ala Thr Leu Ala Gly Ala Val Ala Ala Glu Ala
    50                  55                  60

Phe Thr Leu Ala Ala Arg Gly Phe Gly Val Pro Met Glu Ala Ala Gly
65                  70                  75                  80

Val Trp Glu Glu Gln Ala Gln Ala Ile Pro Val Gly Ala Ile Ala Arg
                85                  90                  95

Ser Val Val Leu Trp Ser Ile Gly Gly Ile Val Leu Ala Val Val Val
            100                 105                 110

Ala Arg Arg Ala Arg Arg Pro Val Arg Ala Phe Val Ala Gly Thr Val
        115                 120                 125

Ala Phe Thr Val Leu Ser Leu Ala Ala Pro Ala Phe Ala Arg Asp Thr
    130                 135                 140

Pro Val Ser Thr Gln Leu Val Leu Ala Gly Thr His Val Ile Ala Gly
145                 150                 155                 160

Ala Val Ile Ile Ser Ile Leu Ala Ala Arg Leu Ala Ala Pro Thr Pro
                165                 170                 175

Pro Arg
```

<210> SEQ ID NO 37
<211> LENGTH: 537
<212> TYPE: DNA
<213> ORGANISM: Micromonospora sp. strain 046-ECO11

<400> SEQUENCE: 37

```
atgttgactg ccgtcgtggc gtccccgcat tctcccgaga acacatcgag gcacccgacc    60
ggaggcgacg ccgtggatga ggccactccc cgaactcccg tcgcggcacg gcccaccttgg   120 tcgccggcca ccgctccggt gtggctggtc ggcgtgctgg ccaccctcgc cggggccgtg   180
gccgcggagg cgttcacgct cgccgcccgg ggcttcggcg taccgatgga ggcggccggc   240
gtctgggagg agcaggcgca ggcgatcccg gtgggggcca tcgcccgcag cgtcgtgctc   300
tggtcgatcg gcggaatcgt cctggcggtg gtcgtggcgc ggcgggcccg gcggcccgtg   360
cgtgccttcg tggccggcac cgtcgcgttc accgtgctgt ccctcgccgc gccgccttc    420
```

```
gcccgggaca ccccggtgtc gacgcagctc gtcctcgccg gcacccacgt gatcgccggc    480
gccgtgatca tctccatcct ggccgcgcgg ctcgccgcgc ccaccccgcc ccggtaa       537
```

<210> SEQ ID NO 38
<211> LENGTH: 661
<212> TYPE: PRT
<213> ORGANISM: Micromonospora sp. strain 046-ECO11

<400> SEQUENCE: 38

```
Met Asp Gly Thr Glu Ser Asn Val Thr Gly Phe Pro Asp Leu Leu Ser
  1               5                  10                  15

Gly Leu Gly Gly Asp Gly Arg Ala Phe Ala Leu Leu His Arg Pro Gly
                 20                  25                  30

Ala Ala Gly Cys Ala Tyr Val Glu Val Leu Thr Gly Glu Val Cys Asp
             35                  40                  45

Val Asp Thr Leu Gly Glu Leu Pro Leu Pro Thr Glu Pro Ala Thr Gly
 50                  55                  60

Ala Arg His Asp Leu Leu Val Ala Val Pro Tyr Arg Gln Val Thr Glu
 65                  70                  75                  80

Arg Gly Phe Asp Cys His Asp Asp Gly Ala Pro Leu Leu Ala Met Arg
                 85                  90                  95

Val His Glu Gln Phe Gly Leu Asp Arg Gly Gln Ala Leu Ala Gly Leu
            100                 105                 110

Pro Glu Arg Gly Val Pro Val Thr Asp Ala Asp Phe Asp Leu Ser Asp
        115                 120                 125

Glu Asp Tyr Ala Ala Ile Val Lys Arg Val Val Gly Asp Glu Ile Gly
130                 135                 140

Leu Gly Ala Gly Ser Asn Phe Val Ile Arg Arg Thr Phe Thr Ala Arg
145                 150                 155                 160

Leu Ala Asp Tyr Ser Ile Ala Thr Glu Leu Ala Leu Phe Arg Arg Leu
                165                 170                 175

Leu Thr Gly Glu Leu Gly Ser Tyr Trp Thr Phe Leu Phe His Ser Gly
            180                 185                 190

Ala Gly Thr Phe Ile Gly Ala Ser Pro Glu Arg His Val Ser Met Ile
        195                 200                 205

Asp Gly Thr Val Ser Met Asn Pro Ile Ser Gly Thr Tyr Arg His Pro
210                 215                 220

Pro Asn Gly Pro Ala Val Ser Gly Leu Leu Glu Phe Leu Asn Asp Pro
225                 230                 235                 240

Lys Glu Ala Asn Glu Leu Tyr Met Val Val Asp Glu Glu Leu Lys Met
                245                 250                 255

Met Ala Arg Met Cys Ala Ser Gly Gly Gln Val His Gly Pro Phe Leu
            260                 265                 270

Lys Glu Met Ala Arg Val Thr His Ser Glu Tyr Ile Leu Thr Gly Arg
        275                 280                 285

Ser Asp Leu Asp Val Arg Asp Val Leu Arg Glu Thr Leu Leu Ala Pro
290                 295                 300

Thr Val Thr Gly Ser Pro Ile Glu Asn Ala Phe Arg Val Ile Thr Arg
305                 310                 315                 320

His Glu Thr Thr Gly Arg Gly Tyr Tyr Gly Val Leu Ala Leu Met
                325                 330                 335

Gly Arg Asp Ser Ala Gly Ser Arg Thr Leu Asp Ser Ala Ile Met Ile
            340                 345                 350
```

Arg Thr Ala Glu Ile Asp Asp Ala Gly Thr Leu Arg Leu Gly Val Gly
            355                 360                 365

Ala Thr Leu Val Arg Asp Ser Lys Pro Glu Ser Glu Val Ala Glu Thr
        370                 375                 380

Arg Ala Lys Ala Gly Ala Met Arg Ala Leu Gly Leu Gly Val Asp
385                 390                 395                 400

Pro Asp Gly Pro Asp Gly Gly Arg Thr Thr Ala Ala Arg Ala Arg Ser
                405                 410                 415

Ser Leu Ala Thr Asp Pro Arg Val Arg Arg Ala Leu Arg Glu Arg Asn
            420                 425                 430

Thr Thr Leu Ser Arg Phe Trp Leu Asp Gly Ala Glu Arg Arg Thr Pro
        435                 440                 445

Asn Pro Ala Leu Thr Gly Arg Arg Val Leu Val Val Asp Asn Glu Asp
450                 455                 460

Thr Phe Met Ala Met Leu Asp His Gln Leu Arg Ala Leu Gly Leu Arg
465                 470                 475                 480

Ser Ser Ile Ala Arg Phe Asp Ser Arg Leu Arg Pro Asp Gly His Asp
                485                 490                 495

Leu Val Val Val Gly Pro Gly Pro Gly Asp Pro Gly Asp Leu Thr Asp
            500                 505                 510

Pro Arg Met Arg Thr Leu Arg Gly Leu Thr Arg Asp Leu Leu Ala Gly
        515                 520                 525

Thr Val Pro Phe Leu Ser Ile Cys Leu Gly His Gln Val Leu Ala Ala
    530                 535                 540

Glu Leu Gly Phe Pro Leu Ala Arg Arg Ala Val Pro Asn Gln Gly Val
545                 550                 555                 560

Gln Lys Arg Ile Asp Leu Phe Gly Arg Pro Glu Leu Val Gly Phe Tyr
                565                 570                 575

Asn Thr Tyr Thr Ala Arg Ser Ala His Asp Val Val Ala Gly Gly Arg
            580                 585                 590

Arg Gly Pro Ile Glu Ile Ser Arg Ser Pro Asp Ser Gly Asp Val His
        595                 600                 605

Ala Leu Arg Gly Pro Gly Phe Arg Ser Val Gln Phe His Leu Glu Ser
    610                 615                 620

Val Leu Thr Gln His Gly Pro Arg Ile Leu Gly Asp Leu Leu Val Ser
625                 630                 635                 640

Leu Leu Ala Asp Gly Thr Ala Ala Ala Ala Glu Ala Ala Gly Arg
                645                 650                 655

Arg Gly Asn Arg Pro
            660

<210> SEQ ID NO 39
<211> LENGTH: 1986
<212> TYPE: DNA
<213> ORGANISM: Micromonospora sp. strain 046-ECO11

<400> SEQUENCE: 39
atggacggga cggaatcgaa cgtgaccgga ttccccgatc tgctgtccgg tctcggcggc      60
gacgggcgcg ccttcgccct gctgcaccgg cccggcgcgg ccgggtgcgc gtacgtggag     120
gttctgaccg cgaggtgtg cgacgtggac actctcggcg agctgcccct gcccaccgag     180
ccggcgaccg gcgcgcggca cgacctgctc gtggcggtgc cgtaccggca ggtcaccgaa     240
cgggggttcg actgccacga cgacggcgcg ccgctgctcg cgatgcgcgt ccacgagcag     300
ttcgggctcg accgcggaca ggcgctggcg ggcctgcccg aacgcggtgt gccggtgacc     360

-continued

```
gacgccgact tcgacctcag cgacgaggac tacgccgcga tcgtcaagcg ggtggtgggt      420
gacgagatcg ggctgggcgc cggatccaac ttcgtcatcc ggcgcacctt caccgcgcgg      480
ctggccgact actcgatcgc cacggaactg gcgctcttcc gccggttgct gaccggcgaa      540
ctgggttcct actggacgtt tctgttccac tccggcgccg gcacgttcat cggcgcgtca      600
ccggaacgac acgtcagcat gatcgacgga accgtctcga tgaatcccat cagcgggacc      660
taccggcacc ccccgaacgg cccggccgtt tccggtctgc tggaattcct gaacgacccg      720
aaagaggcta acgaactcta catggtcgtc gacgaggaac tgaaaatgat ggcgcggatg      780
tgcgcctccg gcggccaggt gcacggcccg ttcctcaagg aaatggcgcg ggtgacgcac      840
tccgagtaca tcctgaccgg ccgcagcgac ctggacgtgc gcgacgtgct gcgggagacc      900
ctgctcgcgc cgacggtcac cggcagcccg atcgagaacg cgttccgggt catcacccgc      960
cacgagacga ccgccgcgg ctactacggc ggcgtgctcg cgttgatggg ccgtgactcg     1020
gccggcagcc gtacgctcga ctcggccatc atgatccgca ccgccgagat cgacgacgcg     1080
ggcacgctgc gcctgggcgt cggcgccacc ctcgtgcggg actccaagcc ggagtcggag     1140
gtggccgaga cgcgggccaa ggcgggcgcc atgcgcgcgg cgctcggcct cggcgtcgac     1200
ccggacggcc cggacggcgg gcggaccacg gccgcgcggg ctcgttcgtc cctggccacc     1260 gaccccgg tacggcgggc gttgcgcgag cgcaacacca cactgtcgag gttctggctc     1320
gacggcgcgg agcggcgcac cccgaacccg cgctgaccg gacgccgcgt gctcgtcgtc     1380
gacaacgagg acacgttcat ggccatgctc gaccaccagt tgcgggccct cgggctgcgg     1440
tcgagcatcg cccggttcga cagccggctg cggccggacg gacacgacct cgtcgtcgtc     1500
ggtcccggcc ccggcgaccc gggcgacctg accgacccgc gtatgcggac cctgcgcggg     1560
ctcacccgcg acctgctcgc cggaacggtg ccgttcctgt ccatctgcct gggccaccag     1620
gtgctcgccg ccgaactggg gttcccctc gcccggcgcg cggtgcccaa ccagggtgtg     1680
cagaagcgga tcgacctgtt cggccggccg gaactcgtgg ggttctacaa cacctacacc     1740
gcccgctccg cgcacgacgt ggtggccggt ggccggcggg gcccgatcga gatcagccgc     1800
agcccggaca gcggggacgt gcacgcgctg cgcggcccgg gattccgttc cgtccagttc     1860
cacctggagt ccgtcctcac ccagcacggc ccacggatcc tgggcgacct gctggtctcc     1920
ctgctcgccg acggcacggc cgccgccgcg gccgaggcgg cgggccggcg cgggaaccgc     1980
ccgtga                                                               1986
```

<210> SEQ ID NO 40
<211> LENGTH: 427
<212> TYPE: PRT
<213> ORGANISM: Micromonospora sp. strain 046-ECO11

<400> SEQUENCE: 40

```
Val Lys Thr Thr Val Asp Val Leu Val Gln Lys Tyr Gly Gly Thr Ser
1               5                   10                  15

Leu Gln Thr Leu Asp Arg Val Arg His Ala Ala Leu Arg Ile Ala Glu
            20                  25                  30

Ala Arg Arg His Gly Ser Ala Val Thr Val Val Ser Ala Arg Gly
        35                  40                  45

Ser Arg Thr Asp Asp Leu Leu Arg Leu Ala Ala Asp Val Gly Ala Ala
    50                  55                  60

Gly Pro Ser Arg Glu Leu Asp Gln Leu Leu Ala Val Gly Glu Ser Glu
65                  70                  75                  80
```

Ser Ala Ala Leu Met Ala Leu Ala Leu Thr Gly Leu Gly Val Pro Ala
                85                  90                  95

Val Ser Leu Thr Gly His Gln Ala Glu Ile His Thr Thr Asp Arg His
            100                 105                 110

Gly Asp Ala Leu Ile Ser Arg Ile Gly Ala Ala Arg Val Glu Ala Ala
        115                 120                 125

Leu Gly Arg Gly Glu Val Ala Val Val Thr Gly Phe Gln Gly Ile Asp
    130                 135                 140

Arg Ala Gly Asp Val Ala Thr Leu Gly Arg Gly Gly Ser Asp Thr Thr
145                 150                 155                 160

Ala Val Ala Leu Ala Ala Arg Leu Arg Ala Ser Ala Cys Glu Ile Tyr
                165                 170                 175

Thr Asp Val Asp Gly Val Phe Ser Ala Asp Pro Arg Ile Leu Pro Ala
            180                 185                 190

Ala Arg Cys Leu Pro Trp Val Glu Pro Gly Val Met Ala Glu Met Ala
        195                 200                 205

Phe Ala Gly Ala Arg Val Leu His Thr Arg Cys Ile Glu Leu Ala Ala
    210                 215                 220

Met Glu Gly Val Glu Val Arg Val Arg Asn Ala Ser Ser Gln Ala Pro
225                 230                 235                 240

Gly Thr Ile Val Val Asp Arg Pro Asp Arg Pro Leu Glu Thr Arg
                245                 250                 255

Arg Ala Val Val Ala Val Thr His Asp Thr Asp Val Val Arg Val Leu
            260                 265                 270

Val His Cys Arg Asp Gly Arg Arg Asp Met Ala Pro Asp Val Phe Glu
        275                 280                 285

Val Leu Ala Ala His Gly Ala Val Ala Asp Leu Val Ala Arg Ser Gly
    290                 295                 300

Pro Tyr Glu Ser Glu Phe Arg Met Gly Phe Thr Ile Arg Arg Ser Gln
305                 310                 315                 320

Ala Glu Ala Val Arg Thr Ala Leu His Asp Leu Thr Ala Ser Phe Asp
                325                 330                 335

Gly Gly Val His Phe Asp Glu Asn Val Gly Lys Val Ser Val Val Gly
            340                 345                 350

Met Gly Leu Leu Ser Arg Pro His Thr Ala Arg Leu Met Ala Ala
    355                 360                 365

Leu Ala Ala Ala Gly Ile Ser Thr Ser Trp Ile Ser Thr Ser Gln Met
370                 375                 380

Arg Leu Ser Val Ile Val Ser Arg Asp Arg Thr Val Asp Ala Val Glu
385                 390                 395                 400

Ala Leu His Arg Ala Phe Arg Leu Asp Arg Ser Glu Pro Ala Asp Ala
                405                 410                 415

Thr Ser Leu Thr Ser Arg Arg Ser Ala Thr Ala
            420                 425

<210> SEQ ID NO 41
<211> LENGTH: 1284
<212> TYPE: DNA
<213> ORGANISM: Micromonospora sp. strain 046-ECO11

<400> SEQUENCE: 41
gtgaagacga ctgtggacgt gctggtccag aaatacgggg gcacctcgct gcagaccctc      60
gaccgcgttc ggcacgccgc gctgcggatc gccgaggcgc ggcggcacgg ctccgccgtg     120

```
acagtggtcg tgtcggcgcg cggcagccgg accgacgacc tgctgcggct ggcggccgac    180
gtcggcgccg cgggtccgtc ccgggaactc gaccagttgc tcgcagtcgg cgagtccgag    240
tcggcggcgc tgatggcgct ggcgttgacc gggctgggag tgccggccgt ctcgctgacc    300
gggcaccagg cggagatcca caccaccgac cggcacggcg acgcgctgat ctcgcggatc    360
ggggcggcgc gggtggaagc ggcgctgggc cgtggcgagg tcgccgtggt caccggattc    420
cagggcatcg accgggccgg tgacgtcgcc acgctgggc gcggcggctc cgacacgaca    480
gcggtggcgc tcgcggcccg gctccgcgcg tcggcgtgcg agatctacac cgacgtggac    540
ggcgtcttca gcgccgaccc ccgcatcctt ccggcggcgc gttgcctgcc gtgggtggag    600
cccggcgtca tggcggagat ggcgttcgcc ggcgcgcggg tcctgcacac ccgatgcatc    660
gagctggccg ccatggaagg ggtcgaagtg cgcgtgcgca acgcgtcgtc gcaggcgccc    720
ggaacgatag tcgtggaccg gcccgacgac cggccgctgg agacccggcg ggccgtggtg    780
gcggtcaccc acgacaccga tgtcgtccgc gtgctggtgc actgccgcga cggccgccgg    840
gacatggcac ccgacgtgtt cgaggtgctg gccgcccatg gggcggtggc ggacctggtg    900
gcccggtccg ggccctacga gagcgagttc cggatggggt tcaccatccg ccgcagccag    960
gccgaagcgg tgcggaccgc gctgcacgac ctcaccgcgt ccttcgacgg cggggtccac   1020
ttcgacgaga acgtcggcaa ggtgtccgtg gtcggcatgg gcctgctcag ccgccccgag   1080
cacacggccc ggctgatggc ggcgctggcc gcggcgggga tctcgacgag ctggatctcc   1140
acctcccaga tgcggctgtc ggtgatcgtg tcgcgggacc gcaccgtcga cgccgtcgaa   1200
gccctgcacc gcgcgttccg cctggaccgg tccgagccgg cggacgccac gtccctgacc   1260
tcccgccgtt ccgccaccgc ctga                                         1284
```

<210> SEQ ID NO 42
<211> LENGTH: 274
<212> TYPE: PRT
<213> ORGANISM: Micromonospora sp. strain 046-ECO11

<400> SEQUENCE: 42

```
Val Ala Val Leu Asn Ala Ser Phe Ala Arg Gly Leu Arg Leu Arg Arg
 1               5                  10                  15

Leu Phe Arg Arg Gly Asp Gly Arg Leu Leu Val Pro Leu Asp His
            20                  25                  30

Ser Val Thr Asp Gly Pro Leu Arg Arg Gly Asp Leu Asn Ser Leu Leu
        35                  40                  45

Gly Glu Leu Ala Gly Thr Gly Val Asp Ala Val Leu His Lys Gly
    50                  55                  60

Ser Leu Arg His Val Asp His Gly Trp Phe Gly Asp Met Ser Leu Ile
65                  70                  75                  80

Val His Leu Ser Val Ser Thr Arg His Ala Pro Asp Pro Asp Ala Lys
                85                  90                  95

Tyr Leu Val Ala His Val Glu Glu Ala Leu Arg Leu Gly Ala Asp Ala
            100                 105                 110

Val Ser Val His Val Asn Leu Gly Ser Pro Gln Glu Ala Arg Gln Ile
        115                 120                 125

Ala Asp Leu Ala Ala Val Ala Gly Glu Cys Asp Arg Trp Asn Val Pro
    130                 135                 140

Leu Leu Ala Met Val Tyr Ala Arg Gly Pro Gln Ile Thr Asp Ser Arg
145                 150                 155                 160

Ala Pro Glu Leu Val Ala His Ala Ala Thr Leu Ala Ala Asp Leu Gly
```

```
                  165                 170                 175
Ala Asp Ile Val Lys Thr Asp Tyr Val Gly Thr Pro Glu Gln Met Ala
            180                 185                 190

Glu Val Val Arg Gly Cys Pro Ile Pro Leu Ile Val Ala Gly Gly Pro
        195                 200                 205

Arg Ser Ala Asp Thr Pro Thr Val Leu Ala Tyr Val Ser Asp Ala Leu
    210                 215                 220

Arg Gly Gly Val Ala Gly Met Ala Met Gly Arg Asn Val Phe Gln Ala
225                 230                 235                 240

Glu Gln Pro Gly Leu Met Ala Ala Val Ala Arg Leu Val His Glu
            245                 250                 255

Pro Arg His Val Pro Asp Arg Tyr Asp Val Asp Asp Arg Leu Ala Leu
            260                 265                 270

Thr Ser

<210> SEQ ID NO 43
<211> LENGTH: 825
<212> TYPE: DNA
<213> ORGANISM: Micromonospora sp. strain 046-ECO11

<400> SEQUENCE: 43
gtggccgtac tcaacgcttc gttcgctcgt ggcctgcgtc tgcgccgact gttccgacgc      60
ggcgacggac gcctgctcgt cgtcccgctc gaccactccg tcaccgacgg ccgctgcgc     120
cgcggcgacc tgaactcgct gctcggtgag ctcgccggca ccggcgtgga cgccgtggtg    180
ctgcacaagg gcagcctgcg gcacgtcgac cacggctggt tcggcgacat gtcgctgatc    240
gtgcatctga gcgtgagcac ccggcacgcc ccggacccgg acgcgaagta cctggtcgcg    300
cacgtggagg aggcgctgcg gctgggcgcc gacgcggtca gcgtgcacgt caacctcggc    360
tcaccgcagg aggcgcggca gatcgccgac ctggcggcgg tggcggggga gtgcgaccgc    420
tggaacgtcc cgctgctggc catggtgtac gcccgcgggc cgcagatcac cgactcccgg    480
gcaccggagc tggtggcgca cgccgcgacg ctcgccgcgg acctcggcgc cgacatcgtc    540
aagaccgact acgtgggcac gcccgagcag atggccgagg tggtgcgcgg ctgcccgatc    600
ccgctgatcg tggccggcgg cccgcgctcg gccgacactc cgacggtgct cgcctacgtc    660
tcggacgcgc tgcgcggcgg cgtggccggg atggccatgg ccgcaacgt gttccaggcc     720
gagcagcccg gcctgatggc cgccgccgtg gcacggctgg tgcacgagcc acggcacgtg    780
ccggaccggt acgacgtcga cgaccggctc gcccttacgt cctga                    825

<210> SEQ ID NO 44
<211> LENGTH: 367
<212> TYPE: PRT
<213> ORGANISM: Micromonospora sp. strain 046-ECO11

<400> SEQUENCE: 44

Val Lys Leu Cys Trp Leu Asp Ile Arg Asn Val Asn Gly Ala Lys Glu
1               5                   10                  15

Ala Ile Val Glu Glu Ala Val His Gln Arg Val Asp Ala Val Val Ala
            20                  25                  30

Ala Asp Pro Ala Asp Leu Glu Thr Leu Pro Pro Thr Val Lys Lys Val
        35                  40                  45

Leu Phe Pro Gln Gly Gly Pro Leu Pro Glu Lys Leu Glu Pro Ala Asp
    50                  55                  60

Leu Val Ile Val Glu Pro Ala Arg His Gly Glu Pro Ala Glu Leu Ala
```

```
                65                  70                  75                  80
Ala Arg Tyr Pro Glu Val Glu Phe Gly Arg Phe Val Glu Ile Val Asp
                    85                  90                  95
Ala Asp Ser Leu Glu Asp Ala Cys Arg Ser Ala Arg His Asp Arg Trp
                100                 105                 110
Ser Leu Leu Tyr Phe Arg Asp Pro Thr Lys Ile Pro Leu Glu Ile Val
            115                 120                 125
Leu Ala Ala Ala Gly Ala Glu Gly Ser Ile Ile Thr Gln Val Ala
        130                 135                 140
Asp Val Glu Glu Ala Glu Ile Val Phe Gly Val Leu Glu His Gly Ser
145                 150                 155                 160
Asp Gly Val Met Leu Ala Pro Arg Ala Val Gly Glu Ala Thr Glu Leu
                165                 170                 175
Arg Thr Ala Ala Val Ser Thr Ala Ala Asp Leu Ser Leu Val Glu Leu
            180                 185                 190
Glu Val Thr Gly Ile Arg Arg Val Gly Met Gly Glu Arg Ala Cys Val
        195                 200                 205
Asp Thr Cys Thr Asn Phe Arg Leu Asp Glu Gly Ile Leu Val Gly Ser
    210                 215                 220
His Ser Thr Gly Met Ile Leu Cys Cys Ser Glu Thr His Pro Leu Pro
225                 230                 235                 240
Tyr Met Pro Thr Arg Pro Phe Arg Val Asn Ala Gly Ala Leu His Ser
                245                 250                 255
Tyr Thr Leu Ser Ala Gly Gly Arg Thr Asn Tyr Leu Ser Glu Leu Val
            260                 265                 270
Ser Gly Gly Arg Val Leu Ala Val Asp Ser Gln Gly Lys Ser Arg Val
        275                 280                 285
Val Thr Val Gly Arg Val Lys Ile Glu Thr Arg Pro Leu Leu Ala Ile
    290                 295                 300
Asp Ala Val Ser Pro Ser Gly Thr Arg Val Asn Leu Ile Val Gln Asp
305                 310                 315                 320
Asp Trp His Val Arg Val Leu Gly Pro Gly Gly Thr Val Leu Asn Val
                325                 330                 335
Thr Glu Leu Thr Ala Gly Thr Lys Val Leu Gly Tyr Leu Pro Val Glu
            340                 345                 350
Lys Arg His Val Gly Tyr Pro Ile Asp Glu Phe Cys Ile Glu Lys
        355                 360                 365

<210> SEQ ID NO 45
<211> LENGTH: 1104
<212> TYPE: DNA
<213> ORGANISM: Micromonospora sp. strain 046-ECO11

<400> SEQUENCE: 45
gtgaagctgt gctggctgga catccgtaac gtcaacggcg ccaaggaggc aatcgtcgag    60
gaggcggtcc accagcgggt ggacgccgtc gtggcggccg atccggccga cctggagacg   120
cttcccccga cggtgaagaa ggtgctgttc ccgcagggcg gccgctgcc ggagaagctg   180 gaaccggccg acctggtgat cgtcgagccg gcccggcacg gcgagcccgc cgagctggcg   240
gcccggtacc cggaggtgga gttcggccgg ttcgtcgaga tcgtcgacgc ggacagcctg   300
gaggacgcct gccggtccgc gcgccacgac cggtggagcc tgctgtactt ccgcgacccc   360
accaagatcc cgctggagat cgtgctggcg gccgcggcgg gcgcggaggg cagcatcatc   420
acccaggtcg ccgacgtcga ggaggcggag atcgtcttcg gcgtcctgga gcacggctcg   480
```

```
gacggagtga tgctggcgcc ccgcgccgtg ggggaggcca ccgagctgcg gaccgccgcg    540
gtgagcacgg cggcggacct gtcgctcgtg gagctggagg tcaccggcat ccggcgggtg    600
ggcatgggcg agcgcgcctg cgtcgacacg tgcacgaact tccgtctgga cgagggcatc    660
ctggtcggct cgcactccac cggcatgatc ctgtgctgca gcgagacgca tccgctgccg    720
tacatgccga cccggccgtt ccgggtcaac gccggcgcgc tgcactcgta cacgctctcc    780
gccggcgggc ggaccaacta cctcagcgag ctggtctccg gcggccgggt gctcgccgtg    840
gactcgcagg ggaagtcccg cgtcgtcaca gtgggacggg tcaagatcga dcgcgtccg    900 ctgctggcga tcgacgcggt ctcccccctcc gggacacgcg tcaacctcat cgtccaggac    960
gactggcacg tgcgcgtgct cgggccgggc ggcaccgtgc tcaacgtgac cgagctgacc    1020
gccggcacga aggtgctcgg ttacctgccg gtggagaagc ggcacgtcgg ctacccgatc    1080
gacgagttct gcatcgagaa gtga                                          1104
```

<210> SEQ ID NO 46
<211> LENGTH: 253
<212> TYPE: PRT
<213> ORGANISM: Micromonospora sp. strain 046-ECO11

<400> SEQUENCE: 46

```
Met Thr Ala Gln Pro Val Leu Asp Phe His Val Arg Leu Ala Pro Arg
1               5                   10                  15

Pro Gly Ala Arg Glu Arg Leu Leu Ala Ala Leu Arg Glu Cys Gly Leu
            20                  25                  30

Ala Arg Ala Val Val Cys Ala Gly Gly Thr Ile Asp Leu Asp Arg Leu
        35                  40                  45

Ser Arg Gln Leu Val Thr Gly Gly His Val Glu Thr Asp Ala Asp Asn
    50                  55                  60

Asp Ala Val Ala Ala Cys Ala Gly Thr Asp Gly Arg Leu Val Pro
65                  70                  75                  80

Phe Phe Phe Ala Asn Pro His Arg Pro Ala Glu Ala Tyr Arg Ala Arg
                85                  90                  95

Ala Ala Glu Phe Arg Gly Leu Glu Ile Ser Pro Ala Val His Gly Val
            100                 105                 110

Ala Leu Thr Asp Pro Arg Val Ala Asp Leu Val Ala Val Ala Ala Glu
        115                 120                 125

Phe Asp His Pro Val Tyr Val Val Cys Leu Asp Arg Pro Gly Ala Gly
    130                 135                 140

Val Ala Asp Leu Val Gly Leu Ser Arg Arg Phe Pro Gln Val Ser Phe
145                 150                 155                 160

Val Leu Gly His Ser Gly Val Gly Asn Ile Asp Leu Tyr Ala Leu Thr
                165                 170                 175

Leu Ile Gln Asp Glu Pro Asn Ile Ser Leu Thr Ser Gly Gly Tyr
            180                 185                 190

Thr Cys Val Ala Glu Ala Ala Leu Arg Arg Leu Gly Asp Asp Arg Val
        195                 200                 205

Val Phe Gly Ser Glu Tyr Pro Leu Gln His Pro Ala Val Glu Leu Ala
    210                 215                 220

Lys Phe Gln Ala Leu Arg Leu Pro Pro Glu Arg Trp Arg Arg Ile Ala
225                 230                 235                 240

Trp Asp Asn Ala His Arg Leu Leu Gly Glu Glu Lys Arg
                245                 250
```

-continued

<210> SEQ ID NO 47
<211> LENGTH: 762
<212> TYPE: DNA
<213> ORGANISM: Micromonospora sp. strain 046-ECO11

<400> SEQUENCE: 47

```
atgaccgcgc agccggtgct ggacttccac gtacgcctgg cgccccggcc cggggcgcgg      60
gagcggctgc tcgccgcgct gcgcgagtgc gggctggcgc gggcggtggt gtgcgcgggc     120
ggcaccatcg acctggaccg gctgtcccgc cagctcgtca ccggcggcca cgtcgagacc     180
gacgccgaca cgacgcggt ggcggcggcc tgcgccggca ccgacggccg gctggtgccg     240
ttcttcttcg ccaacccgca ccggccggcc gaggcgtacc gggcccgcgc cgccgagttc     300
cgcggcctgg agatctcacc cgccgtccac ggcgtcgccc tgaccgaccc gcgggtcgcc     360
gacctcgtgg ccgtggcggc ggagttcgac catccggtgt acgtggtctg cctggaccga     420
cccggcgcgg gcgtggccga cctggtcggc ctgagccgcc ggttcccgca ggtgagcttc     480
gtgctcgggc acagcggcgt cggcaacatc gacctctacg ccctgaccct gatccaggac     540
gagccgaaca tctcgctgga gacctccggc ggctacacct gcgtggccga ggcggcgcta     600
cgccgcctcg cgacgaccg ggtggtgttc ggctccgagt acccgctgca gcacccggcc     660
gtggaactgg ccaagttcca ggcgttgcga ctgccgccgg agcggtggcg gcggatcgcc     720
tgggacaacg cgcatcgact gctaggagag gagaagcggt ga                        762
```

<210> SEQ ID NO 48
<211> LENGTH: 438
<212> TYPE: PRT
<213> ORGANISM: Micromonospora sp. strain 046-ECO11

<400> SEQUENCE: 48

```
Val Ser Glu Pro Ser Ser Leu Pro Arg Leu Gly Gln Trp His Gly
 1               5                  10                  15

Leu Glu Asp Leu Arg Arg Leu Gln Glu Lys Gln Leu Ala Glu Thr Phe
                20                  25                  30

Thr Trp Ala Ala Arg Ser Pro Phe Tyr Arg Ala Arg Leu Ala Ser Gly
            35                  40                  45

Ala Pro Pro Val Thr Pro Ala Asp Leu Ala Asp Leu Pro Leu Thr Thr
        50                  55                  60

Lys Gln Asp Leu Arg Asp Asn Tyr Pro Phe Gly Met Leu Ala Val Pro
65                  70                  75                  80

Arg Glu Arg Leu Ala Thr Tyr His Glu Ser Ser Gly Thr Ala Gly Lys
                85                  90                  95

Pro Thr Pro Ser Tyr Tyr Thr Ala Glu Asp Trp Thr Asp Leu Ala Glu
            100                 105                 110

Arg Phe Ala Arg Lys Trp Ile Gly Met Ser Ala Asp Asp Val Phe Leu
        115                 120                 125

Val Arg Thr Pro Tyr Ala Leu Leu Leu Thr Gly His Leu Ala His Ala
    130                 135                 140

Ala Ala Arg Leu Arg Gly Ala Thr Val Val Pro Gly Asp Asn Arg Ser
145                 150                 155                 160

Leu Ala Met Pro Tyr Ala Arg Val Val Arg Val Met His Asp Leu Asp
                165                 170                 175

Val Thr Leu Thr Trp Ser Val Pro Thr Glu Cys Leu Ile Trp Ala Ala
            180                 185                 190

Ala Ala Ile Ala Ala Gly His Arg Pro Asp Ile Asp Phe Pro Ala Leu
```

```
                195                 200                 205
Arg Ala Leu Phe Val Gly Gly Glu Pro Met Thr Asp Ala Arg Arg
    210                 215                 220

Arg Ile Ser Arg Leu Trp Gly Val Pro Val Ile Glu Glu Tyr Gly Ser
225                 230                 235                 240

Thr Glu Thr Gly Ser Leu Ala Gly Glu Cys Pro Glu Gly Arg Leu His
                245                 250                 255

Leu Trp Ala Asp Arg Ala Leu Phe Glu Val Tyr Asp Pro Asp Thr Gly
            260                 265                 270

Ala Val Arg Ala Asp Gly Asp Gly Gln Leu Val Val Thr Pro Leu Phe
        275                 280                 285

Arg Glu Ala Met Pro Leu Leu Arg Tyr Asn Leu Glu Asp Asn Val Ser
    290                 295                 300

Val Ser Tyr Asp Asp Cys Gly Cys Gly Trp Lys Leu Pro Thr Val Arg
305                 310                 315                 320

Val Leu Gly Arg Ser Ala Phe Gly Tyr Arg Val Gly Gly Thr Thr Ile
                325                 330                 335

Thr Gln His Gln Leu Glu Glu Leu Val Phe Ser Leu Pro Glu Ala His
            340                 345                 350

Arg Val Met Phe Trp Arg Ala Lys Ala Glu Pro Ala Leu Leu Arg Val
        355                 360                 365

Glu Ile Glu Val Ala Ala Ala His Arg Val Ala Ala Glu Ala Glu Leu
    370                 375                 380

Thr Ala Ala Ile Arg Ala Ala Phe Gly Val Asp Ser Glu Val Thr Gly
385                 390                 395                 400

Leu Ala Pro Gly Thr Leu Ile Pro Leu Asp Ala Leu Thr Ser Met Pro
                405                 410                 415

Asp Val Val Lys Pro Arg Ser Leu Phe Gly Pro Asp Glu Asp Trp Ser
            420                 425                 430

Lys Ala Leu Leu Tyr Tyr
        435

<210> SEQ ID NO 49
<211> LENGTH: 1317
<212> TYPE: DNA
<213> ORGANISM: Micromonospora sp. strain 046-ECO11

<400> SEQUENCE: 49
gtgagcgagc caagttcgag cctgccccgg ctcggccagt ggcacggcct cgaggacctg      60
cggcgcctcc aggagaagca actggcggag acgttcacct gggcggcccg gtcgccgttc     120
taccgggcgc ggctggcctc cggcgcgccg ccggtgacgc ccgccgacct ggccgacctg     180
ccgctgacca ccaagcagga cctgcgggac aactacccct tcggcatgct cgccgtgccc     240
cgcgaacggc tggcgaccta ccacgagtcg agcgggaccg ccgggaagcc cacccccctcc    300 tactacaccg cggaggactg gaccgacctg gcggagcgct cgcccgcaa gtggatcggc      360 atgtccgccg acgacgtctt cctggtccgc acgccgtacg cgctgctgct gaccgggcat     420
ctcgcccacg ccgcagcccg gctgcgtggg gccacggtgg tacctggcga caaccggtcg     480
ctggcgatgc cgtacgcccg ggtggtccgg gtgatgcacg acctggacgt cacgctcacc     540
tggtcggtgc cgacggagtg cctgatctgg gccgccgcgg cgatcgcggc cgggcaccgg     600
cccgacatcg acttcccggc gctgcgcgcg ctgttcgtcg cggcgagcc gatgaccgac     660 gcccgccggc ggcggatcag ccgcctgtgg ggggtgccgg tcatcgagga gtacggctcg     720
```

-continued

```
acggagaccg gcagcctggc cggggagtgc cccgagggac gcctgcacct gtgggccgac    780
cgggcgctgt tcgaggtgta cgacccggac accggcgccg tccgcgcgga cggcgacggc    840
cagctcgtgg tcacgccgct gttccgggag gcgatgccgc tgctgcggta caacctggag    900
gacaacgtgt cggtctccta cgacgactgc ggatgcggct ggaagctgcc caccgtgcgg    960
gtgctcggcc ggtcggcgtt cggctaccgg gtcggcggca ccaccatcac ccagcaccag   1020
ctggaggaac tggtcttctc cctgccgagg gcgcaccggg tgatgttctg cggggccaag   1080
gcggagccgg cgctgttgcg ggtcgagatc gaggtggccg ccgcgcaccg gtcgccgcc    1140 gaggcggagc tgaccgccgc gatccgggcc gccttcggcg tggacagcga ggtcaccggc   1200
ctggcgccgg gaaccctgat cccgctcgac gcgctgacca gcatgccgga cgtggtgaag   1260
ccacgcagcc tgttcggtcc ggacgaggac tggagcaaag cgctcctcta ctactga     1317
```

<210> SEQ ID NO 50
<211> LENGTH: 396
<212> TYPE: PRT
<213> ORGANISM: Micromonospora sp. strain 046-ECO11

<400> SEQUENCE: 50

```
Met Pro Gln Met Arg Val Ala Val Ala Gly Ala Gly Ile Ala Gly Leu
1               5                   10                  15

Ala Phe Ala Ala Ala Leu Arg Arg Thr Gly Ile Asp Cys His Val Tyr
                20                  25                  30

Glu Gln Ala Asp Gln Leu Met Glu Val Gly Ala Gly Val Gln Val Ala
            35                  40                  45

Pro Asn Ala Thr Arg Leu Leu His Arg Leu Gly Leu Arg Asp Arg Leu
        50                  55                  60

Arg Thr Val Ala Val Ala Pro Gln Ala Ile Glu Met Arg Arg Trp Asp
65                  70                  75                  80

Asp Gly Thr Leu Leu Gln Arg Thr Gln Leu Gly Ser Val Cys Gly Arg
                85                  90                  95

Arg Phe Gly Ala Pro Tyr Tyr Val Val His Arg Ala Asp Leu His Ser
            100                 105                 110

Ser Leu Leu Ser Leu Val Pro Pro Asp Arg Val His Leu Gly Ala Arg
        115                 120                 125

Leu Thr Ala Val Thr Gln Thr Ala Asp Glu Ala Tyr Leu His Leu Ser
    130                 135                 140

Asn Gly Thr Thr Val Ala Ala Asp Leu Val Val Gly Ala Asp Gly Ile
145                 150                 155                 160

His Ser Val Ala Arg Glu Gln Ile Val Ala Asp Arg Pro Arg Phe Ser
                165                 170                 175

Gly Gln Ser Ile Tyr Arg Gly Leu Val Pro Ala Glu Arg Val Pro Phe
            180                 185                 190

Leu Leu Thr Glu Pro Arg Val Gln Leu Trp Phe Gly Pro Asp Gln His
        195                 200                 205

Cys Val Cys Tyr Pro Val Ser Ala Gly Arg Gln Val Ser Phe Gly Ala
    210                 215                 220

Thr Val Pro Ala Thr Asp Trp Arg Gln Glu Ser Trp Ser Gly Arg Gly
225                 230                 235                 240

Asp Val Thr Gln Leu Ala Ala Ala Tyr Ala Gly Trp His Pro Asp Val
                245                 250                 255

Thr Arg Leu Ile Ala Ala Asp Arg Val Gly Arg Trp Ala Leu His
            260                 265                 270
```

-continued

Asp Arg Asp Ser Ile Asp Arg Leu Ser Ala Gly Arg Val Thr Leu Ile
         275                 280                 285

Gly Asp Ala Ala His Pro Met Leu Pro Phe Gln Ala Gln Gly Ala Asn
     290                 295                 300

Gln Ala Val Glu Asp Ala Val Val Leu Ala Val Cys Leu Ala Gly Val
305                 310                 315                 320

Glu Pro Ala Gly Leu Gly Ala Ala Leu Arg Arg Tyr Glu Arg Ile Arg
                 325                 330                 335

Leu Pro Arg Thr Thr Arg Ile Gln Arg Gln Ser Arg Ala Asn Ala Glu
             340                 345                 350

Met Phe His Leu Ala Asp Gly Ala Asp Gln Arg Arg Arg Asp Val Ala
         355                 360                 365

Ala Gln Ser Ser Ser Gly Leu Asp Arg His Glu Trp Leu Phe Gly Tyr
     370                 375                 380

Asp Ala Glu Lys Ala Thr Thr Thr Ser Gly Ser Ala
385                 390                 395

<210> SEQ ID NO 51
<211> LENGTH: 1191
<212> TYPE: DNA
<213> ORGANISM: Micromonospora sp. strain 046-ECO11

<400> SEQUENCE: 51

| atgccgcaga tgagggtcgc cgtggccggc gccggcatcg ccgggctcgc cttcgccgcc | 60 |
| gcccggcgcc ggaccgggat cgactgccac gtgtacgaac aggccgacca gctcatggag | 120 |
| gtgggcgcgg gcgtgcaggt cgcgccgaac gccacccggc tgctgcaccg gctgggcctg | 180 |
| cgtgaccgcc tgcgtacggt ggctgtcgcg ccgcaggcga tcgagatgcg ccgctgggac | 240 |
| gacggcacgc tgctgcaacg cacccagctg ggcagcgtgt gcggacgccg cttcggcgcg | 300 |
| ccgtactacg tggtgcaccg cgcggacctg cacagcagcc tgctgtcgct ggtgccgccg | 360 |
| gaccgggtgc acctgggcgc ccgcctcacc gccgtgacgc agaccgccga cgaggcgtac | 420 |
| ctgcacctgt ccaacggcac cacggtcgcg gcggatctcg tcgtgggcgc cgacggcatc | 480 |
| cactcggtcg cgcgggagca gatcgtggcg gaccggccgc gcttctccgg acagtccatc | 540 |
| taccgcgggc tggtgccggc cgagcgggtg ccgttcctgc tcaccgaacc ccgggtgcag | 600 |
| ttgtggttcg ggccggacca gcactgcgtc tgctacccgg tgtccgccgg ccggcaggtg | 660 |
| agcttcggcg cgacggtgcc cgccaccgac tggcggcagg agtcgtggtc gggccggggc | 720 |
| gacgtgacgc aactcgcggc cgcgtacgcg ggctggcacc cggacgtcac ccggctgatc | 780 |
| gccgcggccg accgggtcgg caggtgggcg ctgcacgacc gggacagcat cgaccggctc | 840 |
| agcgcgggac gggtgaccct gatcggcgac cgcgcgcacc cgatgctgcc gttccaggcg | 900 |
| cagggcgcga accaggccgt cgaggacgcg gtggtgctcg cggtctgcct ggccggcgtg | 960 |
| gaaccggcgg gcctgggcgc cgcgctgcgc cgctacgaac ggatccgcct gccccggacc | 1020 |
| acccggatcc agcggcagtc ccgggccaac gccgagatgt tccacctggc cgacggcgcc | 1080 |
| gaccagcgcc gccgggacgt cgccgcacaa tcctcgtccg gcctggaccg ccacgaatgg | 1140 |
| ctcttcgggt acgacgccga gaaagccacc acgaccagcg ggagcgcctg a | 1191 |

<210> SEQ ID NO 52
<211> LENGTH: 261
<212> TYPE: PRT
<213> ORGANISM: Micromonospora sp. strain 046-ECO11

<400> SEQUENCE: 52

```
Met Glu Leu Thr Gly Ile Glu Ser Lys Val Ala Leu Val Thr Gly Ala
1               5                   10                  15

Gly Gln Gly Ile Gly Ala Ala Val Ala Gly Val Leu Ala Arg Ala Gly
            20                  25                  30

Ala Gln Val Ala Ala Val Asp Arg Asn Ala Glu Ala Leu Thr Thr Val
        35                  40                  45

Val Thr Lys Leu Ala Ala Glu Gly Asp Ser Ala Arg Ala Tyr Cys Val
    50                  55                  60

Asp Val Cys Asp Ser Glu Ala Val Asp Ala Leu Val Arg Arg Val Glu
65                  70                  75                  80

Asp Glu Met Gly Pro Val Ala Ile Leu Val Asn Ala Ala Gly Val Leu
                85                  90                  95

His Thr Gly Arg Val Val Glu Leu Ser Asp Arg Gln Trp Arg Arg Thr
            100                 105                 110

Phe Ser Val Asn Ala Asp Gly Val Phe His Val Ser Arg Ala Val Ala
        115                 120                 125

Arg Arg Met Val Gly Arg Arg Gly Ala Ile Val Thr Val Ala Ser
    130                 135                 140

Asn Ala Ala Gly Val Pro Arg Thr Glu Met Ala Ala Tyr Ala Ala Ser
145                 150                 155                 160

Lys Ala Ala Ser Ala Gln Phe Thr Arg Cys Leu Gly Leu Glu Leu Ser
                165                 170                 175

Gly Tyr Gly Ile Arg Cys Asn Val Val Ser Pro Gly Ser Thr Asp Thr
            180                 185                 190

Pro Met Leu Arg Ala Met Leu Gly Glu Gly Ala Asp Pro Ser Ala Val
    195                 200                 205

Ile Glu Gly Thr Pro Gly Ala Tyr Arg Val Gly Ile Pro Leu Arg Lys
    210                 215                 220

Leu Ala Gln Pro Arg Asp Val Ala Glu Ala Val Ala Tyr Leu Val Ser
225                 230                 235                 240

Asp Gln Ala Gly His Val Thr Met His Asp Leu Tyr Val Asp Gly Gly
                245                 250                 255

Ala Ala Leu His Val
            260

<210> SEQ ID NO 53
<211> LENGTH: 786
<212> TYPE: DNA
<213> ORGANISM: Micromonospora sp. strain 046-ECO11

<400> SEQUENCE: 53
atggaactga ccggaatcga gtcgaaggtc gccctggtca cgggcgcggg gcagggcatc     60
ggcgccgccg tggccggtgt cctggcgagg gcgggcgcgc aggtggcggc ggtggaccgc    120
aacgccgagg cgctgaccac cgtcgtgacg aagctcgccg ccgagggcga ctcggcgcgc    180
gcctactgcg tcgacgtgtg cgacagcgag gcggtggacg cgctggtgcg ccgggtcgag    240
gacgagatgg gccggtcgc catcctggtc aacgccgccg gcgtgctgca caccggacgg    300
gtcgtcgagc tgtcggaccg gcagtggcgc cggaccttct cggtgaacgc cgacggcgtg    360
ttccacgtgt cccgggcggt ggcgcggcgg atggtgggcc gcgtcgtgg cgcgatcgtc    420 accgtggcgt cgaacgccgc cggggtgccg cgtaccgaga tggccgcgta cgccgcctcc    480
aaggccgcgt ccgcgcagtt caccgcgctgc ctggggcttg agctgtccgg ctacggcatc    540
cggtgcaacg tggtctcgcc cggctccacc gacacccca tgctgcgggc catgctcggc    600
```

```
gagggcgccg acccgagcgc ggtgatcgag ggcacgccgg gcgcgtaccg cgtcggcatc      660
ccgctgcgca agctggccca gccgcgcgac gtggccgagg cggtcgccta tctggtgtcc      720
gaccaggcgg gccacgtgac catgcacgac ctgtacgtcg acggcggcgc ggccctgcac      780
gtgtga                                                                 786
```

<210> SEQ ID NO 54
<211> LENGTH: 224
<212> TYPE: PRT
<213> ORGANISM: Micromonospora sp. strain 046-ECO11

<400> SEQUENCE: 54

```
Met Ala Met Thr Pro Ile Ala Pro Tyr Arg Met Pro Gly Asp Gly Asp
1               5                   10                  15

Leu Pro Gly Thr Ala Leu Pro Trp Arg Pro His Pro Asp Arg Ala Ala
            20                  25                  30

Val Leu Val His Asp Leu Gln Arg Tyr Phe Leu Arg Pro Phe Glu Ala
        35                  40                  45

Gly Glu Ser Pro Met Ala Glu Leu Leu Pro Asn Val Ala Lys Leu Leu
    50                  55                  60

Ala Thr Ala Arg Ala Ala Gly Val Pro Val Leu Tyr Thr Ala Gln Pro
65                  70                  75                  80

Gly Gly Met Ser Arg Gln Asp Arg Gly Leu Leu His Asp Leu Trp Gly
                85                  90                  95

Pro Gly Met Ser Ser Ala Glu Asp Asp Arg Gly Ile Val Asp Asp Val
            100                 105                 110

Ala Pro Gln Pro Gly Asp Thr Val Leu Thr Lys Trp Arg Tyr Ser Ala
        115                 120                 125

Phe Phe Arg Ser Asp Leu Glu Glu Arg Leu Arg Gly Ala Gly Arg Asp
    130                 135                 140

Gln Leu Val Val Cys Gly Val Tyr Ala His Met Gly Cys Leu Ile Thr
145                 150                 155                 160

Ala Cys Asp Ala Phe Ser Arg Asp Ile Glu Ala Phe Leu Val Ala Asp
                165                 170                 175

Ala Leu Ala Asp Leu Ser Arg Glu Asp His Leu Met Ala Leu Arg Tyr
            180                 185                 190

Ala Ala Asp Arg Cys Ala Val Pro Leu Trp Thr Ala Asp Val Leu Asp
        195                 200                 205

Gly Leu Ala Asp Ala Ala Gly Arg Pro Asp Gln Ser Ser Thr Gln Arg
    210                 215                 220
```

<210> SEQ ID NO 55
<211> LENGTH: 675
<212> TYPE: DNA
<213> ORGANISM: Micromonospora sp. strain 046-ECO11

<400> SEQUENCE: 55

```
atggccatga ccccgatcgc gccgtaccgc atgcccggcg acggcgacct gccggcacc       60 gcgctgccct ggcgtccgca cccggaccgg gccgccgtgc tggtgcacga cctgcaacgc     120
tacttcctgc gccgttcga ggccggggag tccccgatgg ccgaactgct ccccaacgtc      180
gcgaagctgc tcgccacggc gcgggcggcc ggcgtgccgg tgctgtacac cgcgcagccc     240
ggcggcatga gccggcagga ccgcgggttg ctgcacgacc tgtggggccc cggcatgagc     300
agcgccgagg acgaccgggg catcgtcgac gacgtcgccc cgcagccggg cgacacggtg     360
```

-continued

```
ctgaccaagt ggcgctacag cgcgttcttc cgcagcgacc tggaggagcg actgcgcggt    420
gcgggacggg accagctcgt ggtctgcggc gtgtacgcgc acatggggtg cctgatcacc    480
gcctgcgacg cgttcagccg cgacatcgag gcgttcctgg tggcggacgc gctggccgac    540
ctatcgcgcg aggaccacct gatggcgctg cgctacgccg cggaccgctg cgcggtgccg    600
ttgtggacgg cggatgtgct ggacgggctg gcggacgccg ccgggcgtcc ggatcagagc    660
agcacccaac gatga                                                     675
```

<210> SEQ ID NO 56
<211> LENGTH: 233
<212> TYPE: PRT
<213> ORGANISM: Micromonospora sp. strain 046-ECO11

<400> SEQUENCE: 56

```
Met Ser Asp Arg Thr Arg Val Val Val Gly Gly Thr Ser Gly Ile
1               5                   10                  15

Gly Arg His Phe Ala Arg Phe Cys Ala Glu Arg Gly Asp Asp Val Val
            20                  25                  30

Ile Thr Gly Arg Ser Ala Ala Arg Thr Lys Thr Val Ala Asp Glu Ile
        35                  40                  45

Gly Gly Arg Thr Arg Gly Leu Ala Leu Asp Leu Ala Glu Pro Glu Thr
    50                  55                  60

Ile Ala Asp Ala Leu Ala Asp Val Pro His Val Asp Arg Leu Val Val
65                  70                  75                  80

Ala Ala Leu Asp Arg Asp Tyr Asn Thr Val Arg Ala Tyr Arg Pro Gly
                85                  90                  95

Asp Ala Ala Arg Leu Leu Thr Val Lys Leu Val Gly Tyr Thr Ala Val
            100                 105                 110

Leu His Ala Leu Ala Pro Arg Met Thr Asp Glu Ser Ala Val Val Leu
        115                 120                 125

Leu Gly Gly Leu Ala Ser His Arg Pro Tyr Pro Gly Ser Thr Ser Val
    130                 135                 140

Thr Thr Ala Asn Gly Gly Ile Ser Ala Leu Val Arg Thr Leu Ala Val
145                 150                 155                 160

Glu Leu Ser Pro Val Arg Val Asn Ala Leu His Pro Ser Ile Val Ser
                165                 170                 175

Asp Thr Pro Phe Trp Ser Asp Lys Pro Ala Ala Arg Glu Ala Ala Ala
            180                 185                 190

Thr Arg Ala Leu Ser Arg Arg Pro Val Thr Met Gln Asp Cys Ala Glu
        195                 200                 205

Ala Ile Asp Phe Leu Leu Thr Asn Arg Ser Ile Asn Gly Val Asn Leu
    210                 215                 220

Asn Ile Asp Gly Gly Asp Val Leu Ile
225                 230
```

<210> SEQ ID NO 57
<211> LENGTH: 702
<212> TYPE: DNA
<213> ORGANISM: Micromonospora sp. strain 046-ECO11

<400> SEQUENCE: 57

```
atgtcggatc ggacccgggt cgtggtcgtc ggcggaacct cggggatcgg cgggcacttc     60
gcccgattct cgccgaacg cggagacgac gtggtgatca ccggccgttc ggcggcccgg    120
accaagaccg tggcggacga gatcgggggg cggacccgtg ggctcgctct cgacctggcc    180
```

-continued

```
gagccggaga cgatcgcgga cgcgctcgcc gacgtgccgc acgtcgaccg gctcgtggtc    240
gcggcgctgg accgcgacta caacaccgtc cgcgcgtacc ggccgggcga cgcggcgcgg    300
ctgctgaccg tcaagctggt cggctacacg gcggtcctgc acgccctcgc ccgcggatg    360 accgacgaga gcgcagtcgt gctgctcggc ggcctggcca ccaccggcc gtatcccggc    420 tccacctccg tcacgaccgc caacggcggg atcagcgcgc tggtgcggac cctggctgtg    480
gaactctcgc cggtccgggt caacgccctg cacccgagca tcgtctccga cacgccgttc    540
tggagcgaca gcccgccgc gcgggaggcc gccgcgaccc gcgcgctcag ccgacggccg    600
gtcaccatgc aggactgcgc cgaggcgatc gacttcctgc tgacgaaccg ctcgataaac    660
ggggtcaacc tgaacatcga cggcgggac gtgctcatct ga                       702
```

<210> SEQ ID NO 58
<211> LENGTH: 246
<212> TYPE: PRT
<213> ORGANISM: Micromonospora sp. strain 046-ECO11

<400> SEQUENCE: 58

```
Met Thr Ser Ala Leu Arg Thr Ser Ala Trp Thr Tyr Asp Asp Phe Thr
  1               5                  10                  15

Ser Arg Glu Leu Asp Pro Ala Arg Trp Ala Ile Met Ser Ile Ala Gly
             20                  25                  30

Ala Asp Gly Gln Thr His Arg Tyr Gln Asp Arg Asn Ala Gln Val Arg
         35                  40                  45

Thr Gly Asp Gly Arg Leu Glu Leu Thr Val Asp Pro Phe Thr Arg Phe
     50                  55                  60

His Asp Thr Asp Pro Arg Gln Asn Asn Ala Lys Gln Met Tyr Arg Ser
 65                  70                  75                  80

Val Arg Arg Phe Ala Val Pro Ala Glu Gly Ser Leu Thr Val Glu Val
                 85                  90                  95

Glu Met Gly Val Arg Thr Tyr Arg Gln Ile Pro His Asp Leu Leu Asp
            100                 105                 110

Ala Phe Gly Thr Val Asn Leu Phe Asp Leu Glu Thr Gly Val Val Phe
        115                 120                 125

Asn Ala Ala Thr Asn Asp Thr Val Tyr Ala Thr Val Glu Arg Leu
    130                 135                 140

Val Leu Pro Gly Val Thr Gln Pro His Glu His Tyr Ile His Arg Val
145                 150                 155                 160

Val Leu Asp Val Pro Thr Glu Pro Gly Arg Ala His Gly Tyr Ala Ile
                165                 170                 175

Thr Tyr Arg Ala Pro Thr Ser Glu Val Glu Phe His Val Asp Gly Arg
            180                 185                 190

Leu Ala Tyr Trp Ala Arg Val Pro Val Pro Val Thr Gly Phe His Ala
        195                 200                 205

Gly Met Ala Leu Phe Ser Ala Arg Asp Leu Ala Arg Tyr Pro Arg Glu
    210                 215                 220

Gln Arg Glu His Gly Gln Gly Ala Thr Gly Trp Trp Gly Pro Trp Arg
225                 230                 235                 240

Ile Ala Ser Gly Val Arg
                245
```

<210> SEQ ID NO 59
<211> LENGTH: 741
<212> TYPE: DNA
<213> ORGANISM: Micromonospora sp. strain 046-ECO11

-continued

<400> SEQUENCE: 59

```
atgacgtcgg cactgagaac cagcgcgtgg acgtacgacg acttcaccag ccgcgagctg      60
gaccccgccc gctgggcgat catgtcgatc gccggcgcgg acgggcagac ccacaggtac     120
caggaccgca acgcccaggt ccgcaccggc gacgggcggc tggagctgac cgtcgacccg     180
ttcacccgct ccacgacac cgatccccgg cagaacaacg ccaagcagat gtaccggtcg      240
gtgcggcgct cgccgtgcc ggcggagggc tcgctgaccg tcgaggtgga gatgggcgtg      300
cggacgtacc ggcagatccc gcacgacctg ctggacgcgt cggcacggt gaacctgttc      360
gacctggaga ccggcgtcgt gttcaacgcc gccgccacga acgacaccgt gtacgcgacg      420
gtcgagcgcc tggtgctgcc cggcgtgacc cagccgcacg agcactacat ccaccgggtg      480
gtcctggacg tgccgacgga gccgggccgg gcgcacggat acgccatcac ctaccgggcg      540
ccgacgtcgg aggtggagtt ccacgtcgac ggccggctcg cctactgggc gcgggtcccg      600
gtgccggtga ccggattcca cgccggcatg gcgctcttct ccgcccgcga cctggcccgg      660
taccccgcg agcagcggga gcacgggcag ggcgcgaccg ggtggtgggg gccgtggcgg      720
atcgcctccg gcgtcagatg a                                                 741
```

<210> SEQ ID NO 60
<211> LENGTH: 111
<212> TYPE: PRT
<213> ORGANISM: Micromonospora sp. strain 046-ECO11

<400> SEQUENCE: 60

```
Met Asp Thr Ala Ala Pro Ala Thr Asp Gly Gly Arg Tyr Leu Ala Val
  1               5                  10                  15

His His Ser Ala Glu Phe Arg Glu Leu Arg Arg Arg Ser Ser Thr Phe
                 20                  25                  30

Thr Leu Trp Ala Ser Val Ala Phe Phe Gly Trp Trp Phe Leu Gly Ser
             35                  40                  45

Leu Leu Ala Thr Tyr Ala Pro Asp Phe Phe Arg Glu Lys Val Ala Gly
 50                  55                  60

Pro Val Asn Val Gly Leu Leu Phe Val Phe Leu Ser Phe Ala Phe Val
 65                  70                  75                  80

Val Thr Leu Ala Ala Phe Tyr Leu Arg Tyr Ala Arg Thr His Leu Asp
                 85                  90                  95

Pro Leu Ser Glu Lys Ile Arg Ala Asp Leu Glu Gly Ala Ser Arg
                100                 105                 110
```

<210> SEQ ID NO 61
<211> LENGTH: 336
<212> TYPE: DNA
<213> ORGANISM: Micromonospora sp. strain 046-ECO11

<400> SEQUENCE: 61

```
atggacacgg cagctccggc aacggacggc ggtcgctacc tcgccgtcca tcacagcgca      60
gagttcaggg aactacggcg acgatcgagc acgttcacgc tctgggccag cgtcgccttc     120
ttcggctggt ggttcctcgg cagcctgctc gccacctacg cgccggactt cttccgggag     180
aaggtggccg gccggtcaa cgtgggtctg ctcttcgtct tcctgtcgtt cgccttcgtg      240
gtgacgctcg ccgccttcta cctgcgttac gcccgcacgc atctcgatcc gctcagcgag      300
aagatccgtg ccgacctgga aggagcgtcc cgatga                                 336
```

-continued

```
<210> SEQ ID NO 62
<211> LENGTH: 559
<212> TYPE: PRT
<213> ORGANISM: Micromonospora sp. strain 046-ECO11

<400> SEQUENCE: 62

Met Ser Val Ile Leu Ala Asp Pro Pro Pro Val Asp Asn Thr Trp
 1               5                  10                  15

Ala Thr Pro Ala Ile Ala Val Pro Val Thr Ile Val Leu Ala Leu Ala
                 20                  25                  30

Val Leu Tyr Leu Val Arg Ser Ala Arg Ala Ser Thr Thr Thr Ala Asp
                 35                  40                  45

Gly Phe Leu Leu Ala Asp Arg Arg Ile Gly Pro Val Gln Asn Ala Leu
     50                  55                  60

Ala Val Ala Ser Ala Pro Leu Met Tyr Ser Thr Met Tyr Ile Ile Thr
 65                  70                  75                  80

Gly His Ile Ala Leu Ser Gly Tyr Asp Ala Ile Leu Leu Met Thr Ala
                 85                  90                  95

Phe Thr Met Gly Thr Met Leu Ala Leu Phe Leu Phe Ala Gly Pro Val
                100                 105                 110

Arg Asn Val Gly Gly Tyr Thr Leu Gly Asp Leu Leu Ala Val Arg Thr
            115                 120                 125

Arg Glu Arg Pro Ala Arg Ile Ala Ser Ala Val Leu Thr Leu Leu Thr
        130                 135                 140

Tyr Val Met Leu Thr Val Ile Met Met Ala Ala Ile Ala Phe Ile Phe
145                 150                 155                 160

Asn Arg Trp Phe Gly Val Asp Ala Leu Val Gly Leu Val Leu Pro Val
                165                 170                 175

Phe Val Val Gly Leu Ile Thr Val Gly Tyr Val Tyr Leu Gly Gly Met
                180                 185                 190

Leu Gly Val Thr Arg Ile Leu Val Phe Lys Leu Val Leu Ser Val Val
            195                 200                 205

Val Val Gly Val Leu Thr Ala Trp Val Leu Ala Arg Phe Asp Leu Asn
        210                 215                 220

Leu Phe Ser Leu Leu Glu Arg Ala Glu Ala Asn Ala Ala Pro Val Pro
225                 230                 235                 240

Ser Gly Ser Asp Leu Leu Gly Pro Gly Arg Leu Phe Gly Glu Gly Ala
                245                 250                 255

Thr Thr Leu Val His Leu Ser Lys Leu Phe Ala Ile Ala Val Gly Val
                260                 265                 270

Ala Ala Ile Pro Phe Leu Phe Met Arg Asn Phe Ala Val Thr Ser Gly
            275                 280                 285

Arg Asp Ala Arg Arg Ser Thr Gly Trp Ala Ser Met Ile Ile Val Gly
        290                 295                 300

Phe Tyr Leu Cys Leu Ser Val Val Gly Leu Gly Ala Val Ala Ile Leu
305                 310                 315                 320

Gly Arg Asp Asn Ile Gly Val Ile Lys Ala His Arg Asp Ile Ser Phe
                325                 330                 335

Pro Lys Leu Ala Asp Glu Leu Gly Gly Pro Val Met Val Gly Ser Leu
                340                 345                 350

Ala Gly Val Ala Val Leu Thr Ile Val Gly Val Phe Ala Pro Leu Leu
            355                 360                 365

His Ser Ala Val Thr Thr Val Thr Lys Asp Leu Asn Val Ile Arg Gly
        370                 375                 380
```

| | | | | | | | | | | | | | | |
|---|---|---|---|---|---|---|---|---|---|---|---|---|---|---|
| Arg | Arg | Leu | Asp | Pro | Ala | Ala | Glu | Leu | Arg | Asp | Ile | Lys | Arg | Asn | Thr |
| 385 | | | | 390 | | | | | 395 | | | | | 400 | |

Leu Ile Ile Gly Val Gly Ser Val Leu Leu Ala Val Val Met Leu Pro
                    405                     410                 415

Val Arg Thr His Ile Phe Ile Pro Thr Ser Ile Asp Ile Ala Gly Ala
                420                     425                 430

Val Val Leu Pro Ile Val Val Tyr Ala Leu Phe Trp Arg Arg Phe Asn
            435                     440                 445

Thr Arg Gly Leu Gln Trp Thr Val Tyr Gly Gly Leu Ala Leu Thr Ala
        450                     455                 460

Phe Leu Val Leu Phe Ser Asn Gly Val Ser Gly Glu Pro Asp Ala Ile
465                 470                     475                 480

Phe Pro Asp Arg Asn Phe Lys Phe Val Asp Val Glu Pro Ala Leu Ile
            485                     490                 495

Thr Val Pro Val Gly Phe Leu Leu Gly Tyr Leu Gly Ser Ile Thr Ser
                500                     505                 510

Arg Glu Arg Asp Asp Ala Ala Phe Ala Glu Met Gln Val Arg Ser Leu
            515                     520                 525

Thr Gly Ala Val Val Thr Gly Pro Pro Arg Pro Ala Ala Val Asp Asp
        530                     535                 540

Glu Asp Arg Asp Gly Arg Gln Asp Arg Ala Pro Ser Pro Val Ser
545                 550                     555

<210> SEQ ID NO 63
<211> LENGTH: 1680
<212> TYPE: DNA
<213> ORGANISM: Micromonospora sp. strain 046-ECO11

<400> SEQUENCE: 63

```
atgagcgtca tcctcgccga cccgccaccc ccggtcgaca cacgtgggc gacgcccgcg    60
atcgccgtgc cggtcaccat cgtcctcgcg ctcgcggtgc tctacctggt ccggtcggcg   120
cgcgccagca ccaccaccgc ggacggcttc ctgctggccg accggcggat cgggccggtg   180
cagaacgcgc tggcggtggc ctccgcgccg ctgatgtact cgacgatgta catcatcacc   240
ggccacatcg cgctcagcgg ctacgacgcc atcctgctga tgaccgcctt caccatgggc   300
accatgctcg cgctgttcct cttcgccggg ccggtgcgca acgtgggcgg ctacacgctc   360
ggtgacctgc tcgcggtccg tacccgggag cggccggcgc ggatcgcgtc ggcggtgctc   420
acgctgctga cgtacgtcat gctgacggtg atcatgatgg ccgccatcgc gttcatcttc   480
aaccgctggt tcggcgtcga cgccctcgtc ggcctggtcc tcccggtgtt cgtcgtcggt   540
ctgatcacgg tggggtacgt gtacctcggc gggatgctcg gggtcacccg catcctggtg   600
ttcaagctgg tgctgtcggt ggtcgtcgtg ggcgtgctga ccgcctgggt gctggcccgc   660
ttcgacctga acctcttcag cctgctggag cgggccgagg cgaacgcggc gccggtgccc   720
agcggcagcg acctgctggg cccgggccgg ctgttcggcg agggcgcgac cacgctcgtg   780
cacctgtcga gctgttcgc catcgccgtc ggagtggcgg ccattccgtt cctgttcatg   840
cgcaacttcg cggtgaccag cgggcgggac gcgcgccggt cgaccgggtg ggcgtcgatg   900
atcatcgtcg ggttctacct gtgcctgtcc gtcgtcgggc tcggtgccgt cgcgatcctc   960
ggccgggaca acatcggcgt catcaaggcc caccgcgaca tcagcttccc caagctcgcc  1020
gacgagctcg cggtccggt gatggtcggc tccctggccg cgtcgcggt cctgacgatc  1080
gtcggcgtct tcgcgccgct gctgcacagc gccgtgacga cggtgaccaa ggaccctgaac  1140
```

```
                                                    -continued gtgatccgcg gccggcggct ggatccggcc gccgagctgc gggacatcaa gcgcaacacc    1200
ctgatcatcg gcgtcggctc cgtgctgctg gcggtcgtga tgctgccggt acggacccac    1260
atcttcatcc cgacctcgat cgacattgcc ggcgcggtgg tcctgccgat cgtcgtctac    1320
gcgttgttct ggcggcgttt caacacccgc ggactgcagt ggacggtcta cggcggcctc    1380
gcgctcaccg cgttcctggt gctgttctcc aacggtgtct cgggcgagcc ggacgccatc    1440
ttcccggacc gcaacttcaa gttcgtggac gtcgagcccg cgctgatcac ggtgccggtc    1500
ggcttcctgc tcggctacct cggctcgatc accagccggg agcgcgacga cgccgcgttc    1560
gccgagatgc aggtccggtc cctcaccgga gctgtcgtca cgggaccgcc gcggccggcc    1620
gccgtggacg acgaggaccg cgacggccgc caggaccggg cgcccagccc ggtgagctga    1680

<210> SEQ ID NO 64
<211> LENGTH: 5960
<212> TYPE: DNA
<213> ORGANISM: Micromonospora sp. strain 046-ECO11

<400> SEQUENCE: 64
ccacacccct cgggaggcaa ctgtggatcc ggtaccggtt ctggtcgtgg gcgcgggccc      60
ggtcggcatg gtcaccgcgc tggcgctcgc ccgtcacggc gtcgcctgcg tcctcgtcga    120
ccagggcttc gagacgtcgg tccatcccaa gctggactac gtcaacgccc gcagcatgga    180
gttcctccgc cagttcggcc tcgccgacga cgtccgtgcc gccggcgtcg cgcccgagca    240
ccgggccgac gtcatctggt cgaccggcct ggccggtgag ccgatcacca ggtgggggct    300
gccctcggtg acgcaggagt ggcgccgcat cgccgagcac aacgacggca cccagccggc    360
cgagcccggc cagcggatct cccagatcga cctggaaccg gtcctgcggg cccgctgccg    420
gcgggagccc cttgtcgacc tgcgcctcgg cgtacggttc gactcgctga cccaggacga    480 cgcggggggtc accagcgtcc tcgccgacga caccggcggc gaggtccggg tgcggtcgga    540
gtacgtggtc gggtgcgacg gcgcgtcgag ccaggtccgc cgggccgtgg gcatcggtga    600 ggagggggttc gacgtgcccg gcctgccggg cgccttcatg gtgcacttca ccagccggga    660
cctggacagc ctgcaccggc acggccggtt ctggcactac ttcgcgttcc ggtacgtgat    720
catcgcccag gacgaggtcg acacctggac cgcgcacgtc aacggcgtcg acccgaacga    780
gttcgacgag ccgccggccg acccggaggc gttcctgctc gacacgatcc gcaccgagct    840
gcggatcgac aagtgctgct caacctcgcg ctggcgtccc ggcttcatgc tcgccgacag    900
gtaccgcgcc ggccgggtgc tgctcgccgg tgactcggcc caccggatgt tccccaccgg    960
cgcgtacggc atgaacaccg gcatcggcga cgccgtcgac gtggcctgga agctggccgc    1020
tgtcgtccgg ggcttcggcg gccccgggct gctcgacagc tacgacgccg aacgccgccc    1080
ggtggggcgg cgcaacatgc gcacctcgca ccggcacctg gcgtgcacc tgcgggcggg    1140 cgagctcctg cgcggcggcg cccgctgcc gtccgtcgcg gccttcctcg acgccgagcg    1200
gggcgagaac gagtaccggg ggatcgagct cggctaccgc tactccggct cgccggtgct    1260
ctggccggag ggcccggggg agccctcgga cgacccgcgg gcgtacgccc gacgacctg    1320 gcccggcgcc cgtccgccca gcctcctgct gagcgacggg cagcagatct tcgaccggtt    1380 cgaccccggcc tcgttcaccc tcgtggactt caccggtgac ggcgccgcgg tccgctgct    1440 ggcggcggcg gccgcgcggg ggctcccggt cacccacacc gtggtgaccg acccccgggc    1500
tcgtgagctg tggaacgcg acctcgtcct gctgcggccg gaccaccacg tcgcctggcg    1560
gggaaacacc gtgccgccgg accccgacgc cgtggtccag cgcgtgcggg gtggcggata    1620
```

```
ggcgcgacgt gccgtcaccg gcggcccggg tcacgcgcac acgcgaccgg ccggtccggc    1680
tgactctcga ctggaggaca gatgcagcaa tccggttcaa cggcggaacg cagcccactc    1740
gggccgtggg agggcatgcc ggcggtccag caaccggact gcaggacca cccggcgtac     1800 gcggagacct gtcaggcgtt ggcgtcggcc ccgccgctgg tcccacccgg ggaggtacgg    1860
gggttccggc agctgttgtc ggagctggcg tcgaccgacg ggctcctgct gcagttgggc    1920
gactgcgccg agagcctcta cgagtgcacc ccccggcaca cctcggacaa gatcgaggtc    1980
atcgaccggc tgggggaccg gctcagcgag ctcaccgggc gcaacgtgct gcgggtgggc    2040
cggatggccg ggcagttcgc caagccccgg tcgcaggcga cggagtggca cgacgcgctg    2100
agcatcccct ccttccgcgg ccacatgatc aattccgagc tggccgcgcc cggtacgcgc    2160
aaggccgacc ctcgccgcat gtggtgggcg tacgaggcga gcgaccgggt gcagcgggtc    2220
ctgcgcgccc accggagggg caaccggcgt gccgcgcgga ccgaggggcc gtggtcgagc    2280
cacgaggccc tggtcgtcga ctacgagtcc cgcctgatcc gccgggaccc ggacacgggc    2340
gagcactacc tggcgtcgac ccacctgccg tgggtggggg agcggacccg ccggtccgcc    2400
gaggcgcacg tggccatgct gtccacggtg gtgaacccgg tcggctgcaa gatcgggccg    2460
gacgccgacc cggacgacgt cctgcgggtg tgcgaggcgc tcgacccgcg cgcgcgatccg   2520 ggccgtctcg tcctgatccc gcggatgggc cgggaccgga tccgggagtc cctgccgccg    2580
atcgtccgcg cggtggtgaa cgcggggcac cccgtgctct ggctgagcga tcccatgcac    2640
ggcaacaccg tcaaggcctc ggtcggcctg aagacgcgcc acctctccga cgtggtcacc    2700
gaggcgctgt ggttccgcga catcctcgac cagcagcggc agcacgccgc cgggctgcac    2760
atcgaggtcc ccgccaccga cgtgaccgag tgcgtcggcg gttcggtggc cggcgaggag    2820
gacctggcgc ggcactacac ctcgctgtgc gacccgcggc tcaacccggg tcaggccacc    2880
gagctgatcg aagcgtgggc caaggacacc gcgacggtcg gcccgggacc gcggcgctcc    2940
ggcccttcgg cgcggccgga ggtcgccgcc tgacgtcgcc ggtctttgcg ccggccgttt    3000
ccgaactgcg ggaaaattga cagaaggaga cctgccggag caaattcggc caggctagcc    3060
gcgccgtagt tcgtcgtcca ctacttgcgt gggtagtgtc aactaccgt gccgggaccg     3120 tcggtggtgt tgctcagcag gaatcccatc gcaatgatgt gtgagaaggc gtaatccttc    3180
gatcggtgac gcgcgtacct catcctatcc gcactgaatc ctgtctcagc tgaagcgagt    3240
gtttccaatg tggggcagct caaacacgct ggaagtgaag gcaacgacg agagattccc      3300 cctgcccgat gcagctacgg aggatcggtc tgtgcttggc gagacggttc cggtttccgc    3360
gctgctgccc ggtgactccc cgcggctggc gggcgagaac gtcgagcaca tccggctgct    3420
ggccgcgatg cacgacctcc cgccgatcct ggtgcaacgc ggcacgatgc gggtgatcga    3480
cggcatgcac cggctgcggg ccgccaagct gcgcggcgac gagaccgtgc gggtgacgtt    3540
cttcgacggg gacgacgccg cggcgttcct gctctcggtc gacgccaaca tcaaacacgg    3600
gctgccgttg tcccgcgccg accgggaggc gccgccacc cgcatcctgc ggttgtatcc     3660
gcagtggtcg gaccgcgccg tcgccgcggc ggccgggctg tcaccgacca cggcgagcgg    3720
catccggcgc cgcctgctgc aaccggcggc gcggagggc agccgggtgg gacgggacgg     3780
gcgggtgcgc ccgctggacg gctcggcggg ccgacgcgcg gccagcgcgg tcatcgcgct    3840
ccggccggac gcgcccctgc gtgccatcgc gcaggaggcc ggggtgtcgg tgggcacggc    3900
gcgggacgtg cgcgcccggt tgcaggcggg ccgggacccc gtcctgacct cgcagcgacc    3960
```

-continued

```
ggcggccgag cccgagccgg ccgccgacga cgggccggag gcgcgcagac gccggctcgg    4020
ccagccctcc gtgccgcctg tcgactggcc ggcggtacgg ggcaacctga tccgggaccc    4080
cgcggtgaag tacgccgagc tgggccgggc cttcgtccgc tgggccgacg ggcacgtggt    4140
ggatccggcg gcctggcgcg agttcgtcga cgccgtgccc ccgtactggc gcaaatcggt    4200
ggccgagctg gcccgttcgt gcgccagcgc ctggctggcg ttcgcccagg aactggagga    4260
ccgggcgtga aaatggcggc cggcatattt acggtggttg ccgacagcgc gtcgcattcc    4320
actgtcgcgg ccactacccg atcgagtagt ggaccggctt gaataacgcg cgttaatgtt    4380
ccttcgatcc gctgccctca tttttcggtg agcacatttt tgcggcggtc caatggagag    4440
gagaattccc ggtgaacatt ctgaggcggc cgcggaaacg gcatctcggg ggtgtcgcgg    4500
ccgtcgccgc ggcgatcgcc ctggtggcgt cgctgacaaa cggtgtggcg gctgccccgc    4560
aggcgccgac cttcgacctc gacaacggga acgccctgac cgacgtcatc tacccggccc    4620
tcaacaccga gccgcgggtc gagtacagcg gccggcccgg gtcctgggcc gcggaccgcg    4680
ccatgctcat cgaactgccg tggttcgacg ccctggcggc gtaccacccc accgcggtcg    4740
gcatcttctc caccatcggc cgccgtcccg ccgaggagca cacgacgcgc aacaagaaca    4800
tcgccgtcat ctactcggcc tacacctcgc tcagcaagct ctaccccag cacgaggcga    4860 cctggcagcg gatgatggcc accgcgggcc tggaccccgc cgtcaccgcg gaggaccgga    4920
ccaccgccag cggcatcggc atcctcgcct cgaagaacgc gatggcggcg cgccggaacg    4980
acggcacgaa ccgcgacggc gacgcgggcg gccgtcgcta caaccgtgag ccgtacgccg    5040
accacaccgg ctaccggccg gtcaacagcc cgtacgagct gcgcttcccg tcgcgctggc    5100
agccgaacac catctccaag cgcgaggtcg tcctgacgca ggagttcgcg acgcccagt    5160 tcggccgggt caagccgatc accttcgagc ggcccgagca gttccggctc accccgccgc    5220
cgaaccacca cctgttgaac ccgaagggct accggaagca ggccgacgag gtgctgcgcg    5280
cctcggcggg cctggacgac cgcaagaaga tgagcgcgga gatcttcagc gacaacatca    5340
cgccgtacgg cgccatcgcg cacacgctcc tgcggggccg gtacaacacc gaggactccg    5400
tccggttcat cgtgatgact gacgtcgccg ggttcgacgt ggcgatcgcg tcctggtact    5460
acatgcgcaa gtacgactcg gtgcagccgt tcagcgcgat ccgccacctg tacccgaaca    5520
agaagctgac cgcgtggggc ggcccgggcc ggggcaccgt caacgacatc accggcaccc    5580
agtggcgcag ctacctcagc tcggtcgcca tcgcggctcc ggattaccg tcggtcaacg    5640 cggcggtctg cgtcgcctac gcccaggtcg cgcgccggtt caccggcacg gacaagctga    5700
ccgtcgtgat cccggtccgc aagggctcct cgatcgtgga accgggcgtg accccggccg    5760
ccgacatgat gctcacctgg aacagctact cggagtgggc cgccgagtgc gggcagagcc    5820
gggtctgggc cggcgagaac ttccccgcct cggtcgcggc cgccgaccag tacgcgccgc    5880
agatcggcga ccgtgccttc gacttcgtcc agagcaagct gaacgggcgc tgacgcccgc    5940
gtaccggtcc gtgctgccgg                                                 5960
```

<210> SEQ ID NO 65
<211> LENGTH: 532
<212> TYPE: PRT
<213> ORGANISM: Micromonospora sp. strain 046-ECO11

<400> SEQUENCE: 65

Val Asp Pro Val Pro Val Leu Val Val Gly Ala Gly Pro Val Gly Met
1               5                   10                  15

```
Val Thr Ala Leu Ala Leu Ala Arg His Gly Val Ala Cys Val Leu Val
            20                  25                  30

Asp Gln Gly Phe Glu Thr Ser Val His Pro Lys Leu Asp Tyr Val Asn
        35                  40                  45

Ala Arg Ser Met Glu Phe Leu Arg Gln Phe Gly Leu Ala Asp Asp Val
 50                  55                  60

Arg Ala Ala Gly Val Ala Pro Glu His Arg Ala Asp Val Ile Trp Ser
 65                  70                  75                  80

Thr Gly Leu Ala Gly Glu Pro Ile Thr Arg Trp Gly Leu Pro Ser Val
                85                  90                  95

Thr Gln Glu Trp Arg Arg Ile Ala Glu His Asn Asp Gly Thr Gln Pro
               100                 105                 110

Ala Glu Pro Gly Gln Arg Ile Ser Gln Ile Asp Leu Glu Pro Val Leu
           115                 120                 125

Arg Ala Arg Cys Arg Arg Glu Pro Leu Val Asp Leu Arg Leu Gly Val
130                 135                 140

Arg Phe Asp Ser Leu Thr Gln Asp Asp Ala Gly Val Thr Ser Val Leu
145                 150                 155                 160

Ala Asp Asp Thr Gly Gly Glu Val Arg Val Arg Ser Glu Tyr Val Val
               165                 170                 175

Gly Cys Asp Gly Ala Ser Ser Gln Val Arg Arg Ala Val Gly Ile Gly
           180                 185                 190

Glu Glu Gly Phe Asp Val Pro Gly Leu Pro Gly Ala Phe Met Val His
           195                 200                 205

Phe Thr Ser Arg Asp Leu Asp Ser Leu His Arg His Gly Arg Phe Trp
        210                 215                 220

His Tyr Phe Ala Phe Arg Tyr Val Ile Ile Ala Gln Asp Glu Val Asp
225                 230                 235                 240

Thr Trp Thr Ala His Val Asn Gly Val Asp Pro Asn Glu Phe Asp Glu
               245                 250                 255

Pro Pro Ala Asp Pro Glu Ala Phe Leu Leu Asp Thr Ile Arg Thr Glu
           260                 265                 270

Leu Arg Ile Asp Lys Val Leu Leu Thr Ser Arg Trp Arg Pro Gly Phe
       275                 280                 285

Met Leu Ala Asp Arg Tyr Arg Ala Gly Arg Val Leu Leu Ala Gly Asp
290                 295                 300

Ser Ala His Arg Met Phe Pro Thr Gly Ala Tyr Gly Met Asn Thr Gly
305                 310                 315                 320

Ile Gly Asp Ala Val Asp Val Ala Trp Lys Leu Ala Ala Val Val Arg
               325                 330                 335

Gly Phe Gly Gly Pro Gly Leu Leu Asp Ser Tyr Asp Ala Glu Arg Arg
           340                 345                 350

Pro Val Gly Arg Arg Asn Met Arg Thr Ser His Arg His Leu Gly Val
           355                 360                 365

His Leu Arg Ala Gly Glu Leu Leu Arg Gly Gly Ala Pro Leu Pro Ser
       370                 375                 380

Val Ala Ala Phe Leu Asp Ala Glu Arg Gly Glu Asn Glu Tyr Arg Gly
385                 390                 395                 400

Ile Glu Leu Gly Tyr Arg Tyr Ser Gly Ser Pro Val Leu Trp Pro Glu
               405                 410                 415

Gly Pro Gly Glu Pro Ser Asp Asp Pro Arg Ala Tyr Ala Pro Thr Thr
           420                 425                 430

Trp Pro Gly Ala Arg Pro Pro Ser Leu Leu Leu Ser Asp Gly Gln Gln
```

```
                    435                 440                 445
Ile Phe Asp Arg Phe Asp Pro Ala Ser Phe Thr Leu Val Asp Phe Thr
    450                 455                 460

Gly Asp Gly Ala Ala Gly Pro Leu Leu Ala Ala Ala Ala Arg Gly
465                 470                 475                 480

Leu Pro Val Thr His Thr Val Val Thr Asp Pro Arg Ala Arg Glu Leu
                485                 490                 495

Trp Glu Arg Asp Leu Val Leu Leu Arg Pro Asp His His Val Ala Trp
            500                 505                 510

Arg Gly Asn Thr Val Pro Pro Asp Pro Asp Ala Val Gln Arg Val
            515                 520                 525

Arg Gly Gly Gly
    530

<210> SEQ ID NO 66
<211> LENGTH: 1599
<212> TYPE: DNA
<213> ORGANISM: Micromonospora sp. strain 046-ECO11

<400> SEQUENCE: 66
gtggatccgg taccggttct ggtcgtgggc gcgggcccgg tcggcatggt caccgcgctg      60
gcgctcgccc gtcacggcgt cgcctgcgtc ctcgtcgacc agggcttcga gacgtcggtc     120
catcccaagc tggactacgt caacgcccgc agcatggagt tcctccgcca gttcggcctc     180
gccgacgacg tccgtgccgc cggcgtcgcg cccgagcacc gggccgacgt catctggtcg     240
accggcctgg ccggtgagcc gatcaccagg tgggggctgc cctcggtgac gcaggagtgg     300
cgccgcatcg ccgagcacaa cgacggcacc cagccggccg agcccggcca gcggatctcc     360
cagatcgacc tggaaccggt cctgcgggcc cgctgccggc gggagcccct tgtcgacctg     420
cgcctcggcg tacggttcga ctcgctgacc caggacgacg cggggtcac cagcgtcctc     480 gccgacgaca ccggcggcga ggtccgggtg cggtcggagt acgtggtcgg gtgcgacggc     540
gcgtcgagcc aggtccgccg ggccgtgggc atcggtgagg aggggttcga cgtgcccggc     600 ctgccggggcg ccttcatggt gcacttcacc agccgggacc tggacagcct gcaccggcac     660
ggccggttct ggcactactt cgcgttccgg tacgtgatca tcgcccagga cgaggtcgac     720
acctggaccg cgcacgtcaa cggcgtcgac ccgaacgagt tcgacgagcc gccggccgac     780
ccggaggcgt tcctgctcga cacgatccgc accgagctgc ggatcgacaa ggtgctgctc     840
acctcgcgct ggcgtcccgg cttcatgctc gccgacaggt accgcgccgg ccgggtgctg     900
ctcgccggtg actcggccca ccggatgttc cccaccggcg cgtacggcat gaacaccggc     960 atcgcgacg ccgtcgacgt ggcctggaag ctggccgctg tcgtccgggg cttcggcggc    1020
cccgggctgc tcgacagcta cgacgccgaa cgccgcccgg tggggcggcg caacatgcgc    1080
acctcgcacg gcacctgggg cgtgcacctg cgggcgggcg agctcctgcg cggcggcgcc    1140
ccgctgccgt ccgtcgcggc cttcctcgac gccgagcggg gcgagaacga gtaccggggg    1200
atcgagctcg gctaccgcta ctccggctcg ccggtgctct ggccggaggg cccgggggag    1260
ccctcggacg acccgcgggc gtacgccccg acgacctggc ccggcgcccg tccgcccagc    1320
ctcctgctga gcgacgggca gcagatcttc gaccggttcg acccgccctc gttcaccctc    1380
gtggacttca ccggtgacgg cgccgccggt ccgctgctgg cggcggcggc cgcgcggggg    1440
ctcccggtca cccacaccgt ggtgaccgac cccggggctc gtgagctgtg gaacgcgac    1500 ctcgtcctgc tgcggccgga ccaccacgtc gcctggcggg gaaacaccgt gccgccggac    1560
```
cccgacgccg tggtccagcg cgtgcggggt ggcggatag                1599

<210> SEQ ID NO 67
<211> LENGTH: 423
<212> TYPE: PRT
<213> ORGANISM: Micromonospora sp. strain 046-ECO11

<400> SEQUENCE: 67

Met Gln Gln Ser Gly Ser Thr Ala Glu Arg Ser Pro Leu Gly Pro Trp
1               5                   10                  15

Glu Gly Met Pro Ala Val Gln Gln Pro Asp Trp Gln Asp His Pro Ala
            20                  25                  30

Tyr Ala Glu Thr Cys Gln Ala Leu Ala Ser Ala Pro Pro Leu Val Pro
        35                  40                  45

Pro Gly Glu Val Arg Gly Phe Arg Gln Leu Leu Ser Glu Leu Ala Ser
    50                  55                  60

Thr Asp Gly Leu Leu Leu Gln Leu Gly Asp Cys Ala Glu Ser Leu Tyr
65                  70                  75                  80

Glu Cys Thr Pro Arg His Thr Ser Asp Lys Ile Glu Val Ile Asp Arg
                85                  90                  95

Leu Gly Asp Arg Leu Ser Glu Leu Thr Gly Arg Asn Val Leu Arg Val
            100                 105                 110

Gly Arg Met Ala Gly Gln Phe Ala Lys Pro Arg Ser Gln Ala Thr Glu
        115                 120                 125

Trp His Asp Ala Leu Ser Ile Pro Ser Phe Arg Gly His Met Ile Asn
    130                 135                 140

Ser Glu Leu Ala Ala Pro Gly Thr Arg Lys Ala Asp Pro Arg Arg Met
145                 150                 155                 160

Trp Trp Ala Tyr Glu Ala Ser Asp Arg Val Gln Arg Val Leu Arg Ala
                165                 170                 175

His Arg Glu Gly Asn Arg Arg Ala Ala Arg Thr Glu Gly Pro Trp Ser
            180                 185                 190

Ser His Glu Ala Leu Val Val Asp Tyr Glu Ser Arg Leu Ile Arg Arg
        195                 200                 205

Asp Pro Asp Thr Gly Glu His Tyr Leu Ala Ser Thr His Leu Pro Trp
    210                 215                 220

Val Gly Glu Arg Thr Arg Arg Ser Ala Glu Ala His Val Ala Met Leu
225                 230                 235                 240

Ser Thr Val Val Asn Pro Val Gly Cys Lys Ile Gly Pro Asp Ala Asp
                245                 250                 255

Pro Asp Asp Val Leu Arg Val Cys Glu Ala Leu Asp Pro Arg Arg Asp
            260                 265                 270

Pro Gly Arg Leu Val Leu Ile Pro Arg Met Gly Arg Asp Arg Ile Arg
        275                 280                 285

Glu Ser Leu Pro Pro Ile Val Arg Ala Val Asn Ala Gly His Pro
    290                 295                 300

Val Leu Trp Leu Ser Asp Pro Met His Gly Asn Thr Val Lys Ala Ser
305                 310                 315                 320

Val Gly Leu Lys Thr Arg His Leu Ser Asp Val Val Thr Glu Ala Leu
                325                 330                 335

Trp Phe Arg Asp Ile Leu Asp Gln Gln Arg Gln His Ala Ala Gly Leu
            340                 345                 350

His Ile Glu Val Ala Ala Thr Asp Val Thr Glu Cys Val Gly Gly Ser
        355                 360                 365

-continued

Val Ala Gly Glu Glu Asp Leu Ala Arg His Tyr Thr Ser Leu Cys Asp
    370                 375                 380

Pro Arg Leu Asn Pro Gly Gln Ala Thr Glu Leu Ile Glu Ala Trp Ala
385                 390                 395                 400

Lys Asp Thr Ala Thr Val Gly Pro Gly Pro Arg Ser Gly Pro Ser
                405                 410                 415

Ala Arg Pro Glu Val Ala Ala
            420

<210> SEQ ID NO 68
<211> LENGTH: 1272
<212> TYPE: DNA
<213> ORGANISM: Micromonospora sp. strain 046-ECO11

<400> SEQUENCE: 68

```
atgcagcaat ccggttcaac ggcggaacgc agcccactcg gccgtgggga gggcatgccg      60
gcggtccagc aaccggactg caggaccac ccggcgtacg cggagacctg tcaggcgttg     120
gcgtcggccc cgccgctggt cccacccggg gaggtacggg ggttccggca gctgttgtcg     180
gagctggcgt cgaccgacgg gctcctgctg cagttgggcg actgcgccga gagcctctac     240
gagtgcaccc cccggcacac ctcggacaag atcgaggtca tcgaccggct ggggaccgg     300
ctcagcgagc tcaccgggcg caacgtgctg cgggtgggcc ggatggccgg cagttcgcc     360
aagccccggt cgcaggcgac ggagtggcac gacgcgctga gcatcccctc cttccgcggc     420
cacatgatca attccgagct ggccgcgccc ggtacgcgca aggccgaccc tcgccgcatg     480
tggtgggcgt acgaggcgag cgaccgggtg cagcgggtcc tgcgcgccca ccgggagggc     540
aaccggcgtg ccgcgcggac cgaggggccg tggtcgagcc acgaggccct ggtcgtcgac     600
tacgagtccc gcctgatccg ccgggacccg gacacgggcg agcactacct ggcgtcgacc     660
cacctgccgt gggtggggga gcggaccgc cggtccgccg aggcgcacgt ggccatgctg     720
tccacggtgg tgaacccggt cggctgcaag atcgggccgg acgccgaccc ggacgacgtc     780
ctgcgggtgt gcgaggcgct cgaccgcgcg gcgatccgg gccgtctcgt cctgatcccg     840
cggatgggcc gggaccggat ccgggagtcc ctgccgccga tcgtccgcgc ggtggtgaac     900
gcggggcacc ccgtgctctg gctgagcgat cccatgcacg gcaacaccgt caaggcctcg     960
gtcggcctga agacgcgcca cctctccgac gtggtcaccg aggcgctgtg gttccgcgac    1020
atcctcgacc agcagcggca gcacgccgcc gggctgcaca tcgaggtcgc gccaccgac    1080
gtgaccgagt gcgtcggcgg ttcggtggcc ggcgaggagg acctggcgcg gcactacacc    1140
tcgctgtgcg acccgcggct caaccgggt caggccaccg agctgatcga agcgtgggcc    1200
aaggacaccg cgacggtcgg cccgggaccg cggcgctccg gcccttcggc gcggccggag    1260
gtcgccgcct ga                                                      1272
```

<210> SEQ ID NO 69
<211> LENGTH: 340
<212> TYPE: PRT
<213> ORGANISM: Micromonospora sp. strain 046-ECO11

<400> SEQUENCE: 69

Met Trp Gly Ser Ser Asn Thr Leu Glu Val Lys Gly Asn Asp Glu Arg
1               5                   10                  15

Phe Pro Leu Pro Asp Ala Ala Thr Glu Asp Arg Ser Val Leu Gly Glu
            20                  25                  30

```
Thr Val Pro Val Ser Ala Leu Leu Pro Gly Asp Ser Pro Arg Leu Ala
        35                  40                  45

Gly Glu Asn Val Glu His Ile Arg Leu Leu Ala Ala Met His Asp Leu
    50                  55                  60

Pro Pro Ile Leu Val Gln Arg Gly Thr Met Arg Val Ile Asp Gly Met
65                  70                  75                  80

His Arg Leu Arg Ala Ala Lys Leu Arg Gly Asp Glu Thr Val Arg Val
                85                  90                  95

Thr Phe Phe Asp Gly Asp Ala Ala Ala Phe Leu Leu Ser Val Asp
               100                 105                 110

Ala Asn Ile Lys His Gly Leu Pro Leu Ser Arg Ala Asp Arg Glu Ala
            115                 120                 125

Ala Ala Thr Arg Ile Leu Arg Leu Tyr Pro Gln Trp Ser Asp Arg Ala
        130                 135                 140

Val Ala Ala Ala Gly Leu Ser Pro Thr Thr Ala Ser Gly Ile Arg
145                 150                 155                 160

Arg Arg Leu Leu Gln Pro Ala Ala Arg Glu Gly Ser Arg Val Gly Arg
                165                 170                 175

Asp Gly Arg Val Arg Pro Leu Asp Gly Ser Ala Gly Arg Arg Ala
            180                 185                 190

Ser Ala Val Ile Ala Leu Arg Pro Asp Ala Pro Leu Arg Ala Ile Ala
        195                 200                 205

Gln Glu Ala Gly Val Ser Val Gly Thr Ala Arg Asp Val Arg Ala Arg
    210                 215                 220

Leu Gln Ala Gly Arg Asp Pro Val Leu Thr Ser Gln Arg Pro Ala Ala
225                 230                 235                 240

Glu Pro Glu Pro Ala Ala Asp Asp Gly Pro Glu Ala Arg Arg Arg
                245                 250                 255

Leu Gly Gln Pro Ser Val Pro Pro Val Asp Trp Pro Ala Val Arg Gly
            260                 265                 270

Asn Leu Ile Arg Asp Pro Ala Val Lys Tyr Ala Glu Leu Gly Arg Ala
        275                 280                 285

Phe Val Arg Trp Ala Asp Gly His Val Val Asp Pro Ala Ala Trp Arg
    290                 295                 300

Glu Phe Val Asp Ala Val Pro Pro Tyr Trp Arg Lys Ser Val Ala Glu
305                 310                 315                 320

Leu Ala Arg Ser Cys Ala Ser Ala Trp Leu Ala Phe Ala Gln Glu Leu
                325                 330                 335

Glu Asp Arg Ala
        340

<210> SEQ ID NO 70
<211> LENGTH: 1023
<212> TYPE: DNA
<213> ORGANISM: Micromonospora sp. strain 046-ECO11

<400> SEQUENCE: 70
atgtggggca gctcaaacac gctggaagtg aagggcaacg acgagagatt ccccctgccc      60
gatgcagcta cggaggatcg gtctgtgctt ggcgagacgg ttccggtttc cgcgctgctg     120
cccggtgact ccccgcggct ggcgggcgag aacgtcgagc acatccggct gctggccgcg     180
atgcacgacc tcccgccgat cctggtgcaa cgcggcacga tgcgggtgat cgacggcatg     240
caccggctgc gggccgccaa gctgcgcggc gacgagaccg tgcgggtgac gttcttcgac     300
ggggacgacg ccgcggcgtt cctgctctcg gtcgacgcca acatcaaaca cgggctgccg     360
```

```
ttgtcccgcg ccgaccggga ggccgccgcc acccgcatcc tgcggttgta tccgcagtgg    420
tcggaccgcg ccgtcgccgc ggcggccggg ctgtcaccga ccacggcgag cggcatccgg    480
cgccgcctgc tgcaaccggc ggcgcgggag ggcagccggg tgggacggga cgggcgggtg    540
cgcccgctgg acggctcggc gggccgacgg cgggccagcg cggtcatcgc gctccggccg    600
gacgcgcccc tgcgtgccat cgcgcaggag gccggggtgt cggtgggcac ggcgcgggac    660
gtgcgcgccc ggttgcaggc gggccgggac cccgtcctga cctcgcagcg accggcggcc    720
gagcccgagc cggccgccga cgacgggccg gaggcgcgca gacgccggct cggccagccc    780
tccgtgccgc ctgtcgactg gccggcggta cggggcaacc tgatccggga ccccgcggtg    840
aagtacgccg agctgggccg ggccttcgtc cgctgggccg acgggcacgt ggtggatccg    900
gcggcctggc gcgagttcgt cgacgccgtg ccgccgtact ggcgcaaatc ggtggccgag    960
ctggcccgtt cgtgcgccag cgcctggctg gcgttcgccc aggaactgga ggaccgggcg   1020
tga                                                                 1023
```

<210> SEQ ID NO 71
<211> LENGTH: 493
<212> TYPE: PRT
<213> ORGANISM: Micromonospora sp. strain 046-ECO11

<400> SEQUENCE: 71

```
Val Asn Ile Leu Arg Arg Pro Arg Lys Arg His Leu Gly Gly Val Ala
1               5                   10                  15

Ala Val Ala Ala Ala Ile Ala Leu Val Ala Ser Leu Thr Asn Gly Val
            20                  25                  30

Ala Ala Ala Pro Gln Ala Pro Thr Phe Asp Leu Asp Asn Gly Asn Ala
        35                  40                  45

Leu Thr Asp Val Ile Tyr Pro Ala Leu Asn Thr Glu Pro Arg Val Glu
    50                  55                  60

Tyr Ser Gly Arg Pro Gly Ser Trp Ala Ala Asp Arg Ala Met Leu Ile
65                  70                  75                  80

Glu Leu Pro Trp Phe Asp Ala Leu Ala Ala Tyr His Pro Thr Ala Val
                85                  90                  95

Gly Ile Phe Ser Thr Ile Gly Arg Arg Pro Ala Glu Glu His Thr Thr
            100                 105                 110

Arg Asn Lys Asn Ile Ala Val Ile Tyr Ser Ala Tyr Thr Ser Leu Ser
        115                 120                 125

Lys Leu Tyr Pro Gln His Glu Ala Thr Trp Gln Arg Met Met Ala Thr
    130                 135                 140

Ala Gly Leu Asp Pro Ala Val Thr Ala Glu Asp Arg Thr Thr Ala Ser
145                 150                 155                 160

Gly Ile Gly Ile Leu Ala Ser Lys Asn Ala Met Ala Ala Arg Arg Asn
                165                 170                 175

Asp Gly Thr Asn Arg Asp Gly Asp Ala Gly Gly Arg Arg Tyr Asn Arg
            180                 185                 190

Glu Pro Tyr Ala Asp His Thr Gly Tyr Arg Pro Val Asn Ser Pro Tyr
        195                 200                 205

Glu Leu Arg Phe Pro Ser Arg Trp Gln Pro Asn Thr Ile Ser Lys Arg
    210                 215                 220

Glu Val Val Leu Thr Gln Glu Phe Ala Thr Pro Gln Phe Gly Arg Val
225                 230                 235                 240

Lys Pro Ile Thr Phe Glu Arg Pro Glu Gln Phe Arg Leu Thr Pro Pro
```

```
                245                 250                 255
Pro Asn His His Leu Leu Asn Pro Lys Gly Tyr Arg Lys Gln Ala Asp
            260                 265                 270
Glu Val Leu Arg Ala Ser Ala Gly Leu Asp Asp Arg Lys Lys Met Ser
            275                 280                 285
Ala Glu Ile Phe Ser Asp Asn Ile Thr Pro Tyr Gly Ala Ile Ala His
            290                 295                 300
Thr Leu Leu Arg Gly Arg Tyr Asn Thr Glu Asp Ser Val Arg Phe Ile
305                 310                 315                 320
Val Met Thr Asp Val Ala Gly Phe Asp Val Ala Ile Ala Ser Trp Tyr
                325                 330                 335
Tyr Met Arg Lys Tyr Asp Ser Val Gln Pro Phe Ser Ala Ile Arg His
            340                 345                 350
Leu Tyr Pro Asn Lys Lys Leu Thr Ala Trp Gly Gly Pro Gly Arg Gly
            355                 360                 365
Thr Val Asn Asp Ile Thr Gly Thr Gln Trp Arg Ser Tyr Leu Ser Ser
            370                 375                 380
Val Ala Ile Ala Ala Pro Asp Tyr Pro Ser Val Asn Ala Ala Val Cys
385                 390                 395                 400
Val Ala Tyr Ala Gln Val Ala Arg Arg Phe Thr Gly Thr Asp Lys Leu
                405                 410                 415
Thr Val Val Ile Pro Val Arg Lys Gly Ser Ser Ile Val Glu Pro Gly
                420                 425                 430
Val Thr Pro Ala Ala Asp Met Met Leu Thr Trp Asn Ser Tyr Ser Glu
            435                 440                 445
Trp Ala Ala Glu Cys Gly Gln Ser Arg Val Trp Ala Gly Glu Asn Phe
            450                 455                 460
Pro Ala Ser Val Ala Ala Asp Gln Tyr Ala Pro Gln Ile Gly Asp
465                 470                 475                 480
Arg Ala Phe Asp Phe Val Gln Ser Lys Leu Asn Gly Arg
                485                 490
```

<210> SEQ ID NO 72
<211> LENGTH: 1482
<212> TYPE: DNA
<213> ORGANISM: Micromonospora sp. strain 046-ECO11

<400> SEQUENCE: 72

```
gtgaacattc tgaggcggcc gcggaaacgg catctcgggg gtgtcgcggc cgtcgccgcg    60
gcgatcgccc tggtggcgtc gctgacaaac ggtgtggcgg ctgccccgca ggcgccgacc   120
ttcgacctcg acaacgggaa cgccctgacc gacgtcatct acccggccct caacaccgag   180
ccgcgggtcg agtacagcgg ccggcccggg tcctgggccg cggaccgcgc catgctcatc   240
gaactgccgt ggttcgacgc cctggcggcg taccacccca ccgcggtcgg catcttctcc   300
accatcggcc gccgtcccgc cgaggagcac acgacgcgca acaagaacat cgccgtcatc   360
tactcggcct acacctcgct cagcaagctc taccccagc acgaggcgac ctggcagcgg   420
atgatggcca ccgcgggcct ggacccggcc gtcaccgcgg aggaccggac caccgccagc   480
ggcatcggca tcctcgcctc gaagaacgcg atggcggcgc gccggaacga cggcacgaac   540
cgcgacggca acgggcgg ccgtcgctac aaccgtgagc cgtacgccga ccacaccggc   600
taccggccgg tcaacagccc gtacgagctg cgcttcccgt cgcgctggca gccgaacacc   660
atctccaagc gcgaggtcgt cctgacgcag gagttcgcga cgcccccagtt cggccgggtc   720
```

-continued

```
aagccgatca ccttcgagcg gcccgagcag ttccggctca ccccgccgcc gaaccaccac    780
ctgttgaacc cgaagggcta ccggaagcag gccgacgagg tgctgcgcgc ctcggcgggc    840
ctggacgacc gcaagaagat gagcgcggag atcttcagcg acaacatcac gccgtacggc    900
gccatcgcgc acacgctcct gcggggccgg tacaacaccg aggactccgt ccggttcatc    960
gtgatgactg acgtcgccgg gttcgacgtg gcgatcgcgt cctggtacta catgcgcaag   1020
tacgactcgg tgcagccgtt cagcgcgatc cgccacctgt acccgaacaa gaagctgacc   1080
gcgtggggcg gcccgggccg ggcaccgtc aacgacatca ccggcaccca gtggcgcagc    1140
tacctcagct cggtcgccat cgcggctccg gattacccgt cggtcaacgc ggcggtctgc   1200
gtcgcctacg cccaggtcgc gcgccggttc accggcacgg acaagctgac cgtcgtgatc   1260
ccggtccgca agggctcctc gatcgtggaa ccgggcgtga ccccgccgc cgacatgatg    1320
ctcacctgga acagctactc ggagtgggcc gccgagtgcg ggcagagccg ggtctgggcc   1380
ggcgagaact tccccgcctc ggtcgcgcc ccgaccagt acgcgccgca gatcggcgac     1440
cgtgccttcg acttcgtcca gagcaagctg aacgggcgct ga                     1482
```

<210> SEQ ID NO 73
<211> LENGTH: 9762
<212> TYPE: DNA
<213> ORGANISM: Micromonospora sp. strain 046-ECO11

<400> SEQUENCE: 73

```
cagccacggc gttccgaccc cccgcaagat ggcttgtata gcaaggtatc ttgcgatgca     60
tggacggggc acgtgagcgg atcactacga acatccgcaa gggcgtgctg gagtactgcg    120
tgctcgccct gctctcgcgg cgcgacatgt acggcctgga actggccgac tggctcgccg    180
tccgcggtct gaccgcgagc gagggcagcc tgtatccgct gctcgcccgc atgcggcagg    240
ccggctccgt gcagacccgg tgggtggccc ccgagcaggg gcacgcccgg cggtactacg    300
cgatcaccga ccaggggcgg gcgcacctgc gggtgttcgc ggcggtgtgg caggagatcc    360
agccgcacgt ggacgacctg atgggggagg aagcatgagc gacgacgcc tcccggaggc    420
ggcgtggacc tatctgcgcg cgctcgacgc ggagttgtcc gacgtcccgt ccggcacggc    480
ggaggagatc gtcgcggatg tccgcgcgca catcgccgac gccctcgaca gcggacggag    540
cgcccacgag atcctcgccg gcctcggcgc cgcgcggac gtggcccggc aggcgcgcga    600
ggagctgggg ctgccggccc aggaccgccc ggcccgggcc ggccggaccc tgtccctggc    660
cgcggtggcg gtcggcgtgc tgatcgccgt gtgcgtgagc ttcctgctgc cgtccgcagt    720
gccggtggag ccgatccagg ccggcccgg cgagcagggc gtcctccgcc ggctcggccc    780
cggaatcgcg ctgctcacgc tgctgccggc gctcgtcgcg gccgcgccgc tcgtggcgcc    840
cgcccgggca cgtgccgggg tacggttcgc cggcgcggcg gtcctgacga tgttcgcctg    900
cgcggccggc gagacgggcc tgtactactt cccgctcgcg ctgatggcct gggcggcggc    960
gatcgtgccg tgggccctgc ggcgcggagc cggtggacgg tggtggcgct atctgaccgg   1020
tggattcgtg gcgatgccg gcgtgctggt ggcggtcgcg tcggccggtg gctcggtcgg   1080
cgtcggctgg gtcggcgcgg cgctgtggat cgccgggccg ctcgcggccg gcgcgctgtg   1140
cgcctacggg atccgggccg gctacgccgt gaccgcgctg gccggcgcgc tggccatagc   1200
gctctcgatg gccgagcgcg gcttcctgtt cgccgccttc tggctgttcg gcgggctgta   1260
cctggcgctc ggcgccgctg cgtacaccgc ctcgcgggcc gtcgacgcg acgccgccgc    1320
gacgcccggc ccgccggccc ggccggaacc cgcgccggcc cccggaggct gacccggggg    1380
```

```
ccgtggcgcc ggccggctag gcggggacgg cctgcgggtc gccggcggcg tcgtgcgcgg    1440
ccatcgtctc ctgccggacg ggctcctcgc gcaggatcgc cgcgtgcagc cacgcgtccg    1500
ggatggcgaa gccgtccacg agcgtgcgca tgtccgggcg cagctccttg agcagcccgt    1560
tcaccacgct ggtgatggtc ttcgagcggg ccggggtgag ccggccgtgc tcgagcagcc    1620
agcccttgtt cgcctcgatc acggtgagcg cgtacaggtc gcagacccgg acagcagtt    1680
ccttgaccgc cgggtcggcg atggcgtcga tcccggcgac gaacgcctcc agcgtcaccc    1740
ggtcgatgtg cgccgcggcg acggcgagga cgtggtcctg gacgtcgttg aagatgtcga    1800
aggggcggtc cttcttggtg gacgcgccac cgcgcaggcg gcggaccgcg ctgtcgagca    1860
ggtgctcctc gcggtcctcg aagagcttga gctgccagcc ccggtcggtg acggcgacct    1920
cgtcgtcgcg cccgggcacg gcgctgacca gacgtgcgat cagcgcccgc gcggcggtgc    1980
gttccagcac catctcgcgt acctgctcgg ccacgaagga ggcgcgtccc cagccgtcga    2040
gcgagccgaa ctcgtcccgg tagccggtca gcagcccctt ggcgaccagt tgcagcagca    2100
ccgtgttgtc gccctcgaag gtggtgaaga catcggtgtc ggccttgagg ctgggcaggc    2160
ggttctcgga caggtagccg cgccgccac acgcctcccg gcagatctgg atggtgcggg    2220
tggcgtgcca ggtctgcgcc gccttcagac cggcggcccg ggactccagc tcccgctgcc    2280
ggtgctcgtc gaccggcccg tcgccgccct ggatgtcgtc gagcgccgcg accagctccg    2340
cctgggcgaa ggtcagcgcg tacgtggtgg ccagcgcggg cagcagcttg cgctggtgcg    2400
ccaggtagtc gttgagcagc acctcgcggt cgccgtcggc gtcggcgaac tgccggcgga    2460
tgtcgccgta gcgcaccgcg atggccagcc ccgacttggt ggccgccgac gcggcgccgc    2520
ccacgctcac ccgccccggg accagggtgc ccagcatggt gaagaagcgc cgggagtcgt    2580
tctcgatcgg gctggagtac gtgccgtcct cggcgacctg cgcgtactgg tccagcagca    2640
tctcccgcgg cacccgcacg tggtcgaagc tgagccgccc gttgtccacg ccgagcaggc    2700
cggccttggg cccggcgtcg ccgatggtca cgccgggcat cggcttgccg tgctcgtcgc    2760
ggatcggcac cagccaggcg tgcacccccgt ggcggcgccc gccggtgacg agctgggcga    2820
acaccacagc catccgcccg tcccgggccg cgttgccgat gtagtccttg cgcgcggcct    2880
cgtgcggggt gtgcaggtcg aaggtctgcg tctgcgggtc gtagacgcag gtggtgcgca    2940
gttgctgcac gtccgagccg tggccggtct cggtcatcgc gaagcagccg aagagccggc    3000
ccgcgacgat gtcccgcagg taggcgtcgt ggtgccgctt cgtgccgagg gcggcgaccg    3060
cgccgccgaa caggccccac tgcacgccgg ccttcaccat cagtgacagg tccacctggg    3120
ccagcatctc ggtggcgacg atcgaggcgc ccacgtcgcc gcggccgccg tactcggcgg    3180
ggaaaccgga ggcgatgccc agctcgacgg ggagttcgga cagcagccgg gtgatgcgct    3240
cgcgggcctg gtcaccggtc tcgccgtaca ccggagggaa gcgttcgtcg aggtgttcgc    3300
ggtgcgcccg gcggacctcg gcccaccggc cgtcgagcgc ttcccgcagg cgtgtgacgt    3360
cgatgcggcc ggatgcgtga tcgagcattg tcactcctcg gggcagcgga catttgcgta    3420
tactctcggc ctgatcaaca ttaccggcgg tgatcgcacc ccgctggcgg agcgcgtggt    3480
gagcccggcc accccggcg gttcggccac ccgtgaagct gaggttaggc tgtcctcact    3540
tcacagcact ggaggcatcc cctcgtgtcc ccgcttcccc ccggcagcgc cgtcaccgcc    3600
cggcacgtgc tccgccaggc gctgcgccgc cagcgccgcc cggtgctgat cggcgtgacc    3660
ctgctcgggc tgcaccaggt caccgaggcg ctcgtgccgg tggcgatcgg cgtcatcatc    3720
```

```
gaccgggccg tggtgaccgg cgacccgtgg gcgctcgcgt actccgtcgc cggcctcgcc   3780
gccctgttca ccgtgctggc gttcgcctac cgcaacggcg cccgccaggc gttcgcggcg   3840
gtggaacggg aggcgcacct gctgcgggtc gagctggccg agcgcgcgct cgacccgcgc   3900
gggcaccgct ccggcctgcg cgacggcgag ctgctctcgg tcgccgcctc cgacgccgaa   3960
ctctccgcgt acgtggtccg ggtggccggc ttcggcgtcg ccgcggtgag cgcgctgacc   4020
gtcgcggcgg tcgcgctgct ggtcatcgac gtcccgctcg gactcggcgt gctcatcggc   4080
gtaccggtgc tggtcctggc gctgcaacgg atggcgccgc tgctgtcccg gcgcagcgcc   4140
tcccagcagg aggccctcgc ggagaccacg gcgctcgccg tggacctcgt ctccggcctg   4200
cgcgtgctgc gcggcatcgg cgcccagcac cacgccgccg gccggtacgc cgaggccagc   4260
cgacgcgccc tcgccgtgac gctgcgcgcc gccaacacca agggcctgca cctcgggctc   4320
accaccgccg cgaacggcct cttcctcgcc ggcgtcgccg gggtcgccgg ctggctcgcg   4380
ctgcgcggcc ggctcaccat cggcgagctg gtcaccgtgg tcgggctcgc gcagttcgtc   4440
gccgagccgg tgcagacgct gggctactgc gtgcagctgt tcgcgatggc ccgcgcctcc   4500
gccgcccggg tcgggcgcgt gctcggcgcc gagccgctga cccggccggg cagcgcgccc   4560
cggccggacc gcacggacgg gccgcggctc gtcctcgacc acgtcggcca cgccgcgctg   4620
gacgggtgt gcctgcgcgt cgacccggga gagatcgtcg gcgtcctggc gtacgacccg   4680
gccgacgcgg acgcgctggt ggcgctgctg tccgggcggg tgcccgcgga ccggcgccgg   4740
ggcacggtac gcgtcgacgg ggtacccgcc gacgacctgg acgtcgacgc gctgcgcggc   4800
gccgtcctgg tcgagccgca cgacgtgacg ctgttcgagg aaccgtggc cgccaacctc   4860
gccgccggga gcaggaccga ggaggggcgc ctgcgcgccg cggtccgggc ggccgcggcg   4920
gacgacgtgg tggacgcgca ccccggcggc ctcggccacc ggctcgtcga gcggggcgcc   4980
aacctctccg gcgggcagcg ccagcggctc gggctggcgc gggcgctgca cgccgacccg   5040
ccggtgctgg tgctgcacga ccccaccacc gccgtggacg cggccaccga ggcccaactc   5100
gccgacggac tggccggcgc gcgccgcgaa gcgccccggg gcacgctgct ggtcaccagc   5160
agccccgccc tgctgcggat caccgaccgg gtggtggtga tcgccgacgg ccgggtgacc   5220
gccgagggga cgcacgagca cctgctggcc accgacgccc gctaccgcga ggagacactg   5280
cggtgaccgc tgacccgcgt accgccgaac ccacccgggt gttgctgccc accgcgaccg   5340
cccggcggac ctggacgacg ctcggcgcgg agttccgccg gcggcccggc ctcagcgccg   5400
ccgcgaccgc cgtgctcgtc gccgccgcca ccggcgggct ggtcgcgccc tgggtgctcg   5460
gccgcctcgt cgacgacgtc atcgccgacg ccccggtctc ccggatcgcc ggccgggtgg   5520
cggtgatcgc cggcgcggca gtgctcaccg gactgctcac cgccgccggg gccgcgctcg   5580
cgtcccgcct gggggagacg gtgctggccc ggctgcgcga gcgggtcctc gaccgggcgc   5640
tgcacctgcc ctcggcgacg ctggaacggg ccggcaccgg cgacctgctg gcccgggtcg   5700
gcgacgacgt ggcggtggtg acgaacgtga tcgcggtcag cggcccggcg ttcgtcggcg   5760
cgctgctgtc cgtggtgctg accgtgttcg ggctggtcgc gctcgactgg cggctcggcc   5820
tcgccgggct ggtcgccgcg cccgcctacg cgctggcgct cgctggtac ctgcgccggt   5880
cggcgccgta ctacgcccgc gagcgcgtcg ccaccggcga gcggacgcag gcgatggccc   5940
gcgcgctgcg tggcgcggcc accgtgcgcg cgtaccggac cgaggacgcg cacgtcgcgg   6000
cgatcgccga gcgctccggc gtggcgcgcg acctgtcgct ggagatcttc aacctgcaca   6060
cccggttcgg gctgcggatc aacaggtcgg agttcctcgg cctggccgcg gtgctcgtcg   6120
```

```
ccgggttctt cctggtccgc gccgacctgg tcacagtggg cgcggcgacc accgccgcgc    6180
tctacttcca ccggctgttc aacccgatcg gcctgctgct gatggagtcc gactcggtgc    6240
tgcaggccgg cgcgagcctc gcccggctgg tcggcgtggc cacgctgccc gacaccgccc    6300
cgtccgggcc cgcgccgtcg gcggccgggc ggcgcggccc ggcggcgctg gacgtcacgg    6360
tccgccggca ccgctacgac gacgacggcc ctctggtcct ggccgacgtc gacctgcgcc    6420
tggcccceggg cgagcgggtc gcgctcgtgg gcgccagcgg cgcgggcaag agcacgctcg    6480
ccggcatcgc cgccgggatc atcgcgccca ccgacgggtc ggtacgcctg gcggcgtgc     6540
cgctgaccga gcggggcgag cacgccgtgc ggcgcgacgt cgcgctggtc agccaggagg    6600
tgcacgtctt cgctggaccg ctcgccgagg atctgcgcct ggctgccccg gacgccaccg    6660
acgccgaact gctcgacgcg ctggaccggg tcggcgccac cacctggctg cgcgcgctgc    6720
cggacgggct ggccacagcg gtcggcgagg cggccaccg gctcaccgcc gcgcaggccc     6780
agcaggtcgc cctggcccgg ctggtgctgg ccgcgcccgc cgtcgccgtg ctggacgagg    6840
ccaccgccga ggccggcagc gccggagcgc gtgacctgga ccgggcggcg ctggccgcca    6900
ccgagggacg gaccacgctg atcgtggcgc accggctcag ccaggcggtc gccgccgacc    6960
ggatcgtcct gctcgaccac gggcggatcg tggagcaggg cacgcactcg gaactgctcg    7020
ccgccgacgg ccggtacggg catctgtggc gctcctggag cgtcccggta tgatcgcgca    7080
ccgcccatcg gcccaggtga ggggaacatg accgacgcgc cggcccgctt cgtgctcttc    7140
ccggggcggc accacctgct gacccggttc caggccgact acctgcggcg gctggccggg    7200
gacgacgcca cagtggtctg ggcggtgacg tcggccaacc acgagaacac caggcgcaac    7260
ccggtgccct accaccggcg ggaggccgcg atcgaacgat tcagcgtgct gagcgggctg    7320
cgctcggtgg tggtgccgat cttcgacacc gcgtacaccg acgcgttcgc cgaggtgacg    7380
ctgaagtcca tcgcggtggc caccgggctc gaactcaccc ccgccgacac cgtgctggcc    7440
tgctccacgc cggaggtcgc gaagctgtac gagcagctcg gcttttcgat cgcgccggtc    7500
gaggcggacc cggacctgcc cgagccgccc gaacggccgt gggacgtgct gctgcgcctg    7560
gccgccgggg acgagacctg gcgcgcgctc acccacccgg ccaccatcga cgtgttcgag    7620
cgctaccgcc tggtcgagtc gatccggtcg gtggtgaacg acccgctcgt cggcgacgag    7680
ggcggtctca cagtgacccg cgactaccgg acctacgtcg aggcgttcgc cacggccgcg    7740
cagcgcaagt gggactcggt acgccggtac gtgcagcccg gccgcatcgt ggacatcggc    7800
tgcggcgcgg gcgccgtcct ggaactcgcc gaccgggagg ccgcgctgcg tgagagcgac    7860
ctgatcggcg tggaggtcgc ccgccacctc taccaggagt gcctgcacaa gaaggcgcag    7920
ggcgtgttcc gcaacgccaa cgtctacttc ttccaccgca acgtcctcgg cggcgcggtg    7980
ttcaaggacc gctcggtcga caccacgctc acgttcgcgc tgacccacga gatctggtcg    8040
tacgggcggc ggcgggagtc gctgctgcag ttcgcccgcc gcatccacga ccacacggtg    8100
cccggcggcc tctggatcaa cagcgacgtg tgcggtccgg acgaccccg gcggcaggtg    8160
ctcctgcgac tgtccaccga cgacggcgac aacccggccg cgccccgccc cgacctcgcc    8220
gagctgacct cggcggaggt ccggcgttac gtcggcgggc tgtcgacgcg ggcgcggctg    8280
gaccagttcg ccgtcgactt cgcgttcgac ttcgactacg agccgctccc cgacggcgcg    8340
gtacgcctga cgctgggcgc cgcgatggac tacctgaccc gcaaggacta cacggacaac    8400
tggctgtcgg agacgcagga gcagttctgc ggcctgagct cgccgactg gacggacctg    8460
```

```
ctcaccgagg cggggttcga gatcggcccg gcgtcggcgc cggtgcgcaa cgagtgggtg    8520
atcgacaacc ggatcgcgcc agtcgcgtcc ctcaccgacc tcgacggccg gccgctggac    8580
tggccgacca cccacgtcct caccgtcgcc caccgccccc gcaaccagtg agaccgacgg    8640
cgcccgccgc gttcggcggg cgccgtcgtc gctcaccggc tcagcgcgat ccggatcgcc    8700
aggacgatca ggatgagccc ggtcagccgt tcgatcacca gcagcacgga cggccgggtc    8760
agccagggct gcaacctgtc gatgagcatg atgtagcagg cccaccagag caccgcgagg    8820
ccgatgaacg tggcggcgag caccgccgta cgggccgccg cccctcgcc gggcttgacg     8880 aactgcggca cgaacgagac gtagaagacg accaccttga cgttcagcag ctggctggtg    8940
acgcccatga cgaacgagcg gcgggccacg tgcggctcgt cggcggccgg ggtgtccggc    9000
accggcgcgg ggccggtgtc cgtgtccggc cggcgccgc ccgcgccgac agtgaccggc     9060
tgcgccgccg ggaccgtccg gcgcggccgg gtcgcccaga ggatcgtgcc gcccaggtag    9120
agcaggtaca gcgcgccggc gacgcgcagc accgtgtaga gcgtcggcga ggagaccagc    9180
agggcggaca ggccggcggt cgcgaacgac gcgtgcacca gcgcggcgac gaacagcccg    9240
gccagcacca cgaacccggc ccgccggccg tacctgacgg tctgccgggt gacgagcgcg    9300
aagtcgacgc cggcacgat gatgatgagc aggctggcgg cgacgaaact gatgatctgg     9360
atgtcagaca cgacgccggc tctcctgtcc tccggcgagc gccggcactg cctcctcgat    9420
gacggagacg ccgctgtcct ggcgtggtcc gtgccggcgc cactgttccc gcagccggat    9480
ccggccgtcc ggcagccgtt cgggccggga ctcgcactcg ccgatgacta tggtgccgtc    9540
ggtgagcacc tccaggtagg cgaagcgcac gacgccctgc gcgtcgcagg tgccggccag    9600
ccggccgtgc cggaccgggc cgccggtgat ctccgcccag accaggtcgc cacgctggtg    9660
gtagtgcccc cgcagcggct cggcgccgtc accggcgtcg tggtccaccg agacgaagac    9720
gcggccgtcg tagtcgaatg tcgtcatcgc gctcacgccc ac                       9762
```

<210> SEQ ID NO 74
<211> LENGTH: 112
<212> TYPE: PRT
<213> ORGANISM: Micromonospora sp. strain 046-ECO11

<400> SEQUENCE: 74

Met Asp Gly Ala Arg Glu Arg Ile Thr Thr Asn Ile Arg Lys Gly Val
1               5                   10                  15

Leu Glu Tyr Cys Val Leu Ala Leu Leu Ser Arg Arg Asp Met Tyr Gly
            20                  25                  30

Leu Glu Leu Ala Asp Trp Leu Ala Val Arg Gly Leu Thr Ala Ser Glu
        35                  40                  45

Gly Ser Leu Tyr Pro Leu Leu Ala Arg Met Arg Gln Ala Gly Ser Val
    50                  55                  60

Gln Thr Arg Trp Val Ala Pro Glu Gln Gly His Ala Arg Arg Tyr Tyr
65                  70                  75                  80

Ala Ile Thr Asp Gln Gly Arg Ala His Leu Arg Val Phe Ala Ala Val
                85                  90                  95

Trp Gln Glu Ile Gln Pro His Val Asp Asp Leu Met Gly Glu Glu Ala
            100                 105                 110

<210> SEQ ID NO 75
<211> LENGTH: 339
<212> TYPE: DNA
<213> ORGANISM: Micromonospora sp. strain 046-ECO11

```
<400> SEQUENCE: 75
atggacgggg cacgtgagcg gatcactacg aacatccgca agggcgtgct ggagtactgc    60
gtgctcgccc tgctctcgcg gcgcgacatg tacggcctgg aactggccga ctggctcgcc   120
gtccgcggtc tgaccgcgag cgagggcagc ctgtatccgc tgctcgcccg catgcggcag   180
gccggctccg tgcagacccg gtgggtggcc cccgagcagg gcacgcccg gcggtactac    240 gcgatcaccg accaggggcg ggcgcacctg cgggtgttcg cggcggtgtg gcaggagatc   300
cagccgcacg tggacgacct gatggggag gaagcatga                           339
```

<210> SEQ ID NO 76
<211> LENGTH: 325
<212> TYPE: PRT
<213> ORGANISM: Micromonospora sp. strain 046-ECO11

<400> SEQUENCE: 76

```
Met Ser Asp Asp Gly Leu Pro Glu Ala Ala Trp Thr Tyr Leu Arg Ala
1               5                   10                  15

Leu Asp Ala Glu Leu Ser Asp Val Pro Ser Gly Thr Ala Glu Glu Ile
            20                  25                  30

Val Ala Asp Val Arg Ala His Ile Ala Asp Ala Leu Asp Ser Gly Arg
        35                  40                  45

Ser Ala His Glu Ile Leu Ala Gly Leu Gly Ala Ala Arg Asp Val Ala
    50                  55                  60

Arg Gln Ala Arg Glu Glu Leu Gly Leu Pro Ala Gln Asp Arg Pro Ala
65                  70                  75                  80

Arg Ala Gly Arg Thr Leu Ser Leu Ala Ala Val Ala Val Gly Val Leu
                85                  90                  95

Ile Ala Val Cys Val Ser Phe Leu Leu Pro Ser Ala Val Pro Val Glu
            100                 105                 110

Pro Ile Gln Ala Gly Pro Gly Glu Gln Gly Val Leu Arg Arg Leu Gly
        115                 120                 125

Pro Gly Ile Ala Leu Leu Thr Leu Leu Pro Ala Leu Val Ala Ala Ala
    130                 135                 140

Pro Leu Val Ala Pro Ala Arg Ala Arg Ala Gly Val Arg Phe Ala Gly
145                 150                 155                 160

Ala Ala Val Leu Thr Met Phe Ala Cys Ala Ala Gly Glu Thr Gly Leu
                165                 170                 175

Tyr Tyr Phe Pro Leu Ala Leu Met Ala Trp Ala Ala Ile Val Pro
            180                 185                 190

Trp Ala Leu Arg Arg Gly Ala Gly Arg Trp Trp Arg Tyr Leu Thr
        195                 200                 205

Gly Gly Phe Val Ala Met Pro Gly Val Leu Val Ala Val Ala Ser Ala
    210                 215                 220

Gly Gly Ser Val Gly Val Gly Trp Val Gly Ala Ala Leu Trp Ile Ala
225                 230                 235                 240

Gly Pro Leu Ala Ala Gly Ala Leu Cys Ala Tyr Gly Ile Arg Ala Gly
                245                 250                 255

Tyr Ala Val Thr Ala Leu Ala Gly Ala Leu Ala Ile Ala Leu Ser Met
            260                 265                 270

Ala Glu Arg Gly Phe Leu Phe Ala Phe Trp Leu Phe Gly Gly Leu
        275                 280                 285

Tyr Leu Ala Leu Gly Ala Ala Ala Tyr Thr Ala Ser Arg Ala Val Asp
    290                 295                 300
```

-continued

```
Gly Asp Ala Ala Ala Thr Pro Gly Pro Pro Ala Arg Pro Glu Pro Ala
305                 310                 315                 320

Pro Ala Pro Gly Gly
            325
```

<210> SEQ ID NO 77
<211> LENGTH: 978
<212> TYPE: DNA
<213> ORGANISM: Micromonospora sp. strain 046-ECO11

<400> SEQUENCE: 77

```
atgagcgacg acggcctccc ggaggcggcg tggacctatc tgcgcgcgct cgacgcggag    60
ttgtccgacg tcccgtccgg cacggcggag gagatcgtcg cggatgtccg cgcgcacatc   120
gccgacgccc tcgacagcgg acggagcgcc cacgagatcc tcgccggcct cggcgccgcg   180
cgggacgtgg cccggcaggc gcgcgaggag ctggggctgc cggcccagga ccgcccggcc   240
cgggccggcc ggaccctgtc cctggccgcg gtggcggtcg gcgtgctgat cgccgtgtgc   300
gtgagcttcc tgctgccgtc cgcagtgccg gtggagccga tccaggccgg ccccggcgag   360
cagggcgtcc tccgccggct cggccccgga atcgcgctgc tcacgctgct gccggcgctc   420
gtcgcggccg cgccgctcgt ggcgcccgcc cgggcacgtg ccggggtacg gttcgccggc   480
gcggcggtcc tgacgatgtt cgcctgcgcg gccggcgaga cgggcctgta ctacttcccg   540
ctcgcgctga tggcctgggc ggcggcgatc gtgccgtggg ccctgcggcg cggagccggt   600
ggacggtggt ggcgctatct gaccggtgga ttcgtggcga tgcccggcgt gctggtggcg   660
gtcgcgtcgg ccggtggctc ggtcggcgtc ggctgggtcg gcgcggcgct gtggatcgcc   720
gggccgctcg cggccggcgc gctgtgcgcc tacgggatcc gggccggcta cgccgtgacc   780
gcgctggccg gcgcgctggc catagcgctc tcgatggccg agcgcggctt cctgttcgcc   840
gccttctggc tgttcggcgg gctgtacctg gcgctcggcg ccgctgcgta caccgcctcg   900
cgggccgtcg acgcgacgc cgccgcgacg cccggcccgc cggcccggcc ggaacccgcg   960
ccggccccg gaggctga                                                  978
```

<210> SEQ ID NO 78
<211> LENGTH: 663
<212> TYPE: PRT
<213> ORGANISM: Micromonospora sp. strain 046-ECO11

<400> SEQUENCE: 78

```
Met Leu Asp His Ala Ser Gly Arg Ile Asp Val Thr Arg Leu Arg Glu
1               5                   10                  15

Ala Leu Asp Gly Arg Trp Ala Glu Val Arg Arg Ala His Arg Glu His
            20                  25                  30

Leu Asp Glu Arg Phe Leu Pro Val Tyr Gly Glu Thr Gly Asp Gln Ala
        35                  40                  45

Arg Glu Arg Ile Thr Arg Leu Leu Ser Glu Leu Pro Val Glu Leu Gly
    50                  55                  60

Ile Ala Ser Gly Phe Pro Ala Glu Tyr Gly Gly Arg Gly Asp Val Gly
65                  70                  75                  80

Ala Ser Ile Val Ala Thr Glu Met Leu Ala Gln Val Asp Leu Ser Leu
                85                  90                  95

Met Val Lys Ala Gly Val Gln Trp Gly Leu Phe Gly Gly Ala Val Ala
            100                 105                 110

Ala Leu Gly Thr Lys Arg His His Asp Ala Tyr Leu Arg Asp Ile Val
        115                 120                 125
```

-continued

```
Ala Gly Arg Leu Phe Gly Cys Phe Ala Met Thr Glu Thr Gly His Gly
    130                 135                 140

Ser Asp Val Gln Gln Leu Arg Thr Thr Cys Val Tyr Asp Pro Gln Thr
145                 150                 155                 160

Gln Thr Phe Asp Leu His Thr Pro His Glu Ala Ala Arg Lys Asp Tyr
                165                 170                 175

Ile Gly Asn Ala Ala Arg Asp Gly Arg Met Ala Val Val Phe Ala Gln
                180                 185                 190

Leu Val Thr Gly Gly Arg Arg His Gly Val His Ala Trp Leu Val Pro
            195                 200                 205

Ile Arg Asp Glu His Gly Lys Pro Met Pro Gly Val Thr Ile Gly Asp
210                 215                 220

Ala Gly Pro Lys Ala Gly Leu Leu Gly Val Asp Asn Gly Arg Leu Ser
225                 230                 235                 240

Phe Asp His Val Arg Val Pro Arg Glu Met Leu Leu Asp Gln Tyr Ala
                245                 250                 255

Gln Val Ala Glu Asp Gly Thr Tyr Ser Ser Pro Ile Glu Asn Asp Ser
            260                 265                 270

Arg Arg Phe Phe Thr Met Leu Gly Thr Leu Val Arg Gly Arg Val Ser
            275                 280                 285

Val Gly Gly Ala Ala Ser Ala Thr Lys Ser Ala Leu Ala Ile Ala
    290                 295                 300

Val Arg Tyr Gly Asp Ile Arg Arg Gln Phe Ala Asp Ala Asp Gly Asp
305                 310                 315                 320

Arg Glu Val Leu Leu Asn Asp Tyr Leu Ala His Gln Arg Lys Leu Leu
                325                 330                 335

Pro Ala Leu Ala Thr Thr Tyr Ala Leu Thr Phe Ala Gln Ala Glu Leu
            340                 345                 350

Val Ala Ala Leu Asp Asp Ile Gln Gly Gly Asp Gly Pro Val Asp Glu
            355                 360                 365

His Arg Gln Arg Glu Leu Glu Ser Arg Ala Ala Gly Leu Lys Ala Ala
    370                 375                 380

Gln Thr Trp His Ala Thr Arg Thr Ile Gln Ile Cys Arg Glu Ala Cys
385                 390                 395                 400

Gly Gly Ala Gly Tyr Leu Ser Glu Asn Arg Leu Pro Ser Leu Lys Ala
                405                 410                 415

Asp Thr Asp Val Phe Thr Thr Phe Glu Gly Asp Asn Thr Val Leu Leu
            420                 425                 430

Gln Leu Val Ala Lys Gly Leu Leu Thr Gly Tyr Arg Asp Glu Phe Gly
        435                 440                 445

Ser Leu Asp Gly Trp Gly Arg Ala Ser Phe Val Ala Glu Gln Val Arg
    450                 455                 460

Glu Met Val Leu Glu Arg Thr Ala Ala Arg Ala Leu Ile Ala Arg Leu
465                 470                 475                 480

Val Ser Ala Val Pro Gly Arg Asp Asp Glu Val Ala Val Thr Asp Arg
                485                 490                 495

Gly Trp Gln Leu Lys Leu Phe Glu Asp Arg Glu Glu His Leu Leu Asp
            500                 505                 510

Ser Ala Val Arg Arg Leu Arg Gly Gly Ala Ser Thr Lys Lys Asp Arg
        515                 520                 525

Pro Phe Asp Ile Phe Asn Asp Val Gln Asp His Val Leu Ala Val Ala
530                 535                 540
```

```
Ala Ala His Ile Asp Arg Val Thr Leu Glu Ala Phe Val Gly Ile
545                 550                 555                 560

Asp Ala Ile Ala Asp Pro Ala Val Lys Glu Leu Leu Ser Arg Val Cys
                565                 570                 575

Asp Leu Tyr Ala Leu Thr Val Ile Glu Ala Asn Lys Gly Trp Leu Leu
            580                 585                 590

Glu His Gly Arg Leu Thr Pro Ala Arg Ser Lys Thr Ile Thr Ser Val
        595                 600                 605

Val Asn Gly Leu Leu Lys Glu Leu Arg Pro Asp Met Arg Thr Leu Val
    610                 615                 620

Asp Gly Phe Ala Ile Pro Asp Ala Trp Leu His Ala Ala Ile Leu Arg
625                 630                 635                 640

Glu Glu Pro Val Arg Gln Glu Thr Met Ala His Asp Ala Ala Gly
                645                 650                 655

Asp Pro Gln Ala Val Pro Ala
            660

<210> SEQ ID NO 79
<211> LENGTH: 1992
<212> TYPE: DNA
<213> ORGANISM: Micromonospora sp. strain 046-ECO11

<400> SEQUENCE: 79
atgctcgatc acgcatccgg ccgcatcgac gtcacacgcc tgcgggaagc gctcgacggc      60
cggtgggccg aggtccgccg ggcgcaccgc gaacacctcg acgaacgctt cctcccggtg     120
tacggcgaga ccggtgacca ggcccgcgag cgcatcaccc ggctgctgtc cgaactcccc     180
gtcgagctgg gcatcgcctc cggtttcccc gccgagtacg gcggccgcgg cgacgtgggc     240
gcctcgatcg tcgccaccga gatgctggcc caggtggacc tgtcactgat ggtgaaggcc     300
ggcgtgcagt ggggcctgtt cggcggcgcg gtcgccgccc tcggcacgaa gcggcaccac     360
gacgcctacc tgcgggacat cgtcgcgggc cggctcttcg gctgcttcgc gatgaccgag     420
accggccacg gctcggacgt gcagcaactg cgcaccacct cgtctacga cccgcagacg      480 cagaccttcg acctgcacac cccgcacgag gccgcgcgca aggactacat cggcaacgcg     540
gcccgggacg gcggatggc tgtggtgttc gcccagctcg tcaccggcgg cgccgccac      600 ggggtgcacg cctggctggt gccgatccgc gacgagcacg gcaagccgat gcccggcgtg     660
accatcggcg acgccgggcc caaggccggc ctgctcggcg tggacaacgg cggctcagc      720 ttcgaccacg tgcgggtgcc gcgggagatg ctgctggacc agtacgcgca ggtcgccgag     780
gacggcacgt actccagccc gatcgagaac gactcccggc gcttcttcac catgctgggc     840
accctggtcc ggggccgggt gagcgtggcc ggcgccgcgt cggcggccac caagtcggcg     900
ctggccatcg cggtgcgcta cggcgacatc cgccggcagt cgccgacgc cgacggcgac      960 cgcgaggtgc tgctcaacga ctacctggcg caccagcgca agctgctgcc cgcgctggcc    1020
accacgtacg cgctgacctt cgcccaggcg gagctggtcg cggcgctcga cgacatccag    1080
ggcggcgacg gccggtcga cgagcaccgg cagcgggagc tggagtcccg gccgccggt      1140 ctgaaggcgg cgcagacctg gcacgccacc cgcaccatcc agatctgccg ggaggcgtgt    1200
ggcggcgccg gctacctgtc cgagaaccgc ctgcccagcc tcaaggccga caccgatgtc    1260
ttcaccacct cgagggcga caacacggtg ctgctgcaac tggtcgccaa ggggctgctg     1320
accggctacc gggacgagtt cggctcgctc gacggctggg acgcgcctc cttcgtggcc     1380 gagcaggtac gcgagatggt gctggaacgc accgccgcgc gggcgctgat cgcacgtctg    1440
```

-continued

```
gtcagcgccg tgcccgggcg cgacgacgag gtcgccgtca ccgaccgggg ctggcagctc    1500
aagctcttcg aggaccgcga ggagcacctg ctcgacagcg cggtccgccg cctgcgcggt    1560
ggcgcgtcca ccaagaagga ccgccccttc gacatcttca cgacgtcca ggaccacgtc     1620 ctcgccgtcg ccgcggcgca catcgaccgg gtgacgctgg aggcgttcgt cgccgggatc    1680
gacgccatcg ccgacccggc ggtcaaggaa ctgctgtccc gggtctgcga cctgtacgcg    1740
ctcaccgtga tcgaggcgaa caagggctgg ctgctcgagc acggccggct caccccggcc    1800
cgctcgaaga ccatcaccag cgtggtgaac gggctgctca aggagctgcg cccggacatg    1860
cgcacgctcg tggacggctt cgccatcccg gacgcgtggc tgcacgcggc gatcctgcgc    1920
gaggagcccg tccggcagga gacgatggcc gcgcacgacg ccgccggcga cccgcaggcc    1980
gtccccgcct ag                                                         1992
```

<210> SEQ ID NO 80
<211> LENGTH: 573
<212> TYPE: PRT
<213> ORGANISM: Micromonospora sp. strain 046-ECO11

<400> SEQUENCE: 80

| Val | Ser | Pro | Leu | Pro | Gly | Ser | Ala | Val | Thr | Ala | Arg | His | Val | Leu |
|---|---|---|---|---|---|---|---|---|---|---|---|---|---|---|
| 1 | | | | 5 | | | | | 10 | | | | | 15 |

Arg Gln Ala Leu Arg Arg Gln Arg Arg Pro Val Leu Ile Gly Val Thr
            20                  25                  30

Leu Leu Gly Leu His Gln Val Thr Glu Ala Leu Val Pro Val Ala Ile
        35                  40                  45

Gly Val Ile Ile Asp Arg Ala Val Val Thr Gly Asp Pro Trp Ala Leu
    50                  55                  60

Ala Tyr Ser Val Ala Gly Leu Ala Ala Leu Phe Thr Val Leu Ala Phe
65                  70                  75                  80

Ala Tyr Arg Asn Gly Ala Arg Gln Ala Phe Ala Ala Val Glu Arg Glu
                85                  90                  95

Ala His Leu Leu Arg Val Glu Leu Ala Glu Arg Ala Leu Asp Pro Arg
            100                 105                 110

Gly His Arg Ser Gly Leu Arg Asp Gly Glu Leu Leu Ser Val Ala Ala
        115                 120                 125

Ser Asp Ala Glu Leu Ser Ala Tyr Val Val Arg Val Ala Gly Phe Gly
    130                 135                 140

Val Ala Ala Val Ser Ala Leu Thr Val Ala Ala Val Ala Leu Leu Val
145                 150                 155                 160

Ile Asp Val Pro Leu Gly Leu Gly Val Leu Ile Gly Val Pro Val Leu
                165                 170                 175

Val Leu Ala Leu Gln Arg Met Ala Pro Leu Leu Ser Arg Arg Ser Ala
            180                 185                 190

Ser Gln Gln Glu Ala Leu Ala Glu Thr Thr Ala Leu Ala Val Asp Leu
        195                 200                 205

Val Ser Gly Leu Arg Val Leu Arg Gly Ile Gly Ala Gln His His Ala
    210                 215                 220

Ala Gly Arg Tyr Ala Glu Ala Ser Arg Arg Ala Leu Ala Val Thr Leu
225                 230                 235                 240

Arg Ala Ala Asn Thr Lys Gly Leu His Leu Gly Leu Thr Thr Ala Ala
                245                 250                 255

Asn Gly Leu Phe Leu Ala Ala Val Ala Gly Val Ala Gly Trp Leu Ala
            260                 265                 270

-continued

```
Leu Arg Gly Arg Leu Thr Ile Gly Glu Leu Val Thr Val Gly Leu
            275                 280                 285

Ala Gln Phe Val Ala Glu Pro Val Gln Thr Leu Gly Tyr Cys Val Gln
        290                 295                 300

Leu Phe Ala Met Ala Arg Ala Ser Ala Ala Arg Val Gly Arg Val Leu
305                 310                 315                 320

Gly Ala Glu Pro Leu Thr Arg Pro Gly Ser Ala Pro Arg Pro Asp Arg
                325                 330                 335

Thr Asp Gly Pro Arg Leu Val Leu Asp His Val Gly His Ala Ala Leu
            340                 345                 350

Asp Gly Val Cys Leu Arg Val Asp Pro Gly Glu Ile Val Gly Val Leu
        355                 360                 365

Ala Tyr Asp Pro Ala Asp Ala Asp Ala Leu Val Ala Leu Leu Ser Gly
    370                 375                 380

Arg Val Pro Ala Asp Arg Arg Gly Thr Val Arg Val Asp Gly Val
385                 390                 395                 400

Pro Ala Asp Asp Leu Asp Val Asp Ala Leu Arg Gly Ala Val Leu Val
                405                 410                 415

Glu Pro His Asp Val Thr Leu Phe Glu Gly Thr Val Ala Ala Asn Leu
            420                 425                 430

Ala Ala Gly Ser Arg Thr Glu Glu Gly Arg Leu Arg Ala Ala Val Arg
        435                 440                 445

Ala Ala Ala Ala Asp Asp Val Val Asp Ala His Pro Gly Gly Leu Gly
    450                 455                 460

His Arg Leu Val Glu Arg Gly Ala Asn Leu Ser Gly Gly Gln Arg Gln
465                 470                 475                 480

Arg Leu Gly Leu Ala Arg Ala Leu His Ala Asp Pro Pro Val Leu Val
                485                 490                 495

Leu His Asp Pro Thr Thr Ala Val Asp Ala Ala Thr Glu Ala Gln Leu
            500                 505                 510

Ala Asp Gly Leu Ala Gly Ala Arg Arg Glu Ala Pro Arg Gly Thr Leu
        515                 520                 525

Leu Val Thr Ser Ser Pro Ala Leu Leu Arg Ile Thr Asp Arg Val Val
    530                 535                 540

Val Ile Ala Asp Gly Arg Val Thr Ala Glu Gly Thr His Glu His Leu
545                 550                 555                 560

Leu Ala Thr Asp Ala Arg Tyr Arg Glu Glu Thr Leu Arg
                565                 570
```

<210> SEQ ID NO 81
<211> LENGTH: 1722
<212> TYPE: DNA
<213> ORGANISM: Micromonospora sp. strain 046-ECO11

<400> SEQUENCE: 81

| | | |
|---|---|---|
| gtgtcccgc ttcccccgg cagcgccgtc accgccggc acgtgctccg ccaggcgctg | 60 |
| cgccgccagc gccgcccggt gctgatcggc gtgaccctgc tcgggctgca ccaggtcacc | 120 |
| gaggcgctcg tgccggtggc gatcggcgtc atcatcgacc gggccgtggt gaccggcgac | 180 |
| ccgtgggcgc tcgcgtactc cgtcgccggc ctcgccgccc tgttcaccgt gctggcgttc | 240 |
| gcctaccgca acggcgcccg ccaggcgttc gcggcggtgg aacgggaggc gcacctgctg | 300 |
| cgggtcgagc tggccgagcg cgcgctcgac ccgcgcgggc accgctccgg cctgcgcgac | 360 |
| ggcgagctgc tctcggtcgc cgcctccgac gccgaactct ccgcgtacgt ggtccgggtg | 420 |

-continued

```
gccggcttcg gcgtcgccgc ggtgagcgcg ctgaccgtcg cggcggtcgc gctgctggtc      480
atcgacgtcc cgctcggact cggcgtgctc atcggcgtac cggtgctggt cctggcgctg      540
caacggatgg cgccgctgct gtcccggcgc agcgcctccc agcaggaggc cctcgcggag      600
accacggcgc tcgccgtgga cctcgtctcc ggcctgcgcg tgctgcgcgg catcggcgcc      660
cagcaccacg ccgccggccg gtacgccgag ccagccgac gcgccctcgc cgtgacgctg       720
cgcgccgcca acaccaaggg cctgcacctc gggctcacca ccgccgcgaa cggcctcttc      780
ctcgccgccg tcgccggggt cgccggctgg ctcgcgctgc gcggccggct caccatcggc      840
gagctggtca ccgtggtcgg gctcgcgcag ttcgtcgccg agccggtgca gacgctgggc      900
tactgcgtgc agctgttcgc gatggcccgc gcctccgccg cccgggtcgg gcgcgtgctc      960
ggcgccgagc cgctgacccg gccgggcagc gcgccccggc cggaccgcac ggacgggccg     1020
cggctcgtcc tcgaccacgt cggccacgcc gcgctggacg gggtgtgcct gcgcgtcgac     1080
ccgggagaga tcgtcggcgt cctggcgtac gaccccggccg acgcggacgc gctggtggcg   1140
ctgctgtccg gcgggtgcc cgcggaccgg cgccggggca cggtacgcgt cgacgggta      1200 cccgccgacg acctggacgt cgacgcgctg cgcggcgccg tcctggtcga ccgcacgac     1260 gtgacgctgt tcgagggaac cgtggccgcc aacctcgccg ccgggagcag gaccgaggag     1320
gggcgcctgc gcgccgcggt ccgggcggcc gcggcggacg acgtggtgga cgcgcacccc     1380
ggcggcctcg gccaccggct cgtcgagcgg ggcgccaacc tctccggcgg gcagcgccag     1440
cggctcgggc tggcgcgggc gctgcacgcc gacccgccgg tgctggtgct gcacgacccc     1500
accaccgccg tggacgcggc caccgaggcc caactcgccg acggactggc cggcgcgcgc     1560
cgcgaagcgc cccggggcac gctgctggtc accagcagcc ccgccctgct gcggatcacc     1620
gaccgggtgg tggtgatcgc cgacggccgg gtgaccgccg aggggacgca cgagcacctg     1680
ctggccaccg acgcccgcta ccgcgaggag acactgcggt ga                        1722
```

<210> SEQ ID NO 82
<211> LENGTH: 596
<212> TYPE: PRT
<213> ORGANISM: Micromonospora sp. strain 046-ECO11

<400> SEQUENCE: 82

```
Val Thr Ala Asp Pro Arg Thr Ala Glu Pro Thr Arg Val Leu Leu Pro
 1               5                  10                  15

Thr Ala Thr Ala Arg Arg Thr Trp Thr Thr Leu Gly Ala Glu Phe Arg
            20                  25                  30

Arg Arg Pro Gly Leu Ser Ala Ala Thr Ala Val Leu Val Ala Ala
        35                  40                  45

Ala Thr Gly Gly Leu Val Ala Pro Trp Val Leu Gly Arg Leu Val Asp
    50                  55                  60

Asp Val Ile Ala Asp Ala Pro Val Ser Arg Ile Ala Gly Arg Val Ala
65                  70                  75                  80

Val Ile Ala Gly Ala Ala Val Leu Thr Gly Leu Leu Thr Ala Ala Gly
                85                  90                  95

Ala Ala Leu Ala Ser Arg Leu Gly Glu Thr Val Leu Ala Arg Leu Arg
            100                 105                 110

Glu Arg Val Leu Asp Arg Ala Leu His Leu Pro Ser Ala Thr Leu Glu
        115                 120                 125

Arg Ala Gly Thr Gly Asp Leu Leu Ala Arg Val Gly Asp Val Ala
    130                 135                 140
```

-continued

```
Val Val Thr Asn Val Ile Ala Val Ser Gly Pro Ala Phe Val Gly Ala
145                 150                 155                 160

Leu Leu Ser Val Val Leu Thr Val Phe Gly Leu Val Ala Leu Asp Trp
                165                 170                 175

Arg Leu Gly Leu Ala Gly Leu Val Ala Ala Pro Ala Tyr Ala Leu Ala
            180                 185                 190

Leu Arg Trp Tyr Leu Arg Arg Ser Ala Pro Tyr Tyr Ala Arg Glu Arg
        195                 200                 205

Val Ala Thr Gly Glu Arg Thr Gln Ala Met Ala Gly Ala Leu Arg Gly
210                 215                 220

Ala Ala Thr Val Arg Ala Tyr Arg Thr Glu Asp Ala His Val Ala Ala
225                 230                 235                 240

Ile Ala Glu Arg Ser Gly Val Ala Arg Asp Leu Ser Leu Glu Ile Phe
                245                 250                 255

Asn Leu His Thr Arg Phe Gly Leu Arg Ile Asn Arg Ser Glu Phe Leu
                260                 265                 270

Gly Leu Ala Ala Val Leu Val Ala Gly Phe Phe Leu Val Arg Ala Asp
            275                 280                 285

Leu Val Thr Val Gly Ala Ala Thr Thr Ala Ala Leu Tyr Phe His Arg
        290                 295                 300

Leu Phe Asn Pro Ile Gly Leu Leu Leu Met Glu Ser Asp Ser Val Leu
305                 310                 315                 320

Gln Ala Gly Ala Ser Leu Ala Arg Leu Val Gly Val Ala Thr Leu Pro
                325                 330                 335

Asp Thr Ala Pro Ser Gly Pro Ala Pro Ser Ala Ala Gly Arg Arg Gly
                340                 345                 350

Pro Ala Ala Leu Asp Val Thr Val Arg Arg His Arg Tyr Asp Asp Asp
            355                 360                 365

Gly Pro Leu Val Leu Ala Asp Val Asp Leu Arg Leu Ala Pro Gly Glu
        370                 375                 380

Arg Val Ala Leu Val Gly Ala Ser Gly Ala Gly Lys Ser Thr Leu Ala
385                 390                 395                 400

Gly Ile Ala Ala Gly Ile Ile Ala Pro Thr Asp Gly Ser Val Arg Leu
                405                 410                 415

Gly Gly Val Pro Leu Thr Glu Arg Gly Glu His Ala Val Arg Arg Asp
                420                 425                 430

Val Ala Leu Val Ser Gln Glu Val His Val Phe Ala Gly Pro Leu Ala
            435                 440                 445

Glu Asp Leu Arg Leu Ala Ala Pro Asp Ala Thr Asp Ala Glu Leu Leu
        450                 455                 460

Asp Ala Leu Asp Arg Val Gly Ala Thr Thr Trp Leu Arg Ala Leu Pro
465                 470                 475                 480

Asp Gly Leu Ala Thr Ala Val Gly Glu Gly Gly His Arg Leu Thr Ala
                485                 490                 495

Ala Gln Ala Gln Val Ala Leu Ala Arg Leu Val Leu Ala Ala Pro
                500                 505                 510

Ala Val Ala Val Leu Asp Glu Ala Thr Ala Glu Ala Gly Ser Ala Gly
            515                 520                 525

Ala Arg Asp Leu Asp Arg Ala Ala Leu Ala Ala Thr Glu Gly Arg Thr
        530                 535                 540

Thr Leu Ile Val Ala His Arg Leu Ser Gln Ala Val Ala Ala Asp Arg
545                 550                 555                 560
```

-continued

Ile Val Leu Leu Asp His Gly Arg Ile Val Glu Gln Gly Thr His Ser
                565                 570                 575

Glu Leu Leu Ala Ala Asp Gly Arg Tyr Gly His Leu Trp Arg Ser Trp
            580                 585                 590

Ser Val Pro Val
        595

<210> SEQ ID NO 83
<211> LENGTH: 1791
<212> TYPE: DNA
<213> ORGANISM: Micromonospora sp. strain 046-ECO11

<400> SEQUENCE: 83

| | | | | | |
|---|---|---|---|---|---|
| gtgaccgctg | acccgcgtac | cgccgaaccc | acccgggtgt | tgctgcccac | cgcgaccgcc | 60 |
| cggcggacct | ggacgacgct | cggcgcggag | ttccgccggc | ggcccggcct | cagcgccgcc | 120 |
| gcgaccgccg | tgctcgtcgc | cgccgccacc | ggcgggctgg | tcgcgccctg | ggtgctcggc | 180 |
| cgcctcgtcg | acgacgtcat | cgccgacgcc | ccggtctccc | ggatcgccgg | ccgggtggcg | 240 |
| gtgatcgccg | gcgcggcagt | gctcaccgga | ctgctcaccg | ccgccggggc | cgcgctcgcg | 300 |
| tcccgcctgg | gggagacggt | gctggcccgg | ctgcgcgagc | gggtcctcga | ccgggcgctg | 360 |
| cacctgccct | cggcgacgct | ggaacgggcc | ggcaccggcg | acctgctggc | cgggtcggc | 420 |
| gacgacgtgg | cggtggtgac | gaacgtgatc | gcggtcagcg | gcccggcgtt | cgtcggcgcg | 480 |
| ctgctgtccg | tggtgctgac | cgtgttcggg | ctggtcgcgc | tcgactggcg | gctcggcctc | 540 |
| gccgggctgg | tcgccgcgcc | cgcctacgcg | ctggcgctgc | gctggtacct | cgccggtcg | 600 |
| gcgccgtact | acgcccgcga | gcgcgtcgcc | accggcgagc | ggacgcaggc | gatggccggc | 660 |
| gcgctgcgtg | gcgcggccac | cgtgcgcgcg | taccggaccg | aggacgcgca | cgtcgcggcg | 720 |
| atcgccgagc | gctccggcgt | ggcgcgcgac | ctgtcgctgg | agatcttcaa | cctgcacacc | 780 |
| cggttcgggc | tgcggatcaa | caggtcggag | ttcctcggcc | tggccgcggt | gctcgtcgcc | 840 |
| gggttcttcc | tggtccgcgc | cgacctggtc | acagtgggcg | cggcgaccac | cgccgcgctc | 900 |
| tacttccacc | ggctgttcaa | cccgatcggc | ctgctgctga | tggagtccga | ctcggtgctg | 960 |
| caggccggcg | cgagcctcgc | ccggctggtc | ggcgtggcca | cgctgcccga | caccgccccg | 1020 |
| tccgggcccg | cgccgtcggc | ggccgggcgg | cgcggcccgg | cggcgctgga | cgtcacggtc | 1080 |
| cgccggcacc | gctacgacga | cgacggccct | ctggtcctgg | ccgacgtcga | cctgcgcctg | 1140 |
| gccccggga | agcgggtcgc | gctcgtgggc | gccagcggcg | cgggcaagag | cacgctcgcc | 1200 |
| ggcatcgccg | ccgggatcat | cgcgcccacc | gacgggtcgg | tacgcctggg | cggcgtgccg | 1260 |
| ctgaccgagc | ggggcgagca | cgccgtgcgg | cgcgacgtcg | cgctggtcag | ccaggaggtg | 1320 |
| cacgtcttcg | ctggaccgct | cgccgaggat | ctgcgcctgg | ctgccccgga | cgccaccgac | 1380 |
| gccgaactgc | tcgacgcgct | ggaccgggtc | ggcgccacca | cctggctgcg | cgcgctgccg | 1440 |
| gacgggctgg | ccacagcggt | cggcgagggc | ggccaccggc | tcaccgccgc | gcaggcccag | 1500 |
| caggtcgccc | tggcccggct | ggtgctggcc | gcgcccgccg | tcgccgtgct | ggacgaggcc | 1560 |
| accgccgagg | ccggcagcgc | cggagcgcgt | gacctggacc | gggcggcgct | ggccgccacc | 1620 |
| gagggacgga | ccacgctgat | cgtggcgcac | cggctcagcc | aggcggtcgc | cgccgaccgg | 1680 |
| atcgtcctgc | tcgaccacgg | gcggatcgtg | gagcagggca | cgcactcgga | actgctcgcc | 1740 |
| gccgacggcc | ggtacgggca | tctgtggcgc | tcctggagcg | tcccggtatg | a | 1791 |

<210> SEQ ID NO 84

```
<211> LENGTH: 507
<212> TYPE: PRT
<213> ORGANISM: Micromonospora sp. strain 046-ECO11

<400> SEQUENCE: 84
```

| Met | Thr | Asp | Ala | Pro | Ala | Arg | Phe | Val | Leu | Phe | Pro | Gly | Arg | His | His |
|---|---|---|---|---|---|---|---|---|---|---|---|---|---|---|---|
| 1 | | | | 5 | | | | | 10 | | | | | 15 | |

| Leu | Leu | Thr | Arg | Phe | Gln | Ala | Asp | Tyr | Leu | Arg | Arg | Leu | Ala | Gly | Asp |
| | | | 20 | | | | | 25 | | | | | 30 | | |

| Asp | Ala | Thr | Val | Val | Trp | Ala | Val | Thr | Ser | Ala | Asn | His | Glu | Asn | Thr |
| | | 35 | | | | | 40 | | | | | 45 | | | |

| Arg | Arg | Asn | Pro | Val | Pro | Tyr | His | Arg | Arg | Glu | Ala | Ala | Ile | Glu | Arg |
| | 50 | | | | | 55 | | | | | 60 | | | | |

| Phe | Ser | Val | Leu | Ser | Gly | Leu | Arg | Ser | Val | Val | Pro | Ile | Phe | Asp |
| 65 | | | | | 70 | | | | | 75 | | | | | 80 |

| Thr | Ala | Tyr | Thr | Asp | Ala | Phe | Ala | Glu | Val | Thr | Leu | Lys | Ser | Ile | Ala |
| | | | | 85 | | | | | 90 | | | | | 95 | |

| Val | Ala | Thr | Gly | Leu | Glu | Leu | Thr | Pro | Ala | Asp | Thr | Val | Leu | Ala | Cys |
| | | | | 100 | | | | | 105 | | | | | 110 | |

| Ser | Thr | Pro | Glu | Val | Ala | Lys | Leu | Tyr | Glu | Gln | Leu | Gly | Phe | Ser | Ile |
| | | | | 115 | | | | | 120 | | | | | 125 | |

| Ala | Pro | Val | Glu | Ala | Asp | Pro | Asp | Leu | Pro | Glu | Pro | Pro | Glu | Arg | Pro |
| | | 130 | | | | | 135 | | | | | 140 | | | |

| Trp | Asp | Val | Leu | Leu | Arg | Leu | Ala | Ala | Gly | Asp | Glu | Thr | Trp | Arg | Ala |
| 145 | | | | | 150 | | | | | 155 | | | | | 160 |

| Leu | Thr | His | Pro | Ala | Thr | Ile | Asp | Val | Phe | Glu | Arg | Tyr | Arg | Leu | Val |
| | | | | 165 | | | | | 170 | | | | | 175 | |

| Glu | Ser | Ile | Arg | Ser | Val | Val | Asn | Asp | Pro | Leu | Val | Gly | Asp | Glu | Gly |
| | | | 180 | | | | | 185 | | | | | 190 | | |

| Gly | Leu | Thr | Val | Thr | Arg | Asp | Tyr | Arg | Thr | Tyr | Val | Glu | Ala | Phe | Ala |
| | | | | 195 | | | | | 200 | | | | | 205 | |

| Thr | Ala | Ala | Gln | Arg | Lys | Trp | Asp | Ser | Val | Arg | Arg | Tyr | Val | Gln | Pro |
| | 210 | | | | | 215 | | | | | 220 | | | | |

| Gly | Arg | Ile | Val | Asp | Ile | Gly | Cys | Gly | Ala | Gly | Ala | Val | Leu | Glu | Leu |
| 225 | | | | | 230 | | | | | 235 | | | | | 240 |

| Ala | Asp | Arg | Glu | Ala | Ala | Leu | Arg | Glu | Ser | Asp | Leu | Ile | Gly | Val | Glu |
| | | | | 245 | | | | | 250 | | | | | 255 | |

| Val | Ala | Arg | His | Leu | Tyr | Gln | Glu | Cys | Leu | His | Lys | Lys | Ala | Gln | Gly |
| | | | 260 | | | | | 265 | | | | | 270 | | |

| Val | Phe | Arg | Asn | Ala | Asn | Val | Tyr | Phe | Phe | His | Arg | Asn | Val | Leu | Gly |
| | | 275 | | | | | 280 | | | | | 285 | | | |

| Gly | Ala | Val | Phe | Lys | Asp | Arg | Ser | Val | Asp | Thr | Thr | Leu | Thr | Phe | Ala |
| | | 290 | | | | | 295 | | | | | 300 | | | |

| Leu | Thr | His | Glu | Ile | Trp | Ser | Tyr | Gly | Arg | Arg | Arg | Glu | Ser | Leu | Leu |
| 305 | | | | | 310 | | | | | 315 | | | | | 320 |

| Gln | Phe | Ala | Arg | Arg | Ile | His | Asp | His | Thr | Val | Pro | Gly | Gly | Val | Trp |
| | | | | 325 | | | | | 330 | | | | | 335 | |

| Ile | Asn | Ser | Asp | Val | Cys | Gly | Pro | Asp | Asp | Pro | Arg | Arg | Gln | Val | Leu |
| | | | 340 | | | | | 345 | | | | | 350 | | |

| Leu | Arg | Leu | Ser | Thr | Asp | Asp | Gly | Asp | Asn | Pro | Ala | Ala | Pro | Arg | Pro |
| | | | 355 | | | | | 360 | | | | | 365 | | |

| Asp | Leu | Ala | Glu | Leu | Thr | Ser | Ala | Glu | Val | Arg | Arg | Tyr | Val | Gly | Gly |
| | 370 | | | | | 375 | | | | | 380 | | | | |

| Leu | Ser | Thr | Arg | Ala | Arg | Leu | Asp | Gln | Phe | Ala | Val | Asp | Phe | Ala | Phe |

-continued

```
            385                 390                 395                 400

Asp Phe Asp Tyr Glu Pro Leu Pro Asp Gly Ala Val Arg Leu Thr Leu
                405                 410                 415

Gly Ala Ala Met Asp Tyr Leu Thr Arg Lys Asp Tyr Thr Asp Asn Trp
                420                 425                 430

Leu Ser Glu Thr Gln Glu Gln Phe Cys Gly Leu Ser Phe Ala Asp Trp
                435                 440                 445

Thr Asp Leu Leu Thr Glu Ala Gly Phe Glu Ile Gly Pro Ala Ser Ala
    450                 455                 460

Pro Val Arg Asn Glu Trp Val Ile Asp Asn Arg Ile Ala Pro Val Ala
465                 470                 475                 480

Ser Leu Thr Asp Leu Asp Gly Arg Pro Leu Asp Trp Pro Thr Thr His
                485                 490                 495

Val Leu Thr Val Ala His Arg Pro Arg Asn Gln
                500                 505
```

<210> SEQ ID NO 85
<211> LENGTH: 1524
<212> TYPE: DNA
<213> ORGANISM: Micromonospora sp. strain 046-ECO11

<400> SEQUENCE: 85

| | | |
|---|---|---|
| atgaccgacg cgccggcccg cttcgtgctc ttcccggggc ggcaccacct gctgacccgg | 60 |
| ttccaggccg actacctgcg gcggctggcc ggggacgacg ccacagtggt ctgggcggtg | 120 |
| acgtcggcca accacgagaa caccaggcgc aacccggtgc cctaccaccg gcgggaggcc | 180 |
| gcgatcgaac gattcagcgt gctgagcggg ctgcgctcgg tggtggtgcc gatcttcgac | 240 |
| accgcgtaca ccgacgcgtt cgccgaggtg acgctgaagt ccatcgcggt ggccaccggg | 300 |
| ctcgaactca ccccgccga caccgtgctg gcctgctcca cgccggaggt cgcgaagctg | 360 |
| tacgagcagc tcggcttttc gatcgcgccg gtcgaggcgg accggacct gcccgagccg | 420 |
| cccgaacggc cgtgggacgt gctgctgcgc ctggccgccg gggacgagac ctggcgcgcg | 480 |
| ctcacccacc cggccaccat cgacgtgttc gagcgctacc gcctggtcga gtcgatccgg | 540 |
| tcggtggtga acgacccgct cgtcggcgac gagggcggtc tcacagtgac ccgcgactac | 600 |
| cggacctacg tcgaggcgtt cgccacggcc gcgcagcgca gtgggactc ggtacgccgg | 660 |
| tacgtgcagc ccggccgcat cgtggacatc ggctgcggcg cgggcgccgt cctggaactc | 720 |
| gccgaccggg aggccgcgct gcgtgagagc gacctgatcg gcgtggaggt cgcccgccac | 780 |
| ctctaccagg agtgcctgca aagaaggcg cagggcgtgt ccgcaacgc caacgtctac | 840 |
| ttcttccacc gcaacgtcct cggcggcgcg gtgttcaagg accgctcggt cgacaccacg | 900 |
| ctcacgttcg cgctgaccca cgagatctgg tcgtacgggc ggcggcggga gtcgctgctg | 960 |
| cagttcgccc gccgcatcca cgaccacacg gtgcccggcg cgtctggat caacagcgac | 1020 |
| gtgtgcggtc cggacgaccc ccggcggcag gtgctcctgc gactgtccac cgacgacggc | 1080 |
| gacaacccgg ccgcgccccg ccccgacctc gccgagctga cctcggcgga ggtccggcgt | 1140 |
| tacgtcggcg ggctgtcgac gcgggcgcgg ctggaccagt tcgccgtcga cttcgcgttc | 1200 |
| gacttcgact acgagccgct ccccgacggc gcggtacgcc tgacgctggg cgccgcgatg | 1260 |
| gactacctga cccgcaagga ctacacggac aactggctgt cggagacgca ggagcagttc | 1320 |
| tgcggcctga gcttcgccga ctggacggac ctgctcaccg aggcggggtt cgagatcggc | 1380 |
| ccggcgtcgg cgccggtgcg caacgagtgg gtgatcgaca accggatcgc gccagtcgcg | 1440 |

-continued

| tccctcaccg acctcgacgg ccggccgctg gactggccga ccacccacgt cctcaccgtc | 1500 |
| gcccaccgcc cccgcaacca gtga | 1524 |

<210> SEQ ID NO 86
<211> LENGTH: 232
<212> TYPE: PRT
<213> ORGANISM: Micromonospora sp. strain 046-ECO11

<400> SEQUENCE: 86

```
Val Ser Asp Ile Gln Ile Ile Ser Phe Val Ala Ala Ser Leu Leu Ile
1               5                   10                  15

Ile Ile Val Pro Gly Val Asp Phe Ala Leu Val Thr Arg Gln Thr Val
            20                  25                  30

Arg Tyr Gly Arg Arg Ala Gly Phe Val Val Leu Ala Gly Leu Phe Val
        35                  40                  45

Ala Ala Leu Val His Ala Ser Phe Ala Thr Ala Gly Leu Ser Ala Leu
    50                  55                  60

Leu Val Ser Ser Pro Thr Leu Tyr Thr Val Leu Arg Val Ala Gly Ala
65                  70                  75                  80

Leu Tyr Leu Leu Tyr Leu Gly Gly Thr Ile Leu Trp Ala Thr Arg Pro
                85                  90                  95

Arg Arg Thr Val Pro Ala Ala Gln Pro Val Thr Val Gly Ala Gly Gly
            100                 105                 110

Ala Gly Pro Asp Thr Asp Thr Gly Pro Ala Pro Val Pro Asp Thr Pro
        115                 120                 125

Ala Ala Asp Glu Pro His Val Ala Arg Arg Ser Phe Val Met Gly Val
    130                 135                 140

Thr Ser Gln Leu Leu Asn Val Lys Val Val Phe Tyr Val Ser Phe
145                 150                 155                 160

Val Pro Gln Phe Val Lys Pro Gly Glu Gly Ala Ala Ala Arg Thr Ala
                165                 170                 175

Val Leu Ala Ala Thr Phe Ile Gly Leu Ala Val Leu Trp Trp Ala Cys
            180                 185                 190

Tyr Ile Met Leu Ile Asp Arg Leu Gln Pro Trp Leu Thr Arg Pro Ser
        195                 200                 205

Val Leu Leu Val Ile Glu Arg Leu Thr Gly Leu Ile Leu Ile Val Leu
    210                 215                 220

Ala Ile Arg Ile Ala Leu Ser Arg
225                 230
```

<210> SEQ ID NO 87
<211> LENGTH: 699
<212> TYPE: DNA
<213> ORGANISM: Micromonospora sp. strain 046-ECO11

<400> SEQUENCE: 87

| gtgtctgaca tccagatcat cagtttcgtc gccgccagcc tgctcatcat catcgtgccg | 60 |
| ggcgtcgact cgcgctcgt cacccggcag accgtcaggt acggccggcg ggccgggttc | 120 |
| gtggtgctgg ccgggctgtt cgtcgccgcg ctggtgcacg cgtcgttcgc gaccgccggc | 180 |
| ctgtccgccc tgctggtctc ctcgccgacg ctctacacgg tgctgcgcgt cgccggcgcg | 240 |
| ctgtacctgc tctacctggg cggcacgatc ctctgggcga cccggccgcg ccggacggtc | 300 |
| ccggcggcgc agccggtcac tgtcggcgcg ggcggcgccg ggccggacac ggacaccggc | 360 |
| cccgcgccgg tgccggacac cccggccgcc gacgagccgc acgtggcccg ccgctcgttc | 420 |

```
gtcatgggcg tcaccagcca gctgctgaac gtcaaggtgg tcgtcttcta cgtctcgttc      480
gtgccgcagt tcgtcaagcc cggcgagggg gcggcggccc gtacggcggt gctcgccgcc      540
acgttcatcg gcctcgcggt gctctggtgg gcctgctaca tcatgctcat cgacaggttg      600
cagccctggc tgaccggcc gtccgtgctg ctggtgatcg aacggctgac cgggctcatc       660
ctgatcgtcc tggcgatccg gatcgcgctg agccggtga                             699
```

```
<210> SEQ ID NO 88
<211> LENGTH: 132
<212> TYPE: PRT
<213> ORGANISM: Micromonospora sp. strain 046-ECO11

<400> SEQUENCE: 88

Val Gly Val Ser Ala Met Thr Thr Phe Asp Tyr Asp Gly Arg Val Phe
1               5                   10                  15

Val Ser Val Asp His Asp Ala Gly Asp Gly Ala Glu Pro Leu Arg Gly
            20                  25                  30

His Tyr His Gln Arg Gly Asp Leu Val Trp Ala Glu Ile Thr Gly Gly
        35                  40                  45

Pro Val Arg His Gly Arg Leu Ala Gly Thr Cys Asp Ala Gln Gly Val
    50                  55                  60

Val Arg Phe Ala Tyr Leu Glu Val Leu Thr Asp Gly Thr Ile Val Ile
65                  70                  75                  80

Gly Glu Cys Glu Ser Arg Pro Glu Arg Leu Pro Asp Gly Arg Ile Arg
                85                  90                  95

Leu Arg Glu Gln Trp Arg Arg His Gly Pro Arg Gln Asp Ser Gly Val
            100                 105                 110

Ser Val Ile Glu Glu Ala Val Pro Ala Leu Ala Gly Gly Gln Glu Ser
        115                 120                 125

Arg Arg Arg Val
    130
```

```
<210> SEQ ID NO 89
<211> LENGTH: 399
<212> TYPE: DNA
<213> ORGANISM: Micromonospora sp. strain 046-ECO11

<400> SEQUENCE: 89
gtgggcgtga gcgcgatgac gacattcgac tacgacggcc gcgtcttcgt ctcggtggac      60
cacgacgccg gtgacggcgc cgagccgctg cggggcact accaccagcg tggcgacctg      120
gtctgggcgg agatcaccgg cggcccggtc cggcacggcc ggctggccgg cacctgcgac      180
gcgcagggct cgtgcgcctt cgcctacctg gaggtgctca ccgacggcac catagtcatc      240
ggcgagtgcg agtcccggcc cgaacggctg ccggacggcc ggatccggct gcgggaacag      300
tggcgccggc acggaccacg ccaggacagc ggcgtctccg tcatcgagga ggcagtgccg      360
gcgctcgccg gaggacagga gagccggcgt cgtgtctga                             399
```

```
<210> SEQ ID NO 90
<211> LENGTH: 296
<212> TYPE: PRT
<213> ORGANISM: Micromonospora echinospora challisensis

<400> SEQUENCE: 90

Met Pro Gly Thr Ser Glu Ala Val Glu Leu Cys Ser Thr Ile Glu Glu
1               5                   10                  15

Ser Ala Arg Leu Leu Asn Val Ala Cys Ser Arg Asp Arg Val Trp Ser
```

```
                  20                  25                  30
Leu Leu Ser Ala Tyr Gly Asp Ala Phe Ala His Pro Gly Ala Val Val
            35                  40                  45
Ala Phe Arg Val Ala Thr Ala Met Arg His Val Gly Glu Leu Asp Cys
        50                  55                  60
Arg Phe Thr Thr His Pro Asp Asp Arg Asp Pro Tyr Ala Arg Ala Leu
65                  70                  75                  80
Ser Arg Gly Leu Thr Pro Glu Thr Asp His Pro Val Gly Thr Leu Leu
                85                  90                  95
Ser Glu Val Gln Gly Arg Cys Pro Val Glu Ser His Gly Ile Asp Phe
            100                 105                 110
Gly Val Val Gly Gly Phe Lys Lys Ile Tyr Ala Phe Phe Thr Pro Asp
        115                 120                 125
Asp Leu Gln Glu Thr Ser Lys Leu Ala Glu Ile Pro Ala Met Pro Arg
    130                 135                 140
Ser Leu Ala Gly Asn Val Glu Phe Phe Ala Arg His Gly Leu Asp Asp
145                 150                 155                 160
Arg Val Gly Val Phe Gly Ile Asp Tyr Pro Ser Arg Thr Val Asn Val
                165                 170                 175
Tyr Phe Asn Asp Val Pro Ala Glu Ser Phe His Ser Glu Thr Ile Arg
            180                 185                 190
Ser Thr Leu Arg Glu Ile Gly Met Ala Glu Pro Ser Glu Arg Met Leu
        195                 200                 205
Lys Leu Gly Glu Lys Ala Phe Gly Leu Tyr Val Thr Leu Gly Trp Asp
    210                 215                 220
Ser Ser Arg Ile Glu Arg Ile Cys Tyr Ala Ala Ala Thr Thr Asp Leu
225                 230                 235                 240
Thr Thr Leu Pro Val Pro Val Glu Pro Glu Ile Glu Lys Phe Val Arg
                245                 250                 255
Ser Val Pro Tyr Gly Gly Glu Asp Arg Lys Phe Val Tyr Gly Val Ala
            260                 265                 270
Leu Thr Pro His Gly Glu Tyr Tyr Lys Leu Glu Ser His Tyr Arg Trp
        275                 280                 285
Lys Pro Gly Ala Met Asp Phe Ile
    290                 295

<210> SEQ ID NO 91
<211> LENGTH: 891
<212> TYPE: PRT
<213> ORGANISM: Micromonospora echinospora challisensis

<400> SEQUENCE: 91

Ala Thr Gly Cys Cys Cys Gly Gly Ala Ala Cys Gly Thr Cys Cys Gly
1               5                   10                  15
Ala Gly Gly Cys Gly Gly Thr Gly Gly Ala Ala Cys Thr Cys Thr Gly
                20                  25                  30
Thr Thr Cys Cys Ala Cys Cys Ala Thr Cys Gly Ala Gly Gly Ala Ala
            35                  40                  45
Thr Cys Gly Gly Cys Cys Gly Gly Cys Thr Gly Cys Thr Cys Gly Ala
        50                  55                  60
Ala Cys Gly Thr Gly Gly Cys Cys Thr Cys Thr Cys Gly Cys Cys Gly
65                  70                  75                  80
Thr Gly Ala Cys Ala Gly Gly Gly Thr Cys Thr Gly Gly Thr Cys Cys
                85                  90                  95
```

-continued

```
Cys Thr Gly Cys Thr Cys Thr Cys Cys Gly Cys Gly Thr Ala Cys Gly
                100                 105                 110
Gly Thr Gly Ala Cys Gly Cys Gly Thr Thr Cys Gly Cys Gly Cys Ala
            115                 120                 125
Cys Cys Cys Cys Gly Gly Thr Gly Cys Cys Gly Thr Gly Gly Thr Cys
        130                 135                 140
Gly Cys Cys Thr Thr Cys Cys Gly Gly Thr Gly Gly Cys Gly Ala
145                 150                 155                 160
Cys Cys Gly Cys Gly Ala Thr Gly Cys Gly Cys Ala Cys Gly Thr
            165                 170                 175
Gly Gly Gly Ala Gly Ala Gly Cys Thr Cys Gly Ala Cys Thr Gly Thr
            180                 185                 190
Cys Gly Gly Thr Thr Cys Ala Cys Gly Ala Cys Gly Cys Ala Cys Cys
        195                 200                 205
Cys Gly Gly Ala Cys Gly Ala Cys Cys Gly Cys Gly Ala Cys Cys
        210                 215                 220
Cys Thr Ala Cys Gly Cys Cys Gly Thr Gly Cys Gly Cys Thr Gly
225                 230                 235                 240
Thr Cys Gly Cys Gly Cys Gly Gly Cys Cys Thr Cys Ala Cys Cys
            245                 250                 255
Cys Gly Gly Ala Gly Ala Cys Gly Gly Ala Cys Cys Ala Cys Cys
        260                 265                 270
Gly Gly Thr Cys Gly Gly Cys Ala Cys Cys Thr Gly Cys Thr Cys
            275                 280                 285
Thr Cys Cys Gly Ala Gly Gly Thr Cys Cys Ala Gly Gly Ala Cys
        290                 295                 300
Gly Thr Thr Gly Thr Cys Cys Gly Gly Thr Gly Gly Ala Gly Ala Gly
305                 310                 315                 320
Cys Cys Ala Cys Gly Gly Cys Ala Thr Cys Gly Ala Cys Thr Thr Cys
            325                 330                 335
Gly Gly Gly Gly Thr Cys Gly Thr Cys Gly Gly Cys Gly Gly Cys Thr
            340                 345                 350
Thr Cys Ala Ala Gly Ala Ala Gly Ala Thr Cys Thr Ala Cys Gly Cys
        355                 360                 365
Gly Thr Thr Cys Thr Thr Cys Ala Cys Cys Cys Gly Gly Ala Cys
        370                 375                 380
Gly Ala Cys Cys Thr Gly Cys Ala Gly Gly Ala Cys Gly Thr
385                 390                 395                 400
Cys Gly Ala Ala Gly Cys Thr Cys Gly Cys Cys Gly Ala Gly Ala Thr
            405                 410                 415
Cys Cys Cys Cys Gly Cys Ala Thr Gly Cys Cys Gly Cys Gly Cys
        420                 425                 430
Ala Gly Cys Cys Thr Gly Gly Cys Cys Gly Gly Gly Ala Ala Cys Gly
            435                 440                 445
Thr Cys Gly Ala Gly Thr Thr Cys Thr Thr Cys Gly Cys Cys Cys Gly
        450                 455                 460
Thr Cys Ala Cys Gly Gly Ala Cys Thr Gly Gly Ala Cys Gly Ala Cys
465                 470                 475                 480
Cys Gly Gly Gly Thr Cys Gly Gly Gly Thr Gly Thr Thr Cys Gly
            485                 490                 495
Gly Gly Ala Thr Cys Gly Ala Cys Thr Ala Cys Cys Gly Ala Gly
        500                 505                 510
Cys Cys Gly Gly Ala Cys Gly Gly Thr Gly Ala Ala Cys Gly Thr Gly
```

-continued

```
        515                 520                 525

Thr Ala Cys Thr Thr Cys Ala Ala Cys Gly Ala Cys Gly Thr Ala Cys
    530                 535                 540

Cys Cys Gly Cys Cys Gly Ala Gly Ala Gly Cys Thr Thr Cys Cys Ala
545                 550                 555                 560
Cys Thr Cys Gly Gly Ala Gly Ala Cys Gly Ala Thr Cys Cys Gly Gly
                565                 570                 575

Thr Cys Gly Ala Cys Gly Cys Thr Cys Cys Gly Gly Gly Ala Gly Ala
            580                 585                 590
Thr Cys Gly Gly Cys Ala Thr Gly Gly Cys Cys Gly Ala Ala Cys Cys
        595                 600                 605

Cys Ala Gly Thr Gly Ala Gly Cys Gly Gly Ala Thr Gly Cys Thr Cys
    610                 615                 620

Ala Ala Gly Cys Thr Cys Gly Gly Cys Gly Ala Gly Ala Ala Gly Gly
625                 630                 635                 640
Cys Gly Thr Thr Cys Gly Gly Ala Cys Thr Gly Thr Ala Thr Gly Thr
                645                 650                 655
Cys Ala Cys Cys Cys Thr Cys Gly Gly Cys Thr Gly Gly Gly Ala Thr
            660                 665                 670

Thr Cys Gly Thr Cys Gly Ala Gly Gly Ala Thr Cys Gly Ala Gly Cys
        675                 680                 685

Gly Gly Ala Thr Cys Thr Gly Cys Thr Ala Cys Gly Cys Cys Gly Cys
    690                 695                 700

Cys Gly Cys Gly Ala Cys Cys Ala Cys Cys Gly Ala Cys Cys Thr Gly
705                 710                 715                 720

Ala Cys Gly Ala Cys Cys Cys Thr Gly Cys Cys Cys Gly Thr Thr Cys
                725                 730                 735

Cys Cys Gly Thr Cys Gly Ala Ala Cys Cys Gly Gly Ala Gly Ala Thr
            740                 745                 750

Cys Gly Ala Gly Ala Ala Gly Thr Thr Cys Gly Thr Ala Cys Gly Gly
        755                 760                 765

Ala Gly Cys Gly Thr Thr Cys Cys Gly Thr Ala Cys Gly Gly Thr Gly
    770                 775                 780

Gly Gly Gly Ala Ala Gly Ala Cys Cys Gly Thr Ala Ala Gly Thr Thr
785                 790                 795                 800

Cys Gly Thr Cys Thr Ala Cys Gly Gly Cys Gly Thr Cys Gly Cys Gly
                805                 810                 815

Thr Thr Gly Ala Cys Cys Cys Cys Gly Cys Ala Cys Gly Gly Cys Gly
            820                 825                 830

Ala Gly Thr Ala Cys Thr Ala Cys Ala Ala Gly Cys Thr Cys Gly Ala
        835                 840                 845

Gly Thr Cys Gly Cys Ala Cys Thr Ala Cys Cys Gly Gly Thr Gly Gly
    850                 855                 860

Ala Ala Gly Cys Cys Cys Gly Gly Gly Gly Cys Gly Ala Thr Gly Gly
865                 870                 875                 880

Ala Cys Thr Thr Cys Ala Thr Cys Thr Gly Ala
                885                 890
```

<210> SEQ ID NO 92
<211> LENGTH: 438
<212> TYPE: PRT
<213> ORGANISM: Micromonospora echinospora challisensis

<400> SEQUENCE: 92

-continued

```
Val Asn Asp Pro Arg Pro Ser Leu Pro Gln Leu Gly Gln Trp His Gly
 1               5                  10                  15

Pro Glu Asp Leu Gln Arg Leu Gln Glu Lys Gln Leu Ser Gln Thr Val
            20                  25                  30

Thr Trp Ala Thr Arg Ser Pro Phe Tyr Arg Asp Arg Leu Asp Pro Gly
            35                  40                  45

Ala Leu Pro Ala Thr Ala Ala Asp Leu Ala Asp Leu Pro Leu Thr Thr
 50                  55                  60

Lys Gln Asp Leu Arg Asp Asn Tyr Pro Phe Gly Met Leu Ala Val Pro
 65                  70                  75                  80

Lys Glu Arg Leu Ala Thr Tyr His Glu Ser Ser Gly Thr Ala Gly Arg
                85                  90                  95

Pro Thr Pro Ser Tyr Tyr Thr Ala Glu Asp Trp Thr Asp Leu Ala Glu
            100                 105                 110

Arg Phe Ala Arg Lys Trp Ile Gly Met Ser Ala Glu Asp Val Phe Leu
            115                 120                 125

Val Arg Thr Pro Tyr Ala Leu Leu Leu Thr Gly His Leu Ala His Ala
            130                 135                 140

Ala Gly Arg Leu Arg Gly Ala Thr Val Val Pro Gly Asp Asn Arg Ser
145                 150                 155                 160

Leu Ala Met Pro Tyr Ala Arg Val Val Arg Val Met His Asp Leu Gly
                165                 170                 175

Val Thr Leu Thr Trp Ser Val Pro Thr Glu Cys Leu Ile Trp Ala Ala
            180                 185                 190

Ala Ala Thr Ala Ala Gly His Arg Pro Asp Val Asp Phe Pro Ala Leu
            195                 200                 205

Arg Ala Leu Phe Val Gly Gly Glu Pro Leu Thr Asp Ala Arg Arg Arg
210                 215                 220

Arg Ile Ser Arg Leu Trp Gly Val Pro Val Ile Glu Glu Tyr Gly Ser
225                 230                 235                 240

Thr Glu Thr Gly Ser Leu Ala Gly Glu Cys Pro Asn Gly Arg Met His
                245                 250                 255

Leu Trp Ala Asp Arg Ala Leu Phe Glu Val Tyr Asp Pro Arg Thr Gly
            260                 265                 270

Thr Val Ser Ala Asp Gly Asp Gly Gln Leu Val Val Thr Pro Leu Phe
            275                 280                 285

Arg Glu Ala Met Pro Leu Leu Arg Tyr Asn Leu Glu Asp Asp Val Thr
            290                 295                 300

Val Ser Tyr Asp Asp Cys Ala Cys Gly Trp Asn Leu Pro Thr Val Arg
305                 310                 315                 320

Val Leu Gly Arg Ala Ala Phe Gly Tyr Arg Val Gly Ala Ala Thr Ile
                325                 330                 335

Thr Gln His Arg Leu Glu Glu Val Val Phe Ser Leu Pro Glu Ser His
            340                 345                 350

Gly Val Val Phe Trp Arg Ala Lys Ala Glu Pro Thr Val Leu Arg Ile
            355                 360                 365

Glu Ile Glu Val Ala Glu Glu His Arg Thr Ala Ala Gln Ala Glu Leu
            370                 375                 380

Thr Ala Ser Val Arg Ala Thr Phe Gly Ile Asp Ser Glu Val Thr Gly
385                 390                 395                 400

Leu Thr Pro Gly Thr Leu Val Pro Arg Glu Ala Leu Thr Ser Met Pro
                405                 410                 415

Asp Val Val Lys Pro Arg Ser Leu Phe Gly Pro Asp Glu Asp Trp Gly
```

Lys Ala Leu Leu Tyr Tyr
        435

<210> SEQ ID NO 93
<211> LENGTH: 1317
<212> TYPE: DNA
<213> ORGANISM: Miicromonospora echinospora challisensis

<400> SEQUENCE: 93

```
gtgaacgacc cacgtccgag cctgcctcaa ctcggccagt ggcacgggcc ggaggacctt      60
cagcgccttc aggagaagca gctgtcgcag acggtcacct gggcgacccg ctcgccgttc     120
taccgcgacc ggctggaccc gggggccctg cccgcgaccg ccgccgacct cgccgacctg     180
ccgctgacca cgaagcagga cctgcgggac aactacccct tcggcatgct cgccgtcccg     240
aaggagcggc tggccaccta ccacgagtcg agcgggacgg caggccggcc cacgccctcc     300
tactacacgg cggaggactg gaccgacctg gccgagcgct tcgcccgcaa gtggatcggg     360
atgtccgccg aggacgtctt cctggtgcgt acgccgtacg cgctgctgct gaccgggcac     420
ctcgcgcacg ccgccggccg gctgcgcggg gccaccgtgg tgcccggcga caaccggtcg     480
ctggccatgc cgtacgcccg ggtggtccgg gtcatgcacg acctgggtgt cacgctgacc     540
tggtcggtgc cgaccgagtg cctcatctgg gccgccgcgg cgaccgcggc cgggcaccgg     600
cccgacgtcg acttccccgc gctgcgcgcg ttgttcgtcg gcggcgagcc gctcaccgac     660
gcccgccgtc gccggatcag ccggctgtgg ggggtgccgg tgatcgagga gtacggctcc     720
acggagaccg gcagcctcgc cggggagtgc ccgaacggcc ggatgcacct ctgggccgac     780
cgggcgctgt tcgaggtgta cgacccgcgc accggcaccg tcagcgcgga cggggacggc     840
cagctcgtgg tcacccccgct gttccgcgag gcgatgccgc tgctgcgcta caacctcgag     900
gacgacgtga cggtctccta cgacgactgc gcgtgcggct ggaacctgcc gaccgtccgg     960
gtgctcggcc gggcggcgtt cggttaccgg gtgggcgccg cgacgatcac ccagcaccgg    1020
ctggaggagg tcgtcttctc cctgccggaa tcccacgggg tggtgttctg gcgggcgaag    1080
gcggaaccga cggtgttgcg catcgagatc gaggtggccg aggagcaccg gaccgccgcc    1140
caggcggagc tgacgcgtc ggtgcgggcc acgttcggga tcgacagcga ggtcaccggg    1200
ttgaccccgg ggactctggt cccgcgtgag gcgctgacca gcatgccgga cgtggtcaag    1260
ccgcgcagcc tgttcgggcc cgacgaggac tggggcaaag cgctcctcta ctactga      1317
```

<210> SEQ ID NO 94
<211> LENGTH: 169
<212> TYPE: PRT
<213> ORGANISM: Streptomyces carzinostaticus neocarzinostaticus

<400> SEQUENCE: 94

Met Phe Ala Thr Ala Gly Ala Ala Glu Leu His Ala Val Val Glu Asp
1               5                   10                  15

Ser Ala Arg Leu Leu Gly Val Thr Cys Ser Pro Asp Thr Val Ala Pro
            20                  25                  30

Ile Leu Ser Thr Tyr Gly Asp Thr Phe Glu His Asp Ala Thr Val Val
        35                  40                  45

Ala Phe Arg Val Ala Thr Gly Lys Arg His Ile Gly Glu Leu Asp Cys
    50                  55                  60

Arg Phe Thr His Pro Thr His Arg Asp Pro Tyr Ala Leu Ala Leu
65                  70                  75                  80

Ser Asn Gly Leu Thr Pro Lys Thr Gly His Pro Val Gly Ser Leu Leu
                85                     90                 95

Ser Ala Leu Gln Glu Arg Leu Pro Ile Asp Ser Tyr Gly Ile Asp Phe
            100                  105              110

Gly Val Gly Gly Phe Lys Lys Ile Tyr Ser Phe Phe Thr Pro Asp
       115                  120              125

Ala Leu Gln Glu Val Ala Ala Leu Ala Gly Ile Pro Ser Met Pro Arg
    130                  135              140

Ser Leu Ala Gly Arg Asp Phe Phe Glu Arg Tyr Gly Cys Thr Thr Gly
145              150              155            160

Arg Val Ile Gly Ile Asp Tyr Pro His
           165

<210> SEQ ID NO 95
<211> LENGTH: 507
<212> TYPE: DNA
<213> ORGANISM: Streptomyces carzinostaticus neocarzinostaticus

<400> SEQUENCE: 95

```
atgttcgcaa ctgccggggc ggcagaactt cacgcggtcg tagaggactc ggctcggctg      60
ctgggcgtca cctgctcgcc cgacacggtg gcgcccatcc tgtccacgta cggcgacacc     120
ttcgagcacg acgccaccgt ggtcgccttc cgggtggcga ccggcaagcg ccacatcggc     180
gaactcgact gccgcttcac gacccatccc acgcaccgcg accccctacg cctcgccctg     240
tcgaacgggc tcacgccgaa gaccggccat cccgtcggct ccctgctctc cgccctgcag     300
gaacggctgc ccatcgacag ttacgggatc gacttcggag tcgtgggcgg cttcaagaag     360
atctactcgt tcttcacccc ggacgccctg caagaggtgg cggcgctcgc cggcattccg     420
tccatgccgc gcagcctggc cggacgggac ttcttcgagc ggtacggctg cacgaccggt     480
cgggtgatcg gcatcgacta cccgcac                                        507
```

<210> SEQ ID NO 96
<211> LENGTH: 438
<212> TYPE: PRT
<213> ORGANISM: Streptomyces carzinostaticus neocarzinostaticus

<400> SEQUENCE: 96

Val Asn Pro Thr Arg Ser Ser Leu Pro Arg Leu Gly Gln Trp Asn Gly
1               5                  10               15

Pro Glu Asp Leu Arg Leu Leu Gln Glu Lys Gln Leu Gln Thr Val
         20                  25              30

Gly Trp Ala Ser Arg Ser Pro Phe Tyr Arg Gly Arg Leu Asp Thr Ala
          35                  40              45

Ala Leu Pro Thr Thr Ile Asp Asp Leu Ala Ser Leu Pro Leu Thr Thr
    50                  55              60

Lys Gln Asp Leu Arg Asp Asn Tyr Pro Phe Gly Met Leu Ala Val Pro
65              70              75            80

Lys Glu Arg Leu Ala Thr Tyr His Glu Ser Ser Gly Thr Ala Gly Arg
         85                  90              95

Pro Thr Pro Ser Tyr Tyr Thr Ala Asp Asp Trp Ile Asp Leu Ala Glu
          100                  105              110

Arg Phe Ala Arg Lys Trp Ile Gly Ile Thr Ala Glu Asp Val Phe Leu
          115                  120              125

Val Arg Thr Pro Tyr Ala Leu Leu Leu Thr Gly His Leu Ala His Ala
    130                  135              140

```
Ala Gly Arg Leu His Gly Ala Thr Val Val Pro Gly Asp Asn Arg Ser
145                 150                 155                 160

Leu Ala Met Pro Tyr Ala Arg Val Val Arg Val Met His Asp Leu Gly
                165                 170                 175

Val Thr Leu Thr Trp Ser Val Pro Thr Glu Cys Leu Ile Trp Ala Ala
            180                 185                 190

Ala Ala Thr Ala Ala Gly His Arg Pro Ser Glu Asp Phe Pro Ala Leu
        195                 200                 205

Arg Ala Leu Phe Val Gly Gly Glu Pro Leu Thr Thr Ala Arg Arg Asp
210                 215                 220

Arg Ile Ser Arg Leu Trp Gly Val Pro Val Ile Glu Glu Tyr Gly Ser
225                 230                 235                 240

Thr Glu Thr Gly Ser Leu Ala Gly Glu Cys Pro His Gly Arg Met His
                245                 250                 255

Leu Trp Ala Asp Arg Ala Leu Phe Glu Val Tyr Asp Pro Gln Thr Gly
            260                 265                 270

Thr Val Arg Ala Glu Gly Glu Gly Gln Leu Val Val Thr Pro Leu Tyr
        275                 280                 285

Arg Glu Ala Met Pro Leu Leu Arg Tyr Asn Leu Glu Asp Asn Val Ser
290                 295                 300

Val Ala Tyr Asp Asp Cys Ala Cys Gly Trp Lys Leu Pro Thr Val Gln
305                 310                 315                 320

Val Leu Gly Arg Ala Ala Phe Gly His Arg Val Gly Ala Thr Thr Val
                325                 330                 335

Thr Gln His Arg Leu Glu Glu Leu Val Phe Ser Leu Pro Asp Ala Tyr
            340                 345                 350

Gln Val Phe Trp Arg Ala Arg Ala Glu Pro Ala Ala Leu Arg Ile
        355                 360                 365

Glu Ile Glu Val Pro Glu His Arg Ala Ala Ala Glu Ala Glu Leu
370                 375                 380

Val His Ser Val Arg Thr Ala Phe Gly Val Asp Ser Thr Val Thr Gly
385                 390                 395                 400

Leu Pro Pro Gly Thr Leu Ile Pro His Gly Ala Leu Thr Ala Met Pro
                405                 410                 415

Asp Val Val Lys Pro Arg Ser Leu Phe Gly Pro Asp Glu Asp Trp Gly
            420                 425                 430

Lys Ala Leu Leu Tyr Tyr
        435
```

<210> SEQ ID NO 97
<211> LENGTH: 1317
<212> TYPE: DNA
<213> ORGANISM: Streptomyces carzinostaticus neocarzinostaticus

<400> SEQUENCE: 97

```
gtgaacccga cacgctcgag tctgcctcgg ctcggccagt ggaacggacc ggaggatctg      60
cggctccttc aggagaagca gcttcagcag accgtcggat gggcgtcccg ctcgccgttc     120
taccgcggcc ggctcgacac ggcggccctg cccacgacca tcgacgacct cgcctccctg     180
ccactgacca ccaaacagga ccttcgggac aactacccct cgggatgct ggccgtcccg      240
aaggagcggc tggccacgta tcacgagtcg agcgggaccg cgggccggcc cacgccctcg     300
tactacacgg ccgacgactg gatcgacctg gccgaacgct tcgcccgcaa gtggatcggc     360
atcaccgccg aggacgtctt cctggtgcgc acaccgtacg cgctgctgct gacggggcat     420
```

```
ctcgcacacg ccgccggccg gctgcacggg gccaccgtcg tgcccggtga caaccgctcg    480
ctggccatgc cgtacgcccg cgtggtgcgg gtcatgcacg acctgggcgt cacgctgacc    540
tggtcggtgc cgaccgaatg cctcatctgg gccgccgcgg cgaccgcggc cgggcaccgg    600
ccctccgagg acttcccggc gctgcgcgca ctgttcgtcg gcggcgagcc gctcaccacc    660
gcccgccgcg accggatcag ccggttgtgg ggcgtcccgg tgatcgagga gtacggctcc    720
accgagaccg gcagcctcgc cggcgagtgt ccgcacggac ggatgcatct gtgggccgac    780
cgggcgctgt tcgaggtgta cgacccgcaa accggcaccg tccgcgcgga gggcgagggc    840
cagctggtgg tcacgcccct gtaccgcgag gcgatgcccc tgctgcgcta caacctcgag    900
gacaacgtgt cggtcgccta cgacgactgc gcgtgcggct ggaagctgcc cacggtccag    960
gtgctcggca gggccgcgtt cggccatcgg gtcggcgcca cgaccgtcac ccagcaccgg   1020
ctggaggaac tcgtcttctc gctcccggac gcctaccagg tggtgttctg gcgggcgcgg   1080
gcggagccgg ccgcgctgcg catcgagatc gaggtgcccg aggagcaccg gcggccgcc    1140 gaggcggaac tggtgcactc ggtgcggacc gcgttcggtg tggacagcac ggtcaccggc   1200
ctccctccgg gcaccctgat ccccacggc gcgctgaccc ccatgcccga cgtggtcaag    1260
ccgcgcagcc tcttcgggcc cgacgaggac tggggcaaag cgctcctcta ctactga     1317
```

<210> SEQ ID NO 98
<211> LENGTH: 290
<212> TYPE: PRT
<213> ORGANISM: Artificial sequence
<220> FEATURE:
<221> NAME/KEY: Miscfeature
<222> LOCATION: (1)..(290)
<223> OTHER INFORMATION: HMM consensus seq based on alignment of Fig 10
      IPTN

<400> SEQUENCE: 98

```
Ala Ala Glu Leu Tyr Ser Val Ile Glu Glu Ser Ala Arg Leu Leu Asp
1               5                   10                  15

Val Ala Cys Ser Arg Asp Arg Val Trp Pro Ile Leu Ser Ala Tyr Gly
            20                  25                  30

Asp Ala Phe Ala His Pro Ala Ala Val Val Ala Phe Arg Val Ala Thr
        35                  40                  45

Ala Leu Arg His Val Gly Glu Leu Asp Cys Arg Phe Thr Thr His Pro
    50                  55                  60

Asp Asp Arg Asp Pro Tyr Ala Leu Ala Leu Ser Arg Gly Leu Thr Pro
65                  70                  75                  80

Lys Thr Asp His Pro Val Gly Ser Leu Leu Ser Glu Val Gln Glu Arg
                85                  90                  95

Leu Pro Val Glu Ser Tyr Gly Ile Asp Phe Gly Val Val Gly Gly Phe
            100                 105                 110

Lys Lys Ile Tyr Ala Phe Phe Thr Pro Asp Glu Leu Gln Glu Val Ala
        115                 120                 125

Ala Leu Ala Gly Ile Pro Ala Met Pro Arg Ser Leu Ala Gly Asn Ala
    130                 135                 140

Asp Phe Phe Glu Arg Tyr Gly Leu Asp Asp Arg Val Gly Val Leu Gly
145                 150                 155                 160

Ile Asp Tyr Pro Ala Arg Thr Val Asn Val Tyr Phe Asn Asp Val Pro
                165                 170                 175

Ala Glu Ser Phe Glu Ser Glu Thr Ile Arg Ser Thr Leu Arg Glu Ile
            180                 185                 190
```

```
Gly Met Ala Glu Pro Ser Glu Arg Met Leu Lys Leu Gly Glu Lys Ala
            195                 200                 205

Phe Gly Leu Tyr Val Thr Leu Gly Trp Asp Ser Ser Glu Ile Glu Arg
        210                 215                 220

Ile Cys Tyr Ala Ala Ala Thr Thr Asp Leu Thr Thr Leu Pro Val Pro
225                 230                 235                 240

Val Glu Pro Glu Ile Glu Lys Phe Val Lys Ser Val Pro Tyr Gly Gly
                245                 250                 255

Glu Asp Arg Lys Phe Val Tyr Gly Val Ala Leu Thr Pro Lys Gly Glu
            260                 265                 270

Tyr Tyr Lys Leu Glu Ser His Tyr Lys Trp Lys Pro Gly Ala Val Asp
        275                 280                 285

Phe Ile
    290

<210> SEQ ID NO 99
<211> LENGTH: 438
<212> TYPE: PRT
<213> ORGANISM: Artificial sequence
<220> FEATURE:
<221> NAME/KEY: Miscfeature
<222> LOCATION: (1)..(438)
<223> OTHER INFORMATION: HMM consensus seq based on alignment of Fig 11
      ADSA

<400> SEQUENCE: 99

Val Asn Glu Pro Arg Ser Ser Leu Pro Arg Leu Gly Gln Trp His Gly
1               5                   10                  15

Pro Glu Asp Leu Arg Arg Leu Gln Glu Lys Gln Leu Ala Gln Thr Val
            20                  25                  30

Thr Trp Ala Ala Arg Ser Pro Phe Tyr Arg Asp Arg Leu Asp Ser Gly
        35                  40                  45

Ala Leu Pro Val Thr Ala Ala Asp Leu Ala Asp Leu Pro Leu Thr Thr
    50                  55                  60

Lys Gln Asp Leu Arg Asp Asn Tyr Pro Phe Gly Met Leu Ala Val Pro
65                  70                  75                  80

Lys Glu Arg Leu Ala Thr Tyr His Glu Ser Ser Gly Thr Ala Gly Arg
                85                  90                  95

Pro Thr Pro Ser Tyr Tyr Thr Ala Glu Asp Trp Thr Asp Leu Ala Glu
            100                 105                 110

Arg Phe Ala Arg Lys Trp Ile Gly Met Ser Ala Glu Asp Val Phe Leu
        115                 120                 125

Val Arg Thr Pro Tyr Ala Leu Leu Leu Thr Gly His Leu Ala His Ala
    130                 135                 140

Ala Gly Arg Leu Arg Gly Ala Thr Val Val Pro Gly Asp Asn Arg Ser
145                 150                 155                 160

Leu Ala Met Pro Tyr Ala Arg Val Val Arg Val Met His Asp Leu Gly
                165                 170                 175

Val Thr Leu Thr Trp Ser Val Pro Thr Glu Cys Leu Ile Trp Ala Ala
            180                 185                 190

Ala Ala Thr Ala Ala Gly His Arg Pro Asp Val Asp Phe Pro Ala Leu
        195                 200                 205

Arg Ala Leu Phe Val Gly Gly Glu Pro Leu Thr Asp Ala Arg Arg Arg
    210                 215                 220

Arg Ile Ser Arg Leu Trp Gly Val Pro Val Ile Glu Glu Tyr Gly Ser
225                 230                 235                 240
```

-continued

```
Thr Glu Thr Gly Ser Leu Ala Gly Glu Cys Pro Glu Gly Arg Leu His
            245                 250                 255

Leu Trp Ala Asp Arg Ala Leu Phe Glu Val Tyr Asp Pro Asp Thr Gly
            260                 265                 270

Thr Val Arg Ala Asp Gly Asp Gly Gln Leu Val Val Thr Pro Leu Phe
            275                 280                 285

Arg Glu Ala Met Pro Leu Leu Arg Tyr Asn Leu Glu Asp Asn Val Ser
        290                 295                 300

Val Ser Tyr Asp Asp Cys Ala Cys Gly Trp Lys Leu Pro Thr Val Arg
305                 310                 315                 320

Val Leu Gly Arg Ala Ala Phe Gly Tyr Arg Val Gly Ala Thr Thr Ile
            325                 330                 335

Thr Gln His Arg Leu Glu Glu Leu Val Phe Ser Leu Pro Glu Ala His
            340                 345                 350

Arg Val Val Phe Trp Arg Ala Lys Ala Glu Pro Ala Val Leu Arg Ile
            355                 360                 365

Glu Ile Glu Val Ala Glu Glu His Arg Val Ala Ala Glu Ala Glu Leu
    370                 375                 380

Thr Ala Ser Val Arg Ala Ala Phe Gly Val Asp Ser Glu Val Thr Gly
385                 390                 395                 400

Leu Ala Pro Gly Thr Leu Ile Pro Arg Glu Ala Leu Thr Ser Met Pro
            405                 410                 415

Asp Val Val Lys Pro Arg Ser Leu Phe Gly Pro Asp Glu Asp Trp Gly
            420                 425                 430

Lys Ala Leu Leu Tyr Tyr
            435
```